(12) United States Patent
Johnson et al.

(10) Patent No.: US 8,406,894 B2
(45) Date of Patent: Mar. 26, 2013

(54) SYSTEMS, APPARATUS, METHODS AND PROCEDURES FOR THE NONINVASIVE TREATMENT OF TISSUE USING MICROWAVE ENERGY

(75) Inventors: Jessi Ernest Johnson, Sunnyvale, CA (US); Mark E. Deem, Mountain View, CA (US); Daniel Francis, Mountain View, CA (US); Steven Kim, Los Altos, CA (US); Alexey Salamini, San Francisco, CA (US); Ted Su, Sunnyvale, CA (US); Peter Smith, Kirkcaldy (GB); Daniel Hallock, Redwood City, CA (US); Yoav Ben-Haim, San Francisco, CA (US); Shailendhar Saraf, San Jose, CA (US)

(73) Assignee: Miramar Labs, Inc., Sunnyvale, CA (US)

( * ) Notice: Subject to any disclaimer, the term of this patent is extended or adjusted under 35 U.S.C. 154(b) by 0 days.

(21) Appl. No.: 13/246,820

(22) Filed: Sep. 27, 2011

(65) Prior Publication Data

US 2012/0022622 A1 Jan. 26, 2012

Related U.S. Application Data

(63) Continuation of application No. 12/747,538, filed as application No. PCT/US2008/013650 on Dec. 12, 2008, which is a continuation-in-part of application No. 12/107,025, filed on Apr. 21, 2008, which is a continuation-in-part of application No.

(Continued)

(51) Int. Cl.
*A61B 18/20* (2006.01)

(52) U.S. Cl. ............... 607/101; 606/9; 606/33; 607/102
(58) Field of Classification Search .................. 607/101, 607/102
See application file for complete search history.

(56) References Cited

U.S. PATENT DOCUMENTS

| 2,407,690 | A | 9/1946 | Southworth |
| 3,307,553 | A | 3/1967 | Liebner |
| 3,527,227 | A | 9/1970 | Fritz |
| 3,693,623 | A | 9/1972 | Harte et al. |
| 3,845,267 | A | 10/1974 | Fitzmayer |
| 4,069,827 | A | 1/1978 | Dominy |
| 4,095,602 | A | 6/1978 | Laveen |

(Continued)

FOREIGN PATENT DOCUMENTS

| EP | 0139607 B1 | 4/1990 |
| EP | 0370890 B1 | 11/1995 |

(Continued)

OTHER PUBLICATIONS

Lehmann et al.; Therapeutic Heat; Therapeutic Heat and Cold, Fourth Ed.; Chapter 9; pp. 417-581; Williams & Wilkins (publishers), Baltimore, MD; Apr. 1990.

(Continued)

*Primary Examiner* — Linda Dvorak
*Assistant Examiner* — Jared W Pike
(74) *Attorney, Agent, or Firm* — Shay Glenn LLP

(57) ABSTRACT

The present invention is directed to systems, apparatus, methods and procedures for the noninvasive treatment of tissue using microwave energy. In one embodiment of the invention a medical device and associated apparatus and procedures are used to treat dermatological conditions using microwave energy.

12 Claims, 62 Drawing Sheets

Related U.S. Application Data

PCT/US2008/060935, filed on Apr. 18, 2008, and a continuation-in-part of application No. PCT/US2008/060929, filed on Apr. 18, 2008, and a continuation-in-part of application No. PCT/US2008/060940, filed on Apr. 18, 2008, and a continuation-in-part of application No. PCT/US2008/060922, filed on Apr. 18, 2008.

(60) Provisional application No. 61/196,948, filed on Oct. 22, 2008, provisional application No. 61/013,274, filed on Dec. 12, 2007, provisional application No. 61/045,937, filed on Apr. 17, 2008.

(56) References Cited

U.S. PATENT DOCUMENTS

| | | |
|---|---|---|
| 4,108,147 A | 8/1978 | Kantor |
| 4,140,130 A | 2/1979 | Storm, III |
| 4,174,713 A | 11/1979 | Mehl |
| 4,190,053 A | 2/1980 | Sterzer |
| 4,190,056 A | 2/1980 | Tapper et al. |
| 4,197,860 A | 4/1980 | Sterzer |
| 4,228,809 A | 10/1980 | Paglione |
| 4,375,220 A | 3/1983 | Matvias |
| 4,378,806 A | 4/1983 | Henley-Cohn |
| 4,388,924 A | 6/1983 | Weissman et al. |
| 4,397,313 A | 8/1983 | Vaguine |
| 4,397,314 A | 8/1983 | Vaguine |
| 4,446,874 A | 5/1984 | Vaguine |
| 4,528,991 A | 7/1985 | Dittmar et al. |
| 4,589,424 A | 5/1986 | Vaguine |
| 4,597,379 A | 7/1986 | Kihn et al. |
| 4,614,191 A | 9/1986 | Perler |
| 4,617,926 A | 10/1986 | Sutton |
| 4,641,649 A | 2/1987 | Walinsky et al. |
| 4,669,475 A | 6/1987 | Turner |
| 4,672,980 A | 6/1987 | Turner |
| 4,690,156 A | 9/1987 | Kikuchi et al. |
| 4,744,372 A | 5/1988 | Kikuchi et al. |
| 4,747,416 A | 5/1988 | Kikuchi et al. |
| 4,800,899 A | 1/1989 | Elliott |
| 4,825,880 A | 5/1989 | Stauffer et al. |
| 4,841,989 A | 6/1989 | Kikuchi et al. |
| 4,841,990 A | 6/1989 | Kikuchi et al. |
| 4,860,752 A | 8/1989 | Turner |
| 4,860,770 A | 8/1989 | Kikuchi et al. |
| 4,873,995 A | 10/1989 | Kikuchi et al. |
| 4,881,543 A | 11/1989 | Trembly et al. |
| 4,891,483 A | 1/1990 | Kikuchi et al. |
| 4,945,912 A | 8/1990 | Langberg |
| 4,974,587 A | 12/1990 | Turner et al. |
| 5,025,810 A | 6/1991 | Kikuchi et al. |
| 5,033,478 A | 7/1991 | Kikuchi et al. |
| 5,059,192 A | 10/1991 | Zaias |
| 5,097,846 A | 3/1992 | Larsen |
| 5,101,836 A | 4/1992 | Lee |
| 5,107,832 A | 4/1992 | Guibert et al. |
| 5,143,063 A | 9/1992 | Fellner |
| 5,148,814 A | 9/1992 | Kikuchi et al. |
| 5,186,181 A | 2/1993 | Franconi et al. |
| 5,190,031 A | 3/1993 | Guibert et al. |
| 5,190,518 A | 3/1993 | Takasu |
| 5,198,776 A | 3/1993 | Carr |
| 5,226,907 A | 7/1993 | Tankovich |
| 5,231,997 A | 8/1993 | Kikuchi et al. |
| 5,234,004 A | 8/1993 | Hascoet et al. |
| 5,246,438 A | 9/1993 | Langberg |
| 5,272,301 A | 12/1993 | Finger et al. |
| 5,295,955 A | 3/1994 | Rosen et al. |
| 5,301,692 A | 4/1994 | Knowlton |
| 5,305,748 A | 4/1994 | Wilk |
| 5,315,994 A | 5/1994 | Guibert et al. |
| 5,316,000 A | 5/1994 | Chapelon et al. |
| 5,364,336 A | 11/1994 | Carr |
| 5,364,394 A | 11/1994 | Mehl |
| 5,383,917 A | 1/1995 | Desai et al. |
| 5,385,544 A | 1/1995 | Edwards et al. |
| 5,405,346 A | 4/1995 | Grundy et al. |
| 5,407,440 A | 4/1995 | Zinreich et al. |
| 5,409,484 A | 4/1995 | Erlich et al. |
| 5,421,819 A | 6/1995 | Edwards et al. |
| 5,425,728 A | 6/1995 | Tankovich |
| 5,433,740 A | 7/1995 | Yamaguchi |
| 5,441,532 A | 8/1995 | Fenn |
| 5,443,487 A | 8/1995 | Guibert et al. |
| 5,462,521 A | 10/1995 | Brucker et al. |
| 5,474,071 A | 12/1995 | Chapelon et al. |
| 5,480,417 A | 1/1996 | Hascoet et al. |
| 5,503,150 A | 4/1996 | Evans |
| 5,507,741 A | 4/1996 | L'Esperance, Jr. |
| 5,507,790 A | 4/1996 | Weiss |
| 5,509,929 A | 4/1996 | Hascoet et al. |
| 5,522,814 A | 6/1996 | Bernaz |
| 5,531,662 A | 7/1996 | Carr |
| 5,540,681 A | 7/1996 | Strul et al. |
| 5,549,639 A | 8/1996 | Ross |
| 5,553,612 A | 9/1996 | Lundback |
| 5,569,237 A | 10/1996 | Beckenstein |
| 5,571,154 A | 11/1996 | Ren |
| 5,575,789 A | 11/1996 | Bell et al. |
| 5,584,830 A | 12/1996 | Ladd et al. |
| 5,586,981 A | 12/1996 | Hu |
| 5,595,568 A | 1/1997 | Anderson et al. |
| 5,660,836 A | 8/1997 | Knowlton |
| 5,662,110 A | 9/1997 | Carr |
| 5,669,916 A | 9/1997 | Anderson |
| 5,683,381 A | 11/1997 | Carr et al. |
| 5,683,382 A | 11/1997 | Lenihan et al. |
| 5,690,614 A | 11/1997 | Carr et al. |
| 5,707,403 A | 1/1998 | Grove et al. |
| 5,724,966 A | 3/1998 | Lundback |
| 5,732,699 A | 3/1998 | Lundback |
| 5,732,700 A | 3/1998 | Lundback |
| 5,733,269 A | 3/1998 | Fuisz |
| 5,735,844 A | 4/1998 | Anderson et al. |
| 5,742,392 A | 4/1998 | Anderson et al. |
| 5,743,899 A | 4/1998 | Zinreich |
| 5,755,753 A | 5/1998 | Knowlton |
| 5,769,879 A | 6/1998 | Richards et al. |
| 5,776,127 A | 7/1998 | Anderson et al. |
| 5,779,635 A | 7/1998 | Carr |
| 5,782,897 A | 7/1998 | Carr |
| 5,810,801 A | 9/1998 | Anderson et al. |
| 5,810,804 A | 9/1998 | Gough et al. |
| 5,814,996 A | 9/1998 | Winter |
| 5,824,023 A | 10/1998 | Anderson |
| 5,830,208 A | 11/1998 | Muller |
| 5,836,999 A | 11/1998 | Eckhouse et al. |
| 5,842,985 A | 12/1998 | Lundback |
| 5,868,732 A | 2/1999 | Waldman et al. |
| 5,871,524 A | 2/1999 | Knowlton |
| 5,879,346 A | 3/1999 | Waldman et al. |
| 5,891,094 A | 4/1999 | Masterson et al. |
| 5,897,549 A | 4/1999 | Tankovich |
| 5,904,709 A | 5/1999 | Arndt et al. |
| 5,919,218 A | 7/1999 | Carr |
| 5,919,219 A | 7/1999 | Knowlton |
| 5,928,797 A | 7/1999 | Vineberg |
| 5,931,860 A | 8/1999 | Reid et al. |
| 5,948,011 A | 9/1999 | Knowlton |
| 5,971,982 A | 10/1999 | Betsill et al. |
| 5,979,454 A | 11/1999 | Anvari et al. |
| 5,983,124 A | 11/1999 | Carr |
| 5,983,900 A | 11/1999 | Clement et al. |
| 6,015,404 A | 1/2000 | Altshuler et al. |
| 6,024,095 A | 2/2000 | Stanley, III |
| 6,026,331 A | 2/2000 | Feldberg et al. |
| 6,026,816 A | 2/2000 | McMillan et al. |
| 6,030,378 A | 2/2000 | Stewart |
| 6,036,632 A | 3/2000 | Whitmore, III et al. |
| 6,047,215 A | 4/2000 | McClure et al. |
| 6,050,990 A | 4/2000 | Tankovich et al. |
| 6,077,294 A | 6/2000 | Cho et al. |
| 6,080,146 A | 6/2000 | Altshuler et al. |
| 6,093,186 A | 7/2000 | Goble |

| | | |
|---|---|---|
| 6,097,985 A | 8/2000 | Kasevich et al. |
| 6,104,959 A | 8/2000 | Spertell |
| 6,106,514 A | 8/2000 | O'Donnell, Jr. |
| 6,113,559 A | 9/2000 | Klopotek |
| 6,113,593 A | 9/2000 | Tu et al. |
| 6,126,636 A | 10/2000 | Naka |
| 6,139,569 A | 10/2000 | Ingle et al. |
| 6,149,644 A | 11/2000 | Xie |
| 6,162,212 A | 12/2000 | Kreindel et al. |
| 6,162,218 A | 12/2000 | Elbrecht et al. |
| 6,171,301 B1 | 1/2001 | Nelson et al. |
| 6,175,768 B1 | 1/2001 | Arndt et al. |
| 6,181,970 B1 | 1/2001 | Kasevich |
| 6,183,773 B1 | 2/2001 | Anderson |
| 6,187,001 B1 | 2/2001 | Azar et al. |
| 6,197,020 B1 | 3/2001 | O'Donnell, Jr. |
| 6,208,903 B1 | 3/2001 | Richards et al. |
| 6,210,367 B1 | 4/2001 | Carr |
| 6,214,034 B1 | 4/2001 | Azar |
| 6,223,076 B1 | 4/2001 | Tapper |
| 6,231,569 B1 | 5/2001 | Bek et al. |
| 6,235,016 B1 | 5/2001 | Stewart |
| 6,241,753 B1 | 6/2001 | Knowlton |
| 6,245,062 B1 | 6/2001 | Berube et al. |
| 6,264,652 B1 | 7/2001 | Eggers et al. |
| 6,273,884 B1 | 8/2001 | Altshuler et al. |
| 6,277,104 B1 | 8/2001 | Lasko et al. |
| 6,277,111 B1 | 8/2001 | Clement et al. |
| 6,277,116 B1 | 8/2001 | Utely et al. |
| 6,280,441 B1 | 8/2001 | Ryan |
| 6,283,956 B1 | 9/2001 | McDaniel |
| 6,283,987 B1 | 9/2001 | Laird et al. |
| 6,287,302 B1 | 9/2001 | Berube |
| 6,290,699 B1 | 9/2001 | Hall et al. |
| 6,293,941 B1 | 9/2001 | Strul et al. |
| 6,306,128 B1 | 10/2001 | Waldman et al. |
| 6,306,130 B1 | 10/2001 | Anderson et al. |
| 6,311,090 B1 | 10/2001 | Knowlton |
| 6,312,427 B1 | 11/2001 | Berube et al. |
| 6,319,211 B1 | 11/2001 | Ito et al. |
| 6,322,584 B2 | 11/2001 | Ingle et al. |
| 6,325,769 B1 | 12/2001 | Klopotek |
| 6,330,479 B1 | 12/2001 | Stauffer |
| 6,334,074 B1 | 12/2001 | Spertell |
| 6,347,251 B1 | 2/2002 | Deng |
| 6,350,263 B1 | 2/2002 | Wetzig et al. |
| 6,350,276 B1 | 2/2002 | Knowlton |
| 6,361,531 B1 | 3/2002 | Hissong |
| 6,364,876 B1 | 4/2002 | Erb et al. |
| 6,377,854 B1 | 4/2002 | Knowlton |
| 6,377,855 B1 | 4/2002 | Knowlton |
| 6,381,498 B1 | 4/2002 | Knowlton |
| 6,383,176 B1 | 5/2002 | Connors et al. |
| 6,383,182 B1 | 5/2002 | Berube et al. |
| 6,387,103 B2 | 5/2002 | Shadduck |
| 6,387,380 B1 | 5/2002 | Knowlton |
| 6,402,739 B1 | 6/2002 | Neev |
| 6,405,090 B1 | 6/2002 | Knowlton |
| 6,409,720 B1 | 6/2002 | Hissong et al. |
| 6,409,722 B1 | 6/2002 | Hoey et al. |
| 6,413,253 B1 | 7/2002 | Koop et al. |
| 6,413,254 B1 | 7/2002 | Hissong et al. |
| 6,413,255 B1 | 7/2002 | Stern |
| 6,425,912 B1 | 7/2002 | Knowlton |
| 6,427,089 B1 | 7/2002 | Knowlton |
| 6,428,532 B1 | 8/2002 | Doukas et al. |
| 6,430,446 B1 | 8/2002 | Knowlton |
| 6,436,094 B1 | 8/2002 | Reuter |
| 6,436,127 B1 | 8/2002 | Anderson et al. |
| 6,438,424 B1 | 8/2002 | Knowlton |
| 6,443,914 B1 | 9/2002 | Costantino |
| 6,443,946 B2 | 9/2002 | Clement et al. |
| 6,451,013 B1 | 9/2002 | Bays et al. |
| 6,451,015 B1 | 9/2002 | Rittman, III et al. |
| 6,453,202 B1 | 9/2002 | Knowlton |
| 6,457,476 B1 | 10/2002 | Elmer et al. |
| 6,461,378 B1 | 10/2002 | Knowlton |
| 6,468,235 B2 | 10/2002 | Ito et al. |
| 6,470,216 B1 | 10/2002 | Knowlton |
| 6,471,662 B1 | 10/2002 | Jaggy et al. |
| 6,471,696 B1 | 10/2002 | Berube et al. |
| 6,475,211 B2 | 11/2002 | Chess et al. |
| 6,480,746 B1 | 11/2002 | Ingle et al. |
| 6,485,484 B1 | 11/2002 | Connors et al. |
| 6,485,703 B1 | 11/2002 | Coté et al. |
| 6,500,141 B1 | 12/2002 | Irion et al. |
| 6,508,813 B1 | 1/2003 | Altshuler |
| 6,514,250 B1 | 2/2003 | Jahns et al. |
| 6,517,532 B1 | 2/2003 | Altshuler et al. |
| 6,529,778 B2 | 3/2003 | Prutchi |
| 6,558,382 B2 | 5/2003 | Jahns et al. |
| 6,575,969 B1 | 6/2003 | Ritman, III et al. |
| 6,577,903 B1 | 6/2003 | Cronin et al. |
| 6,584,360 B2 | 6/2003 | Francischelli et al. |
| 6,585,733 B2 | 7/2003 | Wellman |
| 6,595,934 B1 | 7/2003 | Hissong et al. |
| 6,600,951 B1 | 7/2003 | Anderson |
| 6,605,080 B1 | 8/2003 | Altshuler et al. |
| 6,607,498 B2 | 8/2003 | Eshel |
| 6,626,854 B2 | 9/2003 | Friedman et al. |
| 6,628,990 B1 | 9/2003 | Habib et al. |
| 6,629,974 B2 | 10/2003 | Penny et al. |
| 6,645,162 B2 | 11/2003 | Friedman et al. |
| 6,648,904 B2 | 11/2003 | Altshuler et al. |
| 6,652,518 B2 | 11/2003 | Wellman et al. |
| 6,653,618 B2 | 11/2003 | Zenzie |
| 6,662,054 B2 | 12/2003 | Kreindel et al. |
| 6,663,620 B2 | 12/2003 | Altshuler et al. |
| 6,663,659 B2 | 12/2003 | McDaniel |
| 6,676,654 B1 | 1/2004 | Balle Petersen et al. |
| 6,676,655 B2 | 1/2004 | McDaniel |
| 6,682,501 B1 | 1/2004 | Nelson et al. |
| 6,692,450 B1 | 2/2004 | Coleman |
| 6,723,090 B2 | 4/2004 | Altshuler et al. |
| 6,725,095 B2 | 4/2004 | Fenn et al. |
| 6,736,810 B2 | 5/2004 | Hoey et al. |
| 6,743,222 B2 | 6/2004 | Durkin et al. |
| 6,749,624 B2 | 6/2004 | Knowlton |
| 6,763,836 B2 | 7/2004 | Tasto et al. |
| 6,766,202 B2 | 7/2004 | Underwood et al. |
| 6,807,446 B2 | 10/2004 | Fenn et al. |
| 6,808,532 B2 | 10/2004 | Andersen et al. |
| 6,821,274 B2 | 11/2004 | McHale et al. |
| 6,823,216 B1 | 11/2004 | Salomir et al. |
| 6,824,542 B2 | 11/2004 | Jay |
| 6,856,839 B2 | 2/2005 | Litovitz |
| 6,861,954 B2 | 3/2005 | Levin |
| 6,878,144 B2 | 4/2005 | Altshuler et al. |
| 6,878,147 B2 | 4/2005 | Prakash et al. |
| 6,881,212 B1 | 4/2005 | Clement et al. |
| 6,887,238 B2 | 5/2005 | Jahns et al. |
| 6,887,239 B2 | 5/2005 | Elstrom et al. |
| 6,887,260 B1 | 5/2005 | McDaniel |
| 6,888,319 B2 | 5/2005 | Inochkin et al. |
| 6,897,238 B2 | 5/2005 | Anderson |
| 6,916,316 B2 | 7/2005 | Jay |
| 6,918,908 B2 | 7/2005 | Bonner et al. |
| 6,939,344 B2 | 9/2005 | Kreindel |
| 6,939,346 B2 | 9/2005 | Kannenberg et al. |
| 6,955,672 B2 | 10/2005 | Cense et al. |
| 6,974,415 B2 | 12/2005 | Cerwin et al. |
| 6,974,451 B2 | 12/2005 | Altshuler et al. |
| 6,976,984 B2 | 12/2005 | Cense et al. |
| 6,976,985 B2 | 12/2005 | Altshuler et al. |
| 6,997,923 B2 | 2/2006 | Anderson et al. |
| 7,004,942 B2 | 2/2006 | Laird et al. |
| 7,006,874 B2 | 2/2006 | Knowlton et al. |
| 7,022,121 B2 | 4/2006 | Stern et al. |
| 7,029,469 B2 | 4/2006 | Vasily |
| 7,033,352 B1 | 4/2006 | Gauthier et al. |
| 7,044,959 B2 | 5/2006 | Anderson et al. |
| 7,052,491 B2 | 5/2006 | Erb et al. |
| 7,056,318 B2 | 6/2006 | Black |
| 7,066,929 B1 | 6/2006 | Azar et al. |
| 7,074,218 B2 | 7/2006 | Washington et al. |
| 7,077,840 B2 | 7/2006 | Altshuler et al. |
| 7,081,111 B2 | 7/2006 | Svaasand et al. |
| 7,089,054 B2 | 8/2006 | Palti |

| Patent | Type | Date | Inventor |
|---|---|---|---|
| 7,107,997 | B1 | 9/2006 | Moses et al. |
| 7,115,123 | B2 | 10/2006 | Knowlton et al. |
| 7,115,126 | B2 | 10/2006 | Berube et al. |
| 7,118,590 | B1 | 10/2006 | Cronin |
| 7,122,029 | B2 | 10/2006 | Koop et al. |
| 7,128,739 | B2 | 10/2006 | Prakash et al. |
| 7,135,033 | B2 | 11/2006 | Altshuler et al. |
| 7,136,699 | B2 | 11/2006 | Palti |
| 7,141,049 | B2 | 11/2006 | Stern et al. |
| 7,151,964 | B2 | 12/2006 | Desai et al. |
| 7,153,256 | B2 | 12/2006 | Riehl et al. |
| 7,153,285 | B2 | 12/2006 | Lauman et al. |
| 7,163,536 | B2 | 1/2007 | Godara |
| 7,175,950 | B2 | 2/2007 | Anderson et al. |
| 7,189,230 | B2 | 3/2007 | Knowlton et al. |
| 7,192,429 | B2 | 3/2007 | Trembly |
| 7,204,832 | B2 | 4/2007 | Altshuler et al. |
| 7,217,265 | B2 | 5/2007 | Hennings et al. |
| 7,220,254 | B2 | 5/2007 | Altshuler et al. |
| 7,220,778 | B2 | 5/2007 | Anderson et al. |
| 7,229,436 | B2 | 6/2007 | Stern et al. |
| 7,234,739 | B2 | 6/2007 | Saitoh et al. |
| 7,238,182 | B2 | 7/2007 | Swoyer et al. |
| 7,241,291 | B2 | 7/2007 | Kreindel et al. |
| 7,247,155 | B2 | 7/2007 | Hoey et al. |
| 7,250,047 | B2 | 7/2007 | Anderson et al. |
| 7,252,628 | B2 | 8/2007 | Van Hal et al. |
| 7,258,674 | B2 | 8/2007 | Cribbs et al. |
| 7,267,675 | B2 | 9/2007 | Stern et al. |
| 7,276,058 | B2 | 10/2007 | Altshuler et al. |
| 7,278,991 | B2 | 10/2007 | Morris et al. |
| 7,290,326 | B2 | 11/2007 | Dutton |
| 7,309,335 | B2 | 12/2007 | Altshuler et al. |
| 7,311,674 | B2 | 12/2007 | Gingrich et al. |
| 7,329,273 | B2 | 2/2008 | Altshuler et al. |
| 7,329,274 | B2 | 2/2008 | Altshuler et al. |
| 7,331,951 | B2 | 2/2008 | Eshel et al. |
| 7,344,587 | B2 | 3/2008 | Khan et al. |
| 7,347,855 | B2 | 3/2008 | Eshel et al. |
| 7,351,252 | B2 | 4/2008 | Altshuler et al. |
| 7,354,448 | B2 | 4/2008 | Altshuler et al. |
| 7,367,341 | B2 | 5/2008 | Anderson et al. |
| 7,377,917 | B2 | 5/2008 | Trembly |
| 7,387,627 | B2 | 6/2008 | Erb et al. |
| 7,399,297 | B2 | 7/2008 | Ikadai et al. |
| 7,422,586 | B2 | 9/2008 | Morris et al. |
| 7,422,598 | B2 | 9/2008 | Altshuler et al. |
| 7,431,718 | B2 | 10/2008 | Ikadai |
| 7,431,719 | B2 | 10/2008 | Altshuler et al. |
| 7,470,270 | B2 | 12/2008 | Azar et al. |
| 7,473,251 | B2 | 1/2009 | Knowlton et al. |
| 7,479,101 | B2 | 1/2009 | Hunter et al. |
| 7,481,807 | B2 | 1/2009 | Knudsen et al. |
| 7,481,809 | B2 | 1/2009 | Stern et al. |
| 7,491,171 | B2 | 2/2009 | Barthe et al. |
| 7,524,328 | B2 | 4/2009 | Connors et al. |
| 7,530,356 | B2 | 5/2009 | Slayton et al. |
| 7,530,958 | B2 | 5/2009 | Slayton et al. |
| 7,540,869 | B2 | 6/2009 | Altshuler et al. |
| 7,544,204 | B2 | 6/2009 | Krespi et al. |
| 7,565,207 | B2 | 7/2009 | Turner et al. |
| 7,568,619 | B2 | 8/2009 | Todd et al. |
| 7,588,547 | B2 | 9/2009 | Deem et al. |
| 7,599,745 | B2 | 10/2009 | Palti |
| 7,601,128 | B2 | 10/2009 | Deem et al. |
| 7,613,523 | B2 | 11/2009 | Eggers et al. |
| 7,630,774 | B2 | 12/2009 | Karni et al. |
| 7,643,883 | B2 | 1/2010 | Kreindel |
| 7,682,321 | B2 | 3/2010 | Naldoni |
| 7,713,234 | B2 | 5/2010 | Karanzas |
| 7,722,535 | B2 | 5/2010 | Randlov et al. |
| 7,722,600 | B2 | 5/2010 | Connors et al. |
| 7,722,656 | B1 | 5/2010 | Segal |
| 7,736,360 | B2 | 6/2010 | Mody et al. |
| 7,740,600 | B2 | 6/2010 | Slatkine et al. |
| 7,740,651 | B2 | 6/2010 | Barak et al. |
| 7,749,260 | B2 | 7/2010 | Da Silva et al. |
| 7,758,524 | B2 | 7/2010 | Barthe et al. |
| 7,758,537 | B1 | 7/2010 | Brunell et al. |
| 7,762,964 | B2 | 7/2010 | Slatkine |
| 7,763,060 | B2 | 7/2010 | Baumann |
| 7,771,421 | B2 | 8/2010 | Stewart et al. |
| 7,799,019 | B2 | 9/2010 | Turovskiy et al. |
| 7,805,201 | B2 | 9/2010 | Palti |
| 7,815,570 | B2 | 10/2010 | Eshel et al. |
| 7,815,633 | B2 | 10/2010 | Zanelli et al. |
| 7,824,394 | B2 | 11/2010 | Manstein |
| 7,828,734 | B2 | 11/2010 | Azhari et al. |
| 7,837,694 | B2 | 11/2010 | Tethrake et al. |
| 7,842,029 | B2 | 11/2010 | Anderson et al. |
| 7,854,754 | B2 | 12/2010 | Ting et al. |
| 7,857,773 | B2 | 12/2010 | Desilets et al. |
| 7,857,775 | B2 | 12/2010 | Rosenberg et al. |
| 7,862,564 | B2 | 1/2011 | Goble |
| 7,864,129 | B2 | 1/2011 | Konishi |
| 7,891,362 | B2 | 2/2011 | Domankevitz et al. |
| 7,905,844 | B2 | 3/2011 | Desilets et al. |
| 8,073,550 | B1 | 12/2011 | Spertell |
| 2001/0005775 | A1 | 6/2001 | Samson |
| 2001/0016761 | A1 | 8/2001 | Rudie et al. |
| 2001/0050083 | A1 | 12/2001 | Marchitto et al. |
| 2002/0062124 | A1 | 5/2002 | Keane |
| 2002/0156471 | A1 | 10/2002 | Stern et al. |
| 2002/0165529 | A1 | 11/2002 | Danek |
| 2002/0193851 | A1 | 12/2002 | Silverman et al. |
| 2003/0004082 | A1 | 1/2003 | Masschelein et al. |
| 2003/0060811 | A1 | 3/2003 | McDaniel |
| 2003/0130575 | A1 | 7/2003 | Desai |
| 2003/0130711 | A1 | 7/2003 | Pearson |
| 2003/0158566 | A1 | 8/2003 | Brett |
| 2003/0212393 | A1 | 11/2003 | Knowlton et al. |
| 2003/0216728 | A1 | 11/2003 | Stern et al. |
| 2004/0000316 | A1 | 1/2004 | Knowlton et al. |
| 2004/0049251 | A1 | 3/2004 | Knowlton |
| 2004/0092875 | A1 | 5/2004 | Kochamba |
| 2004/0186535 | A1 | 9/2004 | Knowlton |
| 2004/0206365 | A1 | 10/2004 | Knowlton |
| 2004/0210214 | A1 | 10/2004 | Knowlton |
| 2004/0230260 | A1 | 11/2004 | MacFarland et al. |
| 2004/0243182 | A1 | 12/2004 | Cohen et al. |
| 2004/0243200 | A1 | 12/2004 | Turner et al. |
| 2004/0249426 | A1 | 12/2004 | Hoenig et al. |
| 2005/0010271 | A1 | 1/2005 | Merchant |
| 2005/0137654 | A1 | 6/2005 | Hoenig et al. |
| 2005/0215987 | A1* | 9/2005 | Slatkine ............ 606/9 |
| 2005/0251117 | A1 | 11/2005 | Anderson et al. |
| 2005/0251120 | A1 | 11/2005 | Anderson et al. |
| 2005/0288666 | A1 | 12/2005 | Bertolero et al. |
| 2006/0020309 | A1 | 1/2006 | Altshuler et al. |
| 2006/0036300 | A1 | 2/2006 | Kreindel |
| 2006/0111744 | A1 | 5/2006 | Makin et al. |
| 2006/0112698 | A1 | 6/2006 | Cazzini et al. |
| 2006/0129209 | A1 | 6/2006 | McDaniel |
| 2006/0151485 | A1 | 7/2006 | Cronin |
| 2006/0161228 | A1 | 7/2006 | Lach |
| 2006/0167498 | A1 | 7/2006 | DiLorenzo |
| 2006/0184205 | A1 | 8/2006 | Schuler |
| 2006/0189964 | A1 | 8/2006 | Anderson et al. |
| 2006/0200213 | A1 | 9/2006 | McDaniel |
| 2006/0206110 | A1 | 9/2006 | Knowlton et al. |
| 2006/0259102 | A1 | 11/2006 | Slatkine |
| 2006/0264926 | A1 | 11/2006 | Kochamba |
| 2006/0265034 | A1 | 11/2006 | Aknine et al. |
| 2006/0271028 | A1 | 11/2006 | Altshuler et al. |
| 2006/0276860 | A1 | 12/2006 | Ferren et al. |
| 2007/0010810 | A1 | 1/2007 | Kochamba |
| 2007/0010811 | A1 | 1/2007 | Stern et al. |
| 2007/0016032 | A1 | 1/2007 | Aknine |
| 2007/0020355 | A1 | 1/2007 | Schlebusch et al. |
| 2007/0049918 | A1 | 3/2007 | Van der Weide et al. |
| 2007/0060989 | A1 | 3/2007 | Deem et al. |
| 2007/0078290 | A1 | 4/2007 | Esenaliev |
| 2007/0078502 | A1 | 4/2007 | Weber et al. |
| 2007/0179482 | A1* | 8/2007 | Anderson ............ 606/9 |
| 2007/0179535 | A1 | 8/2007 | Morrissey et al. |
| 2007/0233226 | A1 | 10/2007 | Kochamba et al. |
| 2007/0237620 | A1 | 10/2007 | Mühlhoff et al. |
| 2007/0255274 | A1 | 11/2007 | Stern et al. |

| | | | |
|---|---|---|---|
| 2007/0255355 | A1 | 11/2007 | Altshuler et al. |
| 2007/0255362 | A1 | 11/2007 | Levinson et al. |
| 2007/0265585 | A1 | 11/2007 | Joshi et al. |
| 2007/0265614 | A1 | 11/2007 | Stern et al. |
| 2007/0270925 | A1 | 11/2007 | Levinson |
| 2008/0077201 | A1 | 3/2008 | Levinson et al. |
| 2008/0077202 | A1 | 3/2008 | Levinson |
| 2008/0077211 | A1 | 3/2008 | Levinson et al. |
| 2008/0269851 | A1 | 10/2008 | Deem et al. |
| 2009/0221999 | A1 | 9/2009 | Shahidi |
| 2009/0299361 | A1 | 12/2009 | Flyash et al. |
| 2009/0299364 | A1 | 12/2009 | Batchelor et al. |
| 2009/0318917 | A1 | 12/2009 | Leyh et al. |
| 2010/0016782 | A1 | 1/2010 | Oblong |
| 2010/0049178 | A1 | 2/2010 | Deem et al. |
| 2010/0114086 | A1 | 5/2010 | Deem et al. |
| 2010/0211059 | A1 | 8/2010 | Deem et al. |
| 2010/0268220 | A1 | 10/2010 | Johnson et al. |
| 2011/0028898 | A1 | 2/2011 | Clark, III et al. |
| 2011/0040299 | A1 | 2/2011 | Kim et al. |
| 2011/0196365 | A1 | 8/2011 | Kim et al. |
| 2011/0313412 | A1 | 12/2011 | Kim et al. |
| 2012/0010609 | A1 | 1/2012 | Deem et al. |
| 2012/0041432 | A1 | 2/2012 | Spertell |

FOREIGN PATENT DOCUMENTS

| | | |
|---|---|---|
| EP | 1346753 A2 | 9/2003 |
| JP | 61-364 A | 1/1986 |
| JP | 2001-514921 A | 9/2001 |
| WO | WO 89/02292 A1 | 3/1989 |
| WO | WO 92/07622 A1 | 5/1992 |
| WO | WO 96/41579 A1 | 12/1996 |
| WO | WO 99/46005 A1 | 9/1999 |
| WO | WO 00/24463 A2 | 5/2000 |
| WO | WO 2004/034925 A2 | 4/2004 |
| WO | WO 2006/089227 A2 | 8/2006 |
| WO | WO 2006/090217 A1 | 8/2006 |
| WO | WO 2006/117682 A2 | 11/2006 |
| WO | WO 2007/030367 A2 | 3/2007 |
| WO | WO 2007/038567 A1 | 4/2007 |
| WO | WO 2007/050572 A2 | 5/2007 |
| WO | WO 2007/108516 A1 | 9/2007 |
| WO | WO 2007/131112 A2 | 11/2007 |
| WO | WO 2007140469 A2 * | 12/2007 |

OTHER PUBLICATIONS

Guy, Arthur; Therapeutic Heat and Cold, Fourth Ed.; Chapter 5: Biophysics of High-Frequency Currents and Electromagnetic Radiation; pp. 179R236. Williams and Wilkins (publishers); Apr. 1990.

Basra et al.; The dermatology life quality index 1994R2007: A comprehensive review of validation data and clinical results; Br J Dermatol;159(5); pp. 997R1035; Nov. 2008.

Gabriel et al.; Dielectric parameters relevant to microwave dielectric heating; Chem Soc Rev; 27(3); pp. 213R224; 1998 (month unavailable).

Johnson et al.; Evaluation of a dual-arm Archimedean spiral array for microwave hyperthermia; Int J Hyperthermia; 22(6); pp. 475R490; Sep. 2006.

Rosen et al.; Microwaves treat heart disease; IEEE Microw Mag; 8(1); pp. 70R75; Feb. 2007.

Ross et al.; A pilot study of in vivo immediate tissue contraction with CO2 skin laser resurfacing in a live farm pig; Dermatol Surg; 25(11); pp. 851R856; Nov. 1999.

Ross et al.; Comparison of carbon dioxide laser, erbium: Yag laser, dermabrasion, and dermatome A study of thermal damage, wound contraction, and woundhealing in a live pig model: Implications for skin. resurfacing; J Am Acad Dermatol; 42(1); pp. 92R105; Jan. 2000.

Ross et al.; Use of a novel erbium laser in a yucatan minipig: A study of residual thermal damage, ablation, and wound healing as a function of pulse duration; Lasers Surg Med; 30(2); pp. 93R100; Feb. 2002.

Strutton et al.; US prevalence of hyperhidrosis and impact on individuals with axillary hyperhidrosis: Results from a national survey. J Am Acad Dermatol; 51(2); pp. 241R248; Feb. 2004.

Sullivan et al.; The pig as a model for human wound healing; Wound Repair Regen; 9(2); pp. 66R76; Mar. 2001.

Vander Vorst et al.; RF/microwave interaction with biological tissues; Hoboken, NJ; John Wiley & Sons, Inc.; pp. 264-305; Jan. 2006.

Vardaxis et al.; Confocal laser scanning microscopy of porcine skin: Implications for human wound healing studies; J Anat; 190(04); pp. 601R611; May 1997.

Abraham et al.; Monopolar radiofrequency skin tightening; Facial Plast Surg Clin N Am; 15(2); pp. 169-177; May 2007.

Absar et al.; Efficacy of botulinum toxin type A in the treatment of focal axillary hyperhidrosis; Dermatol Surg; 34(6); pp. 751-755; Jun. 2008.

Alster et al.; Improvement of neck and cheek laxity with a non-ablative radiofrequency device: a lifting experience; Dermatol Surg; 30(4); pp. 503-507; Apr. 2004.

Ball, P.; Radio sweat gland—90 GHz; Nature; 452(7188); p. 676; Apr. 10, 2008; printed Jun. 18, 2012 from website (http://www.nature.com/news/2008/080409/full/452676a.html).

Bindu et al.; Microwave characterization of breast-phantom materials; Microwave and Optical Tech. Letters; 43(6); pp. 506-508; Dec. 20, 2004.

Bioportfolio; Tenex Health Receives FDA clearance for innovative TX1} tissue removal system; 2 pgs.; release dated Mar. 9, 2011; printed on Jun. 18, 2012 from website (http://www.bioportfolio.com/news/article/519143/Tenex-Health-Receives-Fda-Clearance-For-Innovative-Tx1-Tissue-Removal-System.html).

Bu-Lin et al.; A polyacrylamide gel phantom for radiofrequency ablation; Int. J. Hyperthermia; 24(7); pp. 568-576; Nov. 2008.

Burns, Jay A.; Thermage: monopolar radiofrequency; Aesthetic Surg J; 25(6); pp. 638-642; Nov./Dec. 2005.

Campbell et al.; Dielectric properties of female human breast tissue measured in vitro at 3.2 GHz; Phys. Med. Biol.; 37(1); pp. 193-210; Jan. 1992.

Chang et al.; A conductive plastic for simulating biological tissue at microwave frequencies; IEEE Trans on Electromagnetic Compatibility; 42(1); pp. 76-81; Feb. 2000.

CK Electronic GmbH; Scientific Measurements of Skin and Hair (product information); 15 pgs.; published after Sep. 2006.

Covidien; FDA clears Covidien's Evident} microwave ablation system for use in nonresectable liver tumor ablation; 2 pgs.; Dec. 28, 2008; printed Jun. 18, 2012 from website (http://www.medicalnewstoday.com/releases/133800.php).

Darabaneanu et al.; Long-term efficacy of subcutaneous sweat gland suction curettage for axillary hyperhidrosis: a prospective gravimetrically controlled study; Dermatol Surg; 34(9); pp. 1170-1177; Sep. 2008.

Eleiwa et al.; Accurate FDTD simulation of biological tissues for bio-electromagnetic applications; IEEE Proc. SoutheastCon 2001; Clemson, SC; Mar. 30-Apr. 1, 2001; pp. 174-178.

Farace et al.; An automated method for mapping human tissue permittivities by MRI in hyperthermia treatment planning; Phys. Med. Biol.; 42(11); pp. 2159-2174; Nov. 1997.

Fitzpatrick et al.; Multicenter study of noninvasive radiofrequency for periorbital tissue tightening; Lasers Surg Med; 33(4); pp. 232-242; Mar. 2003.

Garber, B. B.; Office microwave treatment of enlarged prostate symptoms; 2 pgs.; printed from website (http://www.garber-online.com/microwave-treatment.htm) on Jun. 18, 2012.

Goldman et al.; Subdermal Nd-YAG laser for axillary hyperhidrosis; Dermatol Surg; 34(6); pp. 756-762; Jun. 2008.

Guidant Corp.; Guidant microwave surgical ablation system; 1 pg.; © 2004; printed Jun. 18, 2012 from website (http://web.archive.org/web/20070306031424/http://www.ctsnet.org/file/vendors/872/pdf/MicrowaveAblationIFU.pdf).

Guy; Analyses of electromagnetic fields induced in biological tissues by thermographic studies on equivalent phantom models; IEEE Trans on Microwave Theory and Techniques; MTT-19(2); pp. 205-214; Feb. 1971.

Jacobsen et al.; Characteristics of microstrip muscle-loaded single-arm archimedean spiral antennas as investigated by FDTD numerical computations; IEEE Trans. On Biomedical Engineering; 52(2); pp. 321-330; Feb. 2005.

Jacobsen et al.; Characterization of a tranceiving antenna concept for microwave heating and thermometry of superficial tumors; PIER; vol. 18; pp. 105-125; (month unavailable) 1998.

Jacobsen et al; Dual-mode antenna design for microwave heating and noninvasive thermometry of superficial tissue disease; IEEE Trans. On Biomedical Engineering; 47(11); pp. 1500-1509; Nov. 2000.

Jacobsen et al.; Multifrequency radiometric determination of temperature profiles in a lossy homogeneous phantom using a dual-mode antenna with integral water bolus; IEEE Trans. on Microwave Theory and Techniques; 50(7); pp. 1737-1746; Jul. 2002.

Jacobsen et al.; Nonparametric 1-D temperature restoration in lossy media using tikhonov regularization on sparse radiometry data; IEEE Trans. on Biomedical Engineering; 50(2); pp. 178-188; Feb. 2003.

Jacobsen et al.; Transceiving antenna for homogenious heating and radiometric thermometry during hyperthermia; Electronic Letters; 36(6); pp. 496-497; Mar. 16, 2000.

Johnson et al.; Automatic temperature controller for multielement array hyperthermia systems; IEEE Trans. on Biomedical Engineering; 53(6); pp. 1006-1015; Jun. 2006.

Juang et al.; Construction of a conformal water bolus vest applicator for hyperthermia treatment of superficial skin cancer; Proc. of the 26th Ann. Int. Conf. of the IEEE EMBS; San Francisco, CA, USA; Sep. 1-5, 2004; pp. 3467-3470.

Kirn, T. F.; Researchers seek to quantify thermage efficacy; Dermatologic Surgery; p. 36; Jan. 2007.

Kirsch et al.; Ultrastructure of collagen thermally denatured by microsecond domain pulsed carbon dioxide laser; Arch Dermatol; 134; pp. 1255-1259; Oct. 1998.

Kumaradas et al.; Optimization of a beam shaping bolus for superficial microwave hyperthermia waveguide applicators using a finite element method; Phys. Med. Biol.; 48(1); pp. 1-18; Jan. 7, 2003.

Lagendijk et al; Hyperthermia dough: a fat and bone equivalent phantom to test microwave/radiofrequency hyperthermia heating systems; Phys. Med. Biol.; 30(7); pp. 709-712; Jul. 1985.

Land et al.; A quick accurate method for measuring the microwave dielectric properties of small tissue samples; Phys. Med. Biol.; 37(1); pp. 183-192; Jan. 1992.

Larson et al.; Microwave treatments for enlared prostate cause blood pressure surges, study shows; 2 pgs.; Apr. 11, 2008; printed on Jun. 18, 2012 from website (http://web.archive.org/web/20080415000815/http://www.sciencedaily.com/releases/2008/04/080408105820.htm).

Lumenis Inc.; Aluma RF Skin Renewal System (product information); copyright 2007 (PB-1013670); 8 pgs.; Oct. 2007 (printed version).

Maccarini et al.; Advances in microwave hyperthermia of large superficial tumors; Microwave Symposium Digest, IEEE MTT-S International; pp. 1797-1800; Jun. 2005.

Maccarini et al.; Electromagnetic optimization of dual mode antennas for radiometry controlled heating of superficial tissue; Proceedings of SPIE; vol. 5698; Bellingham, WA; pp. 71-81; Jan. 2005.

Maccarini et al.; Optimization of a dual concentric conductor antenna for superficial hyperthermia applications; Proc. of the 26th Ann. Int. Conf. of the IEEE EMBS; San Francisco, CA, USA; Sep. 1-5, 2004; pp. 2518-2521.

Mazzurana et al.; A semi-automatic method for developing an anthropomorphic numerical model of dielectric anatomy by MRI; Phys. Med. Biol.; 48(19); pp. 3157-3170; Oct. 7, 2003.

Mrozowski et al.; Parameterization of media dispersive properties for FDTD; IEEE Trans on Antennas and Propagation; 45(9); pp. 1438-1439; Sep. 1997.

Nagaoka et al.; Development of realistic high-resolution whole-body voxel models of Japanese adult males and females of average height and weight, and application of models to radio-frequency electromagnetic-field dosimetry; Phys. Med. Biol.; 49(1); pp. 1-15; Jan. 7, 2004.

Neuman; SAR pattern perturbations from resonance effects in water bolus layers used with superficial microwave hyperthermia applicators; Int. J. Hyperthermia; 18(3); pp. 180-193; May-Jun. 2002.

Popovic et al.; Dielectric spectroscopy of breast tissue—improved model of the precision open-ended coaxial probe; Proc of the 25th Ann Int Conf of the IEEE EMBS; Cancun, Mexico; pp. 3791-3793; Sep. 17-21, 2003.

Popovic et al.; Response characterization of the precision open-ended coaxial probe for dielectric spectroscopy of breast tissue; 2003 IEEE—Anntennas and Propagation Soc. Int. Symp.; vol. 4; pp. 54-57; Jun. 22-27, 2003.

Rolfsnes et al.; Design of spiral antennas for radiometric temperature measurement; Proc. of the 26th Ann. Int. Conf. of the IEEE EMBS; San Francisco, CA, USA; Sep. 1-5, 2004; pp. 2522-2525.

Rossetto et al.; Effect of complex bolus-tissue load configurations on SAR distributions from dual concentric conductor applicators; IEEE Trans. on Biomedical Engineering; 46(11); pp. 1310-1319; Nov. 1999.

Saito et al.; Clinical Trials of Interstitual Microwave Hyperthermia by Use of Coaxial-Slot Antenna With Two Slots; IEEE Trans. on Microwave Theory and Techniques; vol. 52; No. 8; pp. 1987-1991; Aug. 2004.

Sipahioglu et al.; Dielectric properties of vegetables and fruits as a function of temperature, ash, and moisture content; Journal of Food Science; 68(1); pp. 234-239; Jan. 2003.

Surowiec et al.; Dielectric properties of breast carcinoma ind the surrounding tissues; IEEE Trans on Biomedical Engineering; 35(4); pp. 257-263; Apr. 1988.

Spertell et al.; Review of clinical data on hair removal using the MW 2000 microwave delivery system (promotional material); 2000; MW Medical, Inc.; printed from http://www.hairfacts.com/medpubs/mwave/spertell.html on Jun. 23, 2009; 5 pgs.

Spertell; Presentation at the American Academy of Dermatology; MW Medical, Inc.; Mar. 10, 2000; 21 pgs.

Spertell; The application of microwaves to the treatment of cosmetic skin conditions: a technical summary; MW Medical, Inc.; pp. 1-15; May 25, 1999.

SRLI Technologies; BTC-2000} (product information); printed from website: http://www.srli.com/technologies/BTC2000.html on Nov. 16, 2009; 1 pg.

Stauffer et al.; Combination applicator for simultaneous heat and radiation; Proc. of the 26th Ann. Int. Conf. of the IEEE EMBS; San Francisco, CA, USA; Sep. 1-5, 2004; pp. 2514-2517.

Stauffer et al.; Dual mode antenna array for microwave heating and non-invasive thermometry of superficial tissue disease; SPIE Conf. on Thermal Treatment of Tissue with Image Guidance; San Jose, CA; SPIE; vol. 3594; pp. 139-147; Jan. 1999.

Stauffer et al.; Microwave array applicator for rediometry controlled superficial hyperthermia; Proc. of the SPIE; vol. 4247; pp. 19-29; Jun. 2001.

Stauffer et al.; Phantom and animal tissues for modelling the electrical properties of human liver; Int. J. Hyperthermia; 19(1); pp. 89-101; Jan.-Feb. 2003.

Stauffer et al.; Practical induction heating coil designs for clinical hyperthermia with ferromagnetic implants; IEEE Trans. on Biomedical Engineering; 41(1); pp. 17-28; Jan. 1994.

Stauffer et al.; Progress on system for applying simultaneous heat and brachytherapy to large-area surface disease; Proceedings of SPIE; vol. 5698; Bellingham, WA; pp. 82-96; Jan. 2005.

Stauffer et al.; Progress toward radiometry controlled conformal microwave array hyperthermia applicator; Proc. of the 22nd Ann. EMBS Int. Conf.; Chicago, IL; Jul. 23-28, 2000; pp. 1613-1616.

Stoy et al.; Dielectric properties of mammalian tissues from 0.1 to 100 MHz: a summary of recent data; Phys. Med. Bil.; 27(4); pp. 501-513; Apr. 1982.

Stuchly et al.; Diathermy applicators with circular aperture and corrugated flange; IEEE Trans on Microwave Theory and Techniques; MTT-28(3); pp. 267-271; Mar. 1980.

Stuchly et al.; Dielectric properties of animal tissues in vivo at frequencies 10 MHz-1 GHz; Bioelectromagnetics; 2(2); pp. 93-103; Apr. 1981.

Stuchly et al.; Dielectric properties of animal tissues in vivo at radio and microwave frequencies: comparison between species; Phys. Med. Biol.; 27(7); pp. 927-936; Jul. 1982.

Sullivan et al.; Comparison of measured and simulated data in an annular phased array using an inhomogeneous phantom; IEEE Trans on Microwave Theory and Techniques; 40(3); pp. 600-604; Mar. 1992.

Sunaga et al.; Development of a dielectric equivalent gel for better impedance matching for human skin; Bioelectromagnetics; 24; pp. 214-217; Apr. 2003.

Tavernier et al.; Conductivity and dielectric permittivity of dermis and epidermis in nutrient liquid saturation; Engineering in Medicine and Biology Society; 1992 14th Annual Int. Conf of the IEEE; Paris, France; pp. 274-275; Oct. 29-Nov. 1, 1992.

Urolgix, Inc.; Cooled Thermotherapy + Prostiva RF = Durability + Versatility; 1 pg.; printed Jun. 18, 2012 from website (http://www.urologix.com/).

Weiss et al.; Monopolar radiofrequency facial tightening: a retrospective analysis of efficacy and safety in over 600 treatments; J Drugs Dermatol; 5(8); pp. 707-712; Sep. 2006.

Wollina et al.; Tumescent suction curettage versus minimal skin resection with subcutaneous curettage of sweat glands in axillary hyperhidrosis; Dermatol Surg; 34(5); pp. 709-716; May 2008.

Wonnell et al.; Evaluation of microwave and radio frequency catheter ablation in a myocardium-equivalent phantom model; IEEE Trans. on Biomedical engineering; 39(10); pp. 1086-1095; Oct. 1992.

Zelickson et al.; Histological and ultrastructural evaluation of the effects of a radiofrequency-based nonablative dermal remodeling device; Arch Dermatol; 140; pp. 204-209; Feb. 2004.

Zelickson et al.; Ultrastructural effects of an infrared handpiece on forehead and abdominal skin; Dermatol Surg; 32(7); pp. 897-901; Jul. 2006.

Acculis; Microwave Ablation for Healthcare Professionals; 2 pgs.; accessed Jun. 24, 2008; (http://www.acculis.com/mta).

Aesthera US—How it Works; 2 pgs.; accessed Jul. 8, 2008 (http://www.aesthera.com/go/aestheralUS/patients/how_it_works/index.cfm).

Ashby et al.; Cryosurgery for Axillary Hyperhidrosis; British Medical Journal Short Reports; London; pp. 1173-1174; Nov. 13, 1976.

Atkins et al.; Hyperhidrosis: A Review of Current Management; Plast Reconstr Surg; 110(1); pp. 222-228; Jul. 2002.

Beer et al., "Immunohistochemical Differentiation and Localization Analysis of Sweat Glands in the Adult Human Axilla," Plastic and Reconstructive Surgery, vol. 117, No. 6, pp. 2043-2049, May 2006.

Brace et al., "Microwave Ablation with a Trixial Antenna: Results in ex vivo Bovine Liver," IEEE transactions on Microwave Theory and Techniques, vol. 53, No. 1, pp. 215-220 (Jan. 2005).

Candela Corp.; The Cadela SeleroPLUS Laser with Dynamic Cooling Device: The Benefits of Anesthesia without the Risks; Nov. 1998.

Christ et al., "Characterization of the Electromagnetic Near-Field Absorption in Layered Biological Tissue in the Frequency Range from 30 MHz to 6000 MHz," Phys. Med. Biol. 51, pp. 4951-4965; Oct. 2006.

Christ et al., "The Dependence of Electromagnetic Far-Field Absorption on Body Tissue Composition in the Frequency Range from 300 MHz to 6 GHz," IEEE Transactions on Microwave Theory and Techniques, vol. 54, No. 5, pp. 2188-2195 (May 2006).

Copty et al., "Low-power near-field microwave applicator for localized heating of soft matter," Applied Physics Letters, vol. 84, No. 25, pp. 5109-5111 (Jun. 21, 2004).

De Bruijne et al., "Effects of waterbolus size, shape and configuration on the SAR distribution pattern of the Lucite cone applicator," International Journal of Hyperthermia, 22(1): 15-28 (Feb. 2006).

Diederich et al.; Pre-clinical Evaluation of a Microwave Planar Array Applicator for Superficial Hyperthermia; International Journal of Hyperthermia; vol. 9, No. 2; pp. 227-246; Jan. 1993.

Drozd et al.; Comparison of Coaxial Dipole Antennas for Applications in the Near-Field and Far-Field Regions; MW Journal, vol. 47, No. 5 (May 2004), http://www.mwjournal.com/Journal, accessed Dec. 10, 2007.

European Search report dated Mar. 14, 2011 in connection with related European Patent Application No. 08746369.1, entitled "Methods and Apparatus for Reducing Sweat Production", Miramar Labs, Inc.

European Search report dated Mar. 16, 2011 in connection with related European Patent Application No. 08746358.4, entitled "Systems and Methods for Creating an Effect Using Microwave Energy to Specified Tissue", Miramar Labs, Inc., et al.

European Search report dated Mar. 9, 2011 in connection with related European Patent Application No. 08746364.2, entitled "Methods, Devices, & Systems for Non-Invasive Delivery of Microwave Therapy", Miramar Labs, Inc.

European Search report dated Mar. 9, 2011 in connection with related European Patent Application No. 08859299.3, entitled "Systems, Apparatus, Methods and Procedures for the Noninvasive Treat of Tissue Using Microwave Energy", Miramar Labs, Inc.

Gabriel et al.; The dielectric properties of biological tissues: I. literature survey; Phys Med Biol; 41(11); pp. 2231R2249; Nov. 1996.

Gabriel et al.; The dielectric properties of biological tissues: II. Measurements in the frequency range 10 Hz to 20 GHz; Phys Med Biol; 41(11); pp. 2251R2269; Nov. 1996.

Gabriel et al.; The dielectric properties of biological tissues: III. Parametric models for the dielectric spectrum of tissues; Phys Med Biol; 41(11); pp. 2271R2293; Nov. 1996.

Gabriel, et al.; Comparison of the Dielectric Properties of Normal and Wounded Human Skin Material; Bioelectromagnetics; 8; pp. 23-27; Jan. 1987.

Gandhi et al.; Electromagnetic Absorption in the Human Head and Neck for Mobile Telephones at 835 and 1900 MHz; IEEE Transactions on Microwave Theory and Techniques; 44(10); pp. 1884R1897; Oct. 1996.

Gold et al.; Treatment of Wrinkles and Skin Tightening Using Aluma(TM) Skin Renewal System with FACES(TM)(Functional Aspiration Controlled Electrothermal Stimulation) Technology; Lumens, Inc. (Oct. 2005).

Guy, Arthur; History of Biological Effects and Medical Applications of Microwave Energy; IEEE Transactions on Microwave Theory and Techniques; 32(9); pp. 1182-1200; Sep. 1984.

Hey-Shipton, et al.; The Complex Permittivity of Human Tissue at Microwave Frequencies; Phys. Med. Biol.; 27(8); pp. 1067-1071; Aug. 1982.

Hu, Da Zhang, "Electromagnetic Field in Organism of Skin-Fat-Muscle," China Research Institute of Radiowave Propagation IEEE, pp. 807-812 (Aug. 1998).

Kawoos et al., "Issues in Wireless Intracranial Pressure Monitoring at Microwave Frequencies," PIERS Online, vol. 3, No. 6, pp. 927-931; 2007 (month unavailable).

Kobayashi, T.; Electrosurgery Using Insulated Needles: Treatment of Axillary Bromhidrosis and Hyperhidrosis; Journal of Dermatologic Surgery & Oncology; 14(7) pp. 749-752; Jul. 1988.

Krusen, Frank (M.D.); Samuel Hyde Memorial Lecture: Medical Applications of Microwave Diathermy: Laboratory and Clinical Studies. Proceedings of the Royal Society of Medicine; 43(8); pp. 641-658, May 10, 1950.

Lane et al.; Pressure-Induced Bullae and Sweat Gland Necrosis Following Chemotherapy Induction; The American Journal of Medicine; vol. 117; pp. 441-443; Sep. 15, 2004.

Lawrence et al.; Selective Sweat Gland Removal with Minimal Skin Excision in the Treatment of Axillary Hyperhidrosis: A Retrospective Clinical and Histological Review of 15 Patients; British Journal of Dermatology; British Association of Dermatologists; 155(1), pp. 115-118; Jul. 2006.

Lowe et al.; Microwave delivery system for lower leg telangiectasia; Journal of Cutaneous Laser Therapy; 2(1); pp. 3-7; Mar. 2000.

Michel et al.; Design and Modeling of Microstrip—Microslot Applicators with Several Patches and Apertures for Microwave Hyperthermia; Microwave and Optical Technology Letters; vol. 14, No. 2; pp. 121-125; Feb. 5, 1997.

Park et al.; A Comparative Study of the Surgical Treatment of Axillary Osmidrosis by Instrument, Manual, and Combined Subcutaneous Shaving Procedures; 41(5); pp. 488-497; Nov. 1998.

Paulides et al.; A Patch Antenna Design for Application in a Phased-Array Head and Neck Hyperthermia Applicator; IEEE Transactions on Biomedical Engineering; 54(11); pp. 2057-2063; Nov. 2007.

PCT International Search Report for related PCT/US2008/060922 filed Apr. 18, 2008 entitled "Systems and Methods for Creating an Effect using Microwave Energy to Specified Tissue," Deem et al.

PCT International Search Report for related PCT/US2008/060929 filed Apr. 18, 2008 entitled "Methods, Devices, and Systems for Non-Invasive Delivery of Microwave Therapy," Deem et al.

PCT International Search Report for related PCT/US2008/060935 filed Apr. 18, 2008 entitled "Methods and Apparatus for Reducing Sweat Production," Deem et al.

PCT International Search Report for related PCT/US2008/060940 filed Apr. 18, 2008 entitled "Systems and Methods for Creating an Effect using Microwave Energy to Specified Tissue," Deem et al.

PCT International Search Report for related PCT/US2008/13650, filed Dec. 12, 2008 entitled "Systems, Apparatus, Methods and Procedures for the Noninvasive Treatment of Tissue Using Microwave Energy," Miramar Labs, Inc.

PCT International Search Report for related PCT/US2009/02403, filed Apr. 17, 2009 entitled "Systems, Apparatus, Methods & Procedures for the Noninvasive Treatment of Tissue Using Microwave Energy," Miramar Labs, Inc.

PCT International Search Report for related PCT/US2009/05772, filed Oct. 22, 2009 entitled "Systems, Apparatus, Methods and Procedures for the Non-Invasive Treatment of Tissue Using Microwave Energy," Miramar Labs, Inc.

PCT International Search Report for related PCT/US2010/025124, filed Feb. 23, 2010 entitled "Tissue Interface System and Method," Miramar Labs, Inc.

Pozar, David M.; Microwave Engineering, Second Edition; John Wiley & Sons, Inc.; p. 1; Aug. 1997.

Rappaport, C.; Treating Cardiac Disease with Catheter-Based Tissue Heating; IEEE Microwave Magazine; 3(1); pp. 57-64; Mar. 2002.

Sherar et al.; Helical antenna arrays for interstitial microwave thermal therapy for prostate cancer: tissue phantom testing and simulations for treatment; Physics in Medicine and Biology; 46(7); pp. 1905-1918; Jul. 2001.

Shimm, D et al.; Hyperthermia in the Treatment of Malignancies; Therapeutic Heat and Cold Fourth Edition edited by Justin Lehmann M.D., Chapter 14, pp. 674-699, Williams & Wilkins Publishers, Baltimore, MD; Apr. 1990.

Solta Medical, Inc.; Study Published in Facial Plastic Surgery Journal Finds Selective Heating of Fibrous Septae Key to Success and Safety of Thermage(R) ThermaCool(TM) System; Thermage® Press Release; 2 pgs.; Jun. 20, 2005.

Stauffer, Paul R.; Evolving technology for thermal therapy of cancer; International Journal of Hyperthermia; 21(8); pp. 731-744; Dec. 2005.

Stauffer, Paul R.; Thermal Therapy Techniques for Skin and Superficial Tissue Disease; Critical Reviews; SPIE Optical Engineering Press (Bellingham, WA); vol. CR75; pp. 327-367; Jan. 2000.

Sterzer, Fred, Microwave Medical Devices; IEEE Microwave Magazine, 3(1); pp. 65-70; Mar. 2002.

Trembly et al.; Combined Microwave Heating and Surface Cooling of the Cornea; IEEE Transactions on Biomedical Engineering; vol. 38; No. 1; pp. 85-91; Jan. 1991.

Uzunoglu et al.; A 432-MHz Local Hyperthermia System Using an Indirectly Cooled, Water-Loaded Waveguide Applicator; IEEE Trans. on Microwave Theory and Techniques; vol. 35, No. 2; pp. 106-111; Feb. 1987.

Valleylab; Cool-tip(TM) RF Ablation System; (http://www.cool-tiprf.com/physics.html) accessed Jun. 24, 2008.

Van Rhoon et al.; A 433 MHz Lucite Cone Waveguide Applicator for Superficial Hyperthermia; International Journal of Hyperthermia; vol. 14, No. 1; pp. 13-27; Jan.-Feb. 1998.

Vrba, et al.; Evanescent-Mode Applicators (EMA) for Superficial and Subcutaneous Hyperthermia; IEEE Trans. on Biomedical Engineering; vol. 40; No. 5; pp. 397-407; May 1993.

Yang et al.; A Floating Sleeve Antenna Yields Localized Hepatic Microwave Ablation; IEEE Transactions on Biomedical Engineering; 53(3); pp. 533-537; Mar. 2006.

Thermolase Corp.; 510K Pre-Market Notification (No. K950019) and Product User Manual "ThermoLase Model LT100 Q-Switched Nd: YAG, Laser Hair Removal System," Jan. 3, 1995.

Hisada et al.; Hereditary Hemorrhagic Telangiectasia Showing Severe Anemia which was successfully treated with estrogen; International Medicine; vol. 34; No. 6; pp. 589-592; Jun. 1995.

Zhou et al.; Resection of Meningiomas with Implantable Microwave Coagualation; Bioelectromagnetics; vol. 17; No. 2; pp. 85-88; 1996 (pub. month unavailable).

Ben-Haim et al.; U.S. Appl. No. 13/563,656 entitled "Applicator and Tissue Interface Module for Dermatological Device," filed Jul. 31, 2012.

Allergan Pharmaceuticals; Botox® (product insert); 16 pgs.; Oct. 2006.

Arneja et al.; Axillary hyperhidrosis: a 5-year review of treatment efficacy and recurrence rates using a new arthroscopic shaver technique; Plast. Reconstr. Surg.; vol. 119; pp. 562-567; Feb. 2007.

Bechara et al.; Histological and clinical findings in different surgical strategies for focal axillary hyperhidrosis; Dermatol Surg; vol. 34; pp. 1001-1009; Aug. 2008.

Bentel et al.; Variability of the depth of supraclavicular and axillary lymph nodes in patients with breast cancer: is a posterior axillary boost field necessary?; Int J Radiation Oncology Biol Phys; vol. 47(3); pp. 755-758; Jun. 2000.

Blanchard et al.; Relapse and morbidity in patients undergoing sentinel lymph node biopsy alone or with axillary dissection for breast cancer; Arch Surg; vol. 138; pp. 482-488; May 2003.

Cobham; Antenna & Radome Design Aids (product list); 1 pg.; Aug. 2001.

Duparc et al.; Anatomical basis of the variable aspects of injuries of the axillary nerve (excluding the terminal branches in the deltoid muscle); Surg Radiol Anat; vol. 19(3); pp. 127-132; May 1997.

Galloway et al.; Ultrasound imaging of the axillary vein—anatomical basis for central venous access; British ournal of Anaesthesia; 90(5); pp. 589-595; May 2003.

Haedersdal et al.; Evidence-based review of hair removal using lasers and light sources; JEADV; vol. 20; pp. 9-20; Jan. 2006.

Hornberger et al.; Recognition, diagnosis, and treatment of primary focal hyperhidrosis; J Am Acad Dermatol; vol. 51; pp. 274-286; Aug. 2004.

Lowe et al.; Botulinum toxin type A in the treatment of primary axillary hyperhidrosis: A 52-week multicenter double-blind, randomized, placebo-controlled study of efficacy and safety; J Am Acad Dermatol; vol. 56; pp. 604-611; Apr. 2007.

Riddle et al.; Complex permittivity measurements of common plastics over variable temperatures; IEEE Trans on Microwave Theory and Techniques; vol. 51(3); pp. 727-733; Mar. 2003.

Solish et al.; A comprehensive approach to the recognition, diagnosis, and severity-based treatment of focal hyperhidrosis: recommendations of the Canadian hyperhidrosis advisory committee; Dermatol Surg; vol. 33; pp. 908-923; Aug. 2007.

Solish et al.; Prospective open-label study of botulinum toxin type A in patients with axillary hyperhodrosis: effects on functional impairment and quality of life; Dermatol Surg; vol. 31(4); pp. 405-413; Apr. 2005.

* cited by examiner

E-E

K-K

J - J

J - J

F - F

I-I

G - G

US 8,406,894 B2

SYSTEMS, APPARATUS, METHODS AND PROCEDURES FOR THE NONINVASIVE TREATMENT OF TISSUE USING MICROWAVE ENERGY

FIELD OF THE INVENTION

The present application relates to methods, apparatuses and systems for non-invasive delivery of microwave therapy. In particular, the present application relates to methods, apparatuses and systems for non-invasively delivering energy, such as, for example, microwave energy, to the epidermal, dermal and sub-dermal tissue of a patient to achieve various therapeutic and/or aesthetic results.

DESCRIPTION OF THE RELATED ART

It is known that energy-based therapies can be applied to tissue throughout the body to achieve numerous therapeutic and/or aesthetic results. There remains a continual need to improve on the effectiveness of these energy-based therapies and provide enhanced therapeutic results with minimal adverse side effects or discomfort.

BRIEF DESCRIPTION OF THE DRAWINGS

The invention will be understood from the following detailed description of preferred embodiments, taken in conjunction with the accompanying drawings, wherein.

DESCRIPTION OF EMBODIMENTS OF THE INVENTION

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
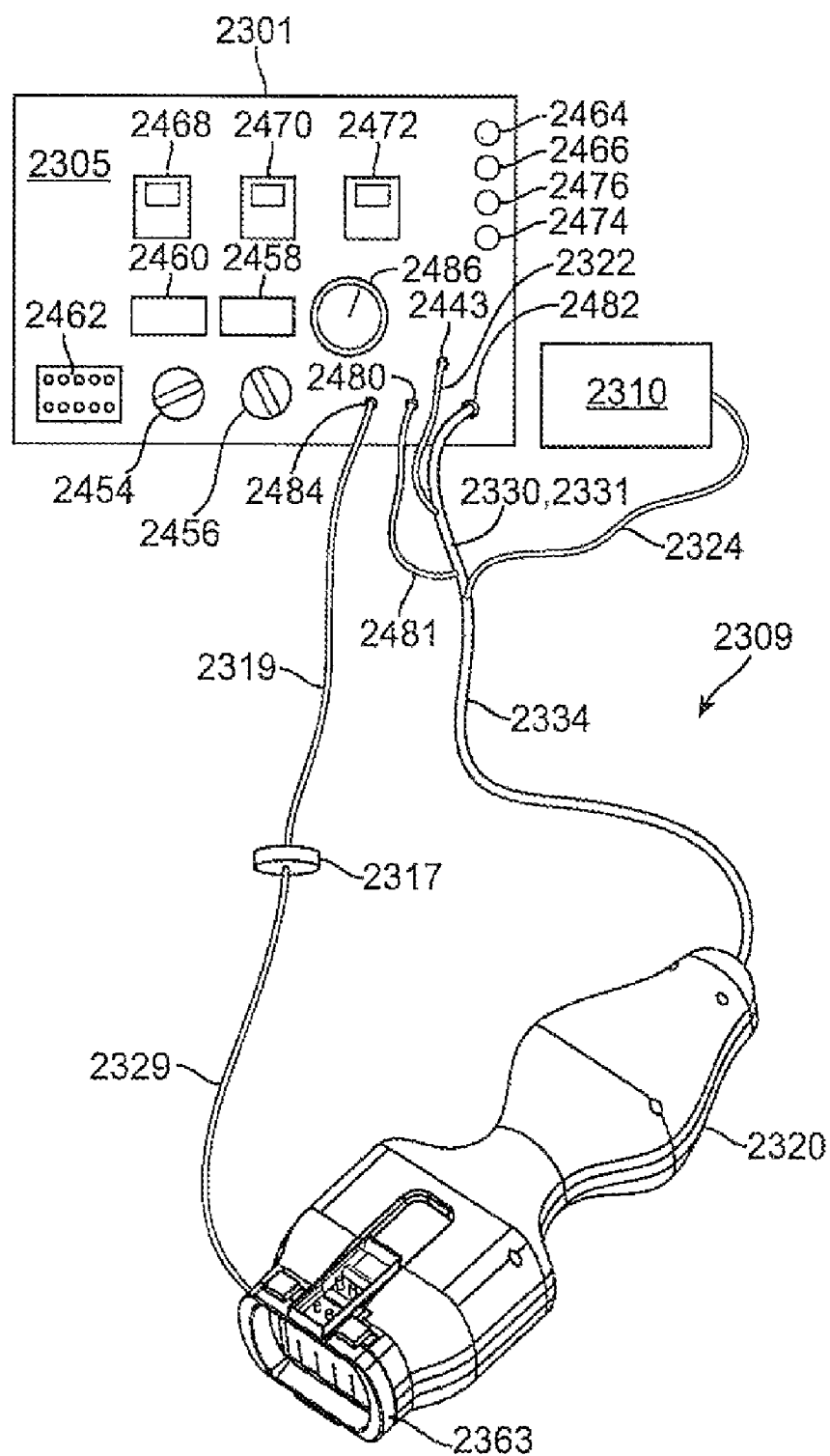
FIG. 1 is an illustration of a system including a generator, applicator and the disposable according to one embodiment of the invention.

FIG. 1 is an illustration of a system 2309 including a generator 2301, applicator 2320 (which may also be referred to as re-usable) and disposable 2363 according to one embodiment of the invention. According to one embodiment of the invention generator 2301 will operate in the ISM band of 5.775 to 5.825 GHz. According to one embodiment of the invention generator 2301 includes circuitry for setting and controlling output power; measuring forward and reverse power and setting alarms. According to one embodiment of the invention generator 2301 may have a Frequency centered at 5.8 GHz. According to one embodiment of the invention generator 2301 may have a power output of between 40 and 100 Watts measured into a 50 ohm load. According to one embodiment of the invention generator 2301 may have a power accuracy of plus or minus 3 Watts. According to one embodiment of the invention disposable 2363 and applicator 2320 may be formed into two separable units. According to one embodiment of the invention disposable 2363 and applicator 2320 may be formed into a single unit. According to one embodiment of the invention when combined disposable 2363 and applicator 2320 may form a medical treatment device 2300. According to one embodiment of the invention generator 2301 may be a microwave generator. According to one embodiment of the invention may be a disposable 2363 tissue head. According to one embodiment of the invention in system 2309 applicator 2320 may be connected to generator 2301 by applicator cable 2334. According to one embodiment of the invention in system 2309 applicator cable 2334 may include coolant conduit 2324, energy cable 2322, coolant thermocouple wires 2331, cooling plate thermocouple wires 2330 and antenna switch signal 2481. According to one embodiment of the invention in system 2309 coolant conduit 2324 may be connected to a coolant source 2310 (which may be, for example, a Nanotherm industrial recirculation chiller with 8 psi pump available from ThermoTek, Inc). According to one embodiment of the invention in system 2309 energy cable 2322 may be connected to generator 2301 by microwave output connector 2443. According to one embodiment of the invention in system 2309 antenna switch signal 2481 may be connected to generator 2301 by antenna switch connector 2480. According to one embodiment of the invention in system 2309 disposable 2363 may be connected to generator 2301 by vacuum tubing 2319 which may include generator bio-barrier 2317, which may be, for example, a hydrophobic filter. According to one embodiment of the invention in system 2309 vacuum tubing 2319 may be connected to generator 2301 by vacuum port connector 2484. According to one embodiment of the invention in system 2309 front panel 2305 of generator 2301 may include power control knob 2454, vacuum control knob 2456, antenna select switch 2462 (which may include both display elements and selection switches), vacuum meter 2486, antenna temperature display 2458, coolant temperature display 2460, pre-cool timer 2468 (which may include both display elements and time set elements), energy timer 2470 (which may include both display elements and time set elements) and post-cool timer 2472 (which may include both display elements and time set elements). According to one embodiment of the invention an error signal is sent to controller 2302 of generator 2301 if a measured signal is outside of the specification for the requested power set by the power control knob 2454 on front panel 2305. According to one embodiment of the invention an error signal is sent to controller 2302 if the measured reverse power is greater than a preset limit on measured reverse power. According to one embodiment of the invention an error signal is sent to controller 2302 if the measured reverse power is greater than approximately twenty-five watts. According to one embodiment of the invention vacuum tube 2319 may include a flexible vacuum hose 2329 and a generator bio-barrier 2317. According to one embodiment of the invention flexible vacuum hose 2329 is adapted to collect fluids, such as, for example sweat or blood, which may escape disposable 2363 so that such fluids do not reach generator 2301. According to one embodiment of the invention generator bio-barrier 2317 may include a hydrophobic filter to keep fluids out of vacuum port connector 2484 of generator 2301. According to one embodiment of the invention generator bio-barrier 2317 may include a hydrophobic filter, such as, for example, a Millex FH Filter made of 0.45 micrometer hydrophobic PTFE which is available from Milipore. According to one embodiment of the invention generator bio-barrier 2317 may be positioned in the flexible hose. According to one embodiment of the invention applicator cable 2334 may connect generator 2301 to applicator 2320. According to one embodiment of the invention applicator cable 2334 may include a coolant conduit 2324, energy cable 2322, antenna switch signal 2481, cooling plate thermocouple wires 2330 and coolant thermocouple wires 2331. According to one embodiment of the invention applicator cable 2334 may further include a thermocouple array cable. According to one embodiment of the invention coolant conduit 2324 may convey cooling fluid from a coolant source 2310 to applicator 2320. According to one embodiment of the invention applicator cable 2334 may convey microwave switch selection data to applicator 2320 and temperature data from thermocouples in applicator 2320 to generator 2301. According to one embodiment of the invention applicator cable 2334 may comprise one or more separate cables and connectors. According to one embodiment of the invention a generator connector may be designed and adapted to connect applicator cable 2334 to the generator 2301, including connections for the cooling fluid conduit, antenna switch control, thermocouples and main microwave connector.

Figure 2:
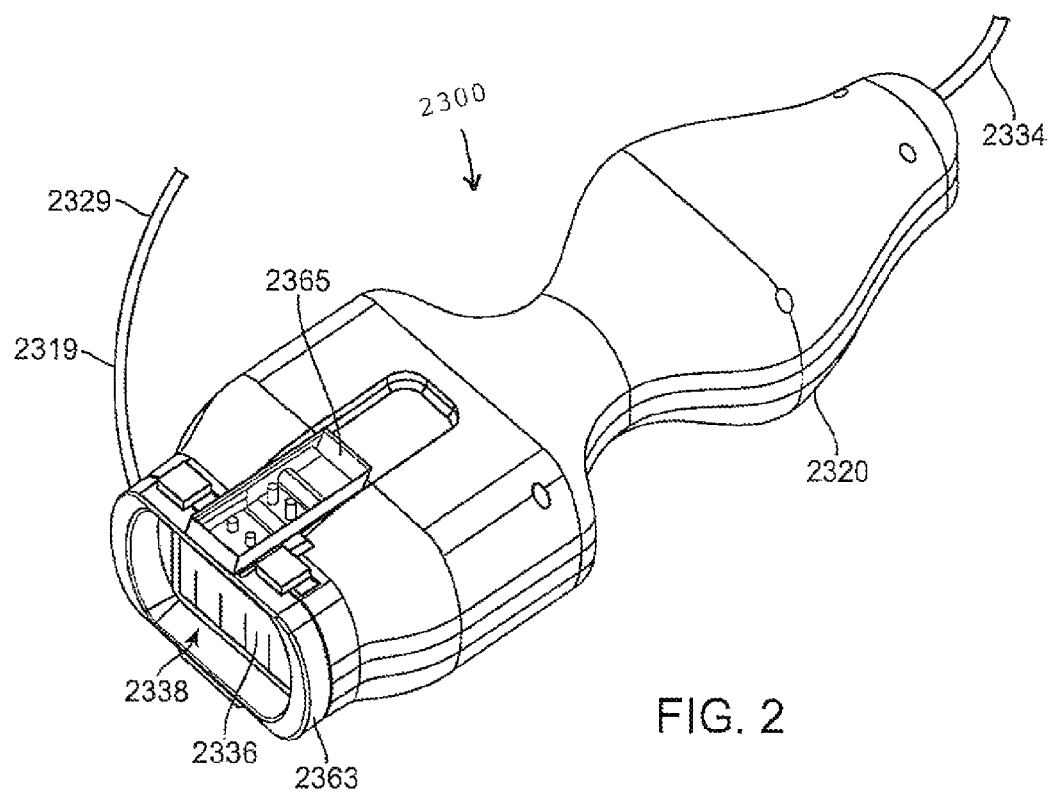
FIG. 2 is a perspective view of an applicator and the disposable according to one embodiment of the invention.

FIG. 2 is a perspective view of applicator 2320 and disposable 2363 according to one embodiment of the invention. According to one embodiment of the invention applicator 2320 may be attached to disposable 2363 by latching mechanism 2365. According to one embodiment of the invention applicator 2320 may include applicator cable 2334. According to one embodiment of the invention disposable 2363 may include vacuum tubing 2319, tissue chamber 2338 and tissue interface surface 2336. According to one embodiment of the invention tissue chamber 2338 may be a cavity where target tissue may be localized for focused treatment. According to one embodiment of the invention tissue interface surface 2336 may include tissue bio-barrier 2337, vacuum ports 2342 and vacuum channel 2350. According to one embodiment of the invention vacuum ports 2342 may be positioned around an outer edge of tissue interface surface 2336. According to one embodiment of the invention vacuum ports 2342 may be arranged to be substantially equidistant from each other. According to one embodiment of the invention vacuum ports 2342 may be arranged evenly around the interface surface. According to one embodiment of the invention vacuum ports 2342 may surround tissue bio-barrier. According to one embodiment of the invention vacuum ports 2342 may be positioned a predetermined distance from the chamber walls 2354. According to one embodiment of the invention vacuum ports 2342 may have a total opening area and positioning sufficient to acquire and hold tissue in tissue chamber 2338. According to one embodiment of the invention vacuum ports 2342 may be evenly distributed around tissue chamber 2338 to facilitate the equal acquisition of tissue across tissue chamber 2338. According to one embodiment of the invention vacuum ports 2342 may be symmetrically distributed around tissue chamber 2338 to facilitate the symmetrical acquisition of tissue. According to one embodiment of the invention there may be, for example, approximately 28 vacuum ports 2342 in tissue interface surface 2336. According to one embodiment of the invention vacuum ports 2342 may contact vacuum channel 2350. According to one embodiment of the invention vacuum ports 2342 connect tissue chamber 2338 to a vacuum circuit 2341. According to one embodiment of the invention vacuum channel 2350 may be positioned around tissue bio-barrier 2337 in flow contact with at least one of the vacuum ports 2342. According to one embodiment of the invention vacuum channel 2350 assists in holding the tissue in place when the vacuum pressure is applied. According to one embodiment of the invention vacuum channel 2350 assists in creating suction marks on the patients skin (such suction marks may be referred to as hickey marks). According to one embodiment of the invention suction marks may be used by a physician or user to identify regions which have been treated. According to one embodiment of the invention laser or other light sources integrated into the disposable 2363 may be used to provide the user with a guide to indicate the treatment region before the applicator is applied to tissue. According to one embodiment of the invention vacuum circuit 2341 may split the vacuum pressure applied through, for example vacuum tubing 2319, between tissue chamber 2338 applicator chamber 2346. According to one embodiment of the invention vacuum circuit 2341 may be adapted to equalize air pressure on either side of tissue bio-barrier while or inhibiting the movement of fluids from tissue chamber 2338 into applicator chamber 2346. According to one embodiment of the invention vacuum channels 2350 in tissue interface surface 2336 may assist in holding tissue and preventing tissue from peeling away from tissue interface surface 2336 during treatment. According to one embodiment of the invention vacuum sounds in tissue chamber 2338 may provide the user with an audio indication of proper tissue acquisition. According to one embodiment of the invention so long as the user is able to hear vacuum sounds, the tissue is not positioned properly in tissue chamber 2338.

Figure 3:
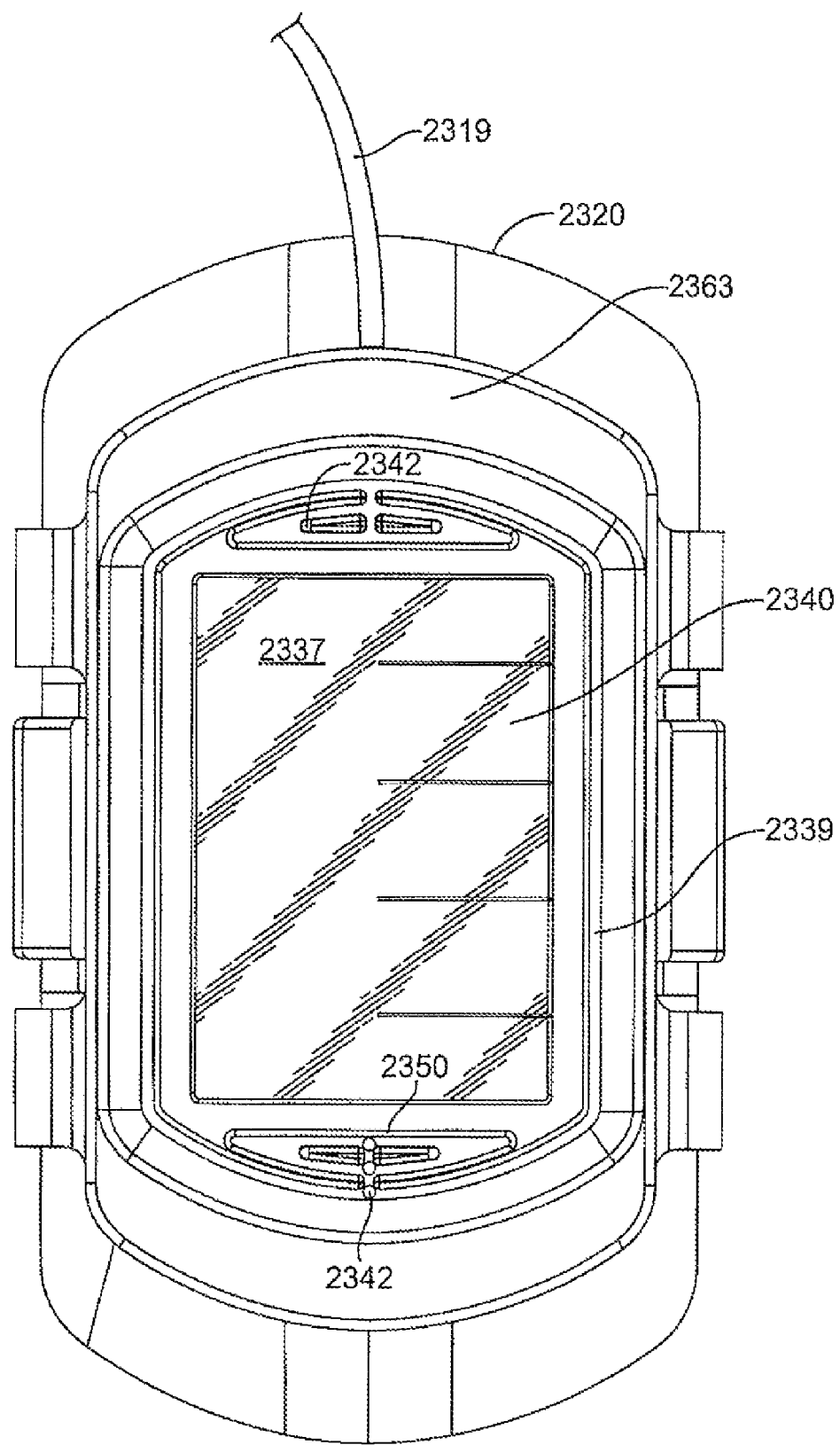
FIG. 3 is an end on view of the distal end of the applicator and the disposable illustrated in FIG. 2.

FIG. 3 is an end on view of the distal end of applicator 2320 and disposable 2363 illustrated in FIG. 2. According to one embodiment of the invention disposable 2363 may include tissue bio-barrier 2337, which may be, for example, a flexible film. According to one embodiment of the invention disposable 2363 may include tissue bio-barrier 2337, which may be, for example, a polyethylene film. According to one embodiment of the invention applicator 2320 may include cooling plate 2340, which may be, for example, positioned behind bio-barrier 2337. According to one embodiment of the invention disposable 2363 may include vacuum ports 2342 and vacuum channels 2350. According to one embodiment of the invention vacuum ports 2342 may be, for example, holes in the distal end of disposable 2363 which may be connected directly or indirectly to vacuum tubing 2319 and to vacuum channels 2350, which may be formed by grooves in disposable 2363. According to one embodiment of the invention disposable 2363 may include a chamber opening 2339. According to one embodiment of the invention chamber opening 2339 may be oval shaped. According to one embodiment of the invention chamber opening 2339 may be approximately 35 millimeters wide by 50 millimeters long. According to one embodiment of the invention tissue chamber 2338 may be approximately 7 millimeters deep.

According to one embodiment of the invention tissue bio-barrier 2337 may be positioned to provide a seal when disposable 2363 is attached to applicator 2320. According to one embodiment of the invention tissue bio-barrier 2337 may be adapted to prevent skin and any bodily fluids on skin from contacting applicator 2320 including cooling plate 2340. According to one embodiment of the invention tissue bio-barrier 2337 may be positioned to stretch across cooling plate 2340 as disposable 2363 is attached to applicator 2320. According to one embodiment of the invention tissue bio-barrier 2337 is designed, at least in part, to minimize the loss of thermal conductivity of the combined cooling plate 2340/tissue bio-barrier 2337 combination. According to one embodiment of the invention tissue bio-barrier 2337 may be a flexible film having a thickness of approximately 0.0005 inches and may vary between approximately 0.0001 inches and approximately 0.030 inches. According to one embodiment of the invention tissue bio-barrier 2337 may be impermeable to fluid and substantially impermeable to air. According to one embodiment of the invention tissue bio-barrier 2337 may be a dielectric material which may be substantially transparent to microwave energy. According to one embodiment of the invention tissue bio-barrier 2337 may be a material which does not perturb microwave fields passing through tissue bio-barrier 2337. According to one embodiment of the invention tissue bio-barrier 2337 may be a low loss material. According to one embodiment of the invention tissue biobarrier 2337 may have a dielectric constant of between two and 15 and preferably between 3 and 3.5. According to one embodiment of the invention tissue bio-barrier 2337 may have a Young's Modulus of between approximately 0.1 GPa and approximately 5 GPa. According to one embodiment of the invention tissue bio-barrier 2337 may have a Young's Modulus of between approximately 0.1 and approximately 3.1 GPa. According to one embodiment of the invention tissue bio-barrier 2337 may have a Young's Modulus of between approximately 0.1 and 1.5 GPa. According to one embodiment of the invention tissue bio-barrier 2337 may be a flexible film, such as polyethylene or PET which may form all or a portion of tissue interface surface 2336. According to one embodiment of the invention tissue bio-barrier 2337 may be a rigid, solid ceramic material with a high thermal conductivity at room temperature of between approximately one watt per meter degree Kelvin and approximately 100 watts per meter degree Kelvin TS. In an alternate embodiment, tissue bio-barrier 2337 may be a rigid, solid ceramic material with a high thermal conductivity at room temperature of between approximately one watt per meter degree Kelvin and approximately 100 watts per meter degree Kelvin TS. According to one embodiment of the invention a rigid tissue bio-barrier 2337 may eliminate the need for the vacuum circuit 2341 in applicator 2320. According to one embodiment of the invention a solid ceramic tissue bio-barrier 2337 may have a microwave permittivity selected for use at 5.8 GHz. According to one embodiment of the invention a rigid tissue bio-barrier 2337 may consist of a material with a dielectric constant that matches or approximately matches the dielectric constant of cooling plate 2340, such as, for example a dielectric constant of approximately 10. According to one embodiment of the invention materials suitable for use as a rigid tissue bio-barrier may include materials having a dielectric constant having values of between 1 and 80 may also be acceptable if the thickness of tissue bio-barrier 2337 is minimized sufficiently to ensure that microwave transparency of tissue bio-barrier 2337 is not impacted by the variation in dielectric constant. According to one embodiment of the invention tissue bio-barrier 2337 may have a thickness of less than approximately 0.001 inches to maximize microwave transparency. According to one embodiment of the invention a rigid tissue bio-barrier 2337 may consist of a material with a dielectric constant that does not add an additional dielectric discontinuity between cooling plate 2340 and tissue engaged in tissue chamber 2338. According to one embodiment of the invention rigid tissue bio-barrier 2337 may be chosen to minimize the overall effective thickness of the cooling plate bio-barrier combination According to one embodiment of the invention a combined thickness of cooling plate 2340 and tissue bio-barrier 2337 may be chosen to minimize a reduction in peak SAR over a cooling plate 2340 alone. According to one embodiment of the invention a combined thickness of cooling plate 2340 and tissue bio-barrier 2337 may be chosen to be less than 0.018" to minimize a reduction in peak SAR over a cooling plate 2340 alone. According to one embodiment of the invention a combined thickness of cooling plate 2340 and tissue bio-barrier 2337 may be chosen to be less than 0.020" to minimize a reduction in peak SAR over a cooling plate 2340 alone.

Figure 4:
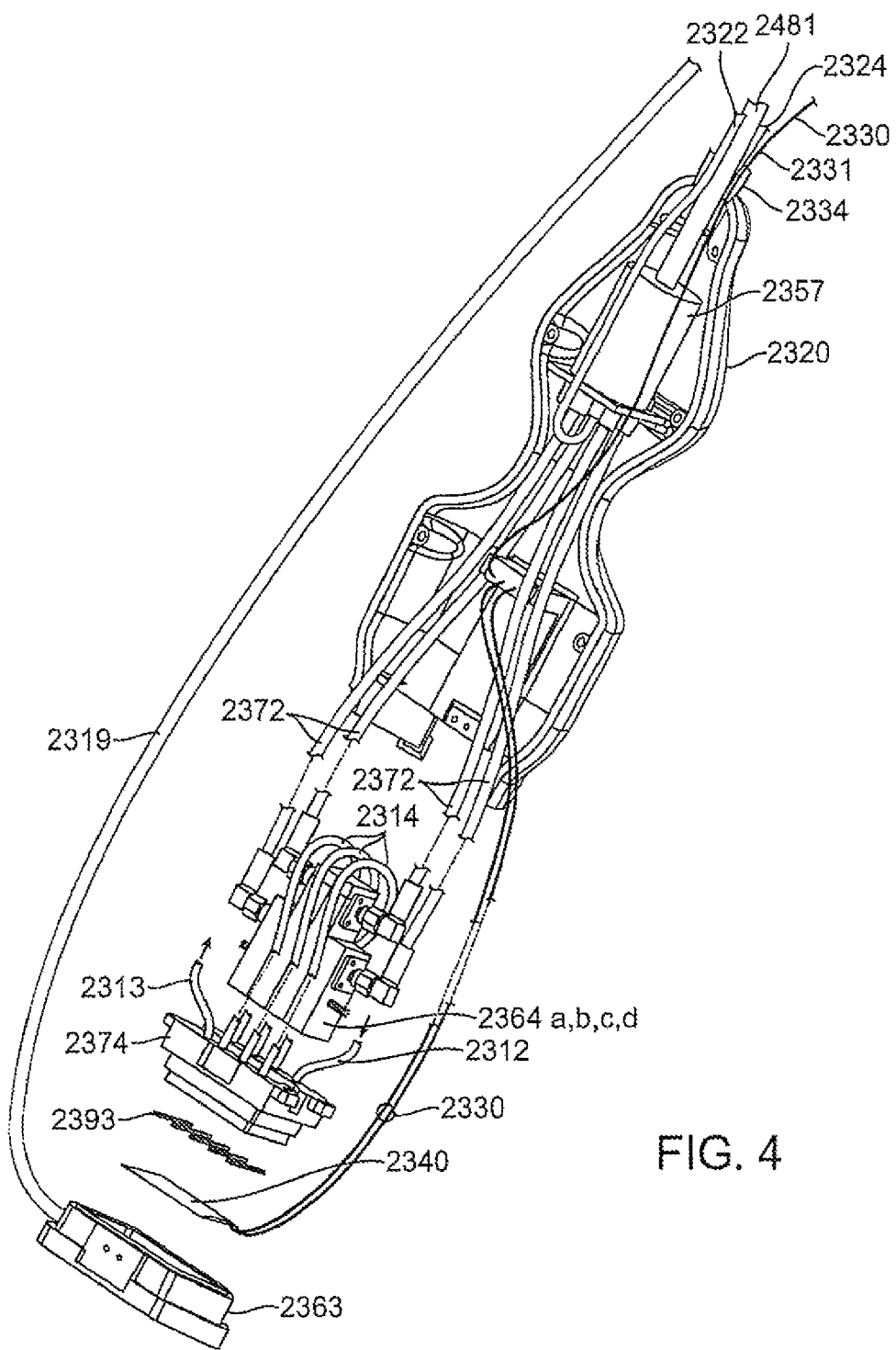
FIG. 4 is an exploded perspective view of the applicator and the disposable illustrated in FIG. 2.

FIG. 4 is an exploded perspective view of applicator 2320 and disposable 2363 illustrated in FIG. 2. According to one embodiment of the invention, applicator 2320 may include a cooling plate 2340, which may include one or more thermocouples attached to cooling plate thermocouple wires 2330. According to one embodiment of the invention applicator 2320 may include separation ribs 2393, antenna cradle 2374, coolant supply tubing 2312, coolant return tubing 2313, waveguide antennas 2364(*a-d*), antenna switch 2357 and applicator cable 2334. According to one embodiment of the invention, applicator cable 2334 may include antenna switch signal 2481, energy cable 2322 and coolant conduit 2324. According to one embodiment of the invention applicator cable 2334 may include cooling plate thermocouple wires 2330 and coolant thermocouple wires 2331. According to one embodiment of the invention, disposable 2363 may include vacuum tubing 2319. According to one embodiment of the invention energy cable 2322 (which may be referred to as microwave cable) conveys microwave energy from generator 2301 to applicator 2320. According to one embodiment of the invention energy cable 2322 conveys microwave energy to an antenna switch 2357 (which may be referred to as a microwave switch) in applicator 2320. According to one embodiment of the invention energy cable 2322 may be designed to match the output of generator 2301 to applicator 2320 at the frequency of interest. According to one embodiment of the invention energy cable 2322 may be designed to match the output of generator 2301 to applicator 2320 at 5.8 GHz. According to one embodiment of the invention energy cable 2322 has less than 2 dB of loss into a 50 ohm load. According to one embodiment of the invention energy cable 2322 may be a six foot coaxial cable with less than 2 dB of loss. According to one embodiment of the invention energy cable 2322 may be a flexible cable to maximize the overall flexibility of applicator cable 2334. According to one embodiment of the invention interconnect cables 2372 leading to waveguide antennas 2364 in antenna array 2355 are preferably balanced and matched such that the output of each waveguide antenna 2364 has the same power. According to one embodiment of the invention interconnect cables 2372 leading to waveguide antennas 2364 in antenna array 2355 are preferably balanced and matched such that the output of each waveguide antenna 2364 has the same power by selecting appropriate lengths and cable types to ensure balanced output between waveguide antennas 2364 and applicator 2320. According to one embodiment of the invention interconnect cables 2372 leading to waveguide antennas 2364 are low loss coaxial cables. According to one embodiment of the invention interconnect cables 2372 leading to waveguide antennas 2364 have losses of less than one dB. According to one embodiment of the invention variations in matching may be compensated by adjusting generator output power or energy delivery time. According to one embodiment of the invention antenna cradle 2374 may include thermocouple guide holes (not shown), which may be sealed to allow thermocouple wires to pass inside the vacuum seal between disposable 2363 and applicator 2320 to prevent vacuum leaks. According to one embodiment of the invention antenna cradle 2374 includes cradle channels 2389 which cooling fluid passes through as part of the coolant circuit. According to one embodiment of the invention alternative antennas may include horn antennas, multi-dielectric fill waveguide antennas, slot antennas, micro-strip antennas, patch antennas and Vivaldi antennas. According to one embodiment of the invention antenna switch 2357 may be adapted to receive a microwave signal and control signals from the generator and, based upon the control signal received, switch the microwave signal between waveguide antennas 2364 in antenna array 2355. According to one embodiment of the invention antenna switch 2357 may be a electro-mechanical coaxial microwave relay, which may be available from, for example, RealComm Technologies. According to one embodiment of the invention one or more of the antennas in applicator 2320 may be activated (e.g. sequentially) via antenna select switches, such as for example antenna select switches which are part of antenna select switch 2462 on generator 2301. According to one embodiment of the invention antenna switch 2357 (which may be referred to as a distribution element) may be adapted to split power from energy cable 2322 between waveguide antennas 2364 powering two or more of waveguide antennas 2364 simultaneously. According to one embodiment of the invention antenna switch 2357 may be a power splitter adapted to split microwave energy between one or more waveguide antennas 2364 simultaneously. According to one embodiment of the invention energy cable 2322 conveys microwave energy to antenna switch 2357. According to one embodiment of the invention feed cables convey microwave power from antenna switch 2357 to individual waveguide antennas 2364. According to one embodiment of the invention cables used to convey microwave energy may be flexible low loss cables. According to one embodiment of the invention cables used to convey microwave energy may have between zero and 2 dB of loss at the frequency of interest. According to one embodiment of the invention cables used to convey microwave energy may have between zero and 2 dB of loss at a frequency of approximately 5.8 GHz. According to one embodiment of the invention cables used to convey microwave energy may have an impedance of approximately 50 ohms.

Figure 5:
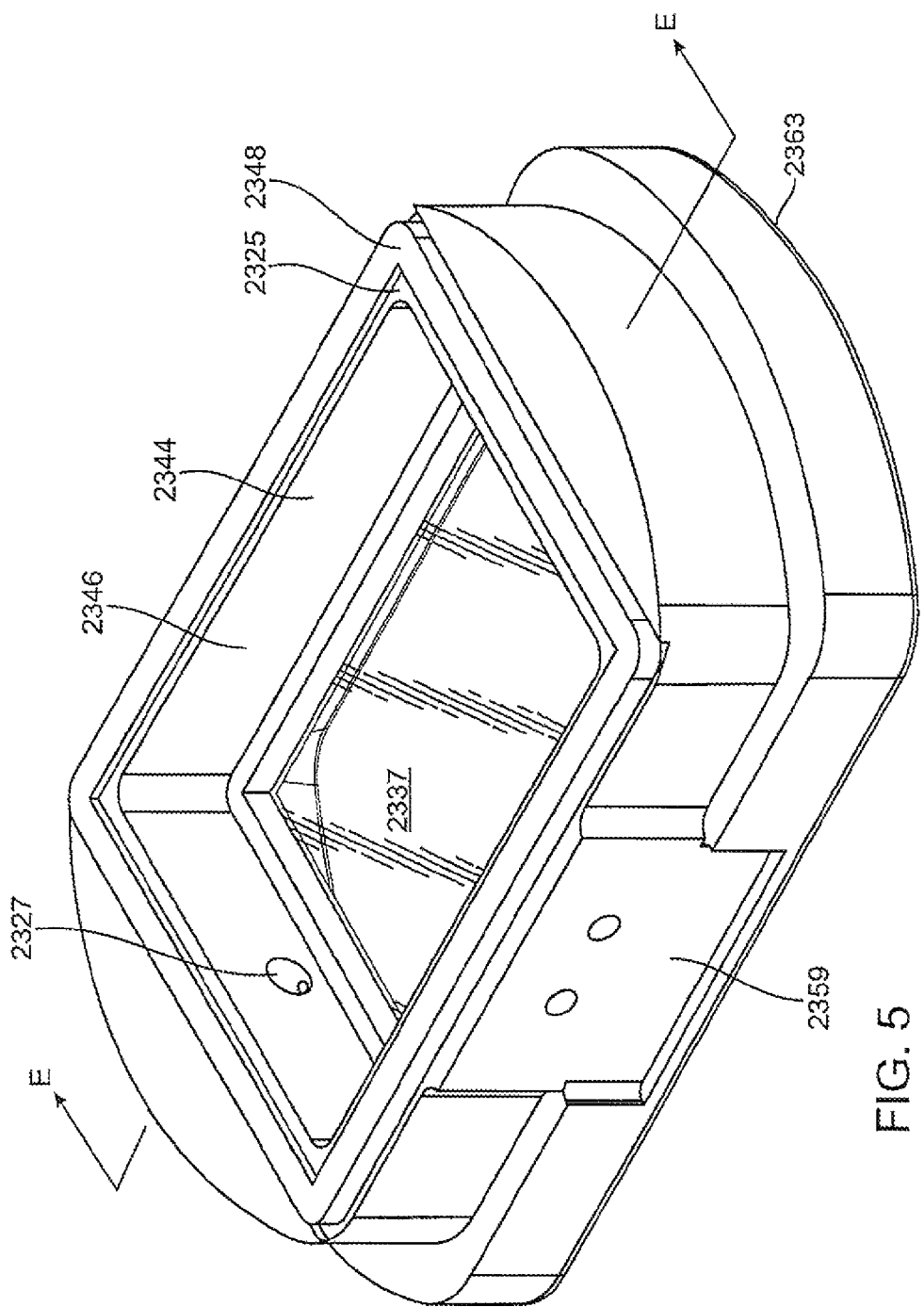
FIG. 5 is a perspective view of the disposable according to one embodiment of the present invention.

FIG. 5 is a perspective view of disposable 2363 according to one embodiment of the present invention. According to one embodiment of the invention, disposable 2363 may include tissue bio-barrier 2337, applicator vacuum port 2327 and applicator chamber 2346, which may also be referred to as a re-usable chamber. According to one embodiment of the invention applicator chamber 2346 may be adapted to receive a distal end of applicator 2320, including cooling plate 2340. According to one embodiment of the invention, disposable 2363 may include applicator interface 2344 (which may also be referred to as re-usable interface). According to one embodiment of the invention applicator interface 2344 includes applicator chamber 2346, vacuum seal 2348, a compression ledge 2325 and latching elements 2359. According to one embodiment of the invention a applicator chamber 2346 may be adapted to receive the distal end of applicator 2320 and to facilitate engagement between the distal end of the applicator 2320 and tissue bio-barrier 2337. According to one embodiment of the invention vacuum seal 2348 may be a gasket, which may be arranged around the outside of the applicator chamber 2346 and may be adapted to engage the distal end of applicator 2320 to seal the applicator chamber 2346 and prevent vacuum leaks when disposable 2363 is attached to applicator 2320. According to one embodiment of the invention when engaged, vacuum seal 2348 may be compressed between approximately twenty percent and approximately fifty percent to ensure good vacuum seal and prevent vacuum leaks. According to one embodiment of the invention vacuum seal 2348 may be compressed a distance sufficient to ensure a good vacuum seal and prevent leaks. According to one embodiment of the invention compression ledge 2325 may be arranged around at least a portion of the applicator chamber 2346. According to one embodiment of the invention compression ledge 2325 may be arranged and positioned to prevent the vacuum seal from being compressed beyond a predetermined point when disposable 2363 is attached to applicator 2320. According to one embodiment of the invention compression ledge 2325 may be arranged and positioned to prevent the vacuum seal from being compressed beyond twenty percent when disposable 2363 is attached to applicator 2320. According to one embodiment of the invention compression ledge 2325 may be arranged and positioned to prevent the vacuum seal from being compressed beyond fifty percent when disposable 2363 is attached to applicator 2320. According to one embodiment of the invention latching elements 2359 may be adapted to facilitate engagement between disposable 2363 and applicator 2320. According to one embodiment of the invention latching elements 2359 on disposable 2363 may be latch keepers, adapted to engage latches on applicator 2320.

Figure 6:
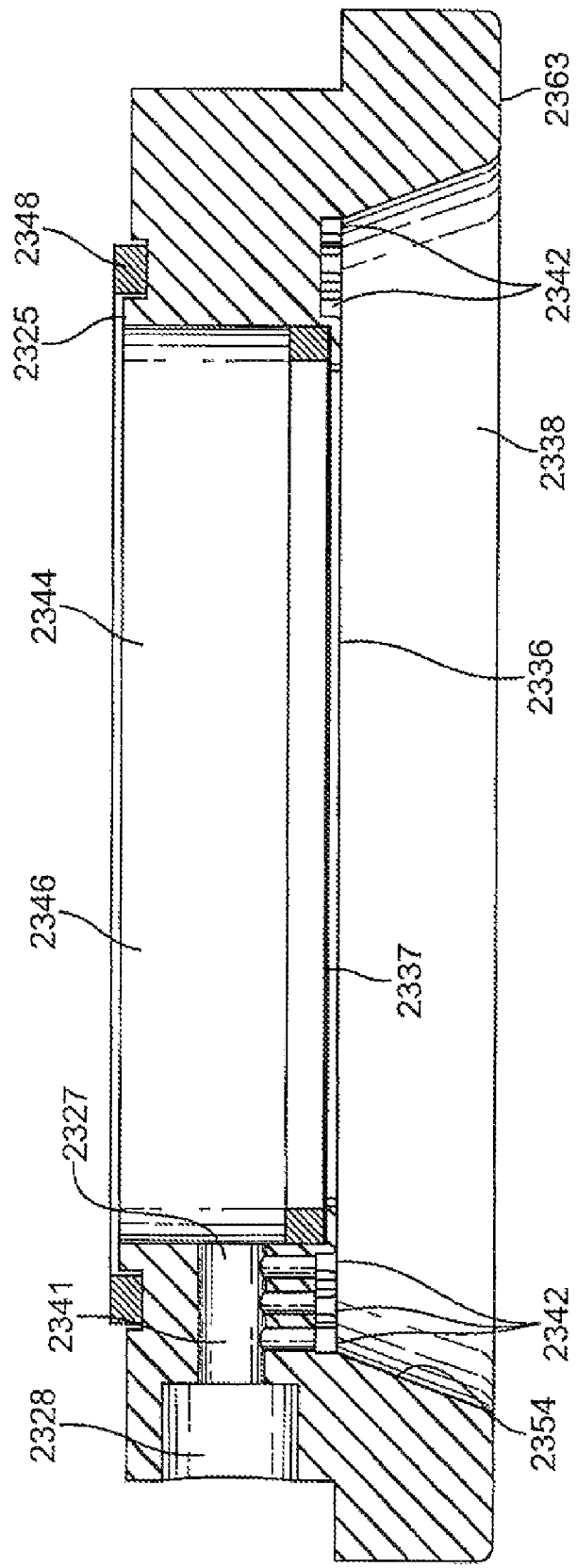
FIG. 6 is a cutaway view along E-E of the disposable illustrated in FIG. 5.

FIG. 6 is a cutaway view of disposable 2363 along E-E in FIG. 5. According to one embodiment of the invention, disposable 2363 includes tissue interface surface 2336, tissue chamber 2338, tissue bio-barrier 2337, applicator chamber 2346, chamber wall 2354 and vacuum ports 2342. According to one embodiment of the invention vacuum ports 2342 may be connected to a vacuum circuit 2341 which may be connected to applicator chamber 2346 by applicator vacuum port 2327 and to a source of vacuum pressure (not shown) by vacuum connector 2328. According to one embodiment of the invention chamber walls 2354 may be transparent or translucent to allow a physician or other user to see into tissue chamber 2338 and to confirm tissue acquisition.

According to one embodiment of the invention chamber walls 2354 may form an angle of between approximately 5 and 20 degrees with tissue interface surface 2336. According to one embodiment of the invention chamber walls 2354 may form an angle of approximately twenty degrees with tissue interface surface 2336. According to one embodiment of the invention chamber walls 2354 may be formed of a rigid polycarbonate or plastic material. According to one embodiment of the invention chamber walls 2354 may be coated with a thin layer of lubricant, such as, for example, silicone oil, Teflon, paralene or other suitable coating material to ease acquisition of tissue. According to one embodiment of the invention tissue interface surface 2336 may be coated with a thin layer of lubricant, such as, for example, silicone oil, Teflon, paralene or other suitable coating material to ease acquisition of tissue. According to one embodiment of the invention surface coatings, such as, for example silicone oil, Teflon, paralene or other suitable coating material applied to tissue chamber 2338, including waveguide walls 2366 and tissue interface surface 2336, facilitate the easy acquisition of tissue and prevent tissue from shifting as it is being acquired. According to one embodiment of the invention waveguide walls 2366 may consist of waveguide tubing with a short at one end or direct plating of the dielectric fill material. According to one embodiment of the invention waveguide walls 2366 may have a thickness of at least 5 times the electric skin depth of the material making up waveguide walls 2366. According to one embodiment of the invention waveguide walls 2366 may be copper plated over dielectric filler 2368. According to one embodiment of the invention waveguide walls 2366 may have thickness of between approximately .0002" and .040" and preferably a thickness of approximately .003 inches. According to one embodiment of the invention waveguide walls 2366 may be formed from solid conductive material. According to one embodiment of the invention waveguide walls 2366 may be formed from a waveguide tube which is cut to a predetermined length and fitted with a conductive short on a side opposite the waveguide antenna aperture. According to one embodiment of the invention waveguide antenna 2364 may have an aperture of approximately .62 inches by .31 inches. According to one embodiment of the invention dielectric filler 2368 may have a dielectric constant selected for use at 5.8GHz. According to one embodiment of the invention temperature measured at cooling plate thermocouple 2395 may be indicative of the temperature of the skin surface underlying the tissue bio-barrier 2337 adjacent cooling plate thermocouple 2395. According to one embodiment of the invention the dielectric filler may have a dielectric constant of approximately 10. According to one embodiment of the invention dielectric filler 2368 should be a low loss material. According to one embodiment of the invention dielectric filler 2368 may have a length of between approximately 20 and 80 millimeters and preferably a length that is approximately an integer multiple of one-half of one guided wavelength at a frequency of interest. According to one embodiment of the invention dielectric filler 2368 may have a length of between approximately 20 and 80 millimeters and preferably a length that is approximately 28.5 millimeters for a short waveguide antenna 2364 and approximately 48 millimeters for a long waveguide antenna 2364. According to one embodiment of the invention dielectric filler 2368 in the longer waveguide antenna 2364 may have a length which may be one or more guided wavelengths longer than the dielectric in the shorter waveguide antenna 2364. According to one embodiment of the invention dielectric filler 2368 in the longer antenna may have a length which is approximately 20 millimeters longer than dielectric filler 2368 in the shorter antenna.

Figure 7:
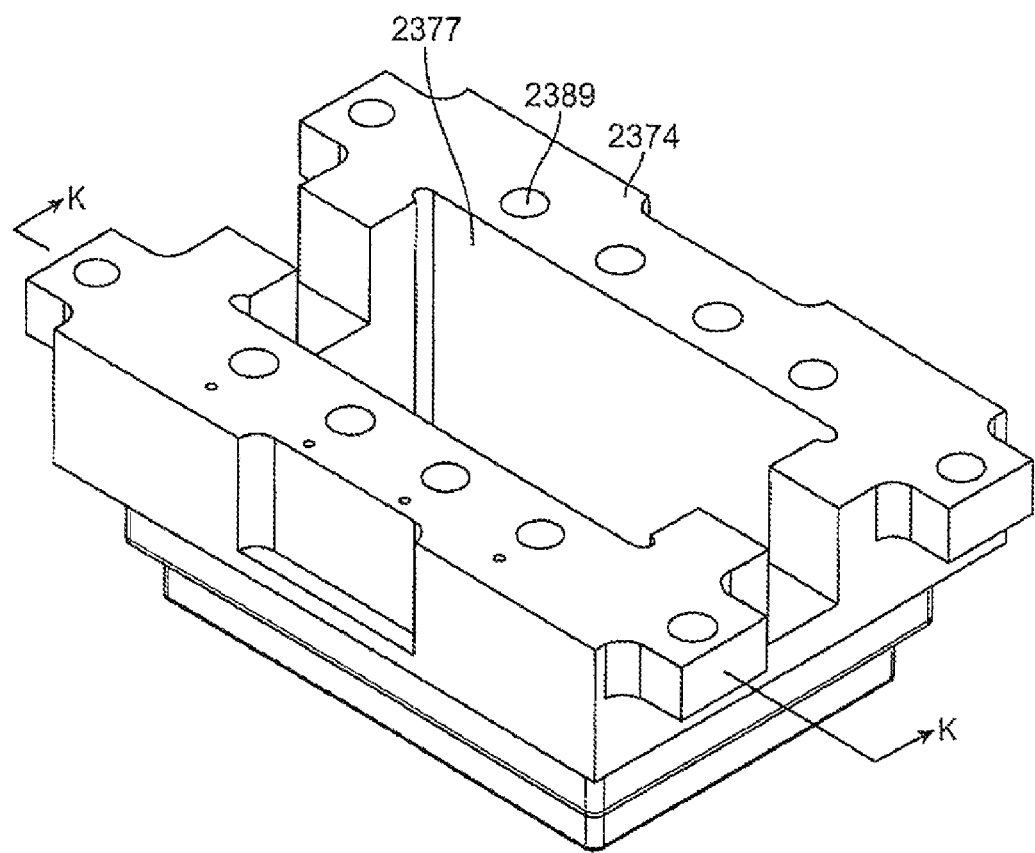
FIG. 7 is a perspective view of an antenna cradle according to one embodiment of the invention.

FIG. 7 is a perspective view of an antenna cradle 2374, which may also be referred to as a waveguide holder, according to one embodiment of the invention. According to one embodiment of the invention antenna cradle 2374 includes cradle channels 2389 and antenna chamber 2377.

Figure 8:
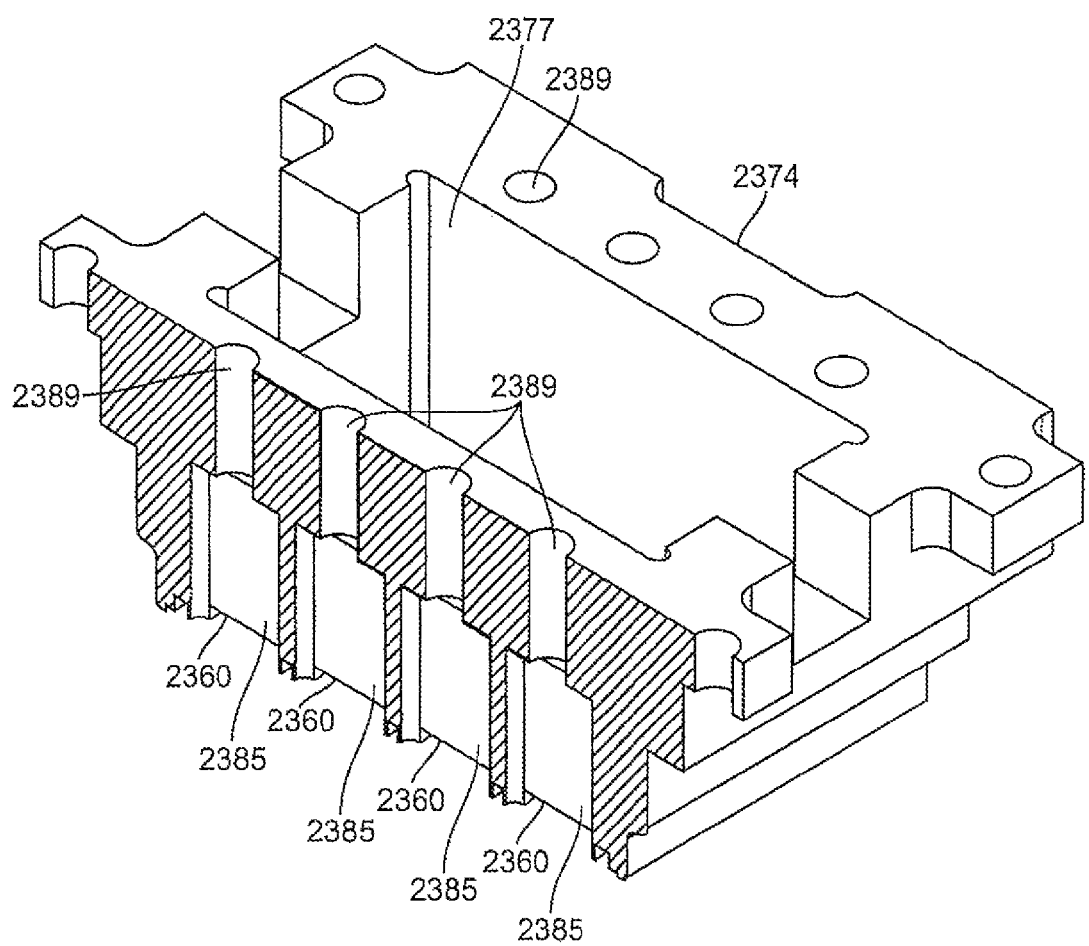
FIG. 8 is a cutaway view along K-K of the antenna cradle illustrated in FIG. 7.

FIG. 8 is a cutaway view of antenna cradle 2374 along K-K in FIG. 7. According to one embodiment of the invention, antenna cradle 2374 includes antenna chamber 2377 and cradle circuit 2385. According to one embodiment of the invention cradle circuit 2385 includes cradle channels 2389 and coolant chambers 2360. According to one embodiment of the invention, cradle circuit 2385 may be used to convey cooling fluid through the antenna cradle. According to one embodiment of the invention, cradle channels 2389 may be connected in parallel, allowing cooling fluid to flow through each cradle channel 2389 and coolant chamber 2360 of cradle circuit 2385 in parallel. According to one embodiment of the invention cradle channels 2389 may be connected in series through, for example, coolant distribution tubing 2314 (illustrated in FIG. 4) allowing cooling fluid to flow through each cradle channel 2389 and coolant chamber 2360 of cradle circuit 2385 sequentially.

Figure 9:
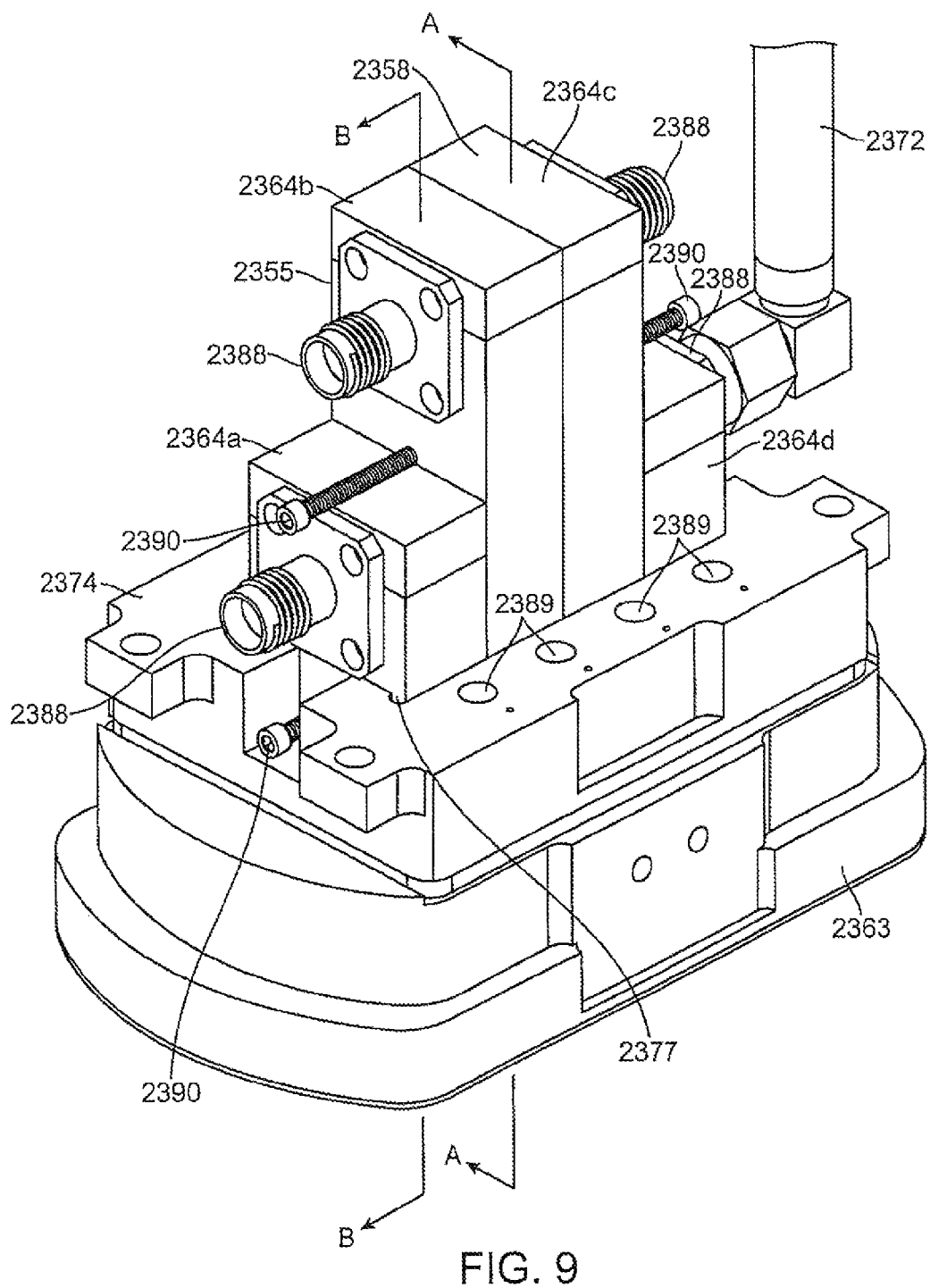
FIG. 9 is a perspective view of an antenna array and the disposable according to one embodiment of the invention.

FIG. 9 is a perspective view of antenna array 2355 and disposable 2363 according to one embodiment of the invention. According to one embodiment of the invention antenna array 2355 may include antenna cradle 2374 and waveguide assembly 2358. According to one embodiment of the invention, antenna cradle 2374 may include cradle channels 2389. According to one embodiment of the invention waveguide assembly 2358 may be positioned in antenna chamber 2377 of antenna cradle 2374 to form antenna array 2355. According to one embodiment of the invention waveguide assembly 2358 may include one or more waveguide antennas 2364. According to one embodiment of the invention waveguide assembly 2358 may include first waveguide antenna 2364a, second waveguide antenna 2364b, third waveguide antenna 2364c and fourth waveguide antenna 2364c. According to one embodiment of the invention waveguide assembly 2358 may include a plurality of tuning elements 2390 (which may be tuning screws) and a plurality of feed connectors 2388, which may be a custom panel mount SMA connector. According to one embodiment of the invention each waveguide antenna 2364 may include a tuning element 2390 and a feed connector 2388. According to one embodiment of the invention microwave energy may be supplied to each waveguide antenna by a interconnect cable 2372. According to one embodiment of the invention tuning element 2390 may include tuning screws which pass through the waveguide walls 2366, forming electrical contact with the waveguide walls 2366, and into the dielectric filler 2368. According to one embodiment of the invention tuning elements 2390 may be positioned approximately ¾ of the guided wavelength from a back wall (such as, for example, shorting element 2373) of waveguide antenna 2364. According to one embodiment of the invention the depth of tuning elements 2390 may be adjusted to tune waveguide antenna 2364 to the frequency of interest. According to one embodiment of the invention the depth of tuning elements 2390 may be adjusted to tune waveguide antenna 2364 to have a center frequency of approximately 5.8 GHz.

Figure 10:
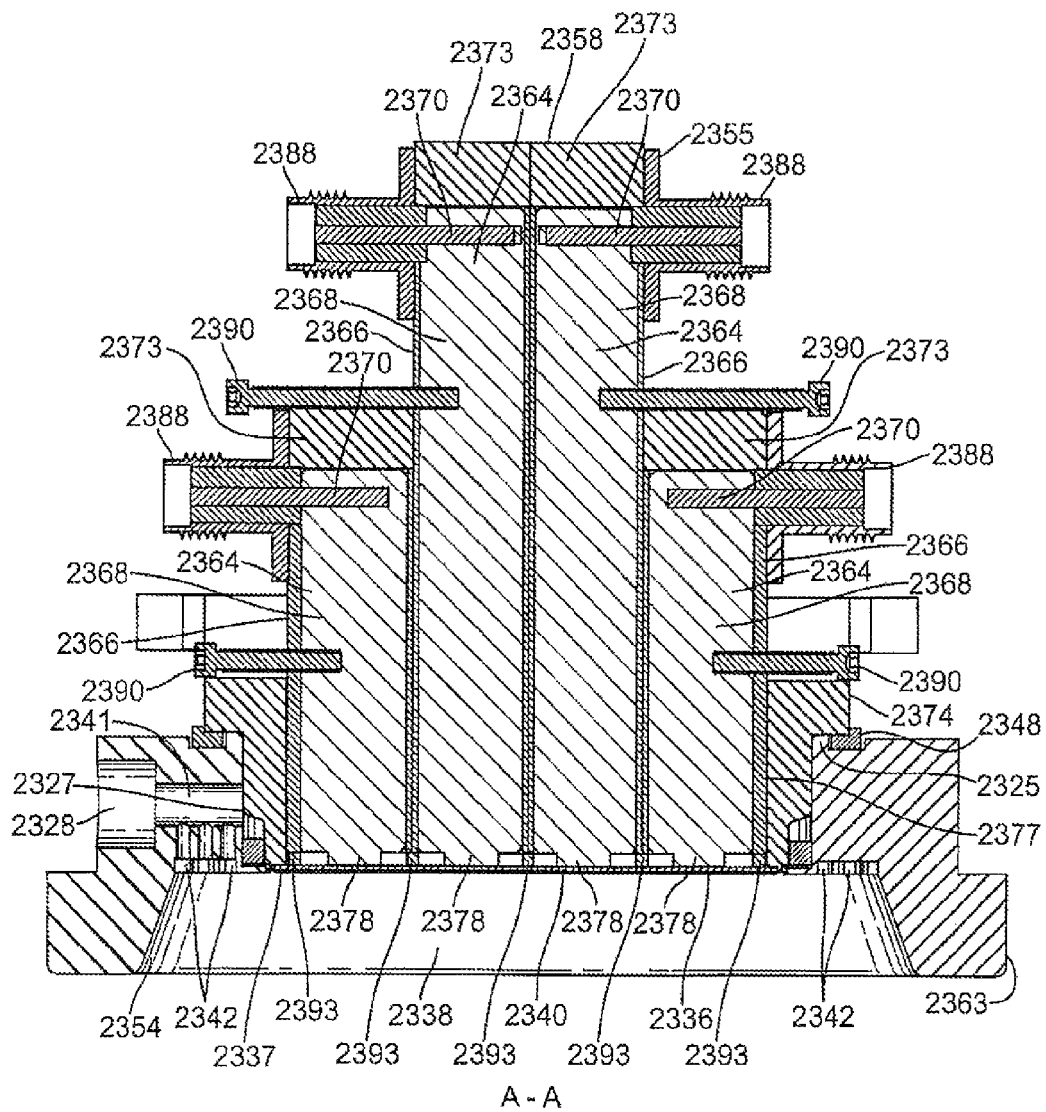
FIG. 10 is a cutaway view along A-A of the antenna array and the disposable illustrated in FIG. 9.

FIG. 10 is a cutaway of antenna array 2355 and disposable 2363 view along A-A in FIG. 9. According to one embodiment of the invention waveguide assembly 2358 is positioned in antenna chamber 2377 of antenna cradle 2374. According to one embodiment of the invention waveguide assembly 2358 includes one or more waveguide antennas 2364. According to one embodiment of the invention signals may be fed into waveguide antenna 2364 through feed connectors 2388 which may include antenna feeds 2370. According to one embodiment of the invention waveguide antennas 2364 may include a dielectric filler 2368, waveguide walls 2366 (which may be, for example waveguide tubing or conductive walls and, more particularly, may be WR62 waveguide tube), a tuning element 2390 and a shorting element 2373, which may be, for example a metal shim. According to one embodiment of the invention waveguide antennas 2364 may be manufactured by, for example, press fitting dielectric filler 2368 into waveguide walls 2366 made from waveguide tubing and brazing shorting element 2373 across one open end of the waveguide tubing. According to one embodiment of the invention disposable 2363 may include tissue chamber 2338, tissue interface surface 2336, which may be, for example, a tissue bio-barrier 2337, vacuum ports 2342 and chamber wall 2354. According to one embodiment of the invention biobarrier 2337 may be, for example a hydrophobic membrane available from GE Osmotics. According to one embodiment of the invention, cooling plate 2340, scattering element 2378 and separation ribs 2393 may be positioned in antenna chamber 2377 between antenna array 2355 and disposable 2363. According to one embodiment of the invention scattering element 2378, which may be referred to as a field spreader, may be, for example, an extension of dielectric filler 2368. According to one embodiment of the invention scattering elements 2378 may be, for example, an absorptive element. According to one embodiment of the invention scattering element 2378 may be an absorptive element which, at least partially mutes the microwave energy radiated from an aperture of waveguide antenna 2364. According to one embodiment of the invention scattering element 2378 may be an absorptive element which, at least partially mutes the microwave energy radiated from an aperture of waveguide antenna 2364 increasing the effective field size of waveguide antenna 2364. According to one embodiment of the invention scattering element 2378 may be an absorptive element which, at least partially mutes the microwave energy radiated from an aperture of waveguide antenna 2364 spreading the SAR pattern in tissue underlying waveguide antenna 2364. According to one embodiment of the invention antenna feed 2370 may be a center conductor of feed connector 2388 which extends into dielectric filler 2368 of waveguide antenna 2364. According to one embodiment of the invention antenna feed 2370 may be positioned such that the microwave signal transitions from feed connector 2388 into waveguide antenna 2364 with minimal reflection resulting from reactive coupling between antenna feed 2370 and a back wall of waveguide antenna 2364, creating impedance matching conditions at a frequency of interest, such as, for example 5.8 GHz. According to one embodiment of the invention antenna feed 2370 may be positioned such that the microwave signal transitions from the feed connector into the waveguide antenna with minimal reflection via reactive coupling between the feed and back wall that creates a 50 ohm matching conditions at 5.8 GHz. According to one embodiment of the invention antenna feed 2370 may be positioned approximately two millimeters from back waveguide wall 2366. According to one embodiment of the invention antenna feed 2370 may be positioned approximately two millimeters from the junction between the shorting element 2373 and the waveguide tube.

Figure 11:
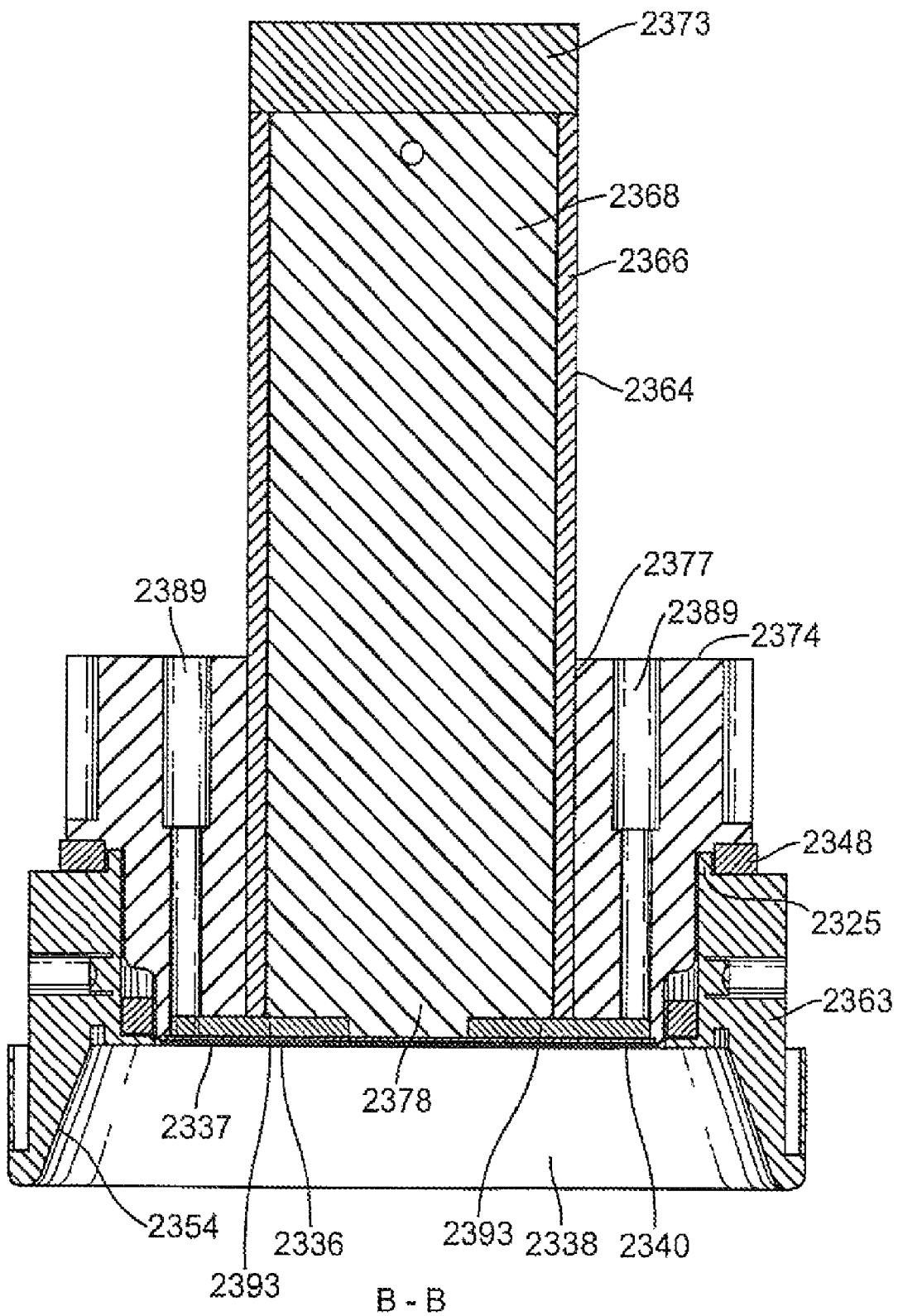
FIG. 11 is a cutaway view along B-B of the antenna array and the disposable illustrated in FIG. 9.

FIG. 11 is a cutaway view of antenna array 2355 and disposable 2363 along B-B in FIG. 9. According to one embodiment of the invention waveguide antenna 2364 may be positioned in antenna chamber 2377 of antenna cradle 2374. According to one embodiment of the invention waveguide antenna 2364 may include dielectric filler 2368, waveguide walls 2366 and shorting element 2373. According to one embodiment of the invention antenna cradle 2374 may include antenna chamber 2377 and cradle channels 2389. According to one embodiment of the invention disposable 2363 may include tissue chamber 2338, tissue interface surface 2336, which may be, for example, a tissue bio-barrier 2337 and chamber wall 2354. According to one embodiment of the invention scattering element 2378, scattering elements 2378 and separation ribs 2393 may be positioned in antenna chamber 2377 between antenna array 2355 and disposable 2363.

Figure 12:
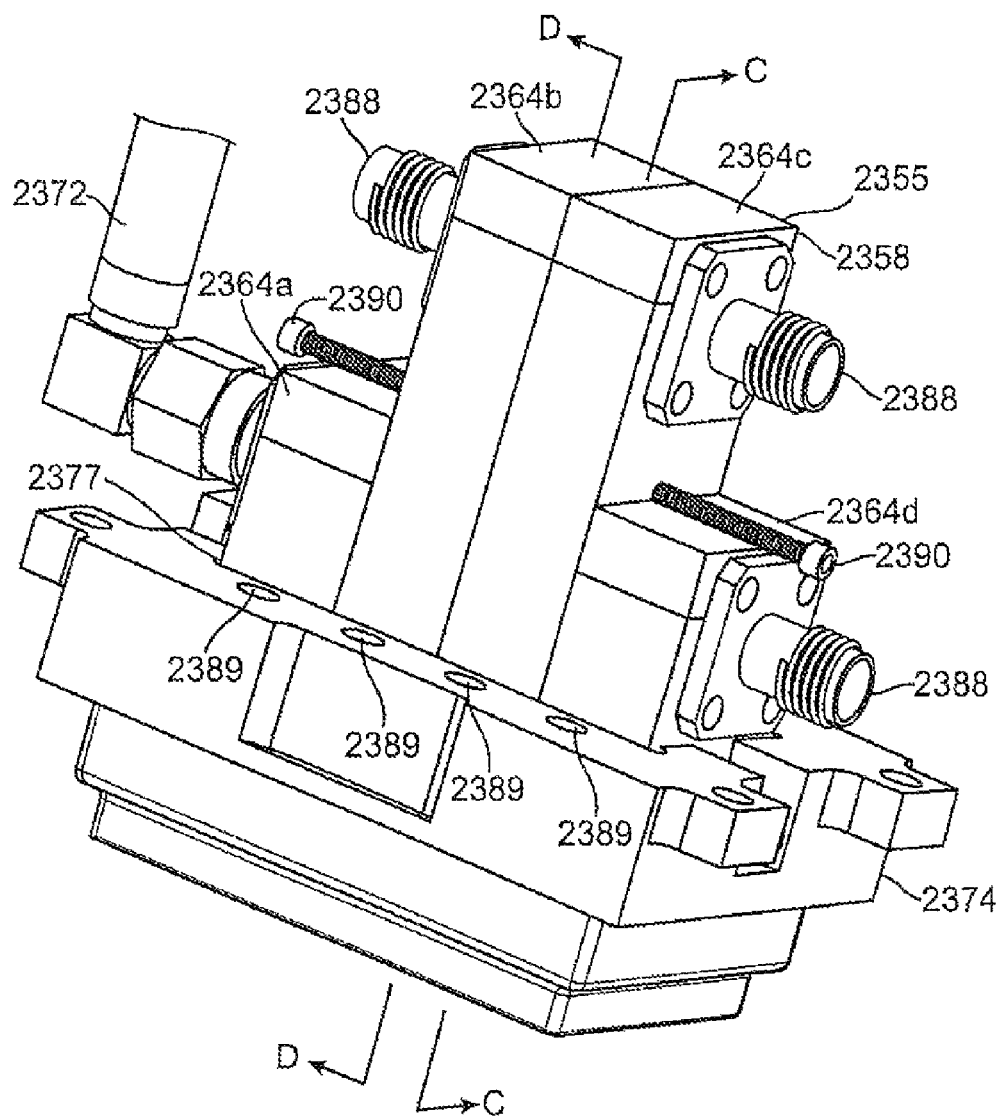
FIG. 12 is a perspective view of an antenna array according to one embodiment of the invention.

FIG. 12 is a perspective view of antenna array 2355 according to one embodiment of the invention. According to one embodiment of the invention waveguide assembly 2358 may include a plurality of tuning elements 2390, which may be tuning screws and a plurality of feed connectors 2388. According to one embodiment of the invention microwave energy may be supplied to each waveguide antenna by a interconnect cable 2372.

Figure 13:
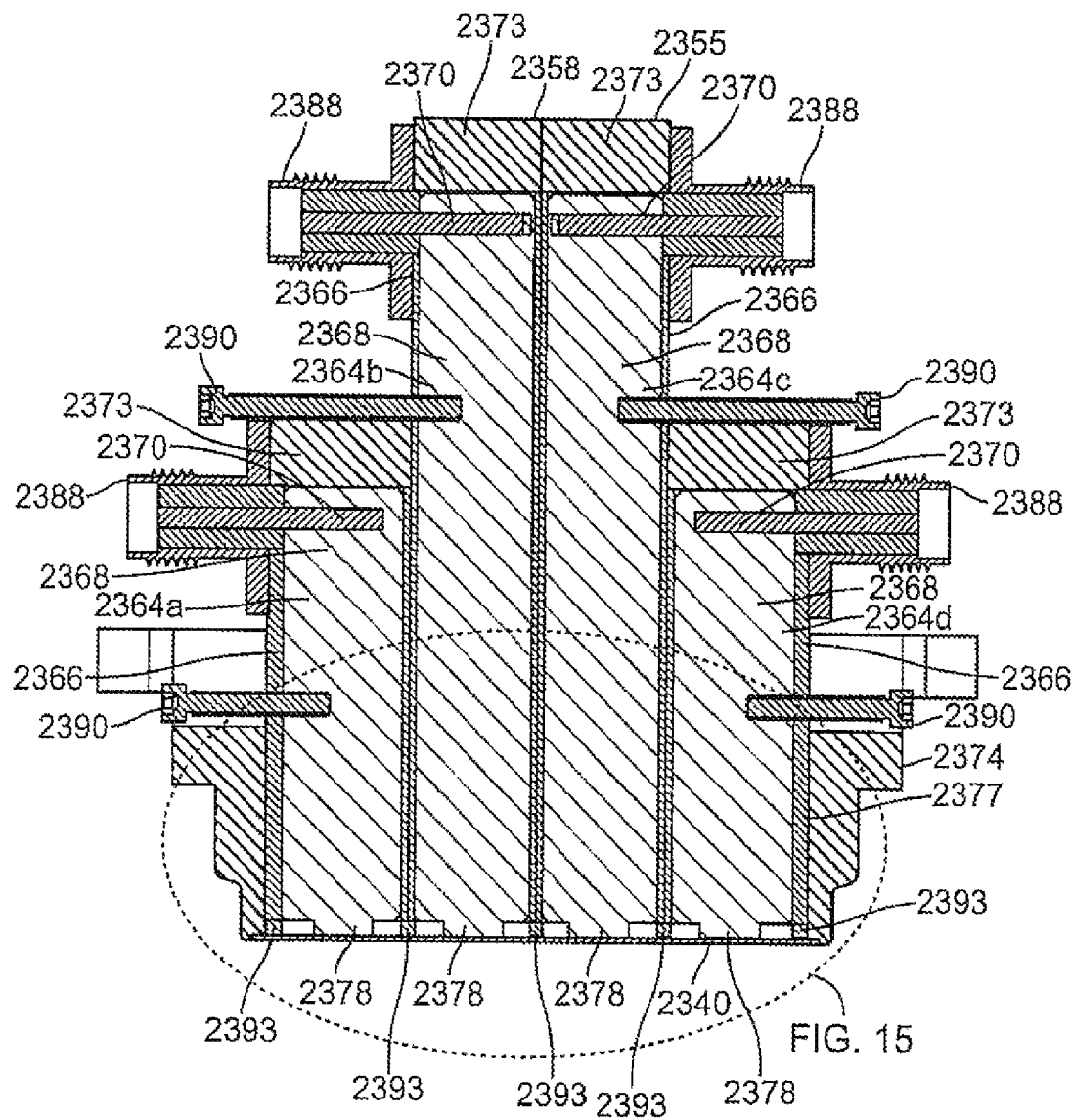
FIG. 13 is a cutaway view along C-C of the antenna array illustrated in FIG. 12.

FIG. 13 is a cutaway view of antenna array 2355 along C-C in FIG. 12. According to one embodiment of the invention waveguide assembly 2358 may be positioned in antenna chamber 2377 of antenna cradle 2374. According to one embodiment of the invention waveguide antennas 2364 may include a dielectric filler 2368, waveguide walls 2366, a tuning element 2390 and a shorting element 2373, which may be, for example a metal shim. According to one embodiment of the invention separation ribs 2393, scattering elements 2378 and cooling plate 2340 may be positioned at a distal end of antenna array 2355.

Figure 14:
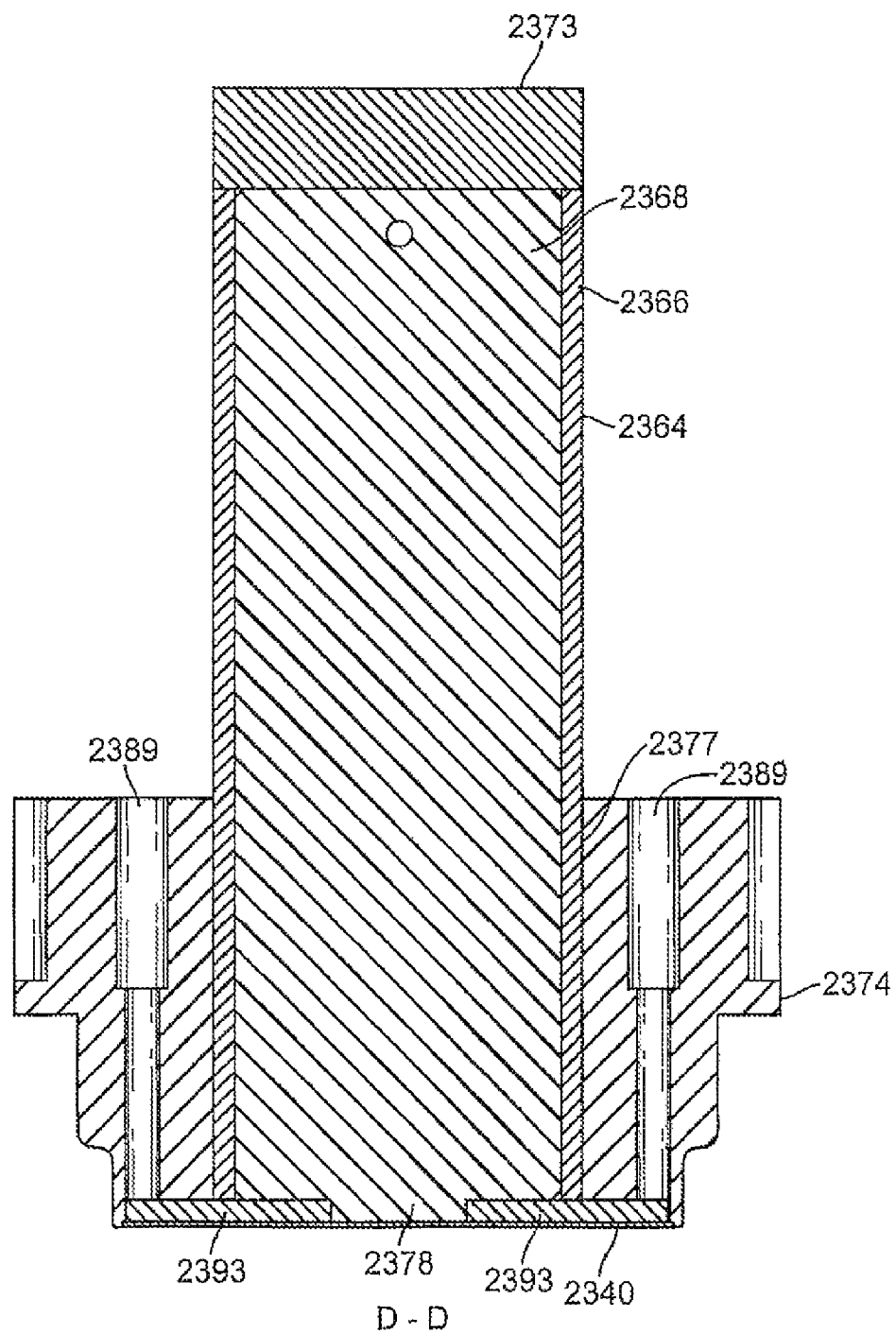
FIG. 14 is a cutaway view along D-D of the antenna array illustrated in FIG. 12.

FIG. 14 is a cutaway view of antenna array 2355 along D-D in FIG. 12. According to one embodiment of the invention scattering element 2378, cooling plate 2340 and separation ribs 2393 may be positioned at a distal end of antenna array 2355 and disposable 2363.

Figure 15:
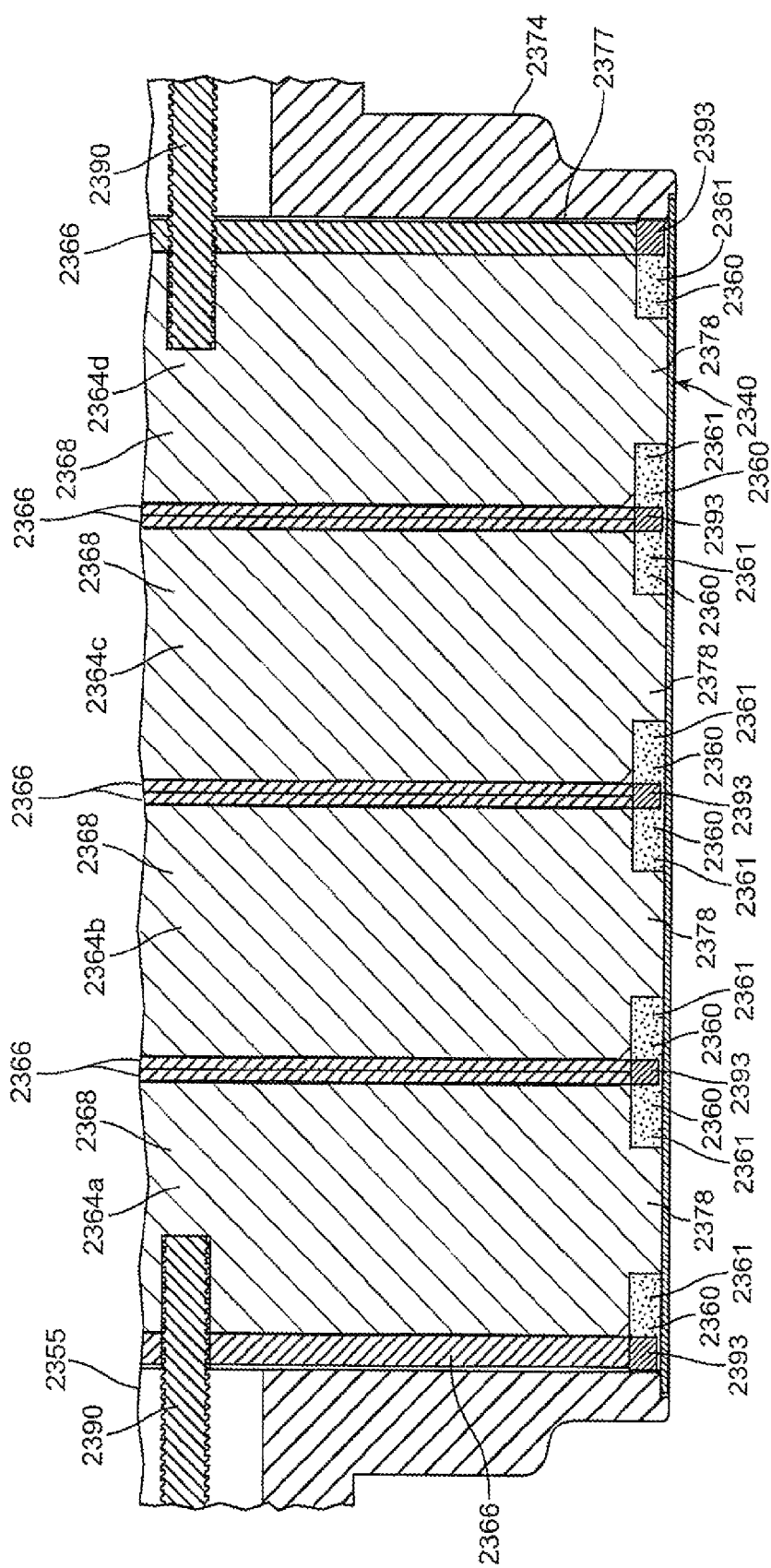
FIG. 15 is a cutaway view along C-C of the distal portion of the antenna array illustrated in FIG. 12.

FIG. 15 is a cutaway view of a distal portion of antenna array 2355 along C-C in FIG. 12. According to one embodiment of the invention waveguide assembly 2358 includes one or more waveguide antennas 2364(a-d). According to one embodiment of the invention waveguide antennas 2364 may include a dielectric filler 2368, waveguide walls 2366 and tuning element 2390. According to one embodiment of the invention scattering elements 2378 and separation ribs 2393 may be positioned in coolant chamber 2360. According to one embodiment of the invention coolant chamber 2360, which may also be referred to as heat exchange channels, may include cooling fluid 2361.

Figure 16:
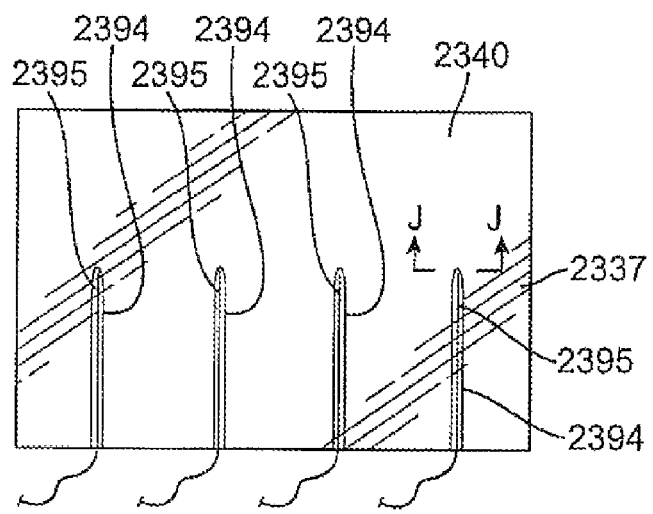
FIG. 16 illustrates a cooling plate and thermocouples according to one embodiment of the invention.

FIG. 16 illustrates a cooling plate and thermocouples according to one embodiment of the invention. According to one embodiment of the invention cooling plate thermocouples 2395 may be positioned in cooling plate grooves 2394. According to one embodiment of the invention cooling plate 2340, cooling plate thermocouples 2395 and cooling plate grooves 2394 may be positioned under tissue bio-barrier 2337.

Figure 17:
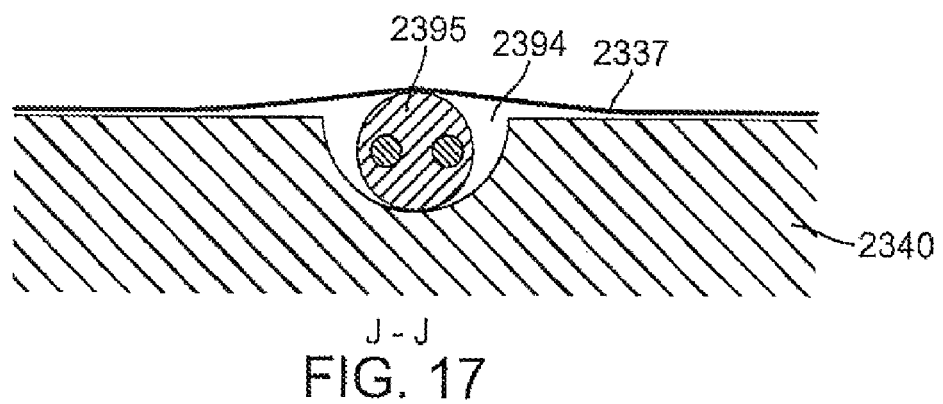
FIG. 17 is a cutaway view along J-J of a portion of the cooling plate and thermocouples illustrated in FIG. 16.
Figure 18:
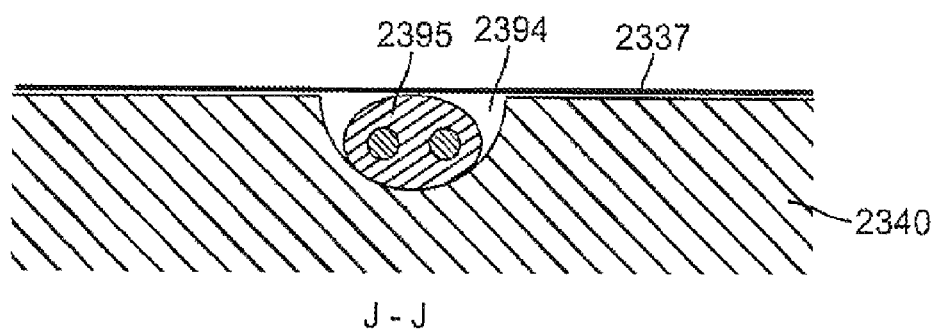
FIG. 18 is a cutaway view along J-J of a portion of the cooling plate and thermocouples illustrated in FIG. 16.

FIG. 17 is a cutaway view of a portion of cooling plate 2340 and cooling plate thermocouple 2395 along J-J in FIG. 16.
FIG. 18 is a cutaway view of a portion of cooling plate 2340 and cooling plate thermocouple 2395 along J-J in FIG. 16. According to one embodiment of the invention cooling plate thermocouple 2395 may be flattened to ensure that tissue bio-barrier 2337 lies flat against a surface of cooling plate 2340. According to one embodiment of the invention cooling plate 2340 may be located at the distal end of applicator 2320. According to one embodiment of the invention cooling plate 2340 may be glued to the distal end of antenna cradle 2374. According to one embodiment of the invention cooling plate 2340 may be positioned to stretch tissue bio-barrier 2337 when disposable 2363 is connected to applicator 2320. According to one embodiment of the invention cooling plate 2340 may be positioned to extend between 0.001 inches and 0.020 inches and preferably 0.010" inches into tissue chamber 2338 when disposable 2363 is attached to applicator 2320. According to one embodiment of the invention cooling plate 2340 may be chosen to have a thickness of between approximately 0.010 inches and 0.014 inches and preferably 0.014 inches. According to one embodiment of the invention cooling plate 2340 may be chosen from a material having rigidity, high thermal conductivity and a dielectric constant chosen to increase coupling of microwave energy into tissue. According to one embodiment of the invention cooling plate 2340 may be a ceramic. According to one embodiment of the invention cooling plate 2340 may be alumina between 90 and 99 percent and preferably of 96 percent. According to one embodiment of the invention cooling plate 2340 may have a thermal conductivity at room temperature of between approximately one watt per meter degree Kelvin and approximately 75 watts per meter degree Kelvin and preferably approximately 30 Watts per meter degree Kelvin TS. According to one embodiment of the invention cooling plate 2340 may have a dielectric constant of between 4 and 15 and preferably 10. According to one embodiment of the invention cooling plate 2340 may be a material which minimizes the microwave energy trapped in cooling plate 2340 in the form of surface waves.

According to one embodiment of the invention a distal surface of cooling plate 2340 may include a plurality of thermocouple channels, such as, for example, cooling plate grooves 2394. According to one embodiment of the invention cooling plate grooves 2394 may have a depth of between approximately 0.003 inches and 0.007 inches and preferably approximately 0.005 inches. According to one embodiment of the invention cooling plate grooves 2394 may have a width of approximately 0.014 inches. According to one embodiment of the invention cooling plate grooves 2394 may be positioned such that they pass directly under the center of the aperture of waveguide antenna 2364. According to one embodiment of the invention cooling plate grooves 2394 may be positioned such that cooling plate thermocouples 2395 are positioned directly under the center of the aperture of waveguide antenna 2364. According to one embodiment of the invention cooling plate grooves 2394 may be positioned such that they pass directly under the center of scattering elements 2378. According to one embodiment of the invention cooling plate grooves 2394 may be positioned such that cooling plate thermocouples 2395 are positioned directly under the center of scattering elements 2378. According to one embodiment of the invention cooling plate grooves 2394 may be positioned such that they cross the portion of the acquired tissue with the highest SAR. According to one embodiment of the invention cooling plate grooves 2394 may be positioned such that cooling plate thermocouples 2395 are positioned above the portion of the acquired tissue with the highest SAR. According to one embodiment of the invention cooling plate grooves 2394 may be positioned such that they are perpendicular to the E-field component of the output of waveguide antenna 2364. According to one embodiment of the invention cooling plate grooves 2394 may be positioned such that the wires of cooling plate thermocouples 2395 lie perpendicular to the E-field component of the output of waveguide antenna 2364. According to one embodiment of the invention cooling plate grooves 2394 may be positioned such that the portion of the wires of cooling plate thermocouples 2395 under the aperture of waveguide antenna 2364 lie perpendicular to the E-field component of the output of waveguide antenna 2364.

According to one embodiment of the invention a proximal surface of cooling plate 2340 may be positioned to contact the distal end of each scattering element 2378. According to one embodiment of the invention cooling plate 2340 may be chosen to have a surface which minimizes the voids or imperfections in the interface between cooling plate 2340 and the distal end of scattering element 2378. According to one embodiment of the invention the interface between cooling plate 2340 and scattering element 2378 interface may be designed to minimize the presence of materials, including air and cooling fluid which may cause perturbations or hot spots at that interface when microwave energy is emitted from waveguide antenna 2364. According to one embodiment of the invention cooling plate 2340 may be substantially flat. According to one embodiment of the invention cooling plate 2340 may have a flatness of less than approximately 0.0002 inches of variability across the surface. According to one embodiment of the invention an adhesive, such as, for example, a dielectric epoxy (e.g. Eccosorb epoxy) may be used to attach cooling plate 2340 to each scattering element 2378.

According to one embodiment of the invention cooling plate thermocouples 2395 may provide feedback indicative of the temperature of tissue adjacent the distal side of cooling plate 2340. According to one embodiment of the invention cooling plate thermocouples 2395 may provide feedback indicative of the temperature of tissue engaged in tissue chamber 2338. According to one embodiment of the invention cooling plate thermocouples 2395 may be positioned in cooling plate grooves 2394 on a distal side of cooling plate 2340. According to one embodiment of the invention cooling plate thermocouples 2395 may be TYPE T, made by laser welding 0.39 gage copper and constantan. According to one embodiment of the invention cooling plate thermocouples 2395 may be printed onto the distal side of cooling plate 2340. According to one embodiment of the invention cooling plate thermocouples 2395 may be oriented such that perturbations in the microwave field caused by cooling plate thermocouples 2395 including cooling plate thermocouple wires are minimized. According to one embodiment of the invention cooling plate thermocouples 2395 may be oriented such that the effect of cooling plate thermocouples 2395 including the cooling plate thermocouple wires on the SAR patterns of applicator 2320 are minimized. According to one embodiment of the invention cooling plate thermocouples 2395 may be oriented such that the effect of cooling plate thermocouples 2395 including thermocouple wires on the creation of lesions within the tissue engaged in tissue chamber 2338 are minimized. According to one embodiment of the invention cooling plate thermocouples 2395 may be oriented such that cooling plate thermocouple lead wires lie perpendicular to the E-field radiated by waveguide antenna 2364. According to one embodiment of the invention, in order to minimize perturbation of the microwave field while maintaining mechanical integrity of cooling plate thermocouple 2395 lead wires, cooling plate thermocouple 2395 lead wires may be chosen to be between approximately 30 gage and approximately 40 gauge and preferably approximately 39 gage. According to one embodiment of the invention cooling plate thermocouples 2395 may be positioned on the distal side of cooling plate 2340 under each waveguide antenna 2364 such that the thermocouple weld lies in the middle of the aperture of waveguide antenna 2364. According to one embodiment of the invention cooling plate thermocouples 2395 may be positioned under each waveguide such that the thermocouple weld lies in the middle of scattering element 2378. According to one embodiment of the invention cooling plate thermocouples 2395 may be positioned in a groove on the surface of cooling plate 2340 such that neither the weld, nor the thermocouple wires extend out of cooling plate groove 2394. According to one embodiment of the invention cooling plate thermocouples 2395 may be positioned in cooling plate grooves 2394 on the surface of cooling plate 2340 such that neither the weld, nor the thermocouple wires push against tissue bio-barrier 2337 by more than approximately 0.003 inches when disposable 2363 is attached to applicator 2320. According to one embodiment of the invention cooling plate thermocouples 2395 may be positioned in cooling plate grooves 2394 on the surface of cooling plate 2340 such that neither the thermocouple weld, nor the thermocouple wires push against tissue bio-barrier 2337 to create air pockets between tissue bio-barrier 2337 and the distal side of cooling plate 2340 when disposable 2363 is attached to applicator 2320. According to one embodiment of the invention cooling plate thermocouple 2395 welds may be flattened to ensure that they fit within cooling plate groove 2394. According to one embodiment of the invention cooling plate thermocouple 2395 welds may be flattened from a cross section of approximately 0.008 inches to create a weld having at least one cross section of approximately 0.004 inches to ensure that cooling plate thermocouple 2395 weld does not extend outside cooling plate groove 2395. According to one embodiment of the invention the number of cooling plate thermocouples 2395 may be generally equal to the number of waveguide antennas 2364 in antenna array 2355. According to one embodiment of the invention the number of cooling plate thermocouples 2395 may be four, one for each waveguide antenna 2364a through 2364d in antenna array 2355. According to one embodiment of the invention cooling plate thermocouples 2395 function to provide feedback to generator 2301 indicative of the temperature of tissue engaged in tissue chamber 2338. According to one embodiment of the invention cooling plate thermocouples 2395 function to provide feedback to generator 2301 indicative of the temperature of tissue underlying each waveguide antenna 2364.

Figure 19:
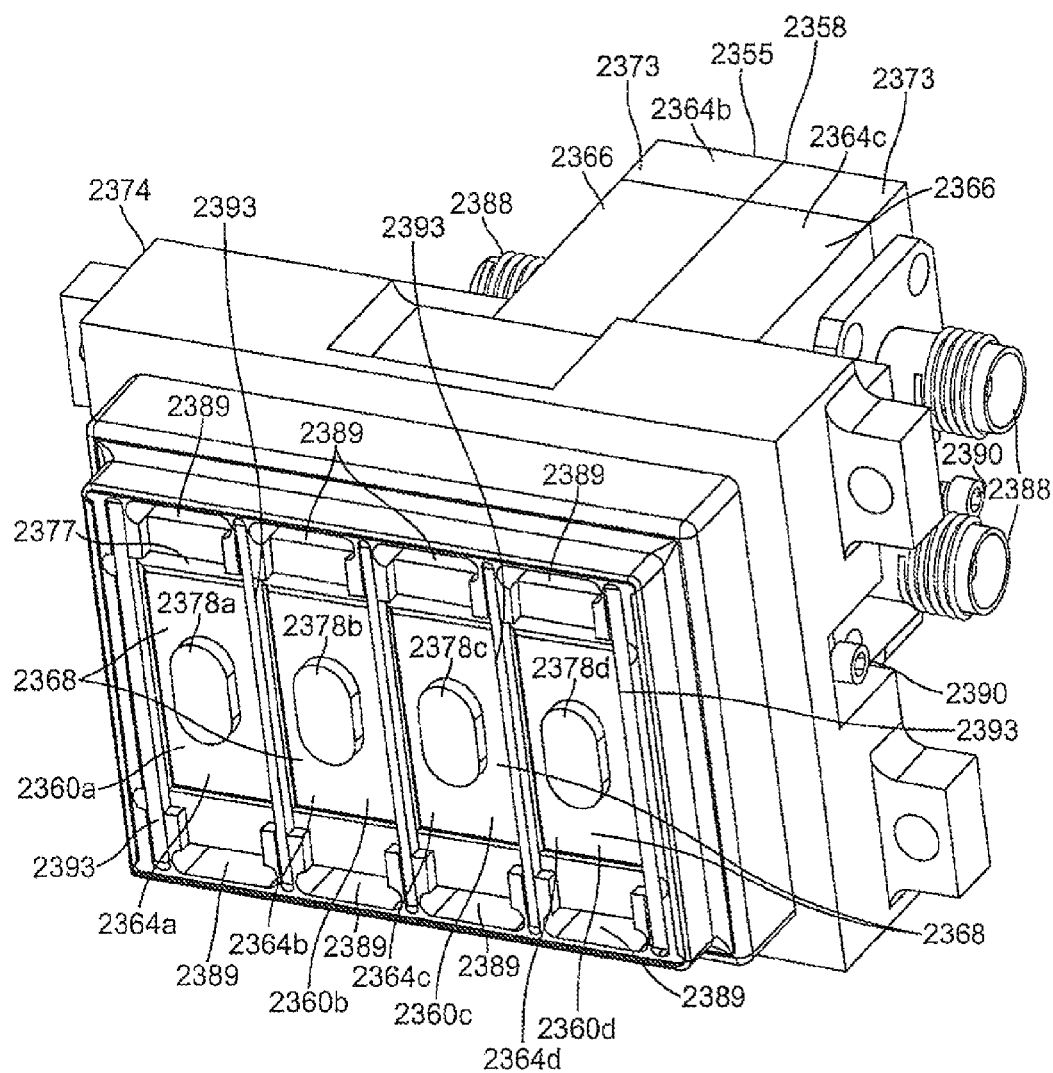
FIG. 19 is a perspective end view of an antenna array, coolant chamber, separation ribs and scattering elements according to one embodiment of the invention.

FIG. 19 is a perspective end view of an antenna array 2355, coolant chambers 2360, separation ribs 2393 and scattering elements 2378 according to one embodiment of the invention. According to one embodiment of the invention waveguide assembly 2358 may include a plurality of tuning elements 2390 and a plurality of feed connectors 2388. According to one embodiment of the invention cradle channels 2389 may be connected to coolant chamber 2360.

Figure 20:
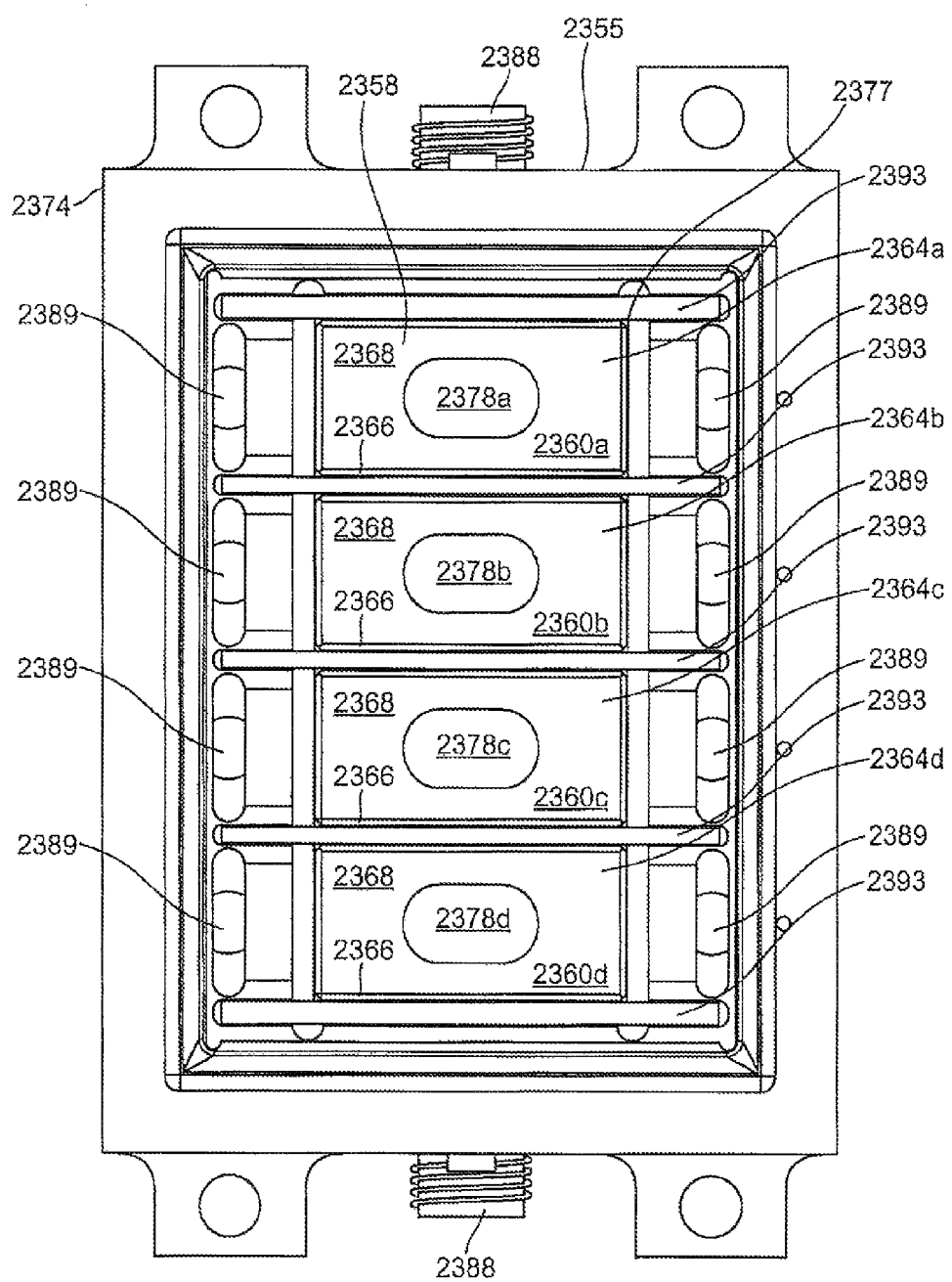
FIG. 20 is an end view of the antenna array, coolant chamber, separation ribs and scattering elements illustrated in FIG. 19.

FIG. 20 is an end view of antenna array 2355, coolant chambers 2360, separation ribs 2393 and scattering elements 2378 according to one embodiment of the invention. According to one embodiment of the invention waveguide assembly 2358 may include one or more waveguide antennas 2364a, 2364b, 2364c and 2364d. According to one embodiment of the invention waveguide assembly 2358 may include a plurality of feed connectors 2388. According to one embodiment of the invention waveguide antennas 2364 may include dielectric fillers 2368 and waveguide walls 2366. According to one embodiment of the invention cradle channels 2389 may be connected to coolant chambers 2360. According to one embodiment of the invention coolant channel 2360a may be located beneath waveguide antenna 2364a. According to one embodiment of the invention coolant channel 2360b may be located beneath waveguide antenna 2364b. According to one embodiment of the invention coolant channel 2360c may be located beneath waveguide antenna 2364c. According to one embodiment of the invention coolant channel 2360d may be located beneath waveguide antenna 2364d. According to one embodiment of the invention scattering element 2378a may be positioned in coolant chamber 2360a. According to one embodiment of the invention scattering element 2378b may be positioned in coolant chamber 2360b. According to one embodiment of the invention scattering element 2378c may be positioned in coolant chamber 2360c. According to one embodiment of the invention scattering element 2378d may be positioned in coolant chamber 2360d. According to one embodiment of the invention cradle channels 2389 may be adapted to supply cooling fluid to coolant chambers 2360. According to one embodiment of the invention separation ribs 2393 may be positioned on either side of coolant chambers 2360a through 2360d.

Figure 21:
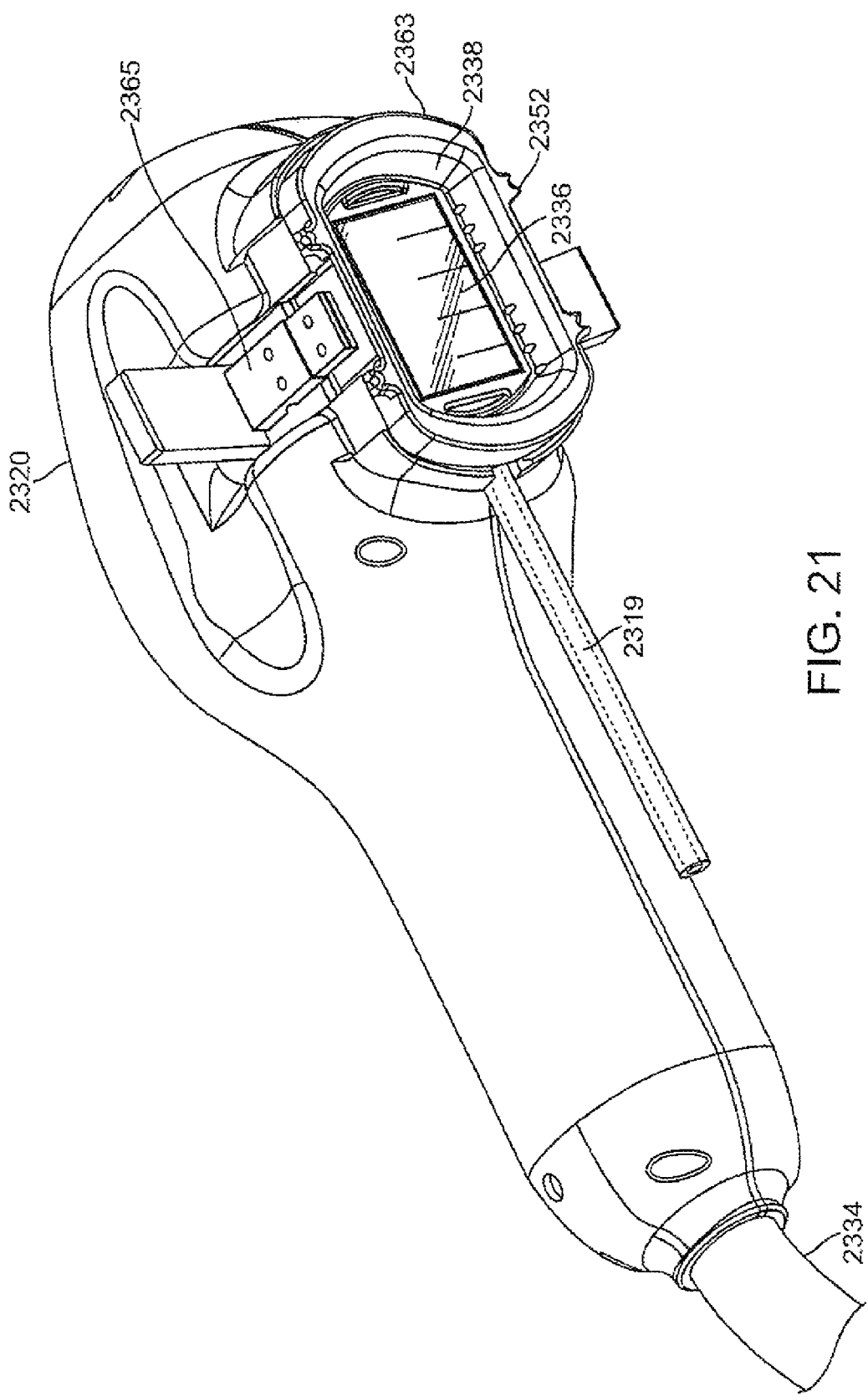
FIG. 21 is a perspective view of an applicator and disposable according to one embodiment of the invention

FIG. 21 is a perspective view of an applicator 2320 and disposable 2363 according to one embodiment of the invention. According to one embodiment of the invention, applicator 2320 may be attached to disposable 2363 by latching mechanism 2365. According to one embodiment of the invention, applicator 2320 may include applicator cable 2334. According to one embodiment of the invention disposable 2363 may include vacuum tubing 2319, tissue chamber 2338, alignment feature 2352 and tissue interface surface 2336. According to one embodiment of the invention alignment features 2352 may be positioned at a distance which facilitate appropriate placement of applicator 2320 during treatment. According to one embodiment of the invention alignment features 2352 may be positioned approximately 30.7 millimeters apart. According to one embodiment of the invention alignment features 2352 may be further positioned and may be designed to assist a physician in positioning applicator 2320 prior to the application of energy. According to one embodiment of the invention alignment features 2352 on disposable 2363 assist the user in properly positioning the applicator prior to treatment and in moving the applicator to the next treatment region during a procedure. According to one embodiment of the invention alignment features 2352 on disposable 2363, when used with marks or landmarks in a treatment region facilitate the creation of a continuous lesion.

Figure 22:
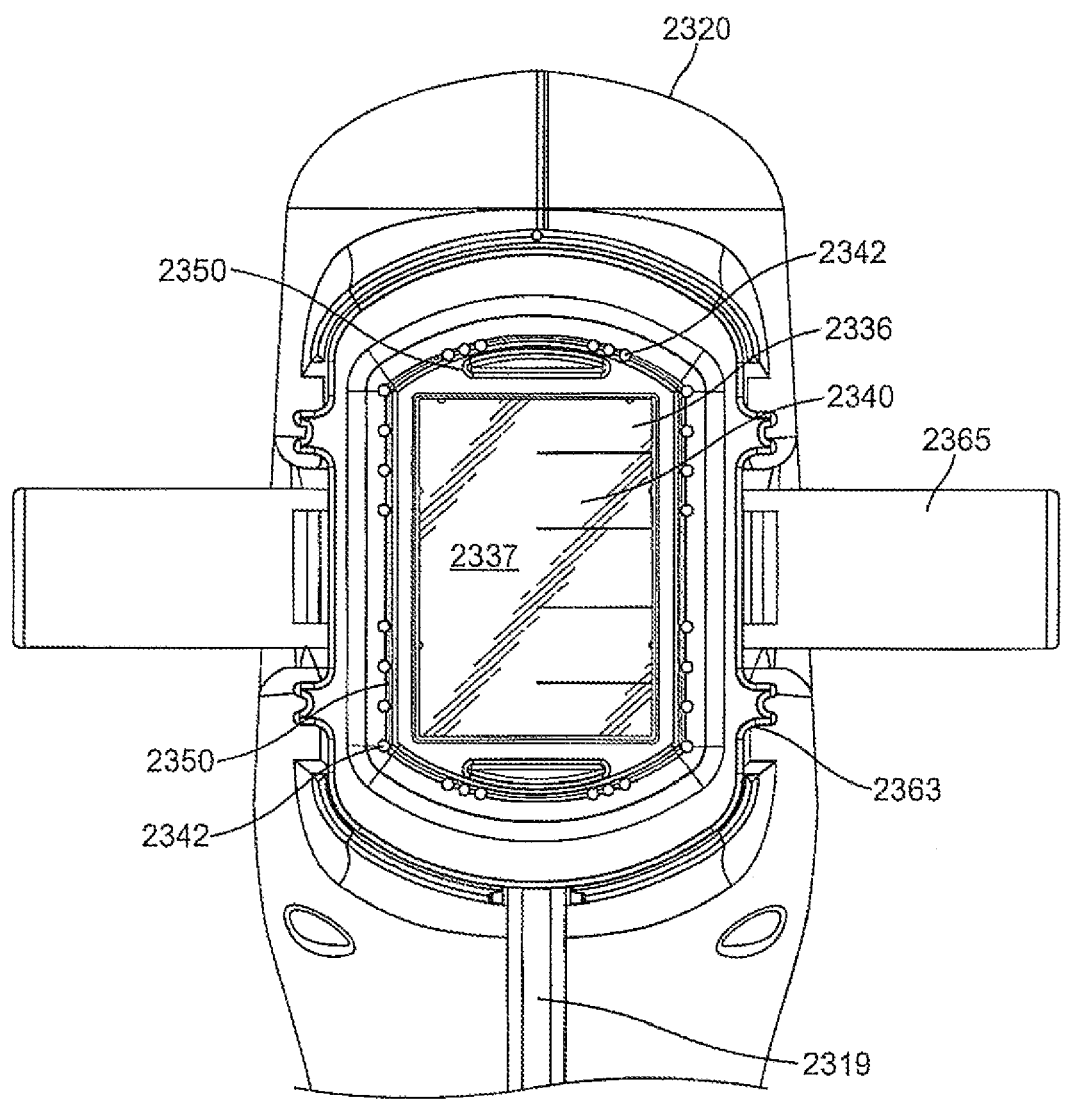
FIG. 22 is an end on view of the distal end of the applicator and the disposable illustrated in FIG. 21.

FIG. 22 is an end on view of the distal end of applicator 2320 and disposable 2363 illustrated in FIG. 21. According to one embodiment of the invention, disposable 2363 may include tissue bio-barrier 2337. According to one embodiment of the invention applicator 2320 may include cooling plate 2340, which may be, for example, positioned behind tissue bio-barrier 2337. According to one embodiment of the invention tissue bio-barrier 2337 may form a portion of tissue interface surface 2336. According to one embodiment of the invention, disposable 2363 may include vacuum ports 2342 and vacuum channels 2350. According to one embodiment of the invention vacuum ports 2342 may be, for example, holes in the distal end of disposable 2363 which may be connected directly or indirectly to vacuum tubing 2319 and to vacuum channels 2350, which may be formed by grooves in disposable 2363. According to one embodiment of the invention latching mechanism 2365 may be used to facilitate the connection of disposable 2363 to applicator 2320.

Figure 23:
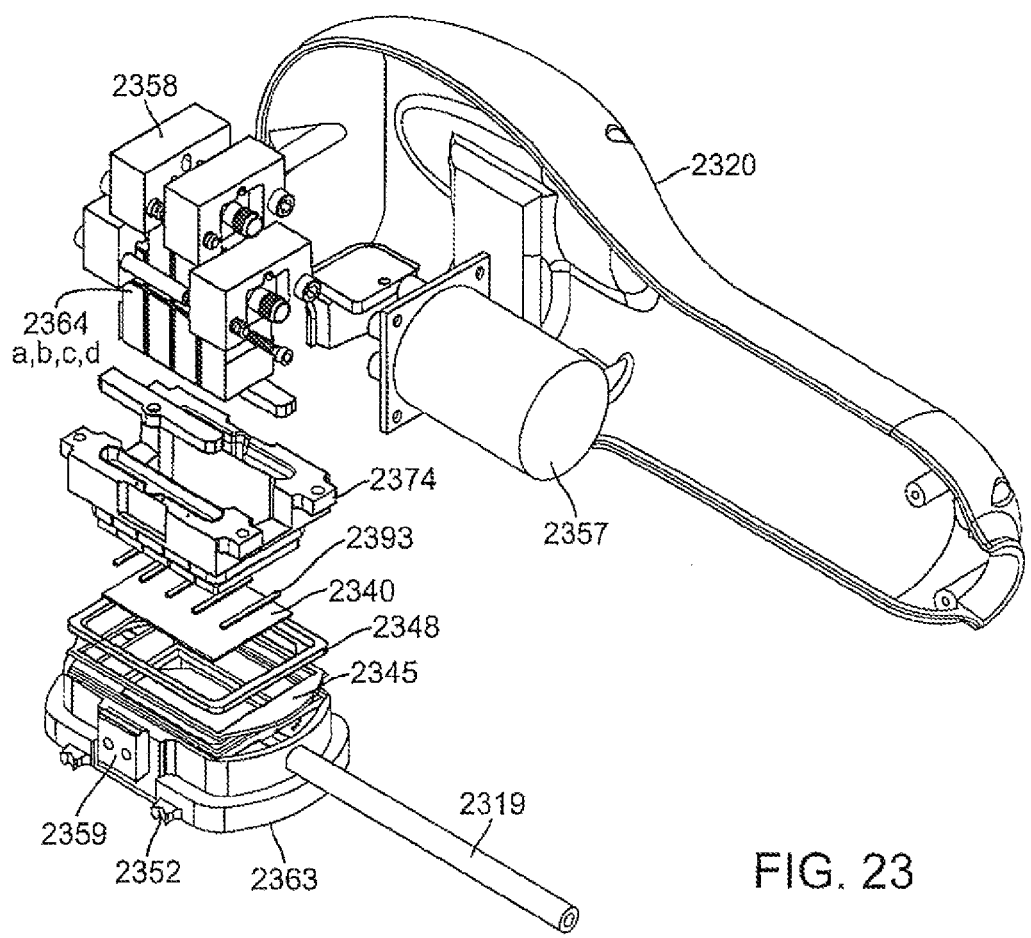
FIG. 23 is an exploded perspective view of the applicator illustrated in FIG. 21.
Figure 27:
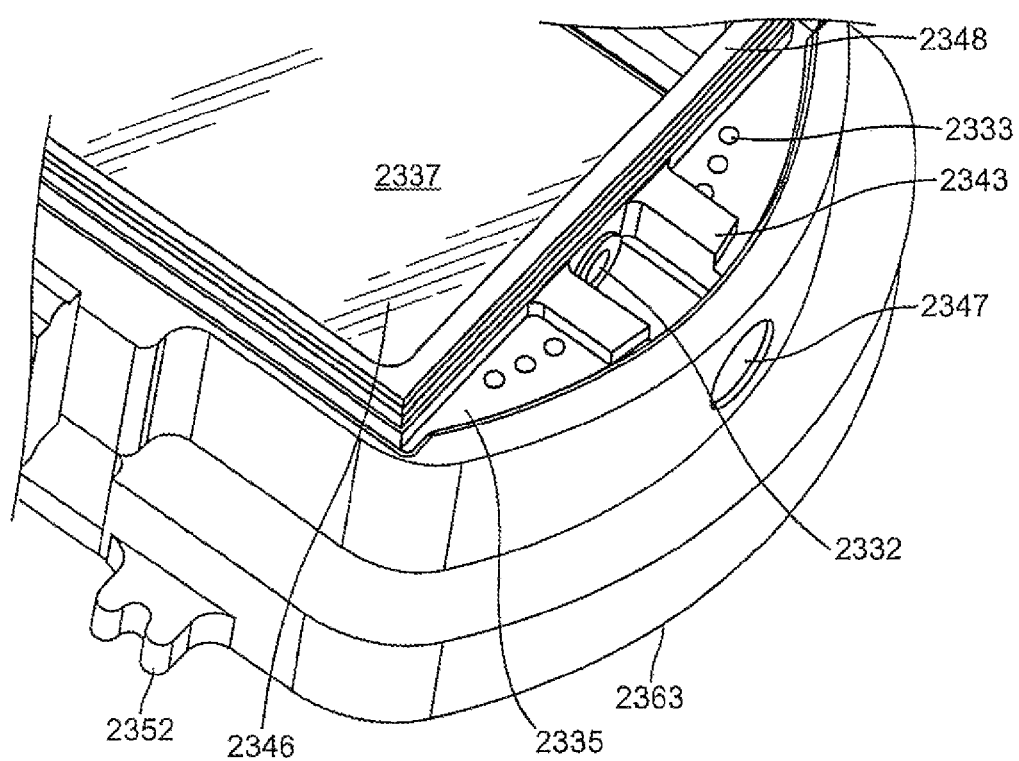
FIG. 27 is a view of a first section of the proximal side of the disposable illustrated in FIG. 26.

FIG. 23 is an exploded perspective view of applicator 2320 and disposable 2363 illustrated in FIG. 21. According to one embodiment of the invention, applicator 2320 may include a cooling plate 2340, separation ribs 2393, antenna cradle 2374, waveguide assembly 2358 and antenna switch 2357. According to one embodiment of the invention waveguide assembly 2358 may include antennas 2364(a-d). According to one embodiment of the invention disposable 2363 may include vacuum tubing 2319, alignment features 2352, latching elements 2359, top vacuum cap 2345 and vacuum seal 2348. According to one embodiment of the invention top vacuum cap 2345 covers and seals at least a portion of main vacuum passage 2335 (FIG. 27).

Figure 24:
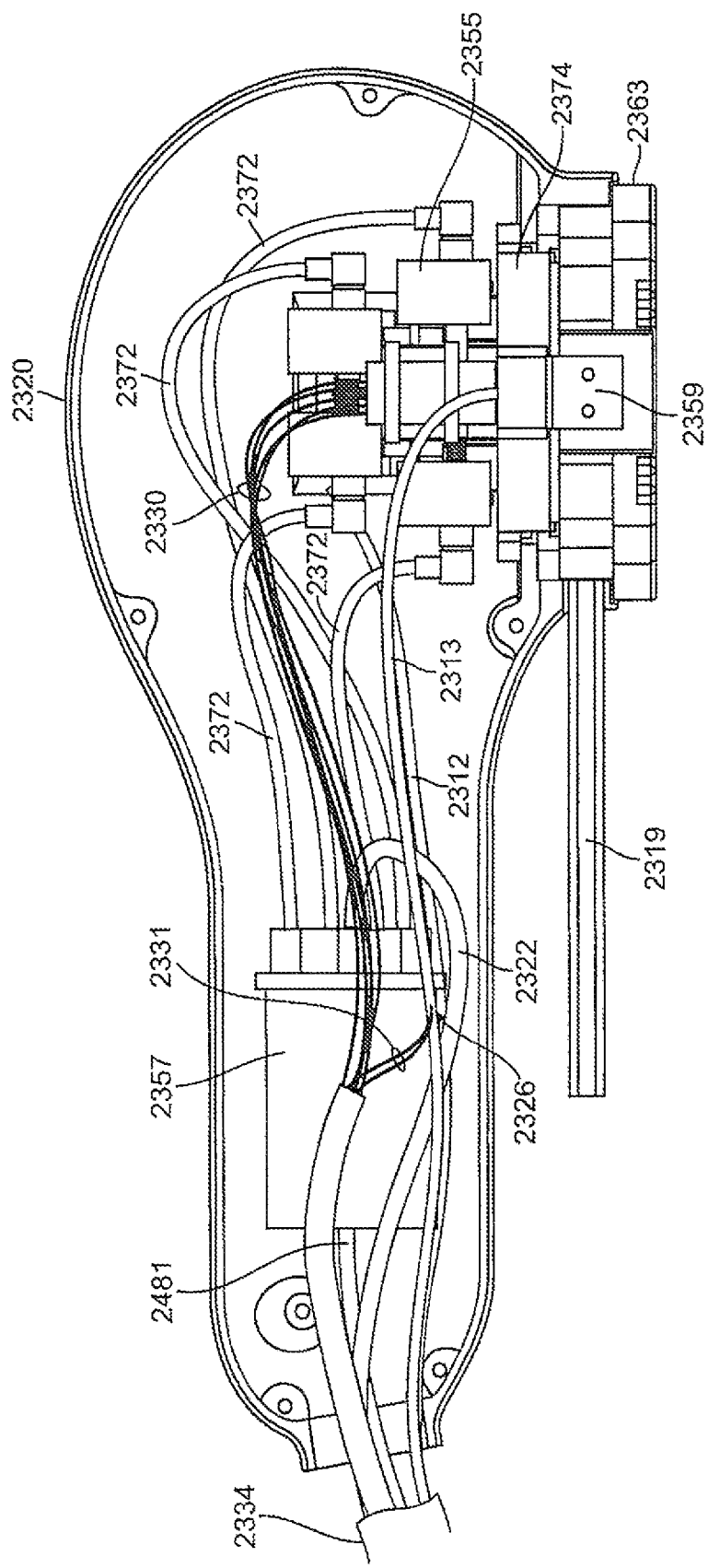
FIG. 24 is a cutaway view of the applicator illustrated in FIG. 21.

FIG. 24 is a cutaway view of applicator 2320 and disposable 2363 illustrated in FIG. 21. According to one embodiment of the invention applicator 2320 may include antenna array 2355, antenna switch 2357 and applicator cable 2334. According to one embodiment of the invention applicator cable 2334 may include cooling plate thermocouple wires 2330, coolant thermocouple wires 2331, coolant supply tubing 2312, coolant return tubing 2313, antenna switch signal 2481, energy cable 2322. According to one embodiment of the invention cooling plate thermocouple wires 2330 may include one or more thermocouple wires which may be attached to one or more thermocouples positioned opposite an output of antenna array 2355. According to one embodiment of the invention coolant thermocouple wires 2331 may include one or more thermocouple wires attached to one or more cooling path thermocouples 2326 which may be positioned to measure coolant fluid, such as, for example, in coolant return tubing 2313. According to one embodiment of the invention one or more cooling path thermocouples 2326 may be positioned to measure the temperature of cooling fluid 2361 after it passes through coolant chamber 2360. According to one embodiment of the invention one or more cooling path thermocouples 2326 may be located in coolant return tubing 2313. According to one embodiment of the invention cooling path thermocouples 2326 function to provide feedback to the generator 2301 indicative of the temperature of cooling fluid 2361 after passing through coolant chamber 2360. According to one embodiment of the invention disposable 2363 may include latching element 2359.

Figure 25:
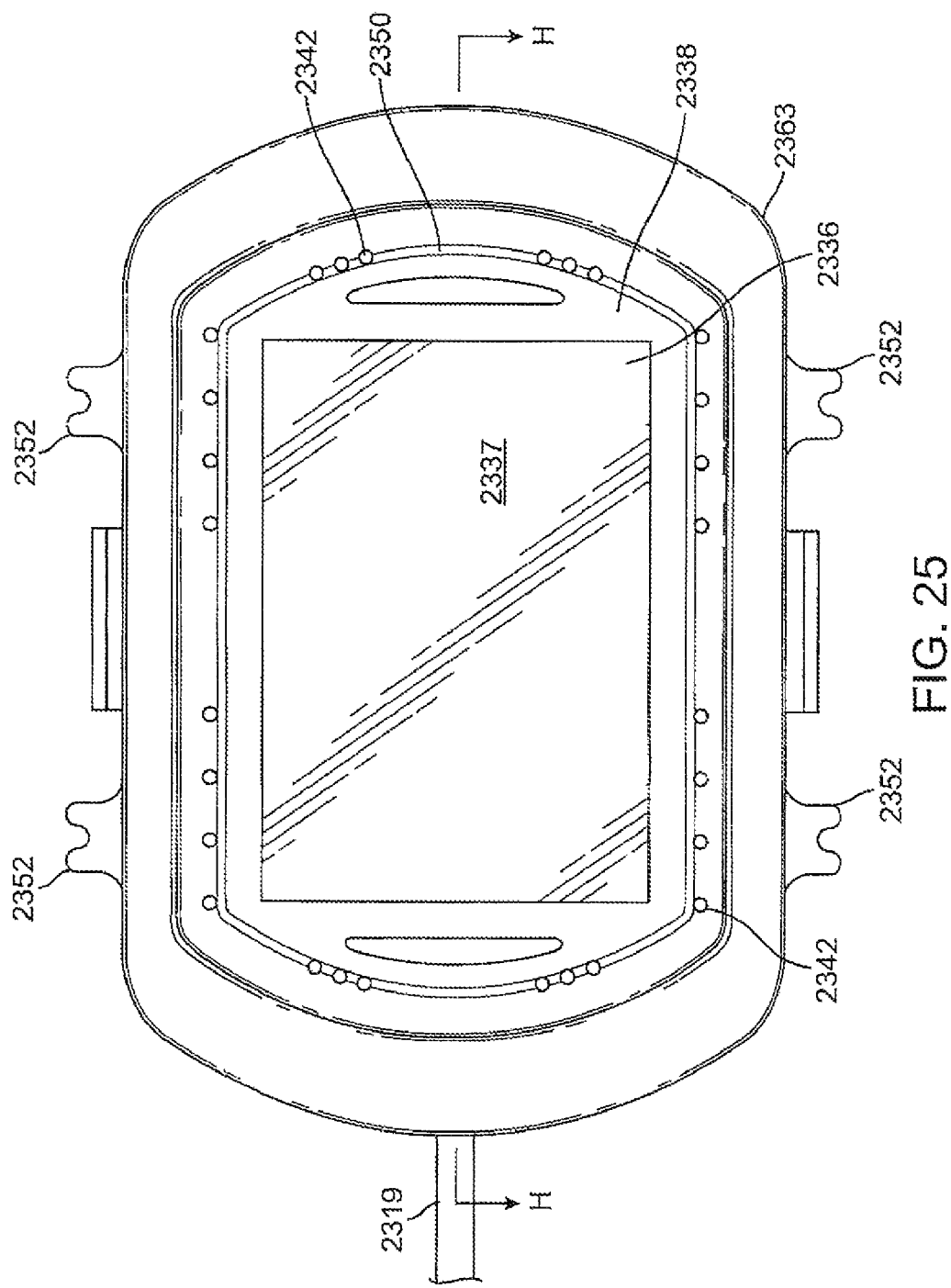
FIG. 25 is a view of the distal end of a the disposable according to one embodiment of the invention.

FIG. 25 is a view of the distal end of disposable 2363 according to one embodiment of the invention. According to one embodiment of the invention disposable 2363 may include tissue interface surface 2336, tissue chamber 2338 and alignment features 2352. According to one embodiment of the invention tissue interface surface 2336 may form a back wall of tissue chamber 2338. According to one embodiment of the invention tissue interface surface 2336 may include tissue bio-barrier 2337, vacuum channel 2350 and vacuum ports 2342. According to one embodiment of the invention disposable 2363 includes alignment features 2352 and vacuum tubing 2319.

Figure 26:
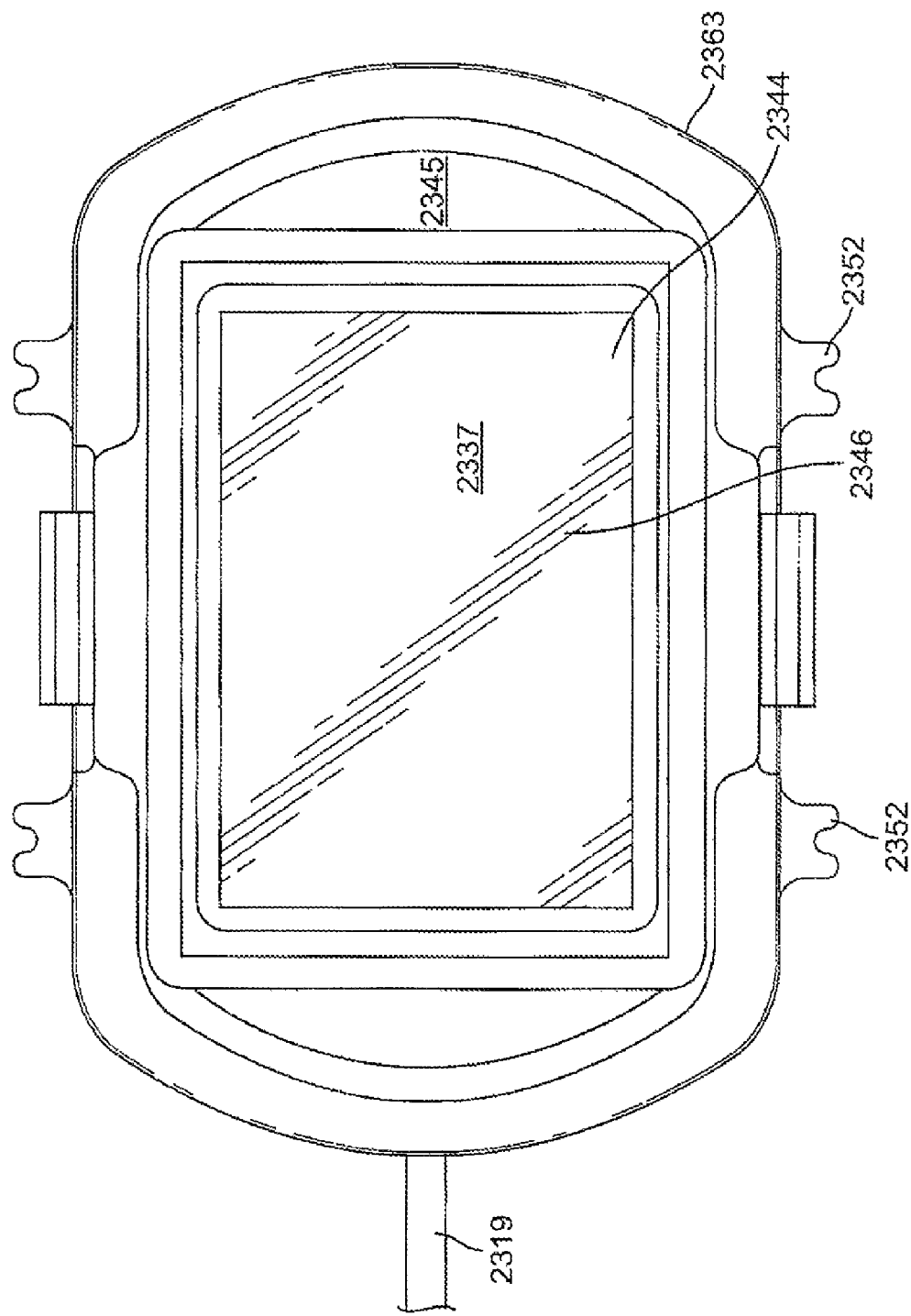
FIG. 26 is a view of the proximal side of the disposable illustrated in FIG. 25.

FIG. 26 is a view of the proximal side of disposable 2363 illustrated in FIG. 25. According to one embodiment of the invention disposable 2363 includes applicator chamber 2346. According to one embodiment of the invention applicator chamber may include an applicator chamber 2346 which may be formed, at least in part, by tissue bio-barrier 2337. According to one embodiment of the invention disposable 2363 includes alignment features 2352 and vacuum tubing 2319. According to one embodiment of the invention disposable 2363 may include top vacuum cap 2345.

FIG. 27 is a view of a first section of the proximal side of disposable 2363 with illustrated in FIG. 26 with top vacuum cap 2345 removed. According to one embodiment of the invention disposable 2363 may include applicator chamber 2346 (which may include tissue bio-barrier 2337), side vacuum cap 2347 and vacuum seal 2348. According to one embodiment of the invention side vacuum cap 2347 covers and seals at least a portion of main vacuum passage 2335. According to one embodiment of the invention disposable 2363 may include applicator bio-barrier 2332 (which may be, for example, a polyethylene film, available from Fisher Scientific) TS, vacuum passages 2333 and vacuum baffles 2343. According to one embodiment of the invention vacuum passages 2333 may connect vacuum connector 2328 to vacuum ports 2342 in tissue chamber 2338 and to applicator bio-barrier 2332. According to one embodiment of the invention vacuum passages 2333 form a direct path to tissue interface surface 2336 and an indirect or circuitous route to applicator bio-barrier 2332. According to one embodiment of the invention vacuum passages 2333 may be adapted to restrict the movement of fluids from tissue chamber 2338 to applicator bio-barrier 2332. According to one embodiment of the invention vacuum connector 2328 may be positioned on the opposite side of disposable 2363 from applicator bio-barrier 2332 to create a long, circuitous path for air to travel as vacuum is applied. According to one embodiment of the invention an indirect path from vacuum connector 2328 to applicator bio-barrier 2332 may be designed to make it harder to pull fluids from tissue chamber 2338 toward applicator bio-barrier 2332, particularly when there is back pressure in vacuum passages 2333, caused by, for example, opening vacuum solenoid 2315 between disposable 2363 and vacuum pump/drive 2307 in the generator or, by a vacuum created in tissue chamber 2338 as tissue is pulled away from tissue interface surface 2336. According to one embodiment of the invention a vacuum pump 2450 and a vacuum solenoid 2315 may be used to support tissue acquisition applicator 2320. According to one embodiment of the invention main vacuum passage 2335 may extend from vacuum connector 2328 to vacuum passages 2333 and applicator bio-barrier 2332. According to one embodiment of the invention vacuum passages 2333 may connect main vacuum passage 2335 to vacuum ports 2342 in tissue interface surface 2336. According to one embodiment of the invention vacuum baffles 2343 may be positioned in main vacuum passage 2335 between vacuum passages 2333 and applicator bio-barrier 2332. According to one embodiment of the invention vacuum baffles 2343 may be adapted to help keep the air pressure in the applicator chamber 2346 and tissue chamber 2338 substantially equal during tissue acquisition by providing a pressure drop between the vacuum passages 2333 and applicator bio-barrier 2332. According to one embodiment of the invention vacuum baffles 2343 may be positioned and adapted to help equalized the pressure between the applicator chamber 2346 and a higher volume of air in tissue chamber 2338 during acquisition of skin. According to one embodiment of the invention vacuum baffles 2343 may be adapted to restrict the amount of backflow pressure which reaches applicator bio-barrier 2332. According to one embodiment of the invention vacuum baffles 2343 may be adapted to restrict the amount of biological fluids which reach applicator bio-barrier 2332 when backflow pressure is applied, as immediately after the vacuum is turned off or as skin is pulled out of tissue chamber 2338 or away from tissue interface surface 2336. According to one embodiment of the invention vacuum baffles 2343 may be positioned and adapted to create a pressure drop so that a majority of any backflow pressure is released through the vacuum passages 2333 into tissue chamber 2338. According to one embodiment of the invention vacuum baffles 2343 may be adapted to provide a mechanical barrier in the circuitous path of vacuum circuit 2341 which increases the pressure on one side of the vacuum baffles 2343 as air flows through main vacuum passage 2335. According to one embodiment of the invention baffles may be adapted to provide a mechanical barrier which increases the length of a circuitous path as air travels through main vacuum passage 2335. According to one embodiment of the invention applicator bio-barrier 2332 may be positioned between vacuum passages 2333 and applicator chamber 2346. According to one embodiment of the invention applicator bio-barrier 2332 may be a membrane which may be adapted to be permeable to air but substantially impermeable to biological fluids such as, for example, blood and sweat. According to one embodiment of the invention applicator bio-barrier 2332 may be a hydrophobic membrane filter. According to one embodiment of the invention applicator bio-barrier 2332 may be made of polyethylene film nylon or other suitable materials. According to one embodiment of the invention applicator bio-barrier 2332 may include pores having sizes sufficient to pass enough air to equalize the vacuum without passing biological fluids. According to one embodiment of the invention applicator bio-barrier 2332 may include pores having sizes of approximately 0.45 micrometers. According to one embodiment of the invention when the vacuum is turned on, and before pressure is equalized, applicator bio-barrier 2332 may induce a minimal pressure drop between vacuum passages 2333 and the applicator chamber 2346.

Figure 28:
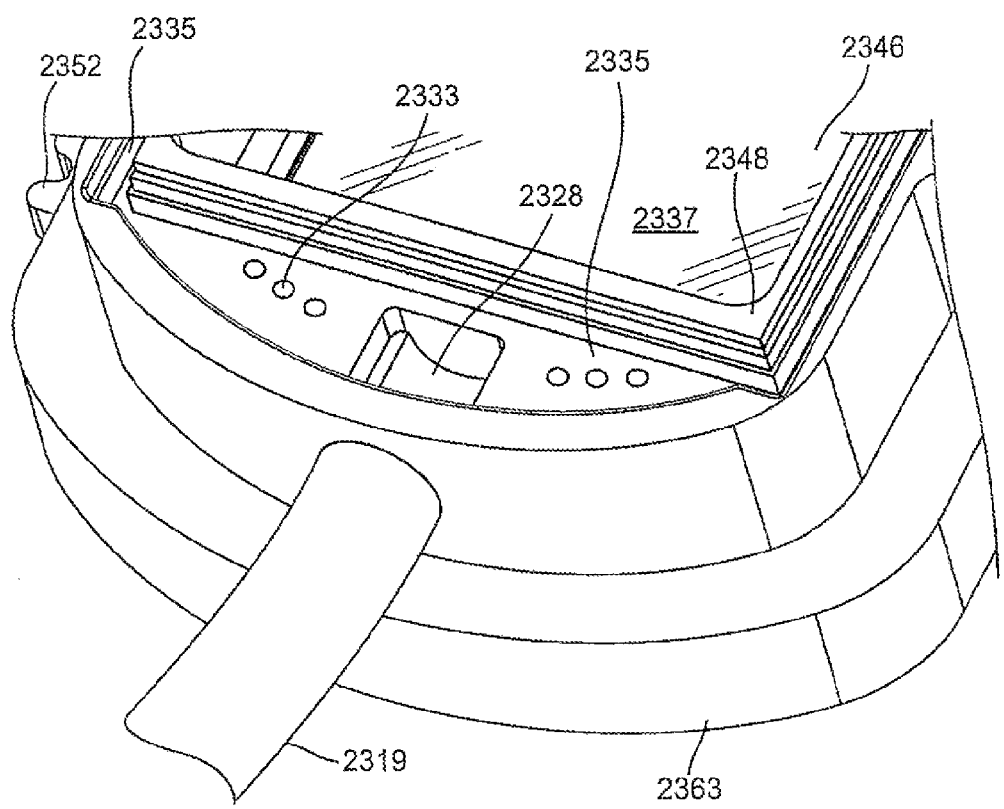
FIG. 28 is a view of a second section of the proximal side of the disposable illustrated in FIG. 26.

FIG. 28 is a view of a second section of the proximal side of disposable 2363 illustrated in FIG. 26 with top vacuum cap 2345 removed. According to one embodiment of the invention disposable 2363 may include applicator chamber 2346 (which may include tissue bio-barrier 2337), and vacuum seal 2348. According to one embodiment of the invention disposable 2363 may include, vacuum passages 2333 and vacuum connector 2328. According to one embodiment of the invention vacuum connector 2328 may connect vacuum passages 2333 to vacuum tubing 2319.

Figure 29:
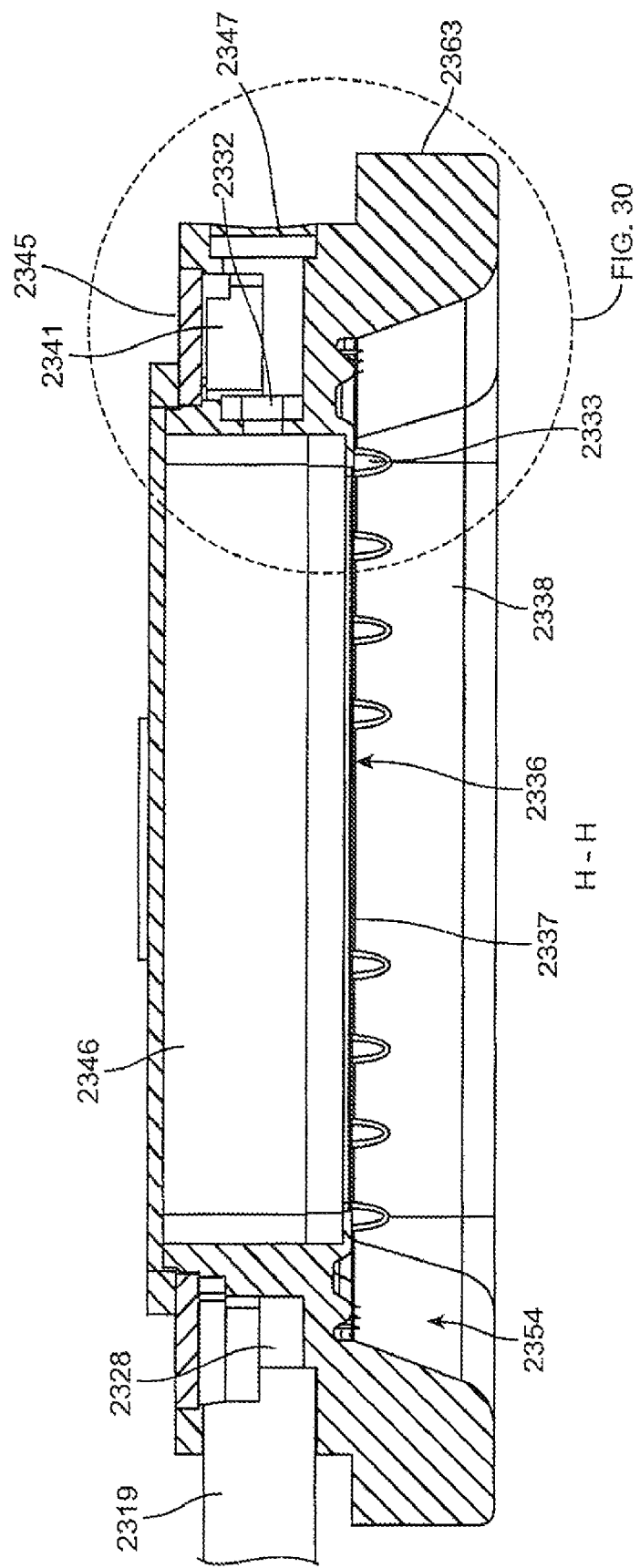
FIG. 29 is a cutaway view along H-H of the disposable illustrated in FIG. 25.

FIG. 29 is a cutaway view of disposable 2363 along H-H in FIG. 25. According to one embodiment of the invention disposable 2363 includes applicator chamber 2346 and tissue chamber 2338. According to one embodiment of the invention applicator chamber 2346 and tissue chamber 2338 may be separated, at least in part, by tissue bio-barrier 2337. According to one embodiment of the invention tissue chamber 2338 may include tissue interface surface 2336 and chamber wall 2354. According to one embodiment of the invention tissue interface surface 2336 may be formed, at least in part, by tissue bio-barrier 2337. According to one embodiment of the invention disposable 2363 may include a vacuum circuit 2341. According to one embodiment of the invention vacuum circuit 2341 may include vacuum tubing 2319, vacuum connector 2328, vacuum baffle 2343, vacuum passages 2333 and applicator bio-barrier 2332. According to one embodiment of the invention vacuum circuit 2341 may connect tissue chamber 2338 to vacuum tubing 2319 through vacuum passages 2333. According to one embodiment of the invention vacuum circuit 2341 may connect applicator chamber 2346 to vacuum tubing 2319 through applicator bio-barrier 2332. According to one embodiment of the invention disposable 2363 may include top vacuum cap 2345 and side vacuum cap 2347. According to one embodiment of the invention top vacuum cap 2345 and side vacuum cap 2347 may seal vacuum circuit 2341.

Figure 30:
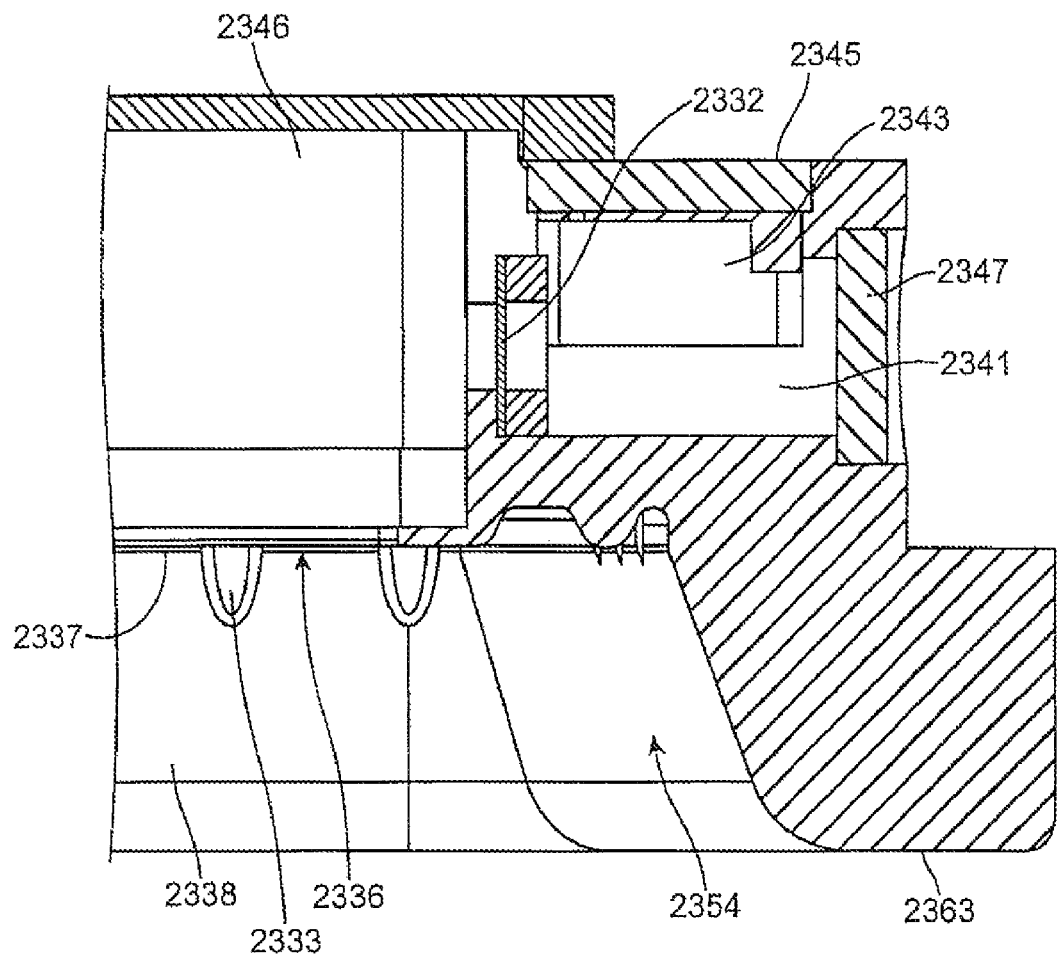
FIG. 30 is a view of a section of the disposable illustrated in FIG. 29.

FIG. 30 is a view of a section of disposable 2363 illustrated in FIG. 30. According to one embodiment of the invention disposable 2363 includes applicator chamber 2346 and tissue chamber 2338. According to one embodiment of the invention applicator chamber 2346 and tissue chamber 2338 may be separated, at least in part, by tissue bio-barrier 2337. According to one embodiment of the invention tissue chamber 2338 may include tissue interface surface 2336 and chamber wall 2354. According to one embodiment of the invention tissue interface surface 2336 may be formed, at least in part, by tissue bio-barrier 2337. According to one embodiment of the invention disposable 2363 may include a vacuum circuit 2341. According to one embodiment of the invention vacuum circuit 2341 may include vacuum baffle 2343, vacuum passages 2333 and applicator bio-barrier 2332. According to one embodiment of the invention vacuum circuit 2341 may be connected to tissue chamber 2338 by vacuum passages 2333. According to one embodiment of the invention vacuum circuit 2341 may connect applicator chamber 2346 to vacuum circuit 2341 through applicator bio-barrier 2332. According to one embodiment of the invention disposable 2363 may include top vacuum cap 2345 and side vacuum cap 2347.

Figure 30A:
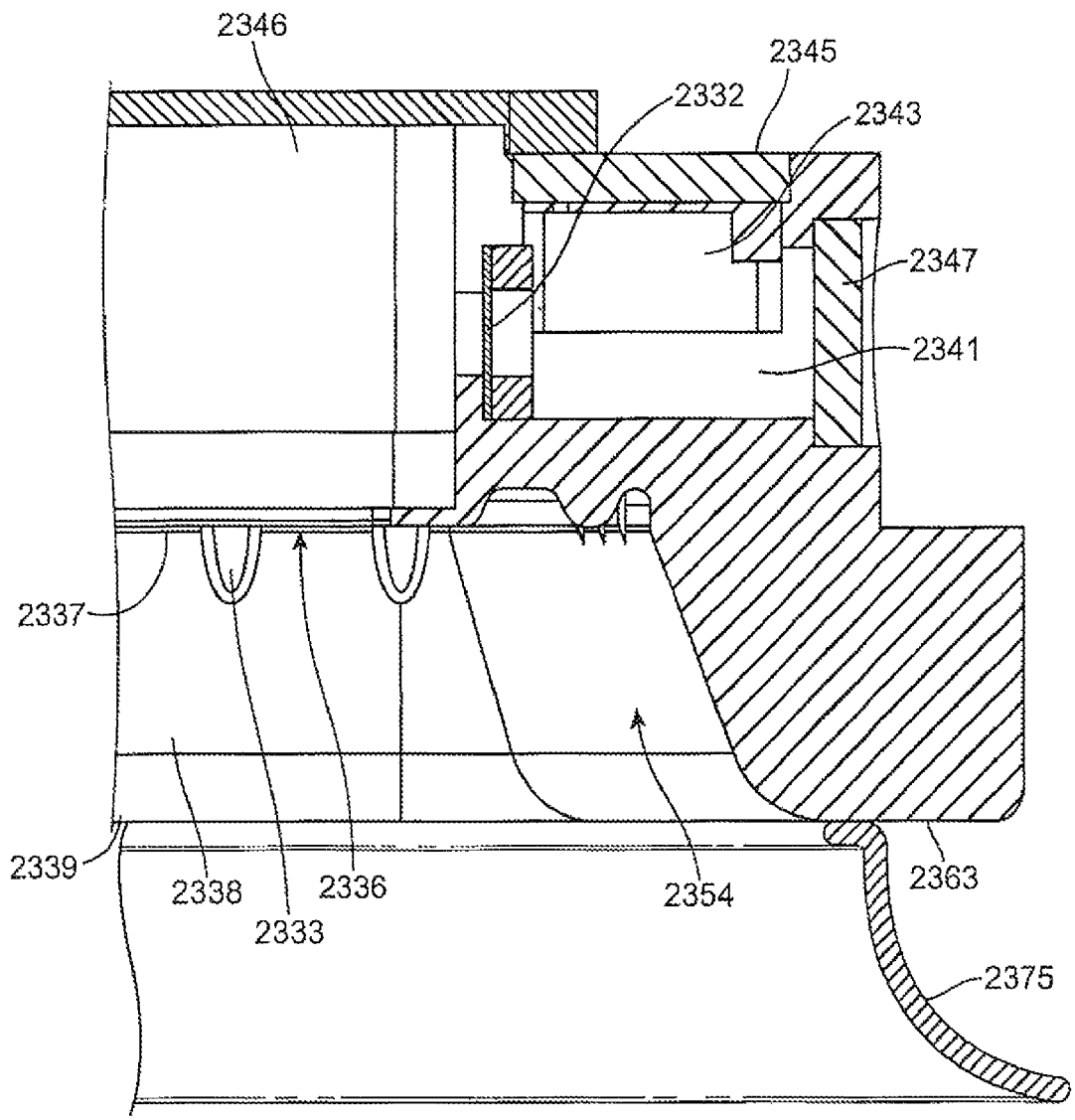
FIG. 30A is a view of a section of the disposable illustrated in FIG. 29 according to an alternate embodiment of the present invention.
Figure 30B:
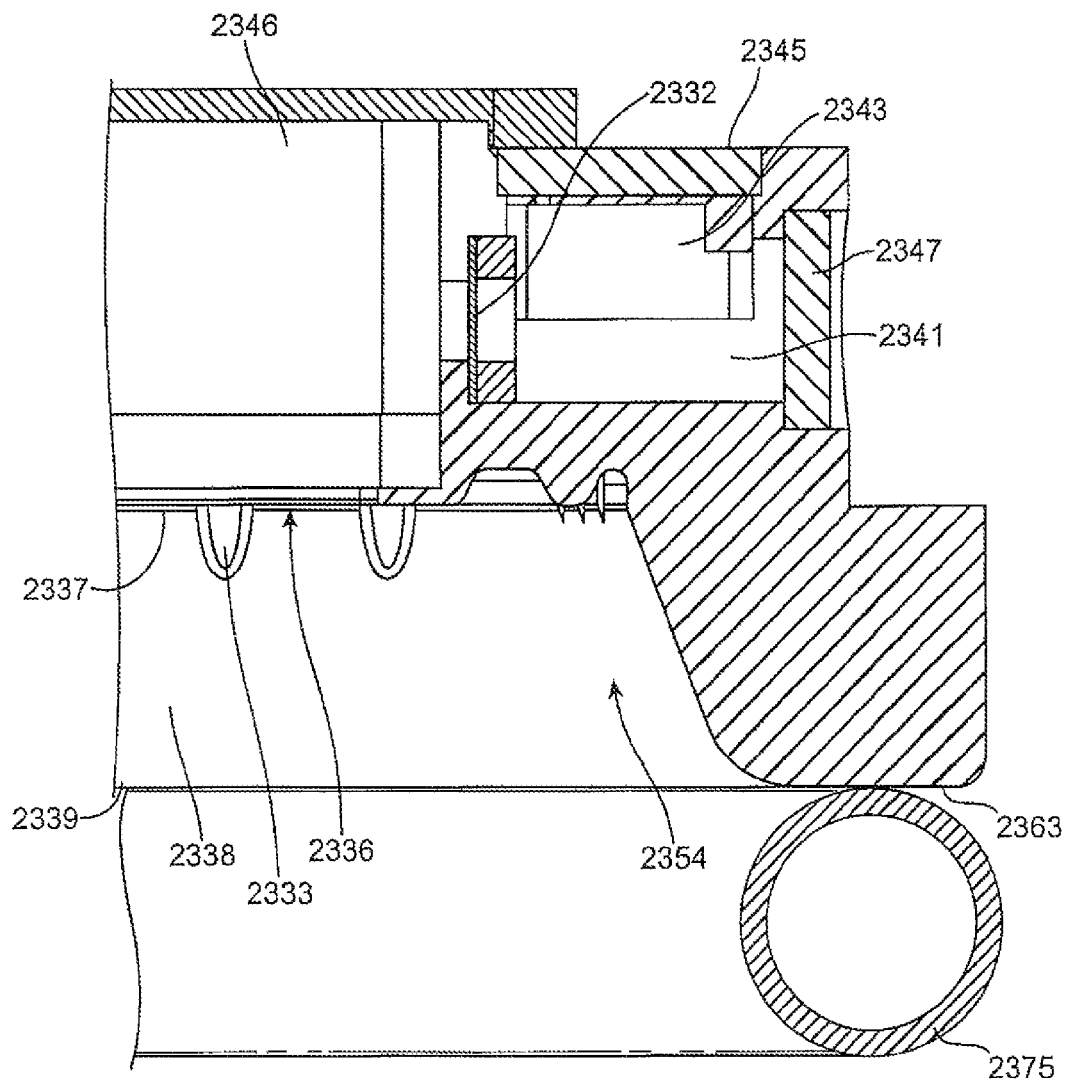
FIG. 30B is a view of a section of the disposable illustrated in FIG. 29 according to an alternate embodiment of the present invention.

FIG. 30A is a view of a section of disposable 2363 illustrated in FIG. 29 according to an alternate embodiment of the present invention. FIG. 30B is a view of a section of disposable 2363 illustrated in FIG. 29 according to an alternate embodiment of the present invention. According to one embodiment of the invention chamber walls 2354 may include a compliant member 2375. According to one embodiment of the invention compliant member 2375 may be formed from a compliant material, such as, for example, rubber, coated urethane foam (with a compliant plastic or rubber seal coating), silicone, polyurethane or heat sealed open cell foam. According to one embodiment of the invention compliant member 2375 may be positioned around the outer edge of tissue chamber 2338 to facilitate the acquisition of tissue. According to one embodiment of the invention compliant member 2375 may be positioned around the outer edge of chamber opening 2339 to facilitate the acquisition of tissue. According to one embodiment of the invention compliant member 2375 may facilitate the engagement of tissue which is not flat, such as, for example tissue in the axilla. According to one embodiment of the invention compliant member 2375 may facilitate the engagement of tissue which is not flat, such as, for example tissue in the outer regions of the axilla. According to one embodiment of the invention compliant member 2375 may provide improved sealing characteristics between the skin and tissue chamber 2338, particularly where the skin is not flat. According to one embodiment of the invention compliant member 2375 may speed the acquisition of tissue in tissue chamber 2338, particularly where the skin is not flat. According to one embodiment of the invention compliant member 2375 may have a height of between approximately 0.15 inches and approximately 0.40 inches above chamber opening 2339 when compliant member 2375 is not compressed. According to one embodiment of the invention compliant member 2375 may have a height of approximately 0.25 inches above chamber opening 2339 when compliant member 2375 is not compressed.

Figure 31:
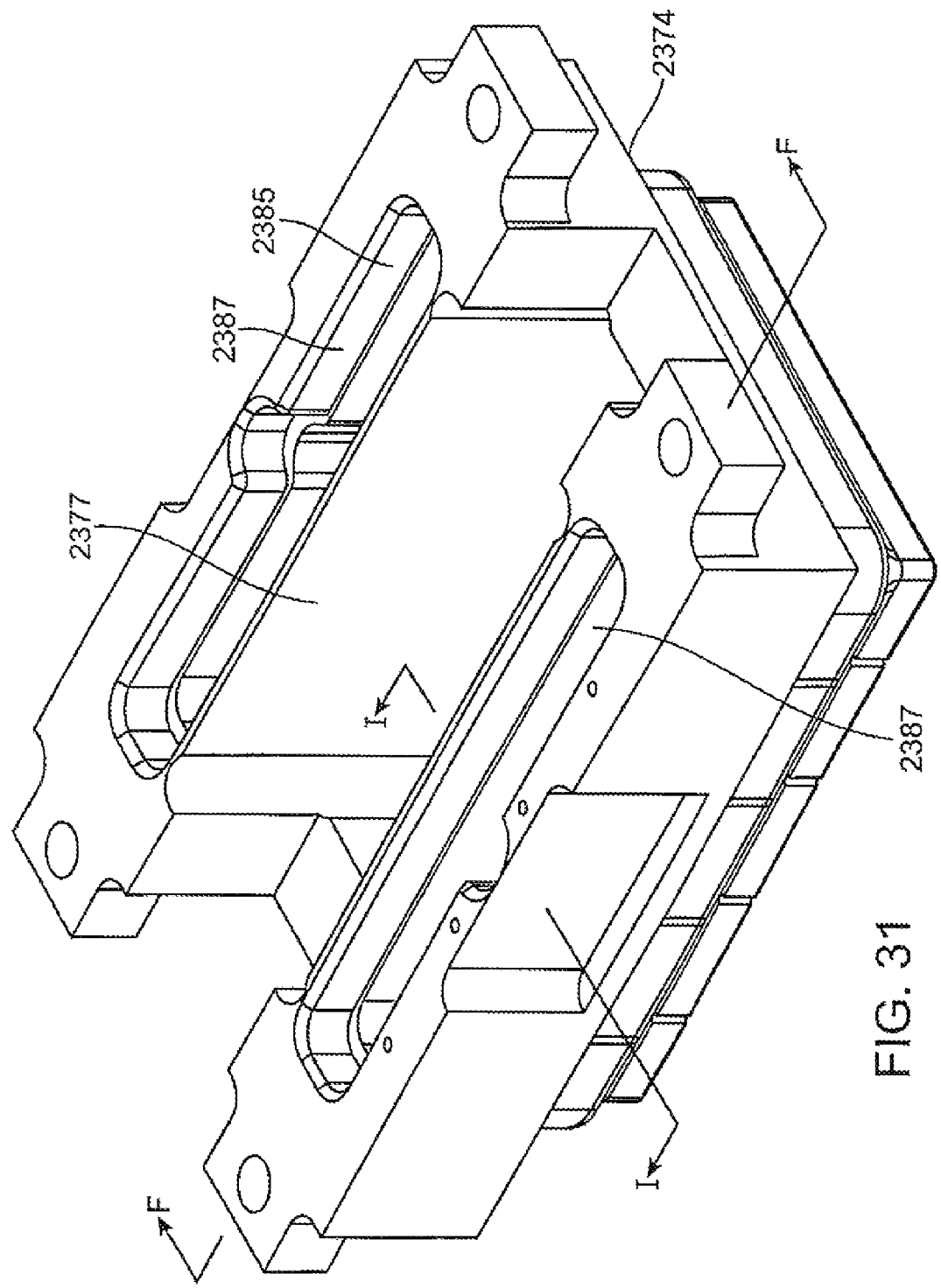
FIG. 31 is a perspective view of an antenna cradle according to one embodiment of the invention.

FIG. 31 is a perspective view of antenna cradle 2374 according to one embodiment of the invention. According to one embodiment of the invention antenna cradle 2374 may include antenna chamber 2377 and cradle circuit 2385. According to one embodiment of the invention cradle circuit 2385 may be adapted to circulate cooling fluid thorough antenna cradle 2374. According to one embodiment of the invention cradle circuit 2385 may include at least one cradle reservoir 2387. According to one embodiment of the invention cradle circuit 2385 may include inlet and outlet cradle reservoirs 2387.

Figure 32:
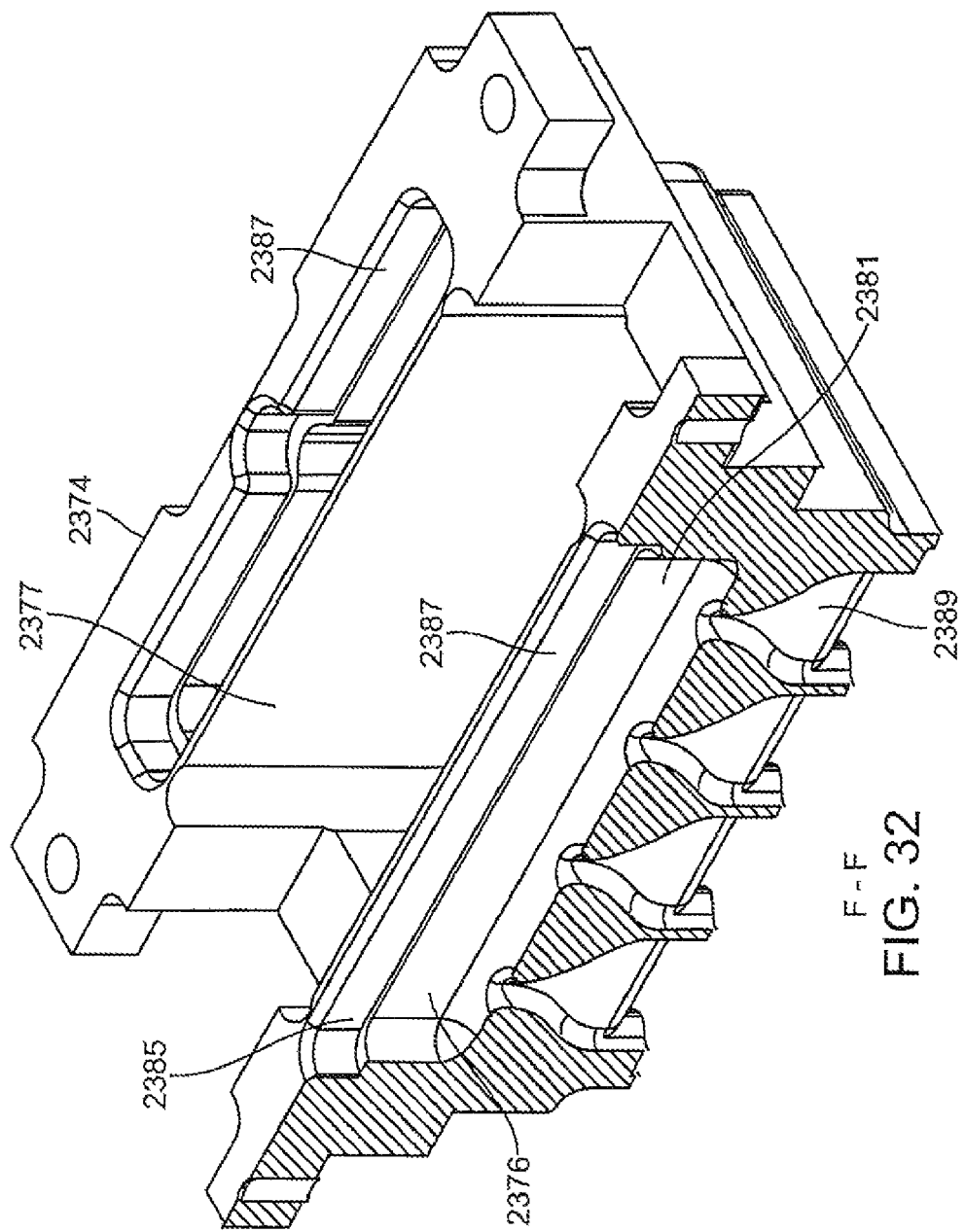
FIG. 32 is a perspective cutaway view along F-F of the antenna cradle illustrated in FIG. 31.

FIG. 32 is a perspective cutaway view of antenna cradle 2374 along F-F in FIG. 31. According to one embodiment of the invention antenna cradle 2374 may include antenna chamber 2377 and cradle circuit 2385. According to one embodiment of the invention cradle circuit 2385 may be adapted to circulate cooling fluid thorough antenna cradle 2374 as part of cooling fluid path 2381. According to one embodiment of the invention cooling fluid path 2381 may be a part of cooling circuit 2376. According to one embodiment of the invention cradle circuit 2385 may include inlet and outlet cradle reservoirs 2387 and cradle channels 2389. According to one embodiment of the invention the elements of cradle circuit 2385 and cooling fluid path 2381 may be designed to facilitate the smooth flow of fluid through cradle circuit 2385 and cooling fluid path 2381. According to one embodiment of the invention the elements of cradle circuit 2385 and cooling fluid path 2381 may be rounded and smoothed to facilitate the smooth flow of fluid through cradle circuit 2385 and cooling fluid path 2381.

Figure 33:
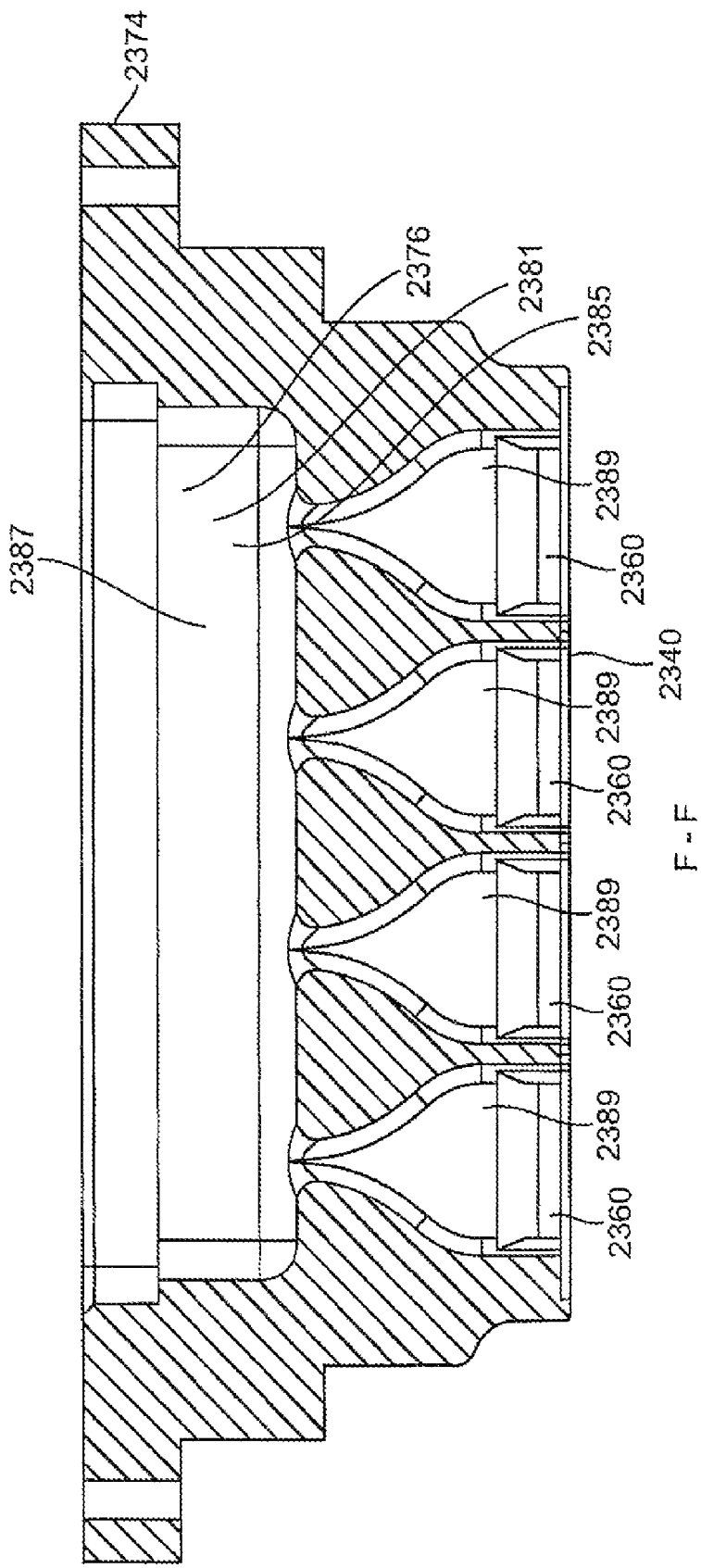
FIG. 33 is a side cutaway view along F-F of the antenna cradle illustrated in FIG. 31.

FIG. 33 is a side cutaway view of antenna cradle 2374 along F-F in FIG. 31. According to one embodiment of the invention cradle circuit 2385 may be adapted to circulate cooling fluid thorough antenna cradle 2374 as part of cooling fluid path 2381. According to one embodiment of the invention cooling fluid path 2381 may include cradle circuit 2385 and coolant chambers 2360. According to one embodiment of the invention coolant chambers 2360 may be formed by affixing cooling plate 2340 to a distal end of antenna cradle 2374. According to one embodiment of the invention cooling plate 2340 may be affixed to antenna cradle 2374 by, for example, gluing cooling plate 2340 to antenna cradle 2374. According to one embodiment of the invention cooling fluid path 2381 may be a part of cooling circuit 2376. According to one embodiment of the invention cradle circuit 2385 may include cradle reservoir 2387 and cradle channels 2389. According to one embodiment of the invention the elements of cradle circuit 2385 and cooling fluid path 2381 may be designed to facilitate the smooth flow of fluid through cradle circuit 2385 and cooling fluid path 2381. According to one embodiment of the invention the elements of cradle circuit 2385 and cooling fluid path 2381 may be rounded and smoothed to facilitate the smooth flow of fluid through cradle circuit 2385 and cooling fluid path 2381.

Figure 34:
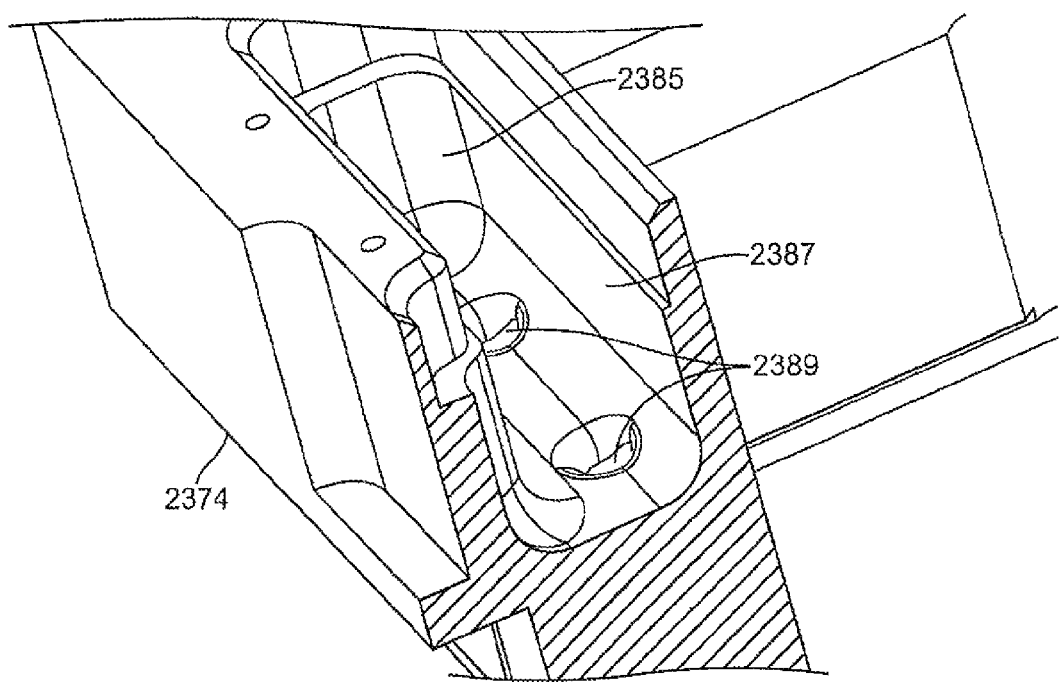
FIG. 34 is a perspective cutaway view along I-I of a section of the antenna cradle illustrated in FIG. 31.

FIG. 34 is a perspective cutaway view of a section of antenna cradle 2374 along I-I in FIG. 31. According to one embodiment of the invention antenna cradle 2374 may include cradle circuit 2385. According to one embodiment of the invention cradle circuit 2385 may include cradle reservoir 2387 and cradle channels 2389.

Figure 35:
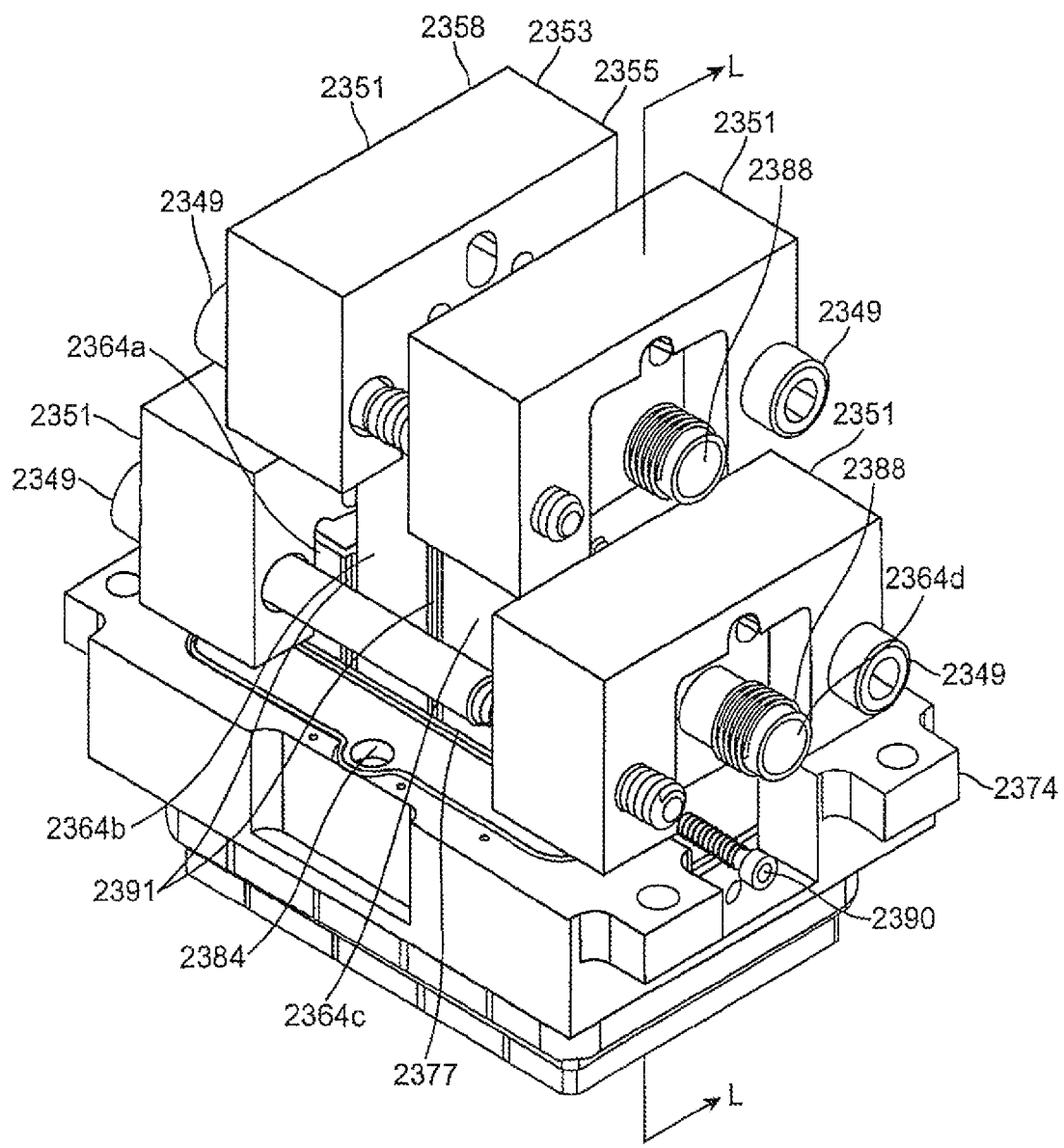
FIG. 35 is a perspective view of an antenna array according to one embodiment of the invention.

FIG. 35 is a perspective view of antenna array 2355 according to one embodiment of the invention. According to one embodiment of the invention, antenna cradle 2374 may include reservoir inlet 2384 and antenna chamber 2377. According to one embodiment of the invention waveguide assembly 2358 may include one or more isolation elements 2391 (which may be, for example, ECCOSORB MF-190 microwave absorber material, available from Emerson & Cuming Microwave Products) positioned between waveguide antennas 2364. According to one embodiment of the invention microwave energy may be supplied to each waveguide antenna through feed connectors 2388. According to one embodiment of the invention waveguide assembly 2358 may be held together by a waveguide assembly frame 2353. According to one embodiment of the invention waveguide assembly frame 2353 may include feed brackets 2351 and assembly bolts 2349. According to one embodiment of the invention antenna array 2355 may include an antenna cradle and at least one waveguide antenna 2364. According to one embodiment of the invention antenna array 2355 may include one or more isolation elements 2391. According to one embodiment of the invention antenna array 2355 may include four waveguide antennas 2364. According to one embodiment of the invention the heights of waveguide antennas 2364 in antenna array 2355 may be staggered to facilitate access to feed connectors 2388.

Figure 36:
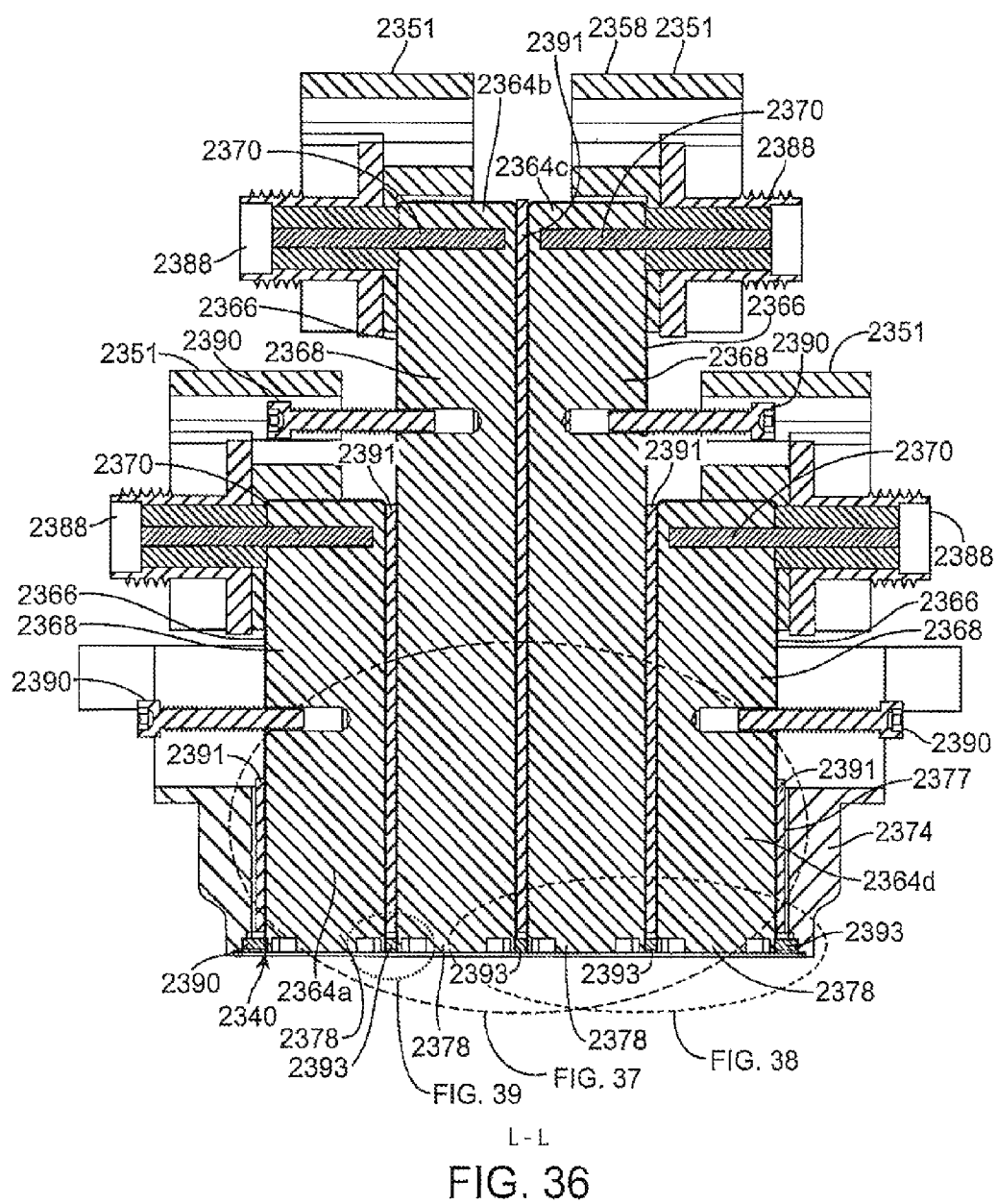
FIG. 36 is a cutaway view along I-I of the antenna array illustrated in FIG. 35.

FIG. 36 is a cutaway view of antenna array 2355 along L-L in FIG. 35. According to one embodiment of the invention waveguide assembly 2358 includes one or more waveguide antennas 2364, one or more feed brackets 2351 and one or more isolation elements 2391. According to one embodiment of the invention waveguide assembly 2358 includes waveguide antennas 2364a, 2364b, 2364c and 2364c. According to one embodiment of the invention waveguide antennas 2364 may include a dielectric filler 2368, waveguide walls 2366 and tuning element 2390. According to one embodiment of the invention waveguide antennas 2364 may be manufactured by plating dielectric filler 2368 with an appropriate plating material such as, for example, copper, gold, silver. According to one embodiment of the invention waveguide walls 2366 may be formed by plating or electroplating dielectric fill material such as, for example, dielectric filler 2368. According to one embodiment of the invention waveguide walls 2366 may be formed by plating or electroplating dielectric fill material directly, covering all faces except a radiating aperture. According to one embodiment of the invention copper may be a preferred plating material. According to one embodiment of the invention scattering element 2378 may also be a separate element. According to one embodiment of the invention scattering element 2378 may also be a separate element formed from, for example, polycarbonate or alumina. According to one embodiment of the invention scattering element 2378 may also be a separate element positioned in coolant chamber 2360. According to one embodiment of the invention scattering element 2378 may also be a separate element positioned in coolant chamber 2360 and centered in an aperture of waveguide antenna 2363.

Figure 37:
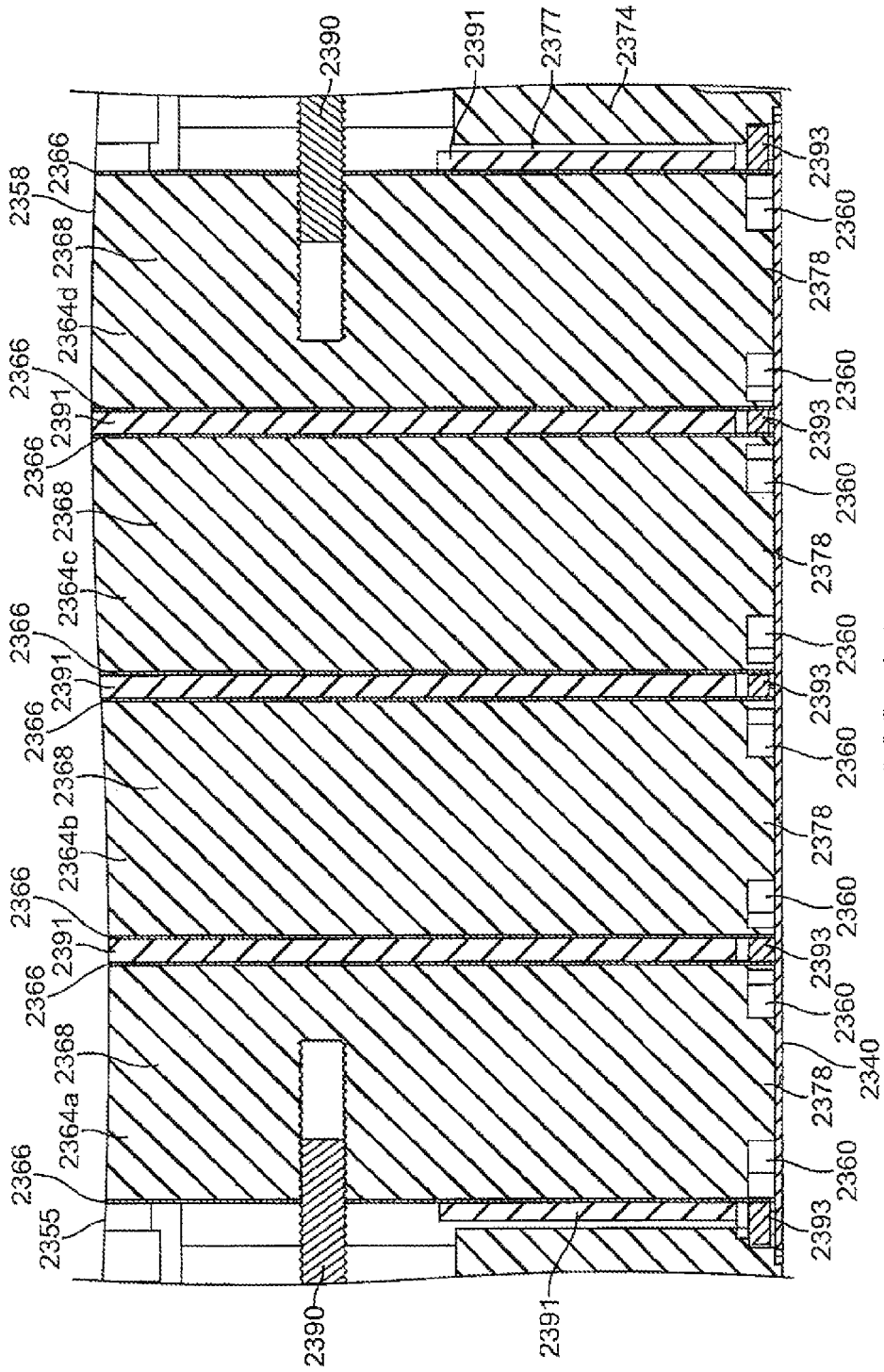
FIG. 37 is a view of a first section of the cutaway view of the antenna array illustrated in FIG. 36.

FIG. 37 is a view of a first section of the cutaway view of antenna array 2355 illustrated in FIG. 36. According to one embodiment of the invention waveguide assembly 2358 may include one or more waveguide antennas 2364(a-d) and one or more isolation elements 2391. According to one embodiment of the invention isolation elements 2391 may be positioned between waveguide antennas 2364 and on either side of waveguide assembly 2358. According to one embodiment of the invention coolant chamber 2360, which may also be referred to as heat exchange channels, may be adapted to receive cooling fluid (not shown).

Figure 38:
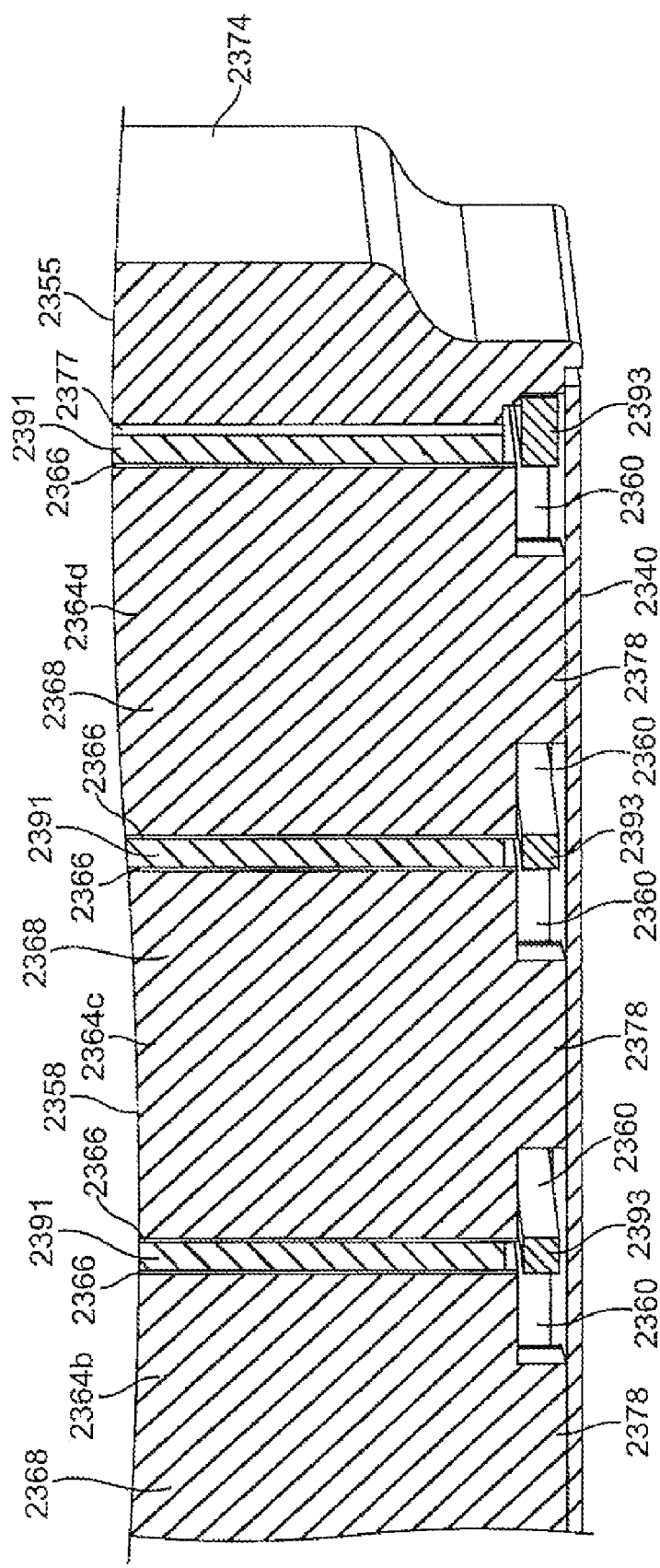
FIG. 38 is a perspective view of a second section of the cutaway view of the antenna array illustrated in FIG. 36.

FIG. 38 is a perspective view of a second section of the cutaway view of antenna array 2355 illustrated in FIG. 36. According to one embodiment of the invention waveguide assembly 2358 may include one or more waveguide antennas 2364(b-d) and one or more isolation elements 2391. According to one embodiment of the invention waveguide antennas 2364 may include a dielectric filler 2368 and waveguide walls 2366. According to one embodiment of the invention coolant chamber 2360, which may also be referred to as heat exchange channels, may be adapted to receive cooling fluid (not shown).

Figure 39:
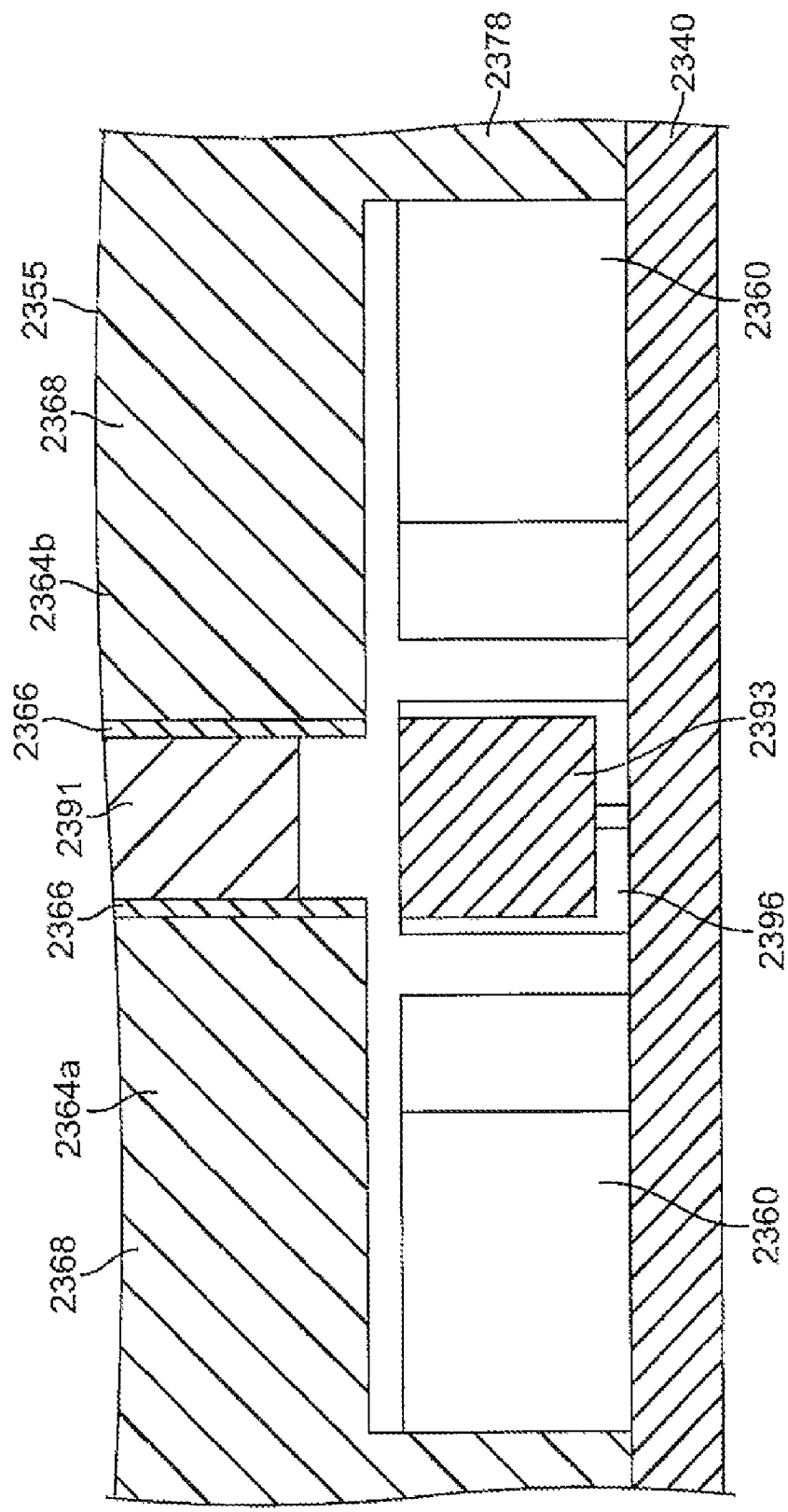
FIG. 39 is a view of a third section of the cutaway view of the antenna array illustrated in FIG. 36.

FIG. 39 is a view of a third section of the cutaway view of antenna array 2355 illustrated in FIG. 36. According to one embodiment of the invention coolant chamber 2360, which may also be referred to as heat exchange channels, may be adapted to receive cooling fluid (not shown). According to one embodiment of the invention separation ribs 2393 may be supported by rib holder 2396. According to one embodiment of the invention scattering element 2378 may be designed, positioned and dimensioned to spread the power loss density pattern (or SAR pattern created in tissue engaged in tissue chamber 2388. According to one embodiment of the invention scattering element 2378 may be formed of the same material as dielectric filler 2368. According to one embodiment of the invention scattering element 2378 may be a low loss dielectric material having a dielectric constant of approximately 10. According to one embodiment of the invention scattering element 2378 may be a low loss dielectric material with a dielectric constant approximately equal to the dielectric constant of filler material 2368. According to one embodiment of the invention scattering element 2378 preferably has a dielectric constant different from the dielectric constant of the cooling fluid. According to one embodiment of the invention scattering element 2378 is preferably low loss such that it does not attenuate or dissipate energy emitted from the aperture of waveguide antenna 2364. According to one embodiment of the invention scattering element 2378 may have a loss of less than approximately 1 at the frequency of interest, such as, for example 5.8 GHz. According to one embodiment of the invention scattering element 2378 with a low loss cooling fluid it may be preferable to have a higher loss scattering element to spread the effective field size (EFS) which may be defined as the ration between the fifty percent SAR contour in a cross section of target tissue and a radiating aperture of the antenna). According to one embodiment of the invention scattering element 2378 may be formed of alumina or Eccostock material. According to one embodiment of the invention scattering element 2378 may be shaped to facilitate laminar flow of coolant around scattering element 2378. According to one embodiment of the invention scattering element 2378 may be shaped to minimize the creation of air bubbles in coolant flowing through cooling chamber 2360. According to one embodiment of the invention scattering element 2378 may be shaped and positioned to optimize the cooling and microwave characteristics of the system. According to one embodiment of the invention scattering element 2378 may be shaped and positioned to minimizing the area of the cooling plate covered by scattering element 2378. According to one embodiment of the invention scattering element 2378 may be shaped and positioned to maximizing the cross-sectional area of peak SAR within the target region at the target depth in tissue engaged by tissue chamber 2338.

According to one embodiment of the invention scattering element 2378 may be located in the center of the aperture of waveguide antenna 2364. According to one embodiment of the invention scattering element 2378 may be rectangular, having dimensions proportional to the dimensions of an aperture of waveguide antenna 2364. According to one embodiment of the invention scattering element 2378 may be oblong. According to one embodiment of the invention scattering element 2378 may be racetrack shaped with elongated sides parallel to the longest sides of the aperture of waveguide antenna 2364. According to one embodiment of the invention scattering element 2378 may have a length of between approximately 1 millimeter and a length of approximately 7 millimeters. According to one embodiment of the invention scattering element 2378 may have a length of approximately as long as the long side of the aperture of waveguide antenna 2364. According to one embodiment of the invention scattering element 2378 may have a width of between approximately 1 millimeter and approximately 4 millimeters. According to one embodiment of the invention scattering element 2378 may have a width as long as the short side of the aperture of waveguide antenna 2364. According to one embodiment of the invention scattering element 2378 may have a height of approximately one-half millimeter. According to one embodiment of the invention scattering element 2378 may have a height approximately equal to the depth of the coolant chamber 2360. According to one embodiment of the invention scattering element 2378 may an area which is proportional to the area of the aperture of waveguide antenna 2364.

According to one embodiment of the invention scattering element 2378 may be positioned between dielectric filler 2368 of waveguide antenna 2364 and a proximal side of cooling plate 2340. According to one embodiment of the invention scattering element 2378 may be positioned to contact both dielectric filler 2368 and a proximal surface of cooling plate 2340. According to one embodiment of the invention scattering element 2378 may be positioned against cooling plate 2340 in a manner which minimizes or eliminates air gaps or other discontinuities at the junction between scattering element 2378 and cooling plate 2340. According to one embodiment of the invention scattering element 2378 may be attached to the cooling plate using for example a dielectric epoxy. According to one embodiment of the invention scattering element 2378 may be positioned such that fields generated by waveguide antenna 2364 do not re-converge while propagating through cooling plate 2340. According to one embodiment of the invention scattering element 2378 may be positioned in the center of the coolant chamber 2360, with equal flow paths on either side of scattering element 2378. According to one embodiment of the invention scattering element 2378 may be oriented such that the longest dimension of scattering element 2378 is aligned along the path taken by cooling fluid through coolant chamber 2360. According to one embodiment of the invention scattering element 2378 may be positioned in the center of the region of maximum E-field strength radiated by waveguide antenna 2364.

Figure 40:
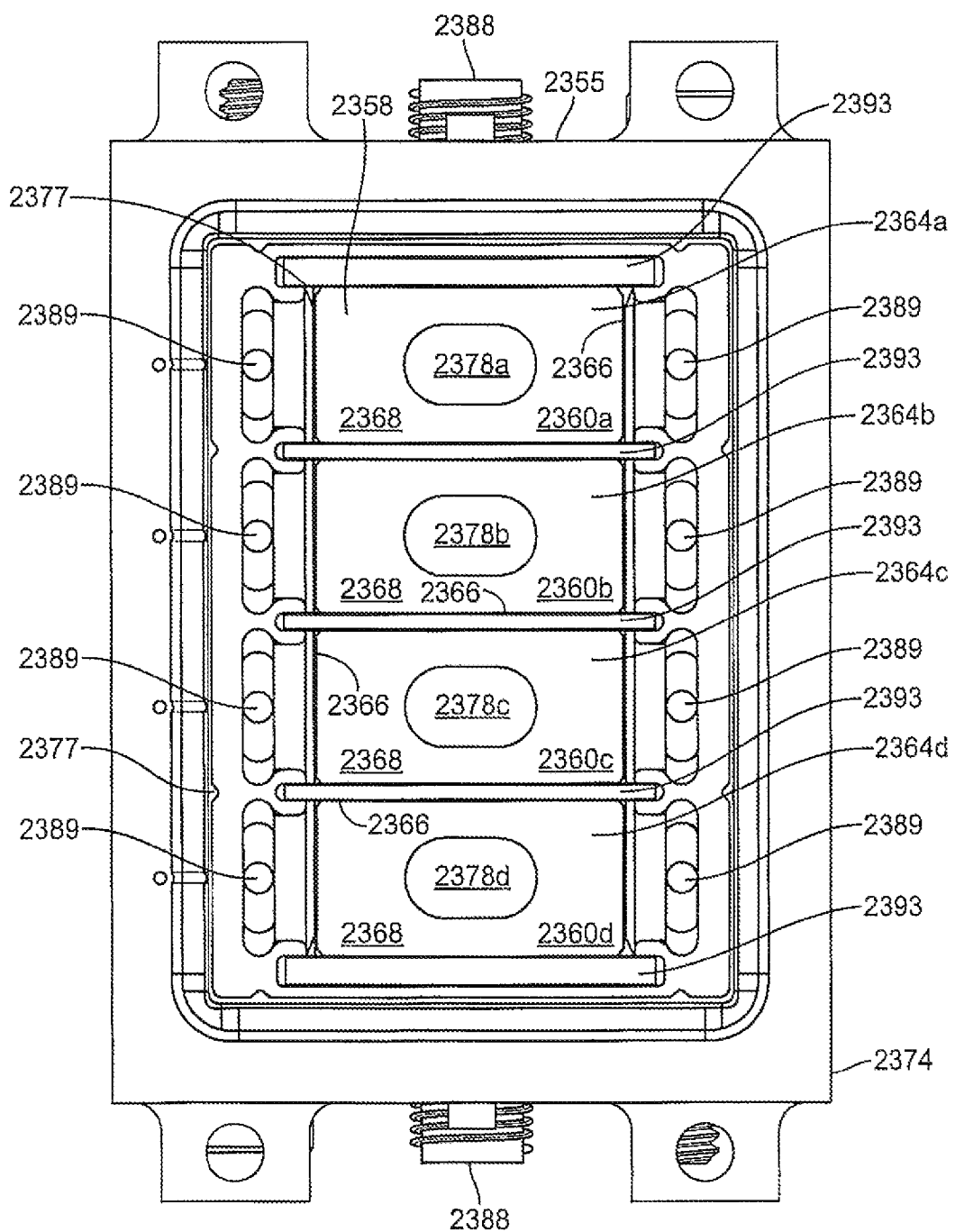
FIG. 40 is an end view of the antenna array illustrated in FIG. 35 without a cooling plate.

FIG. 40 is an end view of the antenna array 2355, coolant chambers 2360, separation ribs 2393 and scattering elements 2378 according to one embodiment of the invention. According to one embodiment of the invention coolant channel 2360*c* may be located beneath waveguide antenna 2364*c*.

According to one embodiment of the invention cooling circuit 2376 may include cooling fluid 2361, coolant conduit 2324, cooling fluid path 2381, coolant supply tubing 2312, coolant return tubing 2313 and coolant distribution tubing 2314. According to one embodiment of the invention cooling fluid path 2381 may include cradle circuit 2385, cooling plate 2340 and coolant chamber 2360. According to one embodiment of the invention cooling fluid path 2381 may include cradle circuit 2385, cooling plate 2340, coolant chamber 2360 and coolant distribution tubing 2314. According to one embodiment of the invention coolant distribution tubing 2314 is used to provide serial flow through cradle circuit 2385 and coolant chambers 2360. According to one embodiment of the invention cooling fluid 2361 may include water, de-ionized water or other suitable fluid. According to one embodiment of the invention cooling fluid 2361 circulates from a coolant source 2310 outside applicator 2320, through applicator 2320 and back to coolant source 2310. According to one embodiment of the invention cooling fluid 2361 may enter cooling fluid path 2381 through coolant supply tubing 2312 and exits cooling fluid path 2381 through coolant return tubing 2313. According to one embodiment of the invention coolant return tubing 2313 may include a thermocouple, such as, for example cooling path thermocouple 2326, to measure the temperature of cooling fluid 2361 leaving cooling circuit 2376. According to one embodiment of the invention elements in cooling fluid path 2381 may be held in place using water sealing adhesives. According to one embodiment of the invention elements in cooling fluid path 2381 may be held in place using adhesives having low water absorption. According to one embodiment of the invention elements in cooling fluid path 2381 may be held in place using epoxy, Tri-Bond FDA-16 (From TraCon) or UV curable adhesives. According to one embodiment of the invention curved surfaces and rounded edges may be used throughout cooling fluid path 2381 to reduce or eliminate turbulence. According to one embodiment of the invention curved surfaces and rounded edges may be used throughout cooling fluid path 2381 to reduce or eliminate air bubbles. According to one embodiment of the invention hydrophilic coatings may be used on selected surfaces in the cooling fluid path 2381 to reduce or eliminate turbulence. According to one embodiment of the invention hydrophilic coatings may be used on selected surfaces in cooling fluid path 2381 to reduce or eliminate air bubbles. According to one embodiment of the invention cradle circuit 2385 includes pathways for the transmission of cooling fluid 2361 through antenna cradle 2374. According to one embodiment of the invention cradle circuit 2385 may be arranged either as a series circuit or a parallel circuit. According to one embodiment of the invention all or a portion of cradle circuit 2385 may be coated with a hydrophilic material to facilitate the smooth flow of coolant and minimize the buildup of bubbles, particularly in coolant chambers 2360. According to one embodiment of the invention, such as, for example where cooling fluid 2361 flows through coolant chambers 2360 in parallel, cradle circuit 2385 may include cradle reservoirs 2387, including, a feed cradle reservoir 2387 and a return cradle reservoir 2387. According to one embodiment of the invention cradle reservoirs 2387 may act as fluidic capacitors, smoothing the flow of cooling fluid 2361 between coolant supply tubing 2312 and coolant chamber 2360. According to one embodiment of the invention cradle reservoirs 2387 may hold a volume of cooling fluid sufficient to ensure pressure is substantially equalized across all coolant chambers 2360. According to one embodiment of the invention cradle reservoirs 2387 may hold a volume of cooling fluid sufficient to ensure flow rate is substantially equalized across all coolant chambers 2360. According to one embodiment of the invention the volume cradle reservoirs 2387 may be selected to equalize pressure across cradle channels 2389. According to one embodiment of the invention the volume cradle reservoirs 2387 may be selected to equalize flow rates across cradle channels 2389. According to one embodiment of the invention a return cradle reservoir 2387 may be designed with equidistant cradle channels 2389 to equalize pressure across cradle channels 2389. According to one embodiment of the invention, wherein cooling fluid 2361 flows through each cooling chamber 2360 in series, the flow through cradle circuit 2385 each cradle channel 2389 is connected directly to a cooling chamber 2360 with a return cradle channel 2389 on the opposite side of cooling chamber 2360. According to one embodiment of the invention inlet and return cradle channels are connected by coolant distribution tubing 2314. According to one embodiment of the invention wherein cooling fluid 2361 flows through each cooling chamber 2360 in parallel, cradle channels 2389 extend in parallel cradle reservoir 2387 to coolant chambers 2360. According to one embodiment of the invention the size, shape and positioning of cradle channels 2389 may be selected to ensure that the flow rate through each coolant chamber is the same. According to one embodiment of the invention the size and shape of cradle channels 2389 may be the same for all cradle channels 2389. According to one embodiment of the invention the inputs to cradle channels 2389 may be spaced equally across the bottom of cradle reservoirs 2387. According to one embodiment of the invention the size, shape and positioning of cradle channels 2389 may be selected to minimize turbulence and air bubbles in coolant chambers 2360. According to one embodiment of the invention the inputs to cradle channels 2389 from cradle reservoirs 2387. According to one embodiment of the invention a cross-section of the section of cradle channels 2389 between cradle reservoir 2387 and the inputs to coolant chambers 2360 may be formed in a wineglass or nozzle shape with the input to coolant chambers 2360 being flared to the width of coolant chamber 2360. According to one embodiment of the invention the opposite cross section of cradle channels 2389 may be formed with flat walls. According to one embodiment of the invention a transition from the cradle channel 2389 to coolant chamber 2360 may be rounded. According to one embodiment of the invention coolant chamber 2360 may include separation ribs 2393. According to one embodiment of the invention cooling fluid flowing through the coolant chamber 2360 may have a flow rate of between TS 200 milliliters per minute and 450 milliliters per minute and preferably 430 milliliters per minute. According to one embodiment of the invention coolant chamber 2360 may be designed to ensure that the flow rate through each coolant chamber 2360 is substantially the same. According to one embodiment of the invention cooling fluid flowing through coolant chamber 2360 may have a temperature of between 8 degrees centigrade and 22 degrees centigrade and preferably approximately 15 degrees centigrade. According to one embodiment of the invention coolant chambers 2360 may be positioned between an aperture of waveguide antenna 2364 cooling plate 2340. According to one embodiment of the invention scattering elements 2378 may extend into at least a portion of coolant chamber 2360. According to one embodiment of the invention scattering elements 2378 may extend through coolant chamber 2360. According to one embodiment of the invention elements of coolant chamber 2360 may be smoothed to promote laminar fluid flow through coolant chamber 2360. According to one embodiment of the invention elements of coolant chamber 2360 may be smoothed to reduce the generation of air bubbles in coolant chamber 2360. According to one embodiment of the invention scattering elements which extend into coolant chamber 2360 may be rounded to promote laminar flow and prevent the buildup of bubbles in coolant chamber 2360. According to one embodiment of the invention square edges or sharp corners in coolant chamber 2360 may result in undesirable flow characteristics, including the generation of air bubbles, as cooling fluid moves through coolant chamber 2360. According to one embodiment of the invention separation ribs 2393 may be used to separate individual coolant chambers 2360. According to one embodiment of the invention separation ribs 2393 may be placed to ensure that each coolant chamber 2360 has a substantially identical cross section. According to one embodiment of the invention separation ribs 2393 may have a square cross section and be approximately 0.030 inches by 0.030 inches in size. According to one embodiment of the invention larger or smaller separation ribs 2393 may be used to ensure that the cross sectional area of each coolant chamber 2360 is the same. According to one embodiment of the invention separation ribs 2393 may be positioned such that they do not contact either the cooling plate or any portion of waveguide antennas 2364. According to one embodiment of the invention separation ribs 2393 may be positioned such that they facilitate equalized cooling across cooling plate 2340. According to one embodiment of the invention separation ribs 2393 may be sized such that they have a width which is equal to or less than the separation distance between apertures of waveguide antennas 2364. According to one embodiment of the invention separation ribs 2393 may be sized and positioned such that they are not positioned an aperture of waveguide antenna 2364. According to one embodiment of the invention separation ribs 2393 may be sized and positioned such that they minimize perturbation of a microwave field as it travels through coolant chamber 2360. According to one embodiment of the invention separation ribs 2393 may be sized and positioned such that they minimize disruption of a microwave field as it travels through coolant chamber 2360. According to one embodiment of the invention separation ribs 2393 may be positioned by placing them in rib holders 2396 at either end of coolant chamber 2360. According to one embodiment of the invention separation ribs 2393 may be positioned such that they do not touch scattering element 2378. According to one embodiment of the invention separation ribs 2393 may be positioned an appropriate distance from a proximal surface of cooling plate 2340 and preferably a distance of approximately 0.010 inches from a proximal surface of the cooling plate 2340. According to one embodiment of the invention separation ribs 2393 may be made of materials which minimize disruption or perturbation of the microwave field. According to one embodiment of the invention separation ribs 2393 may be made of materials which will not rust or degrade in cooling fluid. According to one embodiment of the invention separation ribs 2393 may be made of polycarbonate materials. According to one embodiment of the invention separation ribs 2393 may be made of materials which increase the isolation between waveguide antennas. According to one embodiment of the invention separation ribs 2393 may be made of materials which improve the SAR pattern in tissue. According to one embodiment of the invention separation ribs 2393 may be made of Eccosorb. According to one embodiment of the invention separation ribs 2393 may be made of Eccosorb and coated to prevent separation ribs 2393 from rusting in the cooling fluid.

Figure 41:
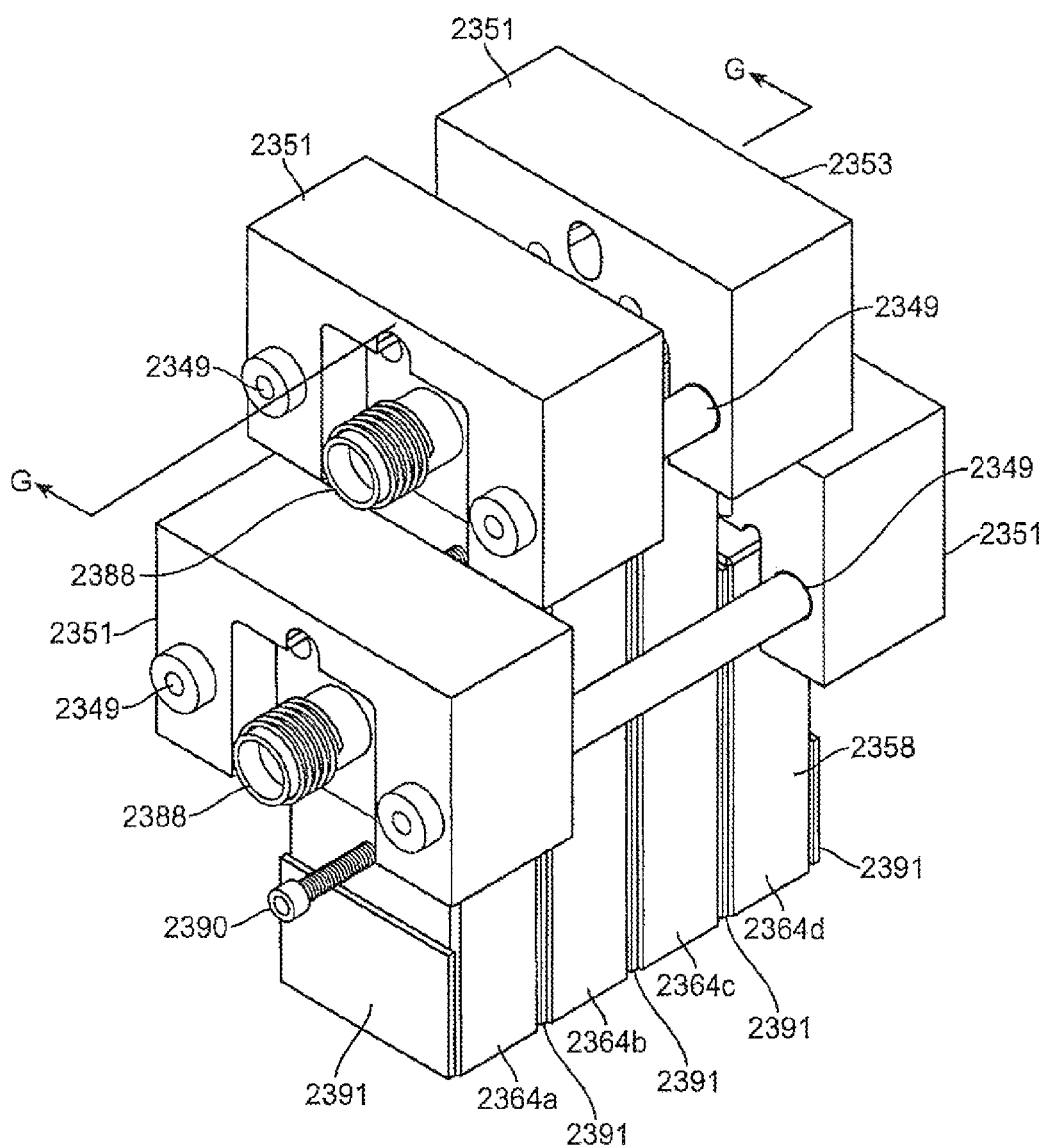
FIG. 41 is a perspective view of a waveguide assembly according to one embodiment of the invention.

FIG. 41 is a perspective view of waveguide assembly 2358 according to one embodiment of the invention. According to one embodiment of the invention waveguide assembly 2358 may include one or more isolation elements 2391 positioned between waveguide antennas 2364a through 2364d. According to one embodiment of the invention waveguide assembly 2358 may include a plurality of tuning elements 2390 and a plurality of feed connectors 2388. According to one embodiment of the invention microwave energy may be supplied to each waveguide antenna through feed connectors 2388. According to one embodiment of the invention waveguide assembly 2358 may be held together by a waveguide assembly frame 2353. According to one embodiment of the invention waveguide assembly frame 2353 may include feed brackets 2351 and assembly bolts 2349.

Figure 42:
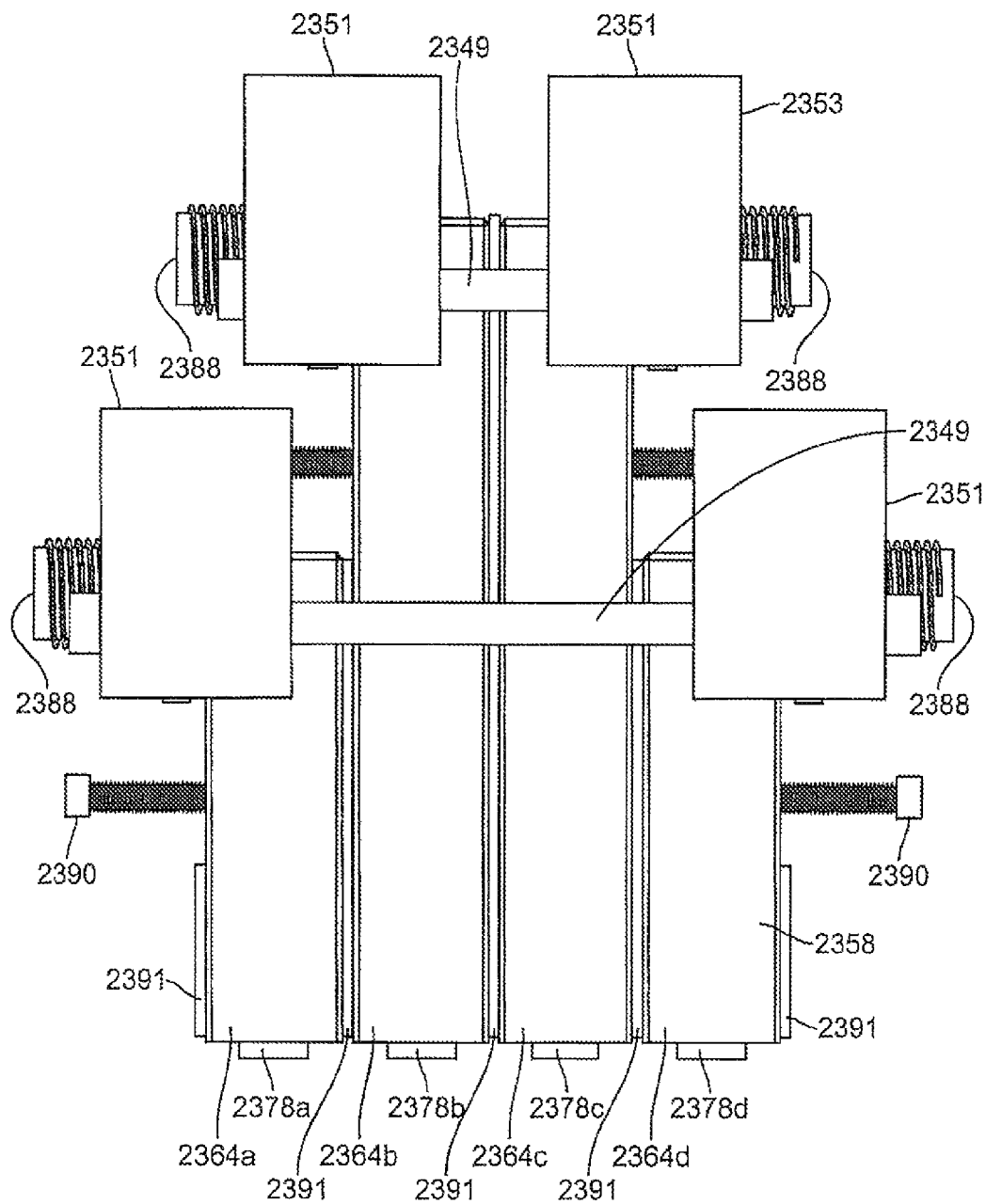
FIG. 42 is a side view of the waveguide assembly illustrated in FIG. 41.

FIG. 42 is a side view of waveguide assembly illustrated in FIG. 41. According to one embodiment of the invention scattering elements 2378 are positioned at an output of waveguide antennas 2364. According to one embodiment of the invention an output of waveguide antenna 2364 may also be referred to as an aperture of antenna 2364. According to one embodiment of the invention scattering element 2378a may be positioned at an output of waveguide antenna 2364a. According to one embodiment of the invention scattering element 2378b may be positioned at an output of waveguide antenna 2364b. According to one embodiment of the invention scattering element 2378c may be positioned at an output of waveguide antenna 2364c. According to one embodiment of the invention scattering element 2378d may be positioned at an output of waveguide antenna 2364d.

Figure 43:
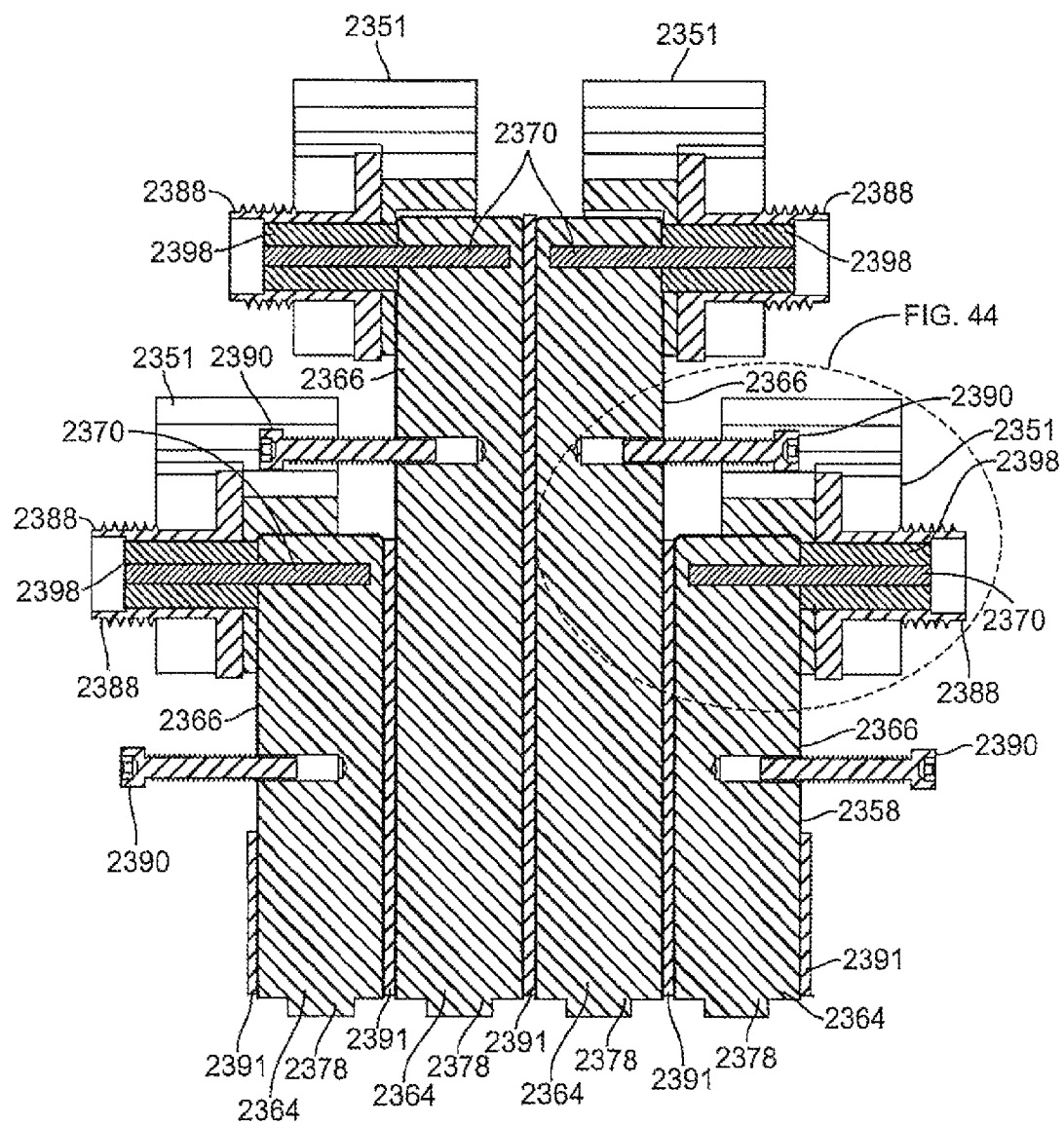
FIG. 43 is a cutaway view along G-G of the waveguide assembly illustrated in FIG. 41.

FIG. 43 is a cutaway view along G-G of waveguide assembly 2358 and scattering elements 2378 illustrated in FIG. 41. According to one embodiment of the invention waveguide assembly 2358 includes one or more waveguide antennas 2364, one or more feed brackets 2351 and one or more isolation elements 2391. According to one embodiment of the invention waveguide assembly 2358 includes waveguide antennas 2364. According to one embodiment of the invention waveguide antennas 2364 may include a dielectric filler 2368, waveguide walls 2366 and tuning element 2390. According to one embodiment of the invention waveguide antennas 2364 may be manufactured by plating dielectric filler 2368 with an appropriate plating material. According to one embodiment of the invention feed shims 2397 may be used to match feed connectors 2388 to waveguide antennas 2364 when waveguide walls 2366 are plated over dielectric filler 2368, ensuring appropriate contact between center insulator 2398 and dielectric filler 2368.

Figure 44:
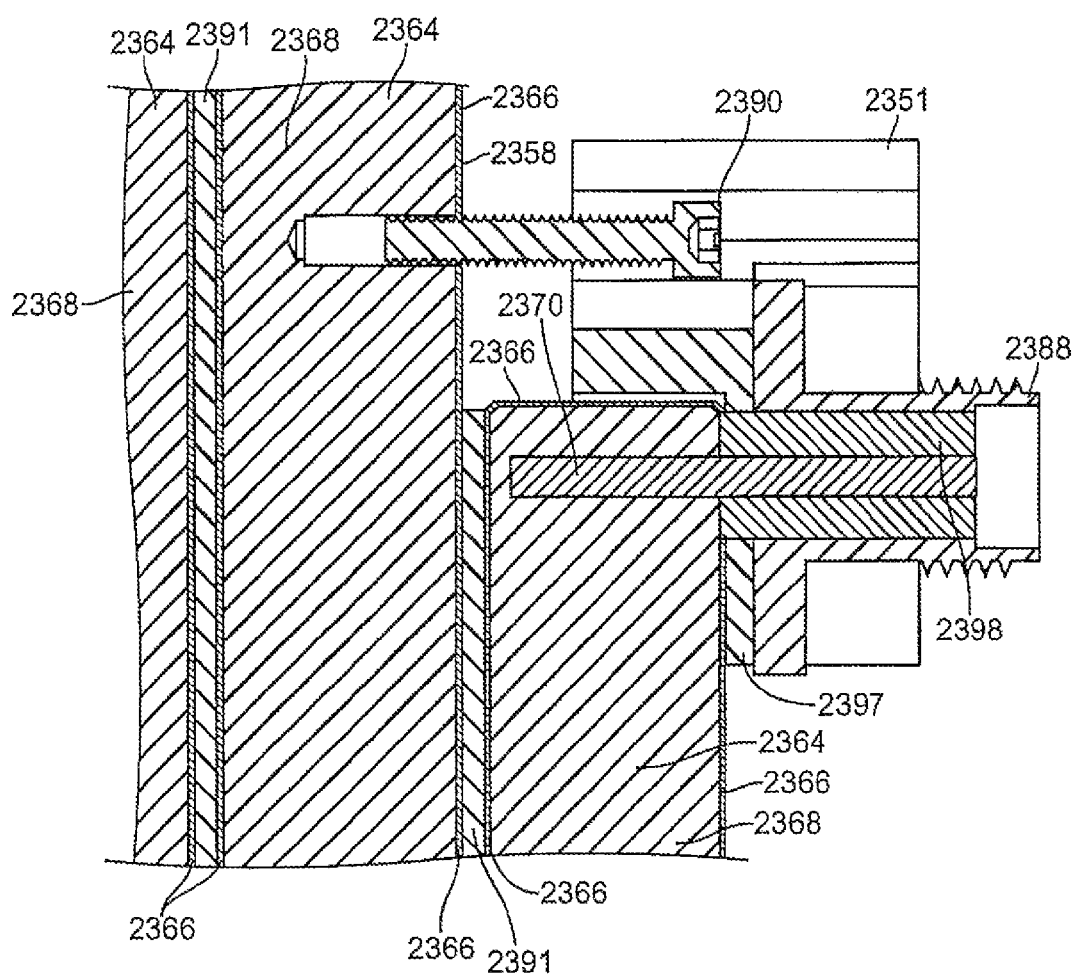
FIG. 44 is a view of a section of cutaway view of the waveguide assembly illustrated in FIG. 43.

FIG. 44 is a view of a section of cutaway view of waveguide assembly 2358 illustrated in FIG. 43. According to one embodiment of the invention waveguide assembly 2358 includes one or more waveguide antennas 2364, one or more feed brackets 2351 and one or more isolation elements 2391. According to one embodiment of the invention waveguide assembly 2358 includes waveguide antennas 2364. According to one embodiment of the invention waveguide antennas 2364 may include a dielectric filler 2368, waveguide walls 2366 and tuning element 2390. According to one embodiment of the invention feed shims 2397 may be used to match feed connectors 2388 to waveguide antennas 2364 when waveguide walls 2366 are plated over dielectric filler 2368, ensuring appropriate contact between center insulator 2398 and dielectric filler 2368.

According to one embodiment of the invention isolation elements 2391 may be designed to isolate the interactions between waveguide antennas 2364 and to balance the loading conditions seen by inner waveguide antennas (such as, for example waveguide antennas 2364a and 2364d) and outer waveguide antennas (such as, for example waveguide antennas 2364b and 2364c). According to one embodiment of the invention isolation elements 2391 may absorb a portion of the microwave energy which is not coupled into tissue engaged by tissue chamber 2338. According to one embodiment of the invention isolation elements 2391 may absorb fringing fields present a the metallic edges of an aperture of waveguide antenna 2364. According to one embodiment of the invention isolation elements 2391 may be designed and positioned to ensure that each waveguide antenna 2364 sees the same loading characteristics on each side of the waveguide antenna 2364.

According to one embodiment of the invention, such as the embodiment illustrated in FIG. 13, the need for isolation elements 2391 may be eliminated where the outer conductive walls of waveguide antennas 2364 are machined to ensure that the width of conductive material (such as, for example, waveguide walls 2366) between the dielectric fillers 2368 of adjacent waveguide antennas 2364 may be the same for all waveguide antennas 2364 in antenna array 2355. According to one embodiment of the invention waveguide walls 2366 of the outer waveguide antennas 2364a and 2364d may be machined such that such wave guide walls 2366 are as thick as the distance between adjacent waveguide antennas 2364 in antenna array 2355. According to one embodiment of the invention waveguide antennas 2364 may be carefully constructed such that the thickness of waveguide walls 2366 are equal on all sides, eliminating the need for isolation elements 2391.

According to one embodiment of the invention isolation elements 2391 may be positioned between antennas and on the outside of outer waveguide antennas 2364a and 2364d in antenna array 2355 to isolate waveguide antennas 2364. According to one embodiment of the invention isolation elements 2391 may be positioned to provide symmetric microwave loading conditions for all waveguide antennas 2364 in the antenna array 2355. According to one embodiment of the invention Isolation elements 2391 may be made from a material which absorbs microwave energy. According to one embodiment of the invention isolation elements 2391 may be made from Eccosorb. According to one embodiment of the invention isolation elements 2391 which rust may be isolated from the cooling fluid.

According to one embodiment of the invention isolation elements 2391 may be designed and positioned to minimize interaction between adjacent waveguide antennas 2364 and balance the load seen by adjacent waveguide antennas 2364. If waveguide antennas are too close together, the SAR patterns they generate may not be symmetrical or of equal strength. If waveguide antennas 2364 are too far apart, the lesions will not be contiguous. According to one embodiment of the invention the space between the dielectric filler 2368 in antenna array 2355 may be made up of the thickness of waveguide walls 2366 of waveguide antenna 2364 and the thickness of the isolation element or elements positioned between microwave antennas. According to one embodiment of the invention the space between dielectric fillers 2368 in antenna array 2355 may be between approximately 0.012 inches and 0.080 inches and preferably approximately 0.030 inches. According to one embodiment of the invention antenna array 2355 may have waveguide walls 2366 with a plating thickness of approximately 0.003 inches, isolation elements 2391 may have a thickness of approximately 0.024 inches. According to one embodiment of the invention wherein the frequency of interest is approximately 5.8 GHz, isolation elements 2391 may have a dielectric constant of between approximately 25 and approximately 40 and preferably of approximately 27. According to one embodiment of the invention wherein the frequency of interest is approximately 5.8 GHz, isolation elements 2391 may have a loss tangent (tan $\delta$) of between approximately 0.02 and approximately 0.07 and preferably of approximately 0.04. According to one embodiment of the invention wherein the frequency of interest is approximately 5.8 GHz, isolation elements 2391 may have a complex permeability of between approximately 1.5+j3.4 and approximately 7+j5.6 and preferably of approximately 2.7+j3.4.

Figure 45:
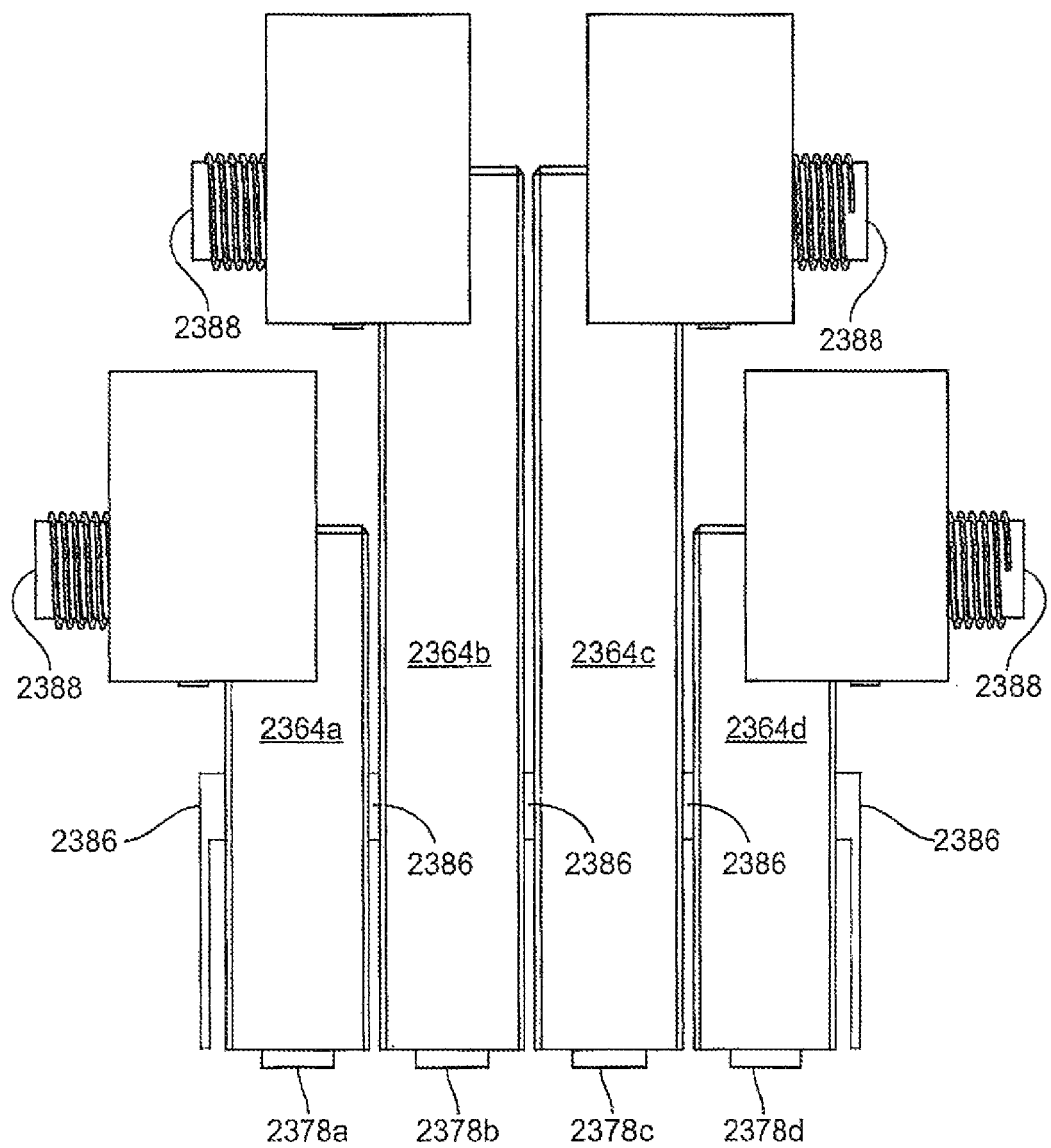
FIG. 45 is a side view of an alternate embodiment of a waveguide assembly according to an embodiment of the invention.
Figure 46:
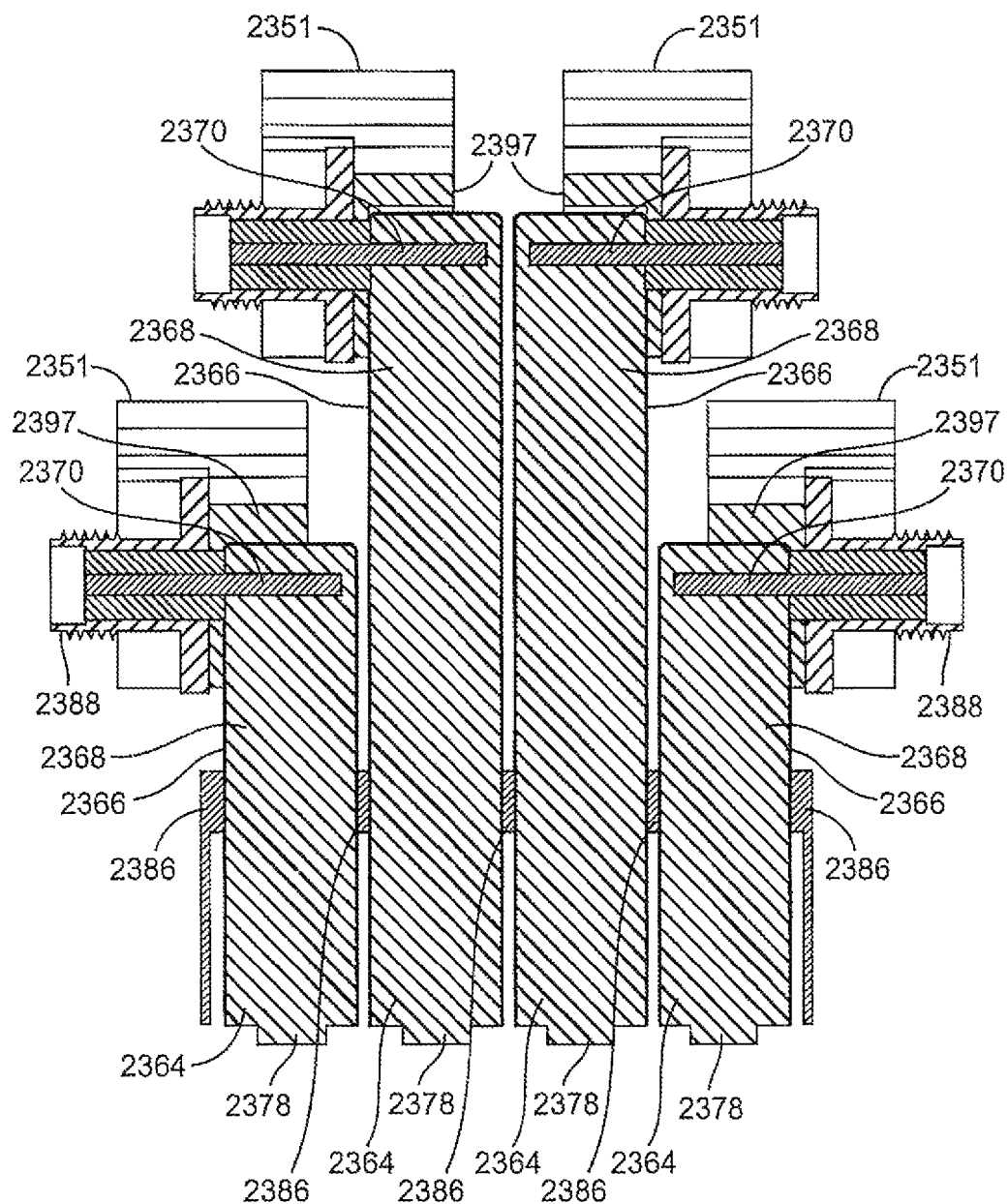
FIG. 46 is a cutaway view of the waveguide assembly illustrated in FIG. 45.

FIG. 45 is a side view of an alternate embodiment of a waveguide assembly according to an embodiment of the invention. FIG. 46 is a cutaway view the waveguide assembly illustrated in FIG. 45. According to one embodiment of the invention microwave chokes 2386 may also be used as isolation elements 2391. According to one embodiment of the invention microwave chokes 2386 may be formed using short metallic shims (set at a fixed distance back from the waveguide aperture) between waveguide antennas 2364 and metal flanges on outside microwave antennas 2364. According to one embodiment of the invention microwave chokes 2386 may be utilized in waveguide assembly 2358 to achieve isolation and SAR consistency among waveguide antennas 2364 in waveguide assembly 2358. According to one embodiment of the invention in the spaces between waveguide antennas 2364, microwave chokes 2386 are created by separating waveguide antennas 2364 with metallic shims of a certain thickness set at a certain distance from the aperture of waveguide antennas 2364. According to one embodiment of the invention on the outer sides of the outer waveguide antennas 2364 microwave chokes 2386 are achieved using a flange consisting of the same size metallic shim set at the same distance from the aperture and a metal plate going from the shim to the face of the waveguide. According to one embodiment of the invention microwave chokes 2386 create a propagation path for fringing fields existing at the long edges of the radiating face of the aperture of waveguide antennas 2364. According to one embodiment of the invention the microwave choke structure allows this fringing signal to be coupled into the microwave chokes 2386 in a symmetric way for both the inner and outer microwave antennas 2364 in waveguide assembly 2358. Thus, the microwave chokes 2386 may enhance the isolation within waveguide assembly 2358 by reducing the interaction between adjacent waveguide antennas 2364, as well as enhance the consistency of the SAR pattern among waveguide antennas 2364 by introducing symmetric loading conditions at the aperture of waveguide antennas 2364.

Figure 47:
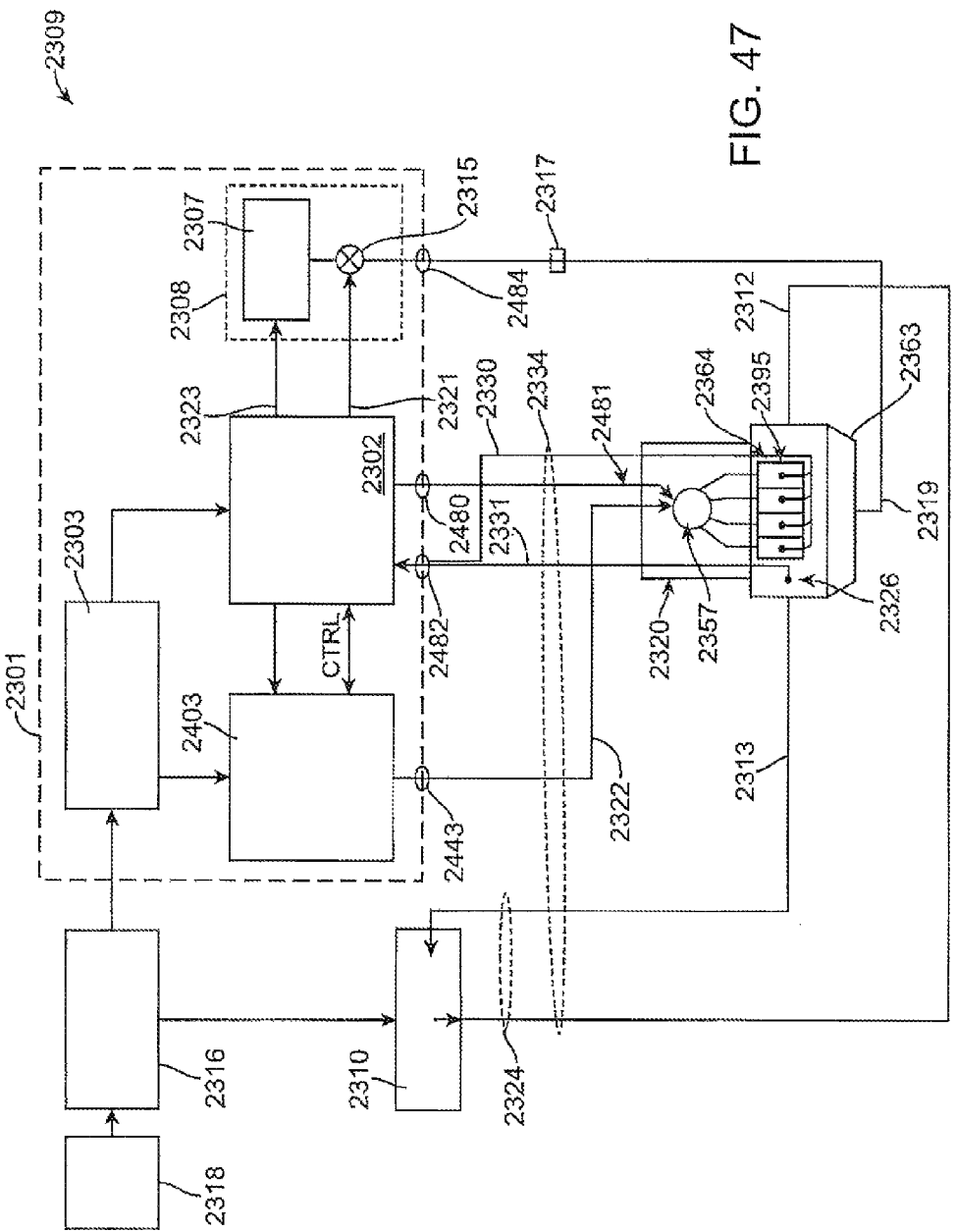
FIG. 47 is a schematic diagram of a system according to one embodiment of the invention.

FIG. 47 is a schematic diagram of system 2309 according to one embodiment of the invention. According to one embodiment of the invention system 2309 may include an isolation transformer 2316, a coolant source 2310 a generator 2301 and applicator 2320. According to one embodiment of the invention isolation transformer 2316 may be connected to AC power supply 2318. According to one embodiment of the invention isolation transformer 2316 may supply power to generator 2301 and coolant source 2310. According to one embodiment of the invention generator 2301 may include DC power supply 2303, controller 2302, microwave chain 2403 (which may be, for example a series of microwave components) and vacuum source 2308. According to one embodiment of the invention controller 2302 may manage all system level inputs and controls such as: power and timer settings from the front panel 2305; input from start button 2464; input from stop button 2466; hardware errors from the microwave circuit (reverse power error, amplifier fault); temperature and installation errors from the applicator; and sending measured data to interface 2420 for recording reverse power, forward power and tissue temperature and coolant temperature at discrete times. According to one embodiment of the invention controller 2302 may also control antenna switch 2357, vacuum pump 2450 and the vacuum solenoid 2315. According to one embodiment of the invention vacuum source 2308 may include vacuum pump/drive 2307 and vacuum solenoid 2315. According to one embodiment of the invention DC power supply 2303 may supply power to microwave chain 2403 and to controller 2302. According to one embodiment of the invention controller 2302 may ensure that microwave chain 2403 operates to specification. According to one embodiment of the invention microwave chain 2403 may be connected to controller 2302. According to one embodiment of the invention controller 2302 may be connected to vacuum pump/drive 2307 by vacuum power signal 2323 and to vacuum solenoid 2315 by solenoid control signal 2321. According to one embodiment of the invention DC Power supply 2303 may be, for example, a medical 650 Watt, +12 Volt switching power supply, model PM650-12C, available from Tumbler Technologies. According to one embodiment of the invention vacuum pump 2450 may be, for example, a rotary vane pump, model number 15988, available from Clark Flow Solutions. According to one embodiment of the invention vacuum solenoid 2315 may be, for example, a solenoid valve, three way, normally closed, exhaust to atmosphere model LW53KK8DGBG12/DC available from Peter Paul Electronics Co. According to one embodiment of the invention applicator 2320 may be connected to generator 2301 by applicator cable 2334. According to one embodiment of the invention applicator cable 2334 may include coolant conduit 2324, energy cable 2322, coolant thermocouple wires 2331, cooling plate thermocouple wires 2330 and antenna switch signal 2481. According to one embodiment of the invention coolant conduit 2324 may be connected to a coolant source 2310. According to one embodiment of the invention coolant conduit 2324 may include coolant supply tubing 2312 and coolant return tubing 2313. According to one embodiment of the invention coolant may be supplied to applicator 2320 through coolant supply tubing 2312. According to one embodiment of the invention coolant is returned to coolant source 2310 thought coolant return tubing 2313. According to one embodiment of the invention energy cable 2322 may be connected to generator 2301 by microwave output connector 2443. According to one embodiment of the invention energy cable 2322 may connect antenna switch 2357 in applicator 2320 to microwave chain 2403 in generator 2301 through microwave output connector 2443. According to one embodiment of the invention coolant thermocouple wires 2331 and antenna thermocouple wires 2330 may be connected to generator 2301 by temperature connector 2482. According to one embodiment of the invention coolant thermocouple wires 2331 may connect cooling path thermocouple 2326 in applicator 2320 to controller 2302 in generator 2301 through temperature connector 2482. According to one embodiment of the invention cooling plate thermocouple wires 2330 may connect cooling plate thermocouples 2395 in applicator 2320 to controller 2302 in generator 2301 through temperature connector 2482. According to one embodiment of the invention antenna switch signal 2481 may be connected to generator 2301 by antenna switch connector 2480. According to one embodiment of the invention antenna switch signal 2481 may connect antenna switch 2357 in applicator 2320 to controller 2302 in generator 2301 through antenna switch connector 2480. According to one embodiment of the invention disposable 2363 may be connected to generator 2301 by vacuum tubing 2319 which may include generator bio-barrier 2317. According to one embodiment of the invention in system 2309 vacuum tubing 2319 may be connected to generator 2301 by vacuum port connector 2484. According to one embodiment of the invention vacuum tubing 2319 may connect disposable 2363 to vacuum solenoid 2315 through vacuum port connector 2484. According to one embodiment of the invention coolant source 2310 supplies cooling fluid 2361 (not shown) to applicator 2320. According to one embodiment of the invention coolant source 2310 may be a NanoTherm Chiller, available from ThemoTek, Inc. According to one embodiment of the invention cooling fluid 2361 from coolant source 2310 has a temperature range of between approximately 5 and 40 degrees centigrade and preferably a temperature of approximately fifteen degrees centigrade. According to one embodiment of the invention coolant source 2310 may have a flow rate of between approximately two hundred and one thousand milliliters per minute and preferably of approximately five hundred millimeters per minute. According to one embodiment of the invention coolant source 2310 may be a solid-state chiller designed to chill cooling fluid 2361 and pump the chilled cooling fluid 2361 through applicator 2320 and coolant chamber 2360 to protect the skin engaged in tissue chamber 2338 from thermal damage. According to one embodiment of the invention coolant source 2310 may be a solid-state chiller designed to chill cooling fluid 2361 and pump the chilled cooling fluid 2361 through applicator 2320 and coolant chamber 2360 to protect a first layer of skin engaged in tissue chamber 2338 from thermal damage.

Figure 48:
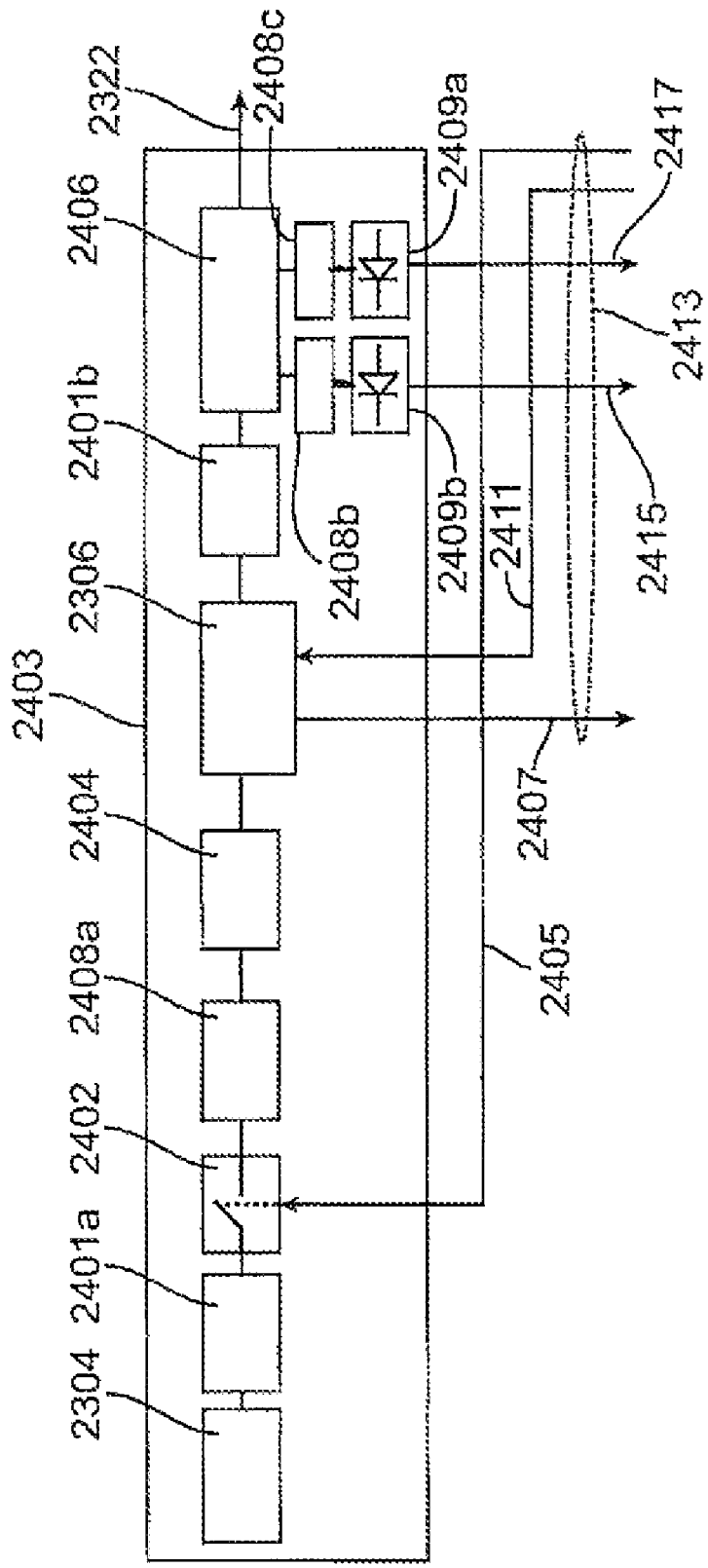
FIG. 48 is a schematic diagram of a microwave chain according to one embodiment of the invention.

FIG. 48 is a schematic diagram of microwave chain 2403 according to one embodiment of the invention. According to one embodiment of the invention oscillator 2304 may be connected to isolator 2401a which may be connected to switch 2402 (which may be, for example, a Single Pole Single Throw SPST reflective pin diode switch) which may be connected to attenuator 2408a (which may be, for example, a fixed attenuator) which may be connected to bandpass filter 2404 which may be connected to amplifier 2306 which may be connected to isolator 2401b which may be connected to directional coupler 2406. According to one embodiment of the invention oscillator 2304 may have an output frequency of approximately 5.8 GHz. According to one embodiment of the invention oscillator 2304 providing a stable 5.8 GHz low power signal. According to one embodiment of the invention isolators 2401a may be used to protect oscillator 2304 from reflected power signals from amplifier 2306. According to one embodiment of the invention filtering circuitry includes bandpass filter 2404 having a center frequency at the frequency of interest. According to one embodiment of the invention filtering circuitry includes bandpass filter 2404 having a center frequency at approximately 5.8 GHz. According to one embodiment of the invention filtering circuitry includes bandpass filter 2404 may be a waveguide cavity filter which eliminates out of band inputs into the power amplifier. According to one embodiment of the invention filtering circuitry includes bandpass filter 2404 may have a 3 dB bandwidth of approximately 25 MHz. According to one embodiment of the invention amplifier 2306 may be an amplifier adapted to amplify signals at the frequency of interest. According to one embodiment of the invention amplifier 2306 may be an amplifier adapted to amplify signals at 5.8 GHz. According to one embodiment of the invention amplifier 2306 may be an S51500-05 amplifier available from Locus Microwave. According to one embodiment of the invention amplifier 2306 may include internal biasing circuitry, matching circuitry and control circuitry adapted to maintain the stability and provide appropriate matching and power output at the frequency of interest. According to one embodiment of the invention amplifier 2306 may be adapted to amplify incoming signals by 54 dB. According to one embodiment of the invention isolator 2401b may be used to protect amplifier 2306 from reflected power signals. According to one embodiment of the invention energy cable 2322 may carry the microwave energy out from directional coupler 2406 out of microwave chain 2403. According to one embodiment of the invention directional coupler 2406 may further be connected to attenuator 2408b which may be connected be connected to power detector 2409b. According to one embodiment of the invention an output of power detector 2409b may be forward power signal 2415. According to one embodiment of the invention directional coupler 2406 may further be connected to attenuator 2408c which may which may be connected to power detector 2409a. According to one embodiment of the invention a pair of power detectors 2409b and 2409a may be used to measure forward and reverse power. According to one embodiment of the invention an output of attenuator 2409a may be reverse power signal 2417. According to one embodiment of the invention microwave chain 2403 may be connected to microwave control signals 2413. According to one embodiment of the invention microwave control signals 2413 may include PWM control signal 2405, fault signal 2407, mute signal 2411, forward power signal 2415 and reverse power signal 2417. According to one embodiment of the invention PWM control signal 2405 may be connected to switch 2402. According to one embodiment of the invention fault signal 2407 may be generated by amplifier 2306. According to one embodiment of the invention mute signal 2411 may be connected to amplifier 2306. According to one embodiment of the invention power detectors 2409 may be, for example, a coaxial tunnel diode detector.

According to one embodiment of the invention power control works by comparing forward power signal 2415 measured at directional coupler 2406 to the requested power from power control knob 2454. According to one embodiment of the invention power may be sampled from the output of amplifier 2306 by directional coupler 2406 which is connected to power detector 2409b. According to one embodiment of the invention directional coupler 2406 may be used to route forward and reflected power to power detectors 2409a and 2409b (which may be, for example, coaxial tunnel diode detectors). According to one embodiment of the invention the output of power detectors 2409a and 2409b may be read by converter circuitry in controller 2302 and fed back to switch 2402 which controls the input to amplifier 2306. According to one embodiment of the invention the duty cycle of switch 2402 may control the output power level from microwave chain 2403 with the percent time on of switch 2402 proportional to the percent of max output power generated from microwave chain 2403. According to one embodiment of the invention a microwave chain with a 100 watt maximum output would may provide a 40 watt output from microwave chain 2403 when switch 2402 is driven at a 40% duty cycle. According to one embodiment of the invention switch 2402 may be operated at a modulation frequency where the output of the pin diode is linear. According to one embodiment of the invention switch 2402 may be operated at a modulation frequency of approximately 7.2 kHz.

Figure 49:
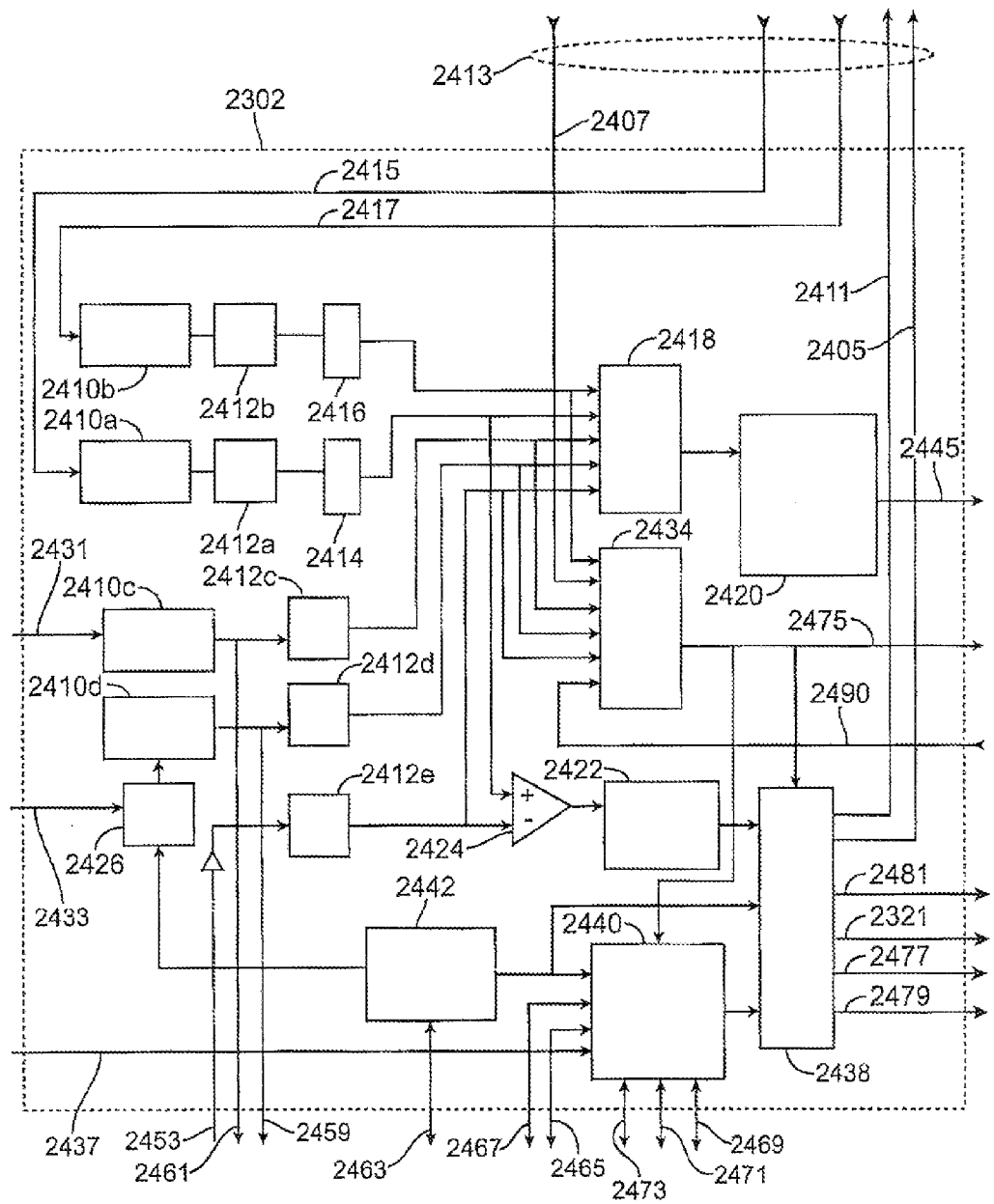
FIG. 49 is a schematic diagram of a controller according to one embodiment of the invention.

FIG. 49 is a schematic diagram of controller 2302 according to one embodiment of the invention. According to one embodiment of the invention conditioning circuitry 2410a may be connected to analog to digital converter 2412a which may be connected to forward power lookup table 2414 which may be connected to multiplexer and UART (Universal Asynchronous Receiver/Transmitter) state machine 2418 which may be connected to interface 2420 (which may be, for example, an isolated RS232 interface). According to one embodiment of the invention forward power lookup table 2414 may also be connected to comparator 2424 (which may be, for example, a digital comparator) which may be connected to pulse width modulation state machine 2422 which may be connected to logic 2438. According to one embodiment of the invention a duty cycle circuit, including logic 2438 may be used to provide a pulse width modulation (PWM) control signal 2405 to control the level of output power through energy cable 2322. According to one embodiment of the invention conditioning circuitry 2410b may be connected to analog to digital converter 2412b which may be connected to reverse power lookup table 2416 which may be connected to multiplexer and UART state machine 2418 and fault logic 2434. According to one embodiment of the invention reverse power look-up table 2416 and conditioning circuit 2410b conditions the voltage from power detector 2409a in order to produce a characteristic measurement of reverse power. According to one embodiment of the invention reverse power look-up table 2416 and conditioning circuit 2410b outputs a signal for downstream circuitry to either record the measured reverse power, or to make safety decisions. According to one embodiment of the invention conditioning circuitry 2410c may be connected to analog to digital converter 2412c which may be connected to multiplexer and UART state machine 2418 and fault logic 2434. According to one embodiment of the invention conditioning circuitry 2410d may be connected to analog to digital converter 2412d which may be connected to multiplexer and UART state machine 2418 and fault logic 2434. According to one embodiment of the invention multiplexer 2426 may be connected to antenna select state machine master controller 2442 which may be connected to timer state machine 2440 which may be connected to logic 2438. According to one embodiment of the invention circuitry antenna select state machine master controller 2442 is provided to control antenna switching in an applicator 2320 employing a multiple antenna array 2355. According to one embodiment of the invention multiplexer 2426 may be connected to conditioning circuitry 2410d. According to one embodiment of the invention antenna select state machine master controller 2442 may be connected to logic 2438. According to one embodiment of the invention analog to digital converter 2412e may be connected to comparator 2424 and multiplexer and UART state machine 2418 and fault logic 2434.

According to one embodiment of the invention microwave control signals 2413 connects microwave chain 2403 to switch 2402. According to one embodiment of the invention forward power signal 2415 may be an input to conditioning circuitry 2410a. According to one embodiment of the invention reverse power signal 2417 may be an input to conditioning circuitry 2410a. According to one embodiment of the invention coolant temperature signal 2431 may be an input to conditioning circuitry 2410c. According to one embodiment of the invention antenna thermocouple cable 2433 may be an input to multiplexer 2426. According to one embodiment of the invention foot pedal signal 2437 may be an input to timers state machine 2440. According to one embodiment of the invention power control signal 2453 may be an input to analog to digital converter 2412e. According to one embodiment of the invention filtered coolant temperature signal 2461 may be an output from conditioning circuitry 2410c. According to one embodiment of the invention filtered antenna temperature signal 2459 may be an output from conditioning circuitry 2410d. According to one embodiment of the invention antenna select signal 2463 may be an input to and output from antenna select state machine master controller 2442. According to one embodiment of the invention stop signal 2467 may be an input to and output from timers state machine 2440. According to one embodiment of the invention start signal 2465 may be an input to and output from timers state machine 2440. According to one embodiment of the invention post-cool timer signal 2473 may be an input to and output of timers state machine 2440. According to one embodiment of the invention energy timer signal 2471 may be input to and an output of timers state machine 2440. According to one embodiment of the invention pre-cool time signal 2469 may be an input to and output of timers state machine 2440. According to one embodiment of the invention buzzer signal 2479 may be an output of logic 2438. According to one embodiment of the invention ready signal 2477 may be an output of logic 2438. According to one embodiment of the invention solenoid control signal 2321 may be an output of logic 2438. According to one embodiment of the invention antenna switch signal 2481 may be an output of logic 2438. According to one embodiment of the invention PWM control signal 2405 may be an output of logic 2438. According to one embodiment of the invention mute signal 2411 may be an output of logic 2438. According to one embodiment of the invention antenna switch signal 2490 may be an input to fault logic 2434. According to one embodiment of the invention fault signal 2475 may be an output of fault logic 2434. According to one embodiment of the invention fault signal 2475 may be an input to logic 2438 and timers state machine 2440. According to one embodiment of the invention serial signal 2445 may be connected to interface 2420.

According to one embodiment of the invention controller 2302 and microwave chain 2403 may include a pulse width modulation (PWM) servo providing feedback to control the power output of amplifier 2306. According to one embodiment of the invention a pulse width modulation servo may control switch 2402 (which may be a pin diode switch), attenuators 2408b and 2408c, power detectors 2409a and 2409b and converter circuitry in controller 2302. According to one embodiment of the invention power output may be controlled by controlling the duty cycle of signal input to amplifier 2306. According to one embodiment of the invention the input power to amplifier 2306 may be maintained through the delivery cycle to ensure stability and linearity in amplifier 2306.

According to one embodiment of the invention controller 2302 generates PWM control signal 2405 to switch 2402 for the purpose of controlling power out of microwave chain 2403. According to one embodiment of the invention controller 2302 works by taking power control signal 2453 (which may be, for example an input reference voltage) from power control knob 2454 on front panel 2305. According to one embodiment of the invention when the user initializes power by pressing start button 2464, power control signal 2453 is used by controller 2302 to generate the requested forward power. According to one embodiment of the invention after a short time the duty cycle circuit will operate according to measured feedback from forward power detector 2409b. According to one embodiment of the invention a comparison of the actual measured forward power signal 2415 against the requested forward power will be carried out. According to one embodiment of the invention controller 2302 shall make small adjustments to PWM control signal 2405 in order to maintain the forward power out of microwave chain 2403 within specification to the requested forward power setting. According to one embodiment of the invention of PWM control signal 2405 may be between approximately 7.0 KHz and approximately 7.5 KHz and preferably approximately 7.2 KHz. According to one embodiment of the invention of PWM control signal 2405 may be approximately 100 percent.

According to one embodiment of the invention forward power look-up table 2414 and conditioning circuitry 2410a (which may include filtering and amplification circuitry) conditions the voltage from power detector 2409b in order to produce a characteristic measurement of forward power. According to one embodiment of the invention forward power look-up table 2414 and conditioning circuitry 2410a outputs a signal for downstream circuitry to either record the measured forward power, or to make control and safety decisions. According to one embodiment of the invention forward power look-up table 2414 and conditioning circuitry 2410a to produce an output voltage signal representing the measured forward power. According to one embodiment of the invention forward power look-up table 2414 may be calibrated to compensate for the characteristics of individual power detectors 2409b and amplifiers 2306. According to one embodiment of the invention reverse power look-up table 2416 may be specifically calibrated to compensate for the characteristics of individual power detector 2409a and amplifier 2306.

Figure 50:
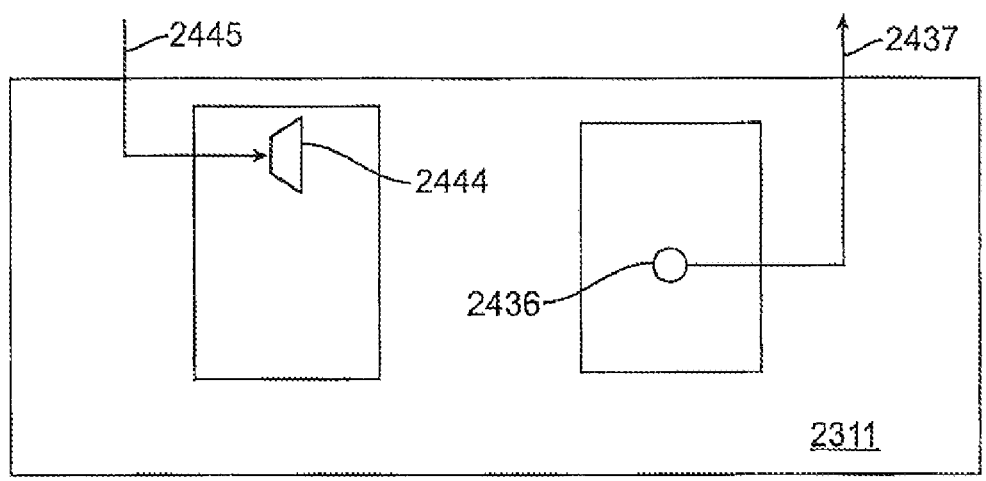
FIG. 50 is a schematic diagram of a back panel according to one embodiment of the invention.

FIG. 50 is a schematic diagram of back panel 2311 according to one embodiment of the invention. According to one embodiment of the invention back panel 2311 includes foot switch connector 2436 and serial interface connector 2444. According to one embodiment of the invention foot switch connector 2436 may be connected to foot pedal signal 2437. According to one embodiment of the invention serial interface connector 2444 may be connected to serial signal 2445.

Figure 51:
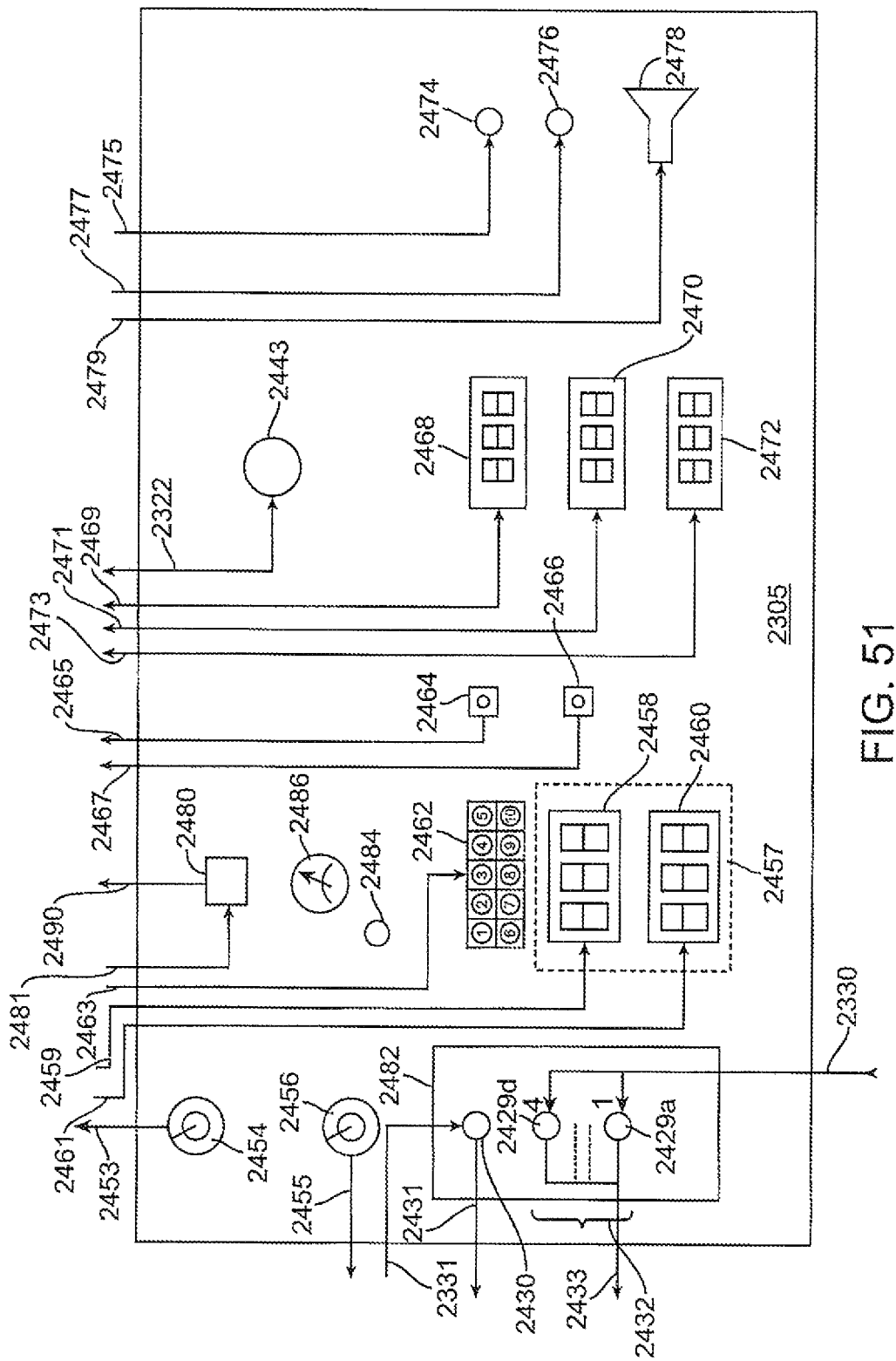
FIG. 51 is a schematic diagram of a front panel according to one embodiment of the invention.

FIG. 51 is a schematic diagram of front panel 2305 according to one embodiment of the invention. According to one embodiment of the invention front panel 2305 may include power control knob 2454, vacuum control knob 2456, temperature connector 2482, antenna switch connector 2480, vacuum meter 2486, vacuum port connector 2484, antenna select switch 2462, temperature display 2457, start button 2464, stop button 2466, microwave output connector 2443, pre-cool timer 2468, energy timer 2470, post-cool timer 2472, fault indicator 2474, ready indicator 2476 and buzzer 2478. According to one embodiment of the invention temperature connector 2482 may include coolant temperature connector 2430 and one or more antenna temperature connector 2429. According to one embodiment of the invention antenna temperature connector 2429 may include antenna temperature connector 2429a through antenna temperature connector 2429d. According to one embodiment of the invention temperature display 2457 may include antenna temperature display 2458 and coolant temperature display 2460.

According to one embodiment of the invention a user interface may be a generator front panel 2305 including user input controls (such as, for example power control knob 2454, vacuum control knob 2456, start button 2464 and stop button 2466, antenna select switch 2462, pre-cool timer 2468, energy timer 2470 and post-cool timer 2472), user feedback (such as, for example vacuum meter 2486, antenna select switch 2462, temperature display 2457, pre-cool timer 2468, energy timer 2470 and post-cool timer 2472) and connectors (such as, for example, temperature connector 2482, vacuum port connector 2484, antenna switch connector 2480 and microwave output connector 2443). According to one embodiment of the invention tissue temperature is measured for each selected waveguide antenna 2364 and displayed on front panel 2305 by antenna temperature display 2458 during energy delivery. According to one embodiment of the invention coolant temperature is continuously measured and displayed on front panel 2305 by coolant temperature display 2460 during energy delivery. According to one embodiment of the invention waveguide antennas 2364 may be selected for microwave energy delivery from front panel 2305 by engaging the appropriate antenna select buttons, such as, for example, energy select buttons associated with antenna select switch 2462. According to one embodiment of the invention energy may be delivered to each selected waveguide antenna 2364 for a predetermined energy timer period.

According to one embodiment of the invention a user interface, such as, for example, generator front panel 2305 may provide user feedback. According to one embodiment of the invention user feedback may include a display of cooling plate temperature (which may be indicative of skin temperature, for each waveguide antenna in the waveguide array using, for example antenna temperature display 2458. According to one embodiment of the invention user feedback may include a display of cooling fluid temperature in the applicator at the output of the cooling fluid path using, for example, coolant temperature display 2460. According to one embodiment of the invention user feedback may include an indication of the vacuum pressure at the vacuum output using, for example, vacuum meter 2486. According to one embodiment of the invention user feedback may include a ready indicator, indicating when the system is ready to use, such as, for example ready indicator 2476. According to one embodiment of the invention user feedback may include a fault indicator, indicating when a fault has occurred, such as, for example, fault indicator 2474. According to one embodiment of the invention antenna temperature display 2458 reports the temperature at the cooling plate thermocouple 2395 positioned under the first active connected waveguide antenna 2364 prior to initiating a therapy cycle. According to one embodiment of the invention temperature measured at cooling plate thermocouple 2395 may be indicative of the temperature of the skin surface underlying the tissue bio-barrier 2337 adjacent cooling plate thermocouple 2395. According to one embodiment of the invention temperature measured at cooling plate thermocouple 2395 may be proportional to the temperature of the skin surface underlying the tissue bio-barrier 2337 adjacent cooling plate thermocouple 2395. According to one embodiment of the invention once a therapy cycle is initiated, antenna temperature display 2458 reports the temperature of the tissue under each waveguide antenna 2364 as it is activated and, once the therapy cycle is complete, the antenna temperature display 2458 continues to show the tissue temperature under the last active waveguide antenna 2364.

According to one embodiment of the invention power control signal 2453 may be an output from power control knob 2454. According to one embodiment of the invention vacuum control input signal 2455 may be an output from vacuum control knob 2456. According to one embodiment of the invention coolant thermocouple wires 2331 may be an input to coolant temperature connector 2430. According to one embodiment of the invention coolant temperature signal 2431 may be an output from coolant temperature connector 2430. According to one embodiment of the invention cooling plate thermocouple wires 2330 may be an input to antenna temperature connector 2429. According to one embodiment of the invention antenna thermocouple cable 2433 may be an output from antenna temperature connector 2429. According to one embodiment of the invention antenna switch signal 2481 may be an input to antenna switch connector 2480. According to one embodiment of the invention antenna switch signal 2490 may be an output from antenna switch connector 2480. According to one embodiment of the invention antenna select signal 2463 may be an input to and output from antenna select switch 2462. According to one embodiment of the invention filtered antenna temperature signal 2459 may be an input to antenna temperature display 2458. According to one embodiment of the invention filtered coolant temperature signal 2461 may be an input to coolant temperature display 2460. According to one embodiment of the invention start signal 2465 may be an input to and output from start button 2464. According to one embodiment of the invention stop signal 2467 may be an input to and output from stop button 2466. According to one embodiment of the invention energy cable 2322 may be an input to microwave output connector 2443. According to one embodiment of the invention pre-cool time signal 2469 may be an input to and output from pre-cool timer 2468. According to one embodiment of the invention energy timer signal 2471 may be an input to energy timer 2470. According to one embodiment of the invention post-cool timer signal 2473 may be an input to and output from post-cool timer 2472. According to one embodiment of the invention fault signal 2475 may be an input to fault signal 2474. According to one embodiment of the invention ready signal 2477 may be an input to ready indicator 2476. According to one embodiment of the invention buzzer signal 2479 may be an input to buzzer 2478.

Figure 52:
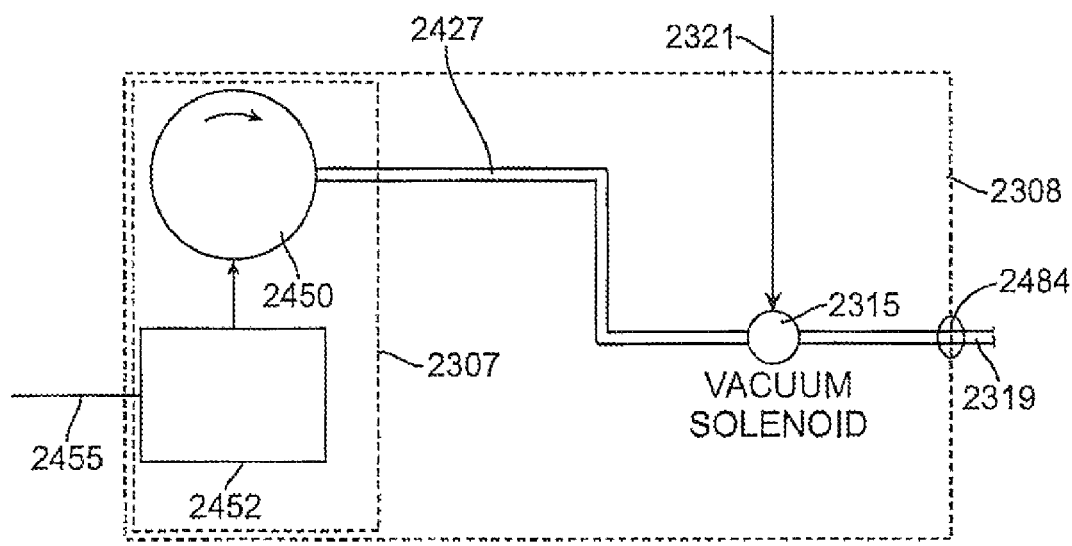
FIG. 52 is a schematic diagram of vacuum source according to one embodiment of the invention.

FIG. 52 is a schematic diagram of vacuum source 2308 according to one embodiment of the invention. According to one embodiment of the invention vacuum source 2308 may include vacuum solenoid 2315 and vacuum pump/drive 2307. According to one embodiment of the invention vacuum pump/drive 2307 may include variable voltage drive 2452 and vacuum pump 2450. According to one embodiment of the invention vacuum control input signal 2455 may be an input to variable voltage drive 2452 and solenoid control signal 2321 may be an input to vacuum solenoid 2315. According to one embodiment of the invention solenoid control signal 2321 may be an input to vacuum solenoid 2315. According to one embodiment of the invention vacuum pump/drive 2307 may be connected to vacuum solenoid 2315 by tubing 2427.

Figure 53:
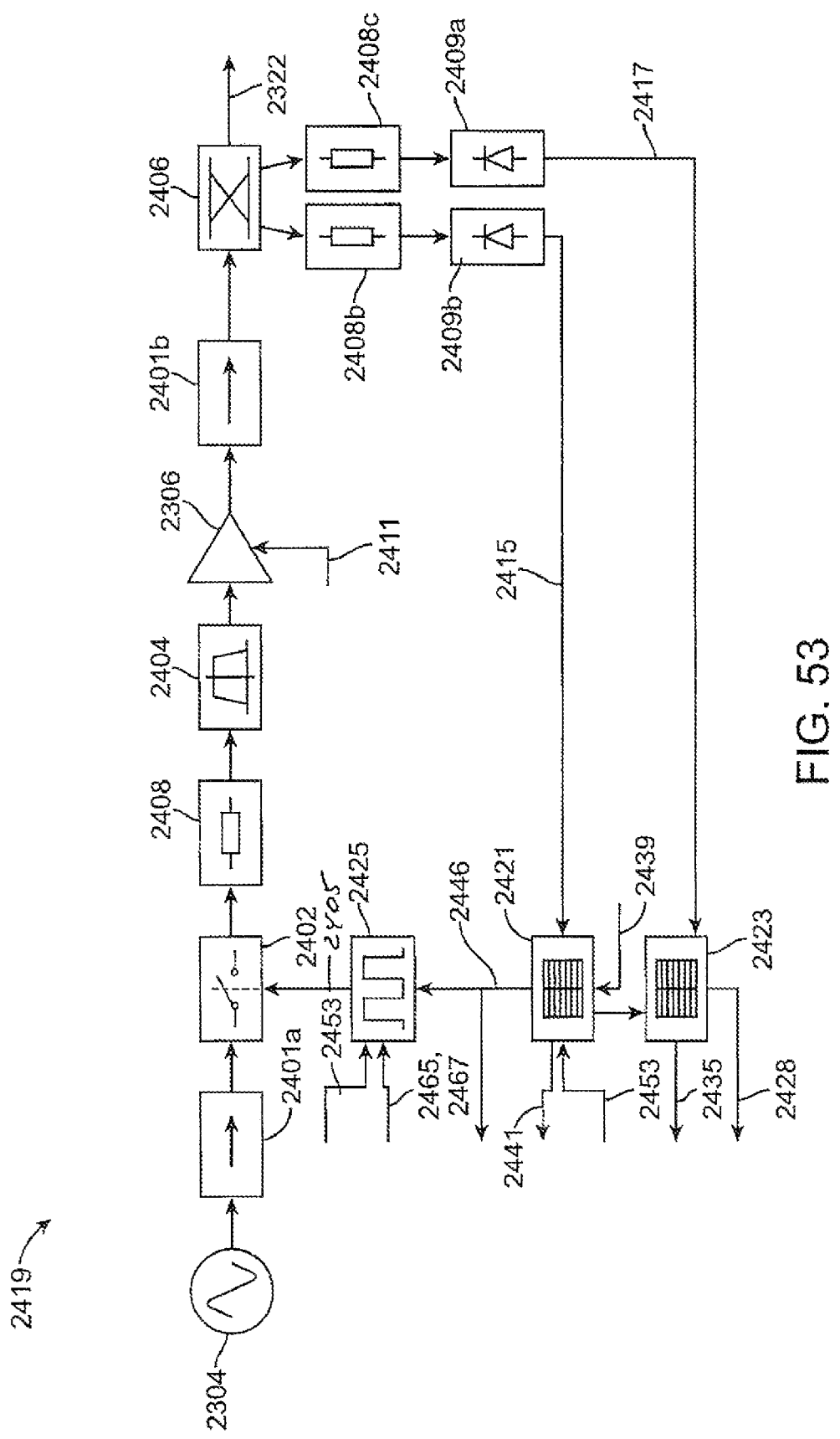
FIG. 53 is a schematic diagram of a microwave control circuit according to one embodiment of the invention.
Figure 54:
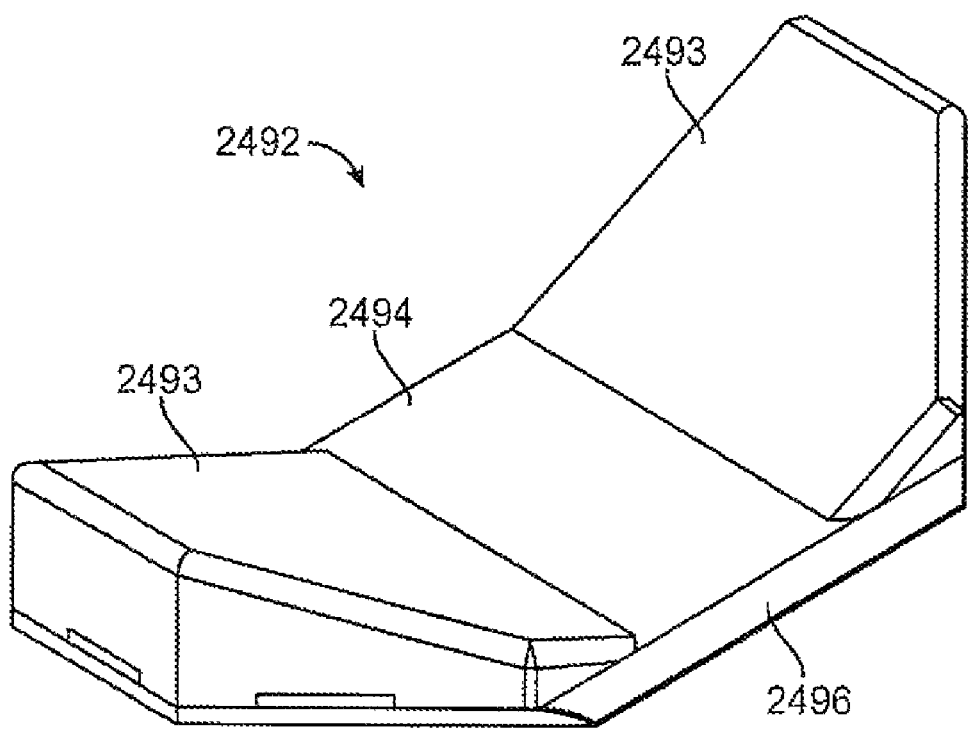
FIGS. 54 to 58 are schematic diagrams of a patient positioning apparatus according to one embodiment of the invention.
Figure 55:
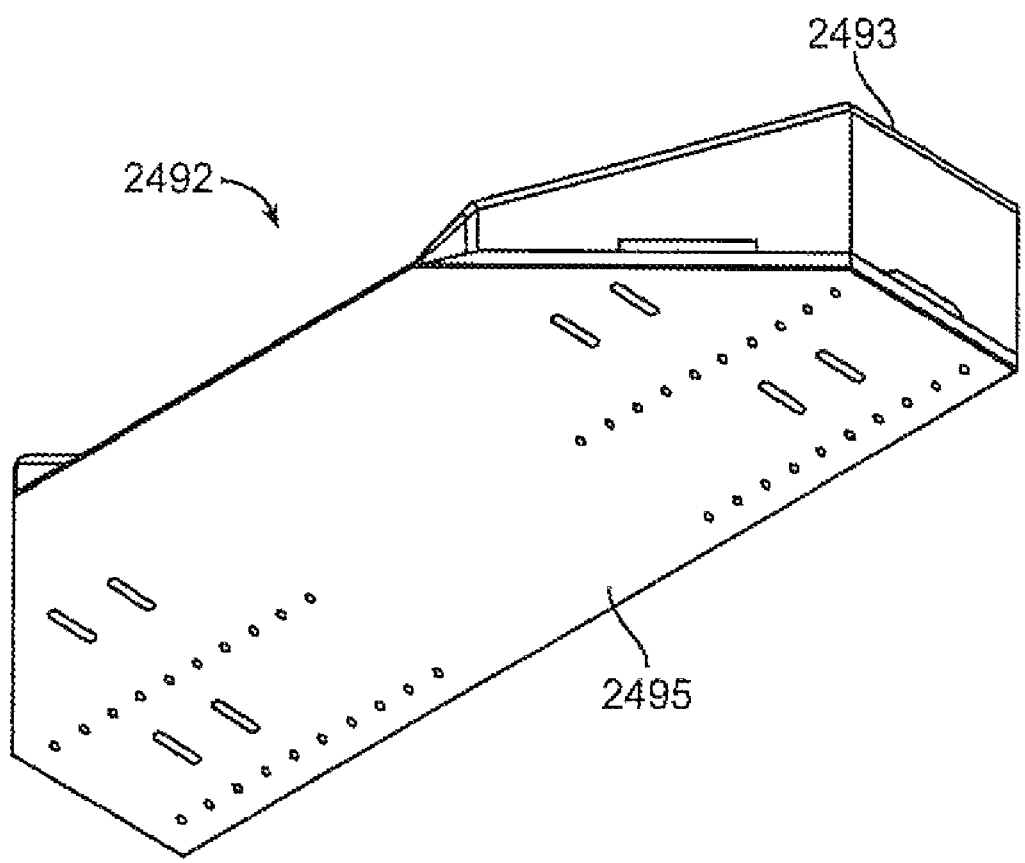
Figure 56:
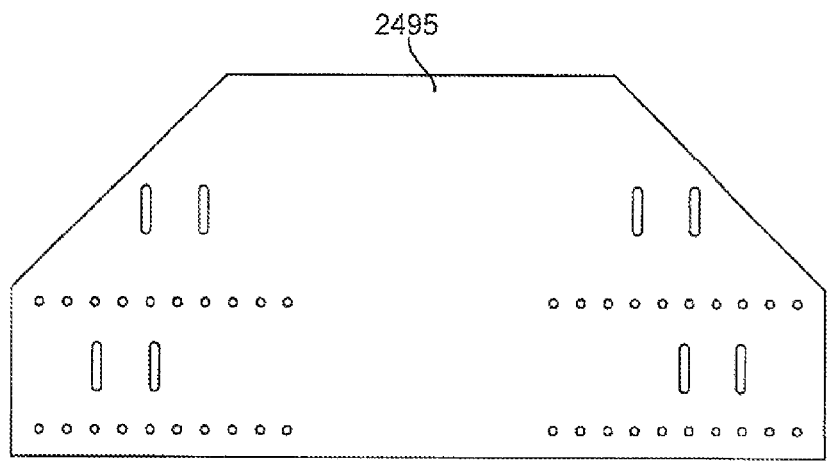
Figure 57:
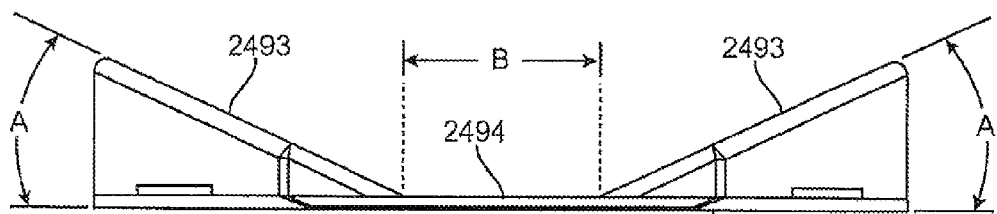
Figure 58:
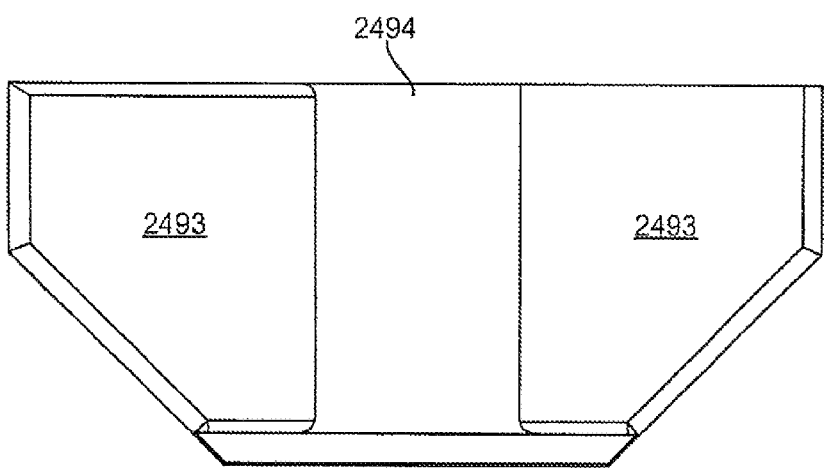

FIG. 53 is a schematic diagram of a microwave control circuit 2419 according to one embodiment of the invention. According to one embodiment of the invention microwave control circuit may be a pulse width modulation (PWM) control circuit adapted to control energy output at 2322. According to one embodiment of the invention microwave control circuit 2419 may include oscillator 2304, isolator 2401a, switch 2402, attenuator 2408a, bandpass filter 2404, amplifier 2306, isolator 2401b and directional coupler 2406. According to one embodiment of the invention mute signal 2411 may be an input to amplifier 2306. According to one embodiment of the invention microwave control circuit 2419 may have an output energy cable 2322 which may carry microwave energy to an applicator 2320. According to one embodiment of the invention microwave control circuit 2419 may include attenuators 2408b and 2408c, power detectors 2409a and 2409b. According to one embodiment of the invention an output of power detector 2409a may be reverse power signal 2417. According to one embodiment of the invention an output of power detector 2409b may be forward power signal 2415. According to one embodiment of the invention reverse power signal 2417 may be an input to reverse power lookup table and conditioning circuitry 2423. According to one embodiment of the invention reverse power lookup table and conditioning circuitry 2423 may output reverse power error signal 2428. According to one embodiment of the invention reverse power lookup table and conditioning circuitry 2423 may output reverse power reading 2435. According to one embodiment of the invention forward power signal 2415 may be an input to forward power lookup table and conditioning circuitry 2421. According to one embodiment of the invention energy delivery on/off signal 2439 may be an input to forward power look-up table and conditioning circuitry 2421. According to one embodiment of the invention power control signal 2453 may be an input to forward power look-up table and conditioning circuitry 2421. According to one embodiment of the invention forward power look-up table and conditioning circuitry 2421 may have an input to reverse power lookup table and conditioning circuitry 2423. According to one embodiment of the invention forward power look-up table and conditioning circuitry 2421 may output forward output power error 2441. According to one embodiment of the invention forward power look-up table and conditioning circuitry 2421 may output forward output power error 2441. According to one embodiment of the invention forward power look-up table and conditioning circuitry 2421 may output forward power signal 2446. According to one embodiment of the invention forward power look-up table and conditioning circuitry 2421 may output forward power signal 2446 to duty cycle circuit 2425. According to one embodiment of the invention power control signal 2453 and start signal 2465 may be inputs to duty cycle circuit 2425. According to one embodiment of the invention two modules, using forward power look-up table and conditioning circuitry 2421 and reverse power look-up table and conditioning circuitry 2423 to convert forward and reverse power readings to usable control signals and fault signals. According to one embodiment of the invention a look-up table is included in reverse power look-up table and conditioning circuit 2423 to produce the output voltage signal representing the measured reverse power. According to one embodiment of the invention each look-up table in reverse power look-up table and conditioning circuit 2423 is calibrated to the diode and amplifier in the circuit.

FIGS. 54 to 58 are schematic diagrams of a patient positioning apparatus 2492 according to one embodiment of the invention. According to one embodiment of the invention patient positioning apparatus 2492 includes arm supports 2493. According to one embodiment of the invention patient positioning apparatus 2492 includes center support 2494. According to one embodiment of the invention patient positioning apparatus 2492 includes base 2495. According to one embodiment of the invention patient positioning apparatus 2492 includes head rest 2496. According to one embodiment of the invention patient positioning apparatus 2492 may be used to properly position the patient. According to one embodiment of the invention, according to one embodiment of the invention arm supports 2493 may form an angle (A) of between approximately 15 degrees and approximately 35 degrees with center support 2494. According to one embodiment of the invention, according to one embodiment of the invention arm supports 2493 may form an angle of approximately twenty-five degrees with center support 2494. According to one embodiment of the invention, according to one embodiment of the invention patent positioning apparatus 2492 may have a dimension (B) of approximately 22 centimeters between arm supports 2493. According to one embodiment of the invention patient positioning apparatus 2492 may further include a disposable cover (not shown) which may be changed for each patient.

Figure 59:
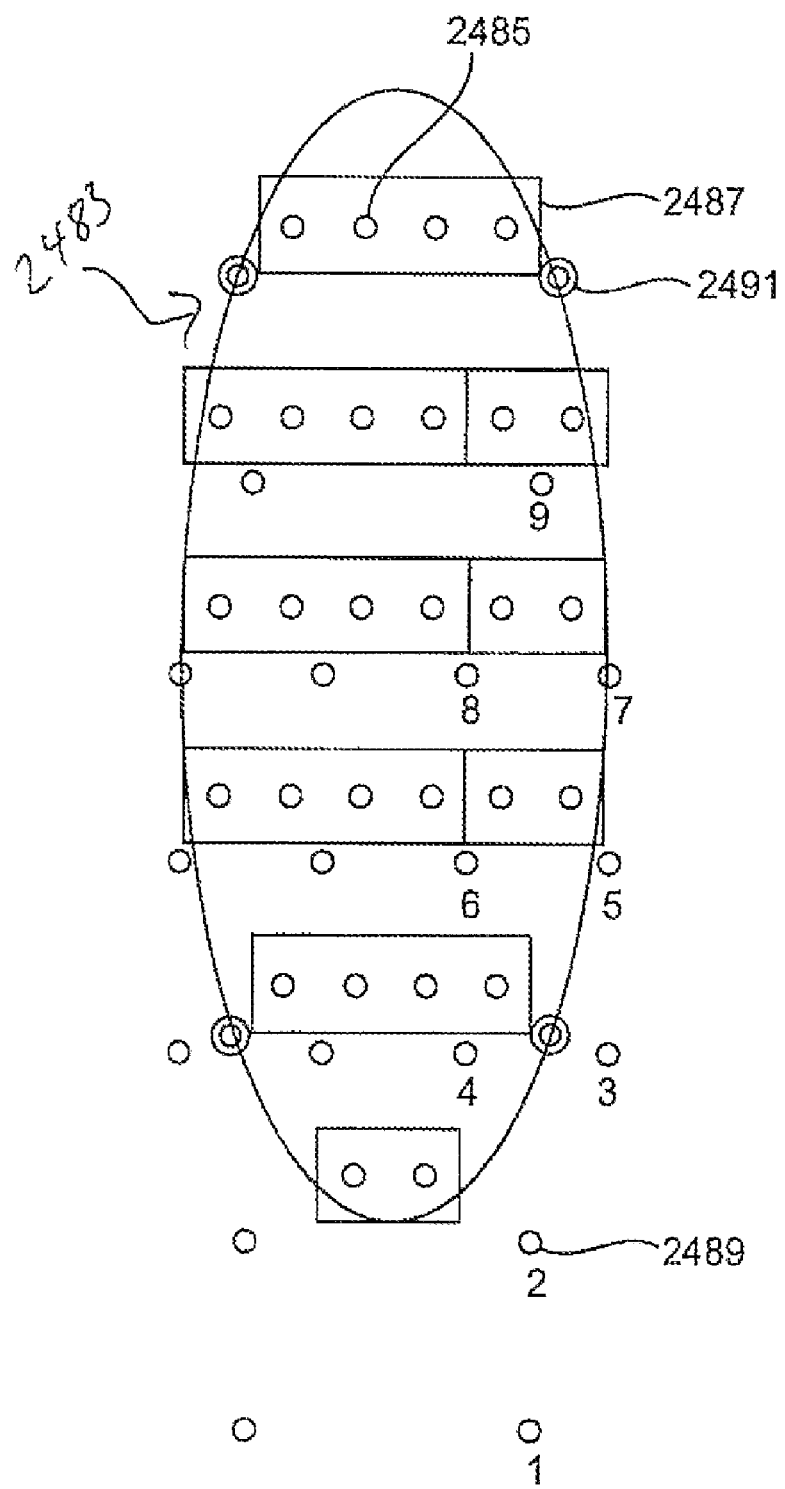
FIG. 59 is a schematic diagram of a treatment template according to one embodiment of the invention.

FIG. 59 is a schematic diagram of a treatment template 2483 according to one embodiment of the invention. According to one embodiment of the invention treatment template 2483 may be a flexible, transparent base. According to one embodiment of the invention a suitable treatment template 2483 may include a number of openings arranged in a predetermined pattern. According to one embodiment of the invention each opening or group of openings may be used to identify a particular treatment element. According to one embodiment of the invention an opening or group of openings, such as, for example, device position sites 2487, may be used to mark an area of the treatment region where applicator 2320 is to be placed. According to one embodiment of the invention an opening or group of openings, such as, for example applicator placement marks 2489, may be used to mark the skin where the applicator alignment features 2352 may be to be positioned. According to one embodiment of the invention an opening or group of openings, such as, for example, anesthesia injection marks 2485 may be used to mark the skin where the anesthesia is to be injected. According to one embodiment of the invention injecting anesthesia under the center of the antenna aperture may increase predictability of the outcome and reduce the amount of fluid needed for each treatment. According to one embodiment of the invention marks on the template may also be used to indicate how many of the antennas in an array may be used according to the position of the applicator on the axilla. According to one embodiment of the invention holes in the template, such as, for example, landmark alignment marks 2491 may also be used to align treatment template 2493 with landmarks (such as, for example tattoos, temporary tattoos, skin tags, skin folds, hair patterns, sharpie marks or moles) on the patient.

Figure 60:
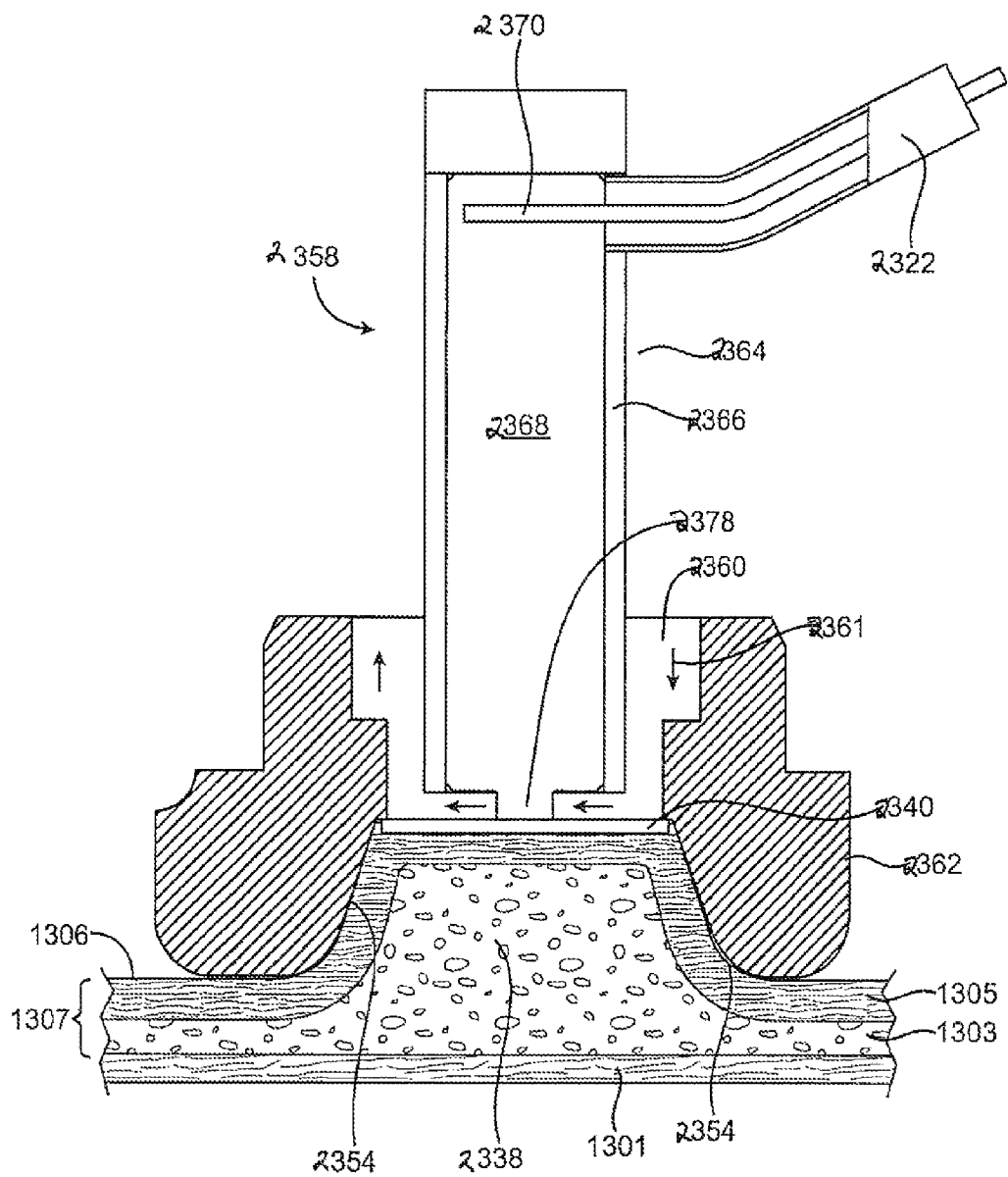
FIG. 60 is simplified cutaway view of a medical treatment device with tissue engaged according to one embodiment of the invention.

FIG. 60 is simplified cutaway view of a medical treatment device 2300 with tissue engaged according to one embodiment of the invention. In the embodiment of the invention illustrated in FIG. 60 skin 1307 is engaged in tissue chamber 2338. In the embodiment of the invention illustrated in FIG. 60 dermis 1305 and hypodermis 1303 are engaged in tissue chamber 2338. In the embodiment of the invention illustrated in FIG. 60, skin surface 1306 is engaged in tissue chamber 2338 such that skin surface 1306 is in contact with at least a portion of chamber wall 2354 and in thermal contact with at least a portion of cooling plate 2340. In the embodiment of the invention illustrated in FIG. 60, skin surface 1306 is engaged in tissue chamber 2338 such that skin surface 1306 is in contact with at least a portion of tissue interface 2336. As illustrated in FIG. 60, a vacuum pressure may be used to elevate dermis 1305 and hypodermis 1303, separating dermis 1305 and hypodermis 1303 from muscle 1301. As illustrated in FIG. 60, vacuum pressure may be used to elevate dermis 1305 and hypodermis 1303, separating dermis 1305 and hypodermis 1303 from muscle 1301 to, for example, protect muscle 1301 by limiting or eliminating the electromagnetic energy which reaches muscle 1301.

Figure 61:
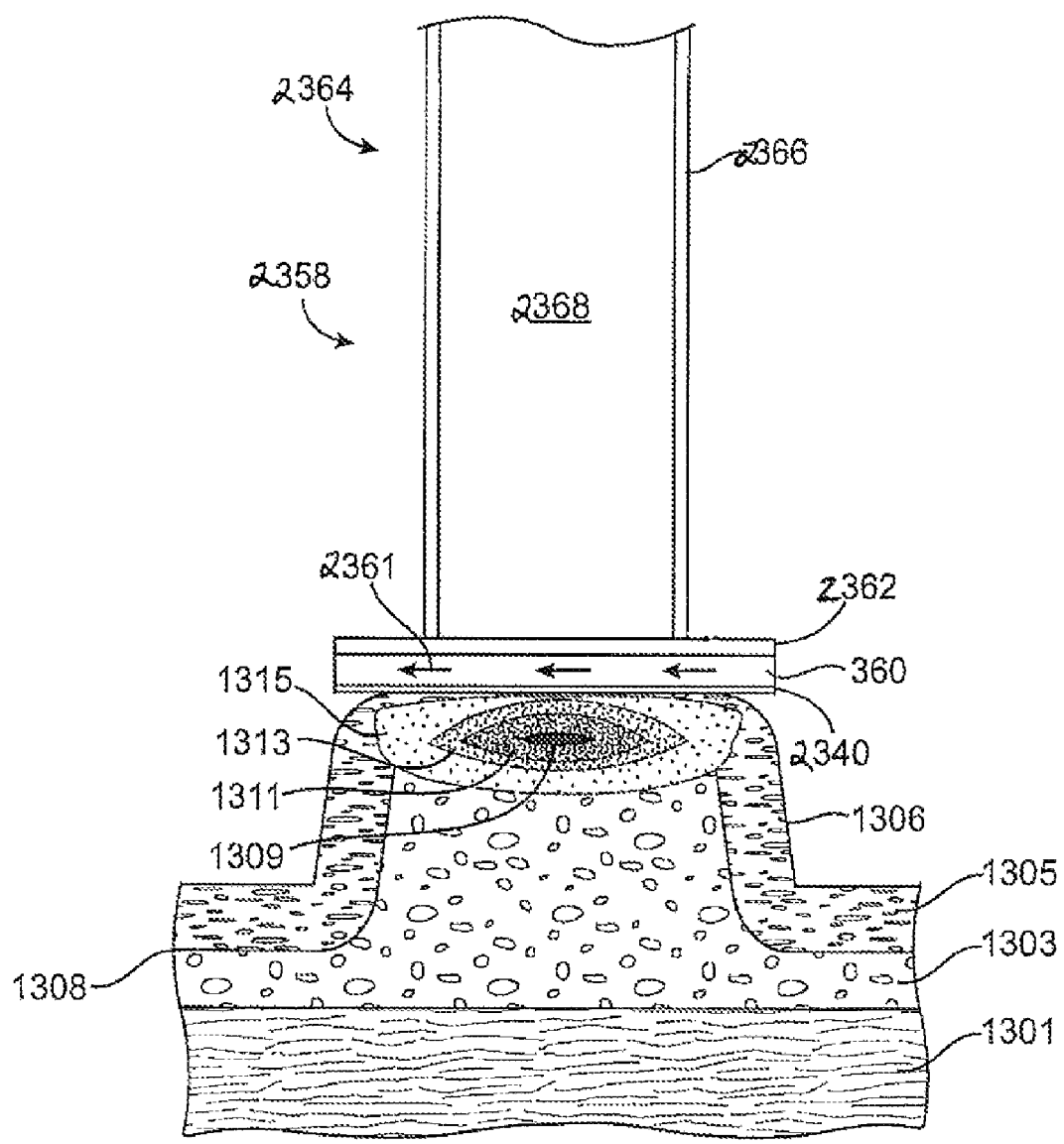
FIG. 61 illustrates a tissue profile and simplified view of a medical treatment device according to one embodiment of the invention.
Figure 62:
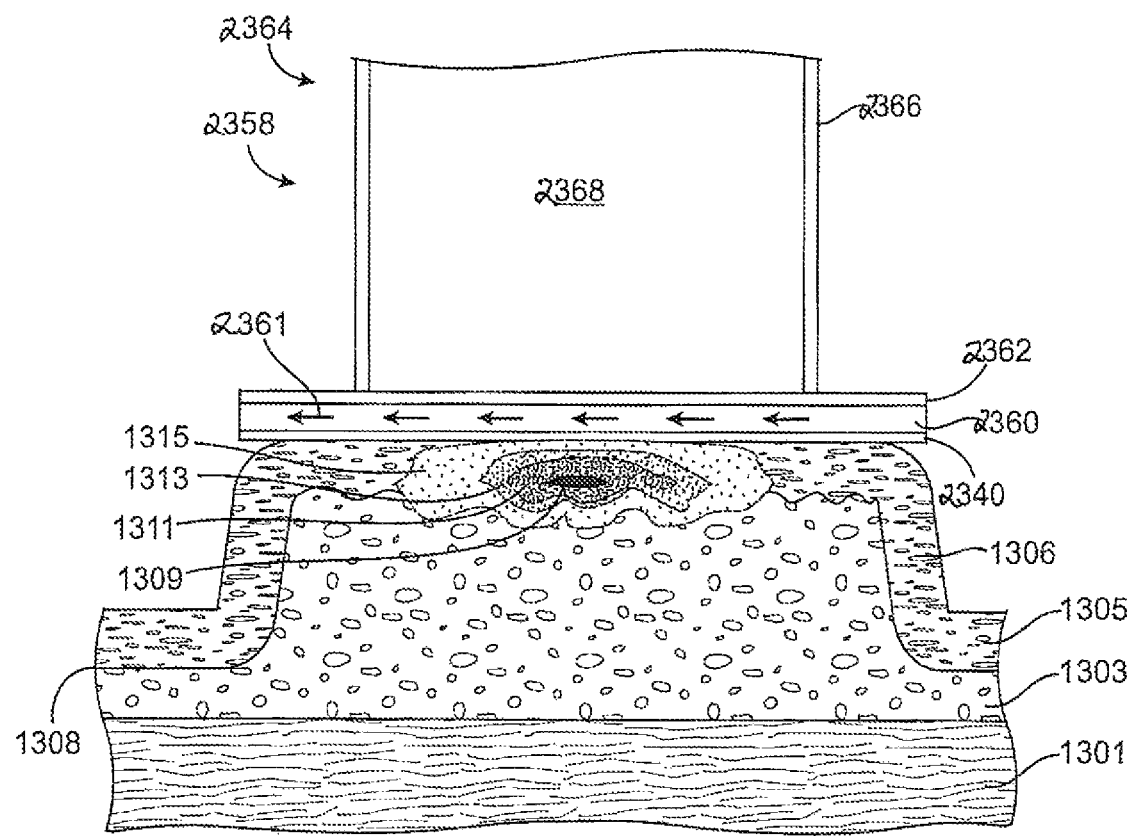
FIG. 62 illustrates a tissue profile and simplified view of a medical treatment device according to one embodiment of the invention.
Figure 63:
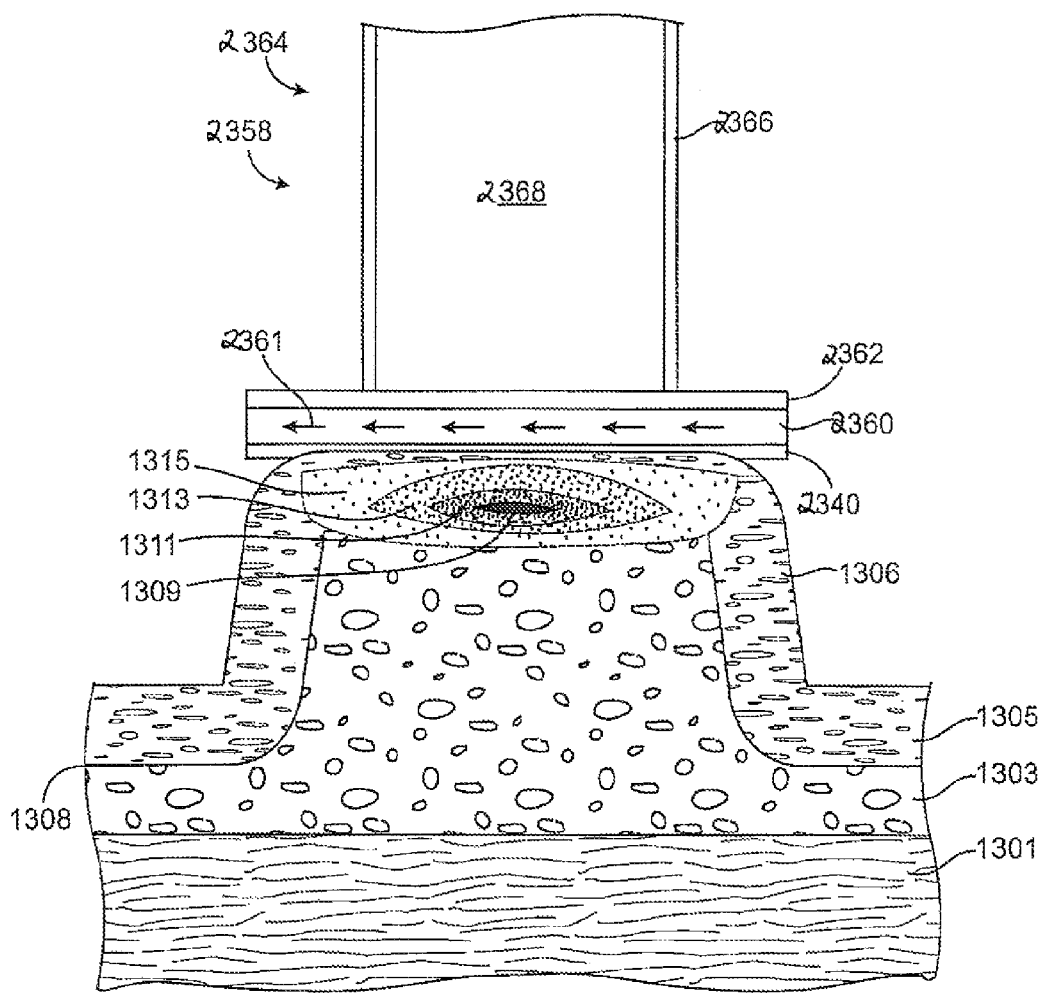
FIG. 63 illustrates a tissue profile and simplified view of a medical treatment device according to one embodiment of the invention.
Figure 64:
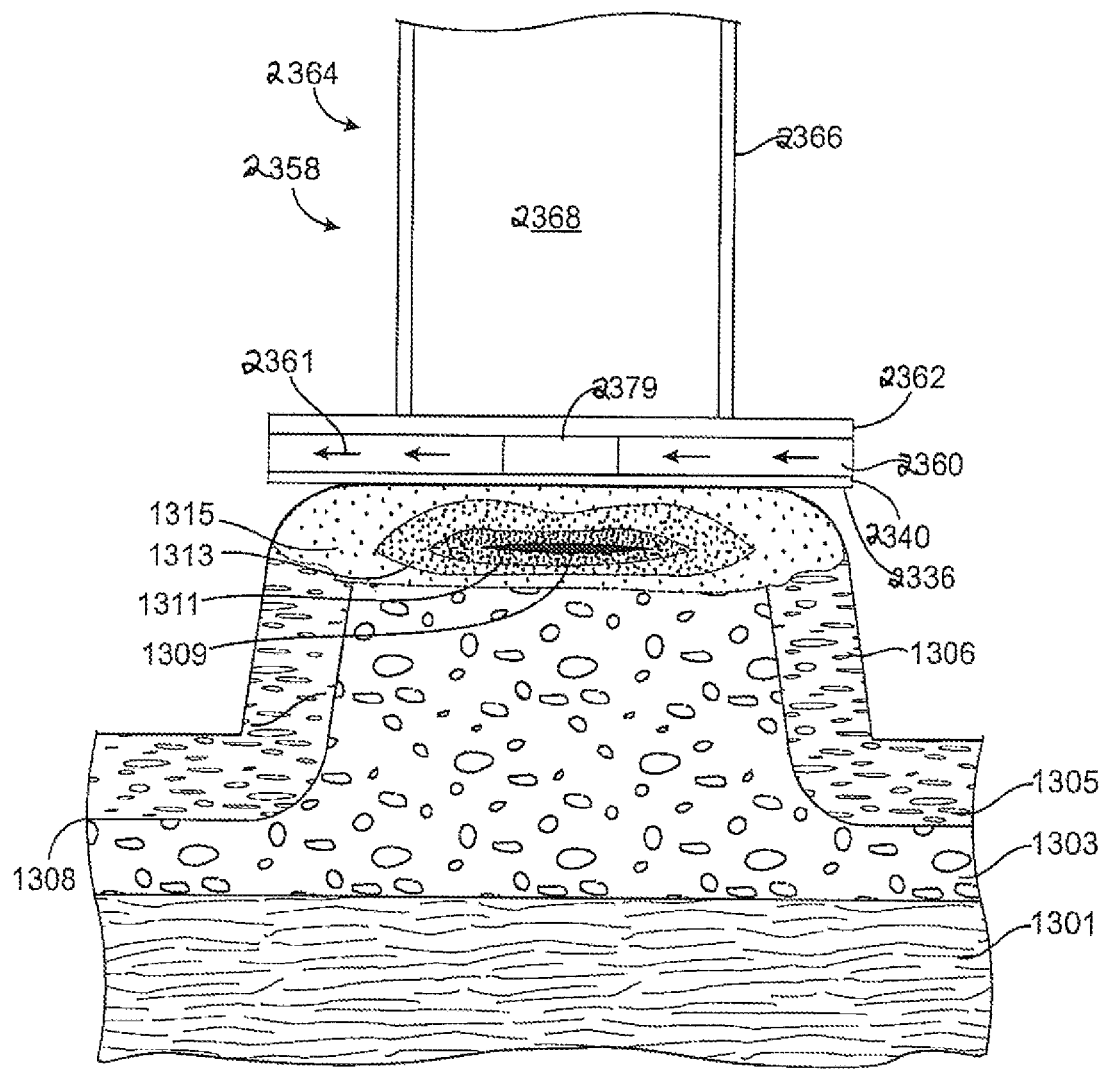
FIG. 64 illustrates a tissue profile simplified view of a medical treatment device according to one embodiment of the invention.

FIGS. 61 through 64 illustrate tissue profiles and a simplified diagram of a medical treatment device 2300 according to embodiments of the invention. According to one embodiment of the invention waveguide assembly 2358 may include waveguide antenna 2364. According to one embodiment of the invention electromagnetic energy, such as, for example, microwave energy may be radiated into dermis 1305 through tissue head 2362 which may be, for example an integrated or attached disposable 2363. According to one embodiment of the invention medical treatment device 2300 may include coolant chamber 2360 and cooling plate 2340. In the embodiment of the invention illustrated in FIGS. 61 through 64, a peak which may be, for example, a peak SAR, peak power loss density or peak temperature, is generated in first tissue region 1309. In the embodiment of the invention illustrated in FIGS. 61 through 64, a reduced magnitude which may be, for example, a reduced SAR, reduced power loss density or reduced temperature, is generated in second tissue region 1311 with further reduced magnitudes in third tissue region 1313 and fourth tissue region 1315. As illustrated in FIGS. 61 through 64 dermis 1305 is separated from hypodermis 1303 by interface 1308. As illustrated in FIGS. 61, 63 and 64 interface 1308 may be idealized as a substantially straight line for the purposes of simplified illustration, however, as illustrated in FIG. 64, in actual tissue, interface 1308 may be a non-linear, non continuous, rough interface which may also include many tissue structures and groups of tissue structures which cross and interrupt tissue interface 1308. As illustrated in FIGS. 61 through 64, hypodermis 1303 lies over muscle tissue 1301. According to one embodiment of the invention electromagnetic radiation may be radiated at a frequency of, for example, between 5 and 6.5 GHz. According to one embodiment of the invention electromagnetic radiation may be radiated at a frequency of, for example, approximately 5.8 GHz. According to one embodiment of the invention field spreader 2379 (which may be, for example a scattering element 2378) may be located in coolant chamber 2360. In embodiments of the invention, such as, for example, the embodiment illustrated in FIG. 64 field spreader 2379 may be used to, for example, spread and flatten first tissue region 1309. In the embodiment of the invention illustrated in FIG. 64 field spreader 2379 may be used to, for example, spread and flatten lesions formed in first tissue region 1309. According to one embodiment of the invention the creation of lesions, such as, for example, the lesions illustrated in FIGS. 61 through 64 may be used to treat the skin of patients. According to one embodiment of the invention the creation of lesions, such as, for example, the lesions illustrated in FIGS. 61 through 64 may be used to damage or destroy structures, such as, for example, sweat glands in the skin of a patient.

According to one embodiment of the invention disposable 2363 includes a number of advantageous features. According to one embodiment of the invention vacuum pressure may be evenly distributed to either side of tissue bio-barrier 2337. According to one embodiment of the invention vacuum pressure may be evenly distributed to tissue chamber 2338 and the applicator chamber 2346 when equilibrium is achieved. According to one embodiment of the invention use of a stretchable tissue bio-barrier 2337 and vacuum balance ensures that tissue bio-barrier 2337 will conform to the distal end of applicator 2320 to prevent air bubbles from forming between tissue bio-barrier 2337 and the distal end of applicator 2320. According to one embodiment of the invention use of a stretchable tissue bio-barrier 2337 and vacuum balance ensures that tissue bio-barrier 2337 will conform to the distal side of cooling plate 2340 to prevent air bubbles from forming between tissue bio-barrier 2337 and the distal side of cooling plate 2340. According to one embodiment of the invention vacuum balance ensures that tissue bio-barrier 2337 is sealed to both the distal end of applicator 2320 and the surface of skin engaged in tissue chamber 2338, reducing or eliminating air pockets which can cause unwanted perturbations in the microwave field. According to one embodiment of the invention vacuum balance ensures that tissue bio-barrier 2337 is sealed to both the distal side of cooling plate 2340 and the surface of skin engaged in tissue chamber 2338, reducing or eliminating air pockets which can cause unwanted perturbations in the microwave field.

According to one embodiment of the invention stretching tissue bio-barrier 2337 ensures that it lies flat against the distal end of applicator 2320. According to one embodiment of the invention tissue bio-barrier 2337 stretches to form a substantially wrinkleless interface with the distal end of applicator 2320. According to one embodiment of the invention stretching tissue bio-barrier 2337 creates an interference fit between tissue bio-barrier 2337 and the distal end of applicator 2320. According to one embodiment of the invention extending the distal end of applicator 2320 into tissue chamber 2338 stretches tissue bio-barrier 2337 and ensures an interference fit between tissue bio-barrier 2337 and the distal end of applicator 2320. According to one embodiment of the invention applicator 2320 may be recessed into the applicator chamber by up to approximately 0.020 inches. According to one embodiment of the invention the distal end of applicator 2320 may extend between zero and 0.030 and preferably approximately 0.010 inches into tissue chamber 2338 to stretch tissue bio-barrier 2337 and create an interference fit between the distal end of applicator 2320 and tissue bio-barrier 2337. According to one embodiment of the invention the combination of an interference fit and vacuum in the applicator chamber 2346 minimizes air pockets, folds and wrinkles which might otherwise occur in stretchable tissue bio-barrier 2337.

According to one embodiment of the invention biological fluids may be isolated from the generator 2301 by generator bio-barrier 2317. According to one embodiment of the invention biological fluids may be isolated from applicator 2320 by applicator bio-barrier 2332. According to one embodiment of the invention biological fluids may be isolated from applicator 2320 by tissue bio-barrier 2337. According to one embodiment of the invention applicator bio-barrier 2332 provides isolation between tissue chamber 2338 and applicator 2320, allowing air to pass but preventing biological or other (e.g. KY Jelly) fluids from reaching applicator 2320. According to one embodiment of the invention vacuum baffles 2343 and circuitous path in vacuum circuit 2341 help to isolate biological or other fluids from applicator bio-barrier 2332. According to one embodiment of the invention the combination of applicator bio-barrier 2332, a circuitous path in vacuum circuit 2341, vacuum baffles 2343 and the placement of vacuum passages 2333 before the vacuum baffles 2343 prevent back pressure (which may happen, for example, when the vacuum is terminated by venting the vacuum tube to atmospheric pressure) from forcing biological or other fluids into the applicator chamber 2346. According to one embodiment of the invention applicator bio-barrier 2332 may be a hydrophobic filter available from Harrington Plastics with a pore size of between approximately 0.1 micrometer and 1.0 micrometers of approximately 0.45 micrometers.

According to one embodiment of the invention Applicator 2320 includes a number of advantageous features. According to one embodiment of the invention antenna array 2355 facilitates the creation of a large lesion or lesion region with a single placement of applicator 2320. According to one embodiment of the invention antenna array 2355 facilitates the creation of a lesion of up to approximately thirty millimeters by approximately eight millimeters in cross section. According to one embodiment of the invention the creation of contiguous lesions may be facilitated by rapidly switching microwave energy between waveguide antennas 2364 in antenna array 2355. According to one embodiment of the invention the creation of non-contiguous lesions may be facilitated by the application of microwave energy to selected waveguide antennas 2364 in antenna array 2355. According to one embodiment of the invention the creation of lesions under a portion of tissue interface surface 2336 may be facilitated by the application of microwave energy to selected waveguide antennas 2364 in antenna array 2355. According to one embodiment of the invention antenna array 2355 may be used to selectively develop lesions where the user wants them.

According to one embodiment of the invention generator 2301 includes a number of advantageous features. According to one embodiment of the invention generator 2301 will not initiate or will discontinue treatment when it detects fault conditions such as, for example, when: energy cable 2322 is not connected, one or more cooling plate thermocouples 2395 or cooling path thermocouple 2326 are not connected; temperature measured at one or more of cooling plate thermocouples 2395 exceeds a predetermined limit such as, for example 45 degrees centigrade; the temperature measured at cooling path thermocouple 2326, which may be indicative of the temperature of coolant chamber 2360 exceeds a predetermined limit such as, for example 45 degrees centigrade; there is fault in amplifier 2306; reflected power exceeds a predetermined limit, such as, for example, 19.5 Watts. According to one embodiment of the invention generator 2301 will not initiate or will discontinue treatment when it detects fault conditions in the PWM servo circuit such as, for example, when: power out of microwave chain 2403 is not maintained within a predetermined window; power out of microwave chain 2403 is not set within 400 ms of command; power out of microwave chain 2403 is not maintained within a predetermined range such as, for example plus or minus 13 Watts of requested power; the ratio of reflected to forward power measured at directional coupler 2406 exceeds a predetermined limit. According to one embodiment of the invention generator 2301 will not initiate or will discontinue treatment when it detects fault conditions such as, for example, when: the rate of temperature increase or decrease measured at one or more of cooling plate thermocouples 2395 or cooling path thermocouple 2325 exceeds a predetermined limit; the rate increase or decrease of temperature measured at one or more of cooling plate thermocouples 2395 or cooling path thermocouples 2325 exceeds a predetermined limit. According to one embodiment of the invention generator 2301 may be capable of delivering output power in the range of 40 to 100 Watts. According to one embodiment of the invention generator 2301 may be capable of increasing or decreasing output power in increments of 5 Watts. According to one embodiment of the invention generator 2301 may be capable of maintaining an accuracy of plus or minus 3 Watts within the output power range. According to one embodiment of the invention generator 2301 may be capable of maintaining an output frequency of 5.8 GHz plus or minus approximately 25 KHz. According to one embodiment of the invention chiller 2310 may be capable of controlling the temperature of cooling fluid 2361 within a range of approximately −5 to approximately 600 C with an accuracy of approximately plus or minus 2.50 C.

According to one embodiment of the invention the invention includes a patient positioning procedure According to one embodiment of a procedure according to the invention a patient may be positioned in a supine position, using, for example, patient positioning apparatus 2492. According to one embodiment of a procedure according to the invention a patient may be positioned by positioning the patient's arm to expose the axilla, by, for example raising the patient's arm and placing the patient's hand under their head. According to one embodiment of a procedure according to the invention the user may identify, or generate, landmarks on the patient's axilla. According to one embodiment of a procedure according to the invention such landmarks may be, for example, moles, freckles scars or other individual characteristics. According to one embodiment of a procedure according to the invention such landmarks may be generated using, for example, a pen, permanent marker, a tattoo or small sterile India ink mark.

According to one embodiment of the invention the invention includes a treatment roadmap. According to one embodiment of a procedure according to the invention once the patient is positioned and suitable landmarks are identified or generated, the landmarks may be used to create a treatment roadmap. According to one embodiment of the invention a treatment roadmap may be created using, for example, a template such as, for example, treatment template 2483. According to one embodiment of a procedure according to the invention treatment template 2483 may be used to identify the position of various roadmap elements of the treatment regimen. According to one embodiment of a procedure according to the invention treatment template 2483 may be used to mark roadmap elements in the treatment region, such as, for example, the axilla with various elements of the treatment region. According to one embodiment of a procedure according to the invention such elements may include, for example, one or more anesthesia injection sites 2485 and one or more device position sites 2487. According to one embodiment of a procedure according to the invention such elements may include, for example, one or more anesthesia injection sites 2485 and one or more applicator placement mark 2489. According to one embodiment of a procedure according to the invention such elements may include, for example, one or more anesthesia injection sites 2485 and one or more landmark alignment marks 2491 (which may be, for example tattoo alignment marks). According to one embodiment of a procedure according to the invention treatment template 2483 may be positioned using identified or created landmarks in the treatment region prior to marking the position of the roadmap elements on the patient's skin. According to one embodiment of a procedure according to the invention marks identifying the roadmap elements may be used to by the physician to guide the treatment regimen.

According to one embodiment of a procedure according to the invention in some instances, there may be a time period, such as, for example several weeks, between treatments, sufficient to require the provision of additional anesthesia prior to continuing to treat a treatment region. According to one embodiment of a procedure according to the invention where there has been an event or a passage of time sufficient to remove or obliterate previously generated marks identifying the roadmap elements, it may be necessary to re-establish those marks, by, for example, aligning treatment template 2483 with previously identified or generated landmarks and re-marking the skin using treatment template 2483. According to one embodiment of a procedure according to the invention photographs of the treatment region may be used to help generate or align treatment template 2483 for subsequent treatments.

According to one embodiment of a procedure according to the invention once the entire treatment region has been treated, areas which require touch ups may be treated by, for example using a touch-up tool which treats only the areas which require touch up.

According to one embodiment of the invention the invention includes an anesthesia procedure. According to one embodiment of a procedure according to the invention treatment regimen may include anesthetizing at least a portion of the treatment region. According to one embodiment of a procedure according to the invention where the treatment regimen includes anesthetizing the area to be treated, anesthesia injection sites 2485 on treatment template 2483 may be used to identify and mark locations in the treatment region where anesthesia is to be injected. According to one embodiment of a procedure according to the invention suitable anesthesia might include lidocaine or lidocaine with epinephrine. According to one embodiment of a procedure according to the invention anesthesia may be injected into the subcutaneous layer. According to one embodiment of a procedure according to the invention suitable lidocaine concentrations may include 2%, 3%, 4% or 5% solutions of lidocaine. According to one embodiment of a procedure according to the invention suitable epinephrine concentrations may include a 1 to 100,000 solution. According to one embodiment of a procedure according to the invention suitable injection patterns may include ring block or infiltrative patterns. According to one embodiment of a procedure according to the invention in one treatment, anesthesia consisting of 2% lidocaine with epinephrine in 1:100,000 concentration may be injected into the treatment region at maximum concentrations of approximately 0.4 cc per square centimeter (1.2 cc per 3 square centimeters) of skin surface in the treatment region. According to one embodiment of a procedure according to the invention a suitable volume of anesthesia may be approximately 0.3 cc per injection site for an applicator with an antenna array 2355 including four waveguide antennas 2364. According to one embodiment of a procedure according to the invention anesthesia injection sites may be positioned under the center of the aperture of waveguide antennas 2364. According to one embodiment of a procedure according to the invention approximately 10 cc of anesthesia may be used per axilla. According to one embodiment of a procedure according to the invention approximately 20 cc of anesthesia may be used per axilla. According to one embodiment of a procedure according to the invention a minimum concentration of anesthetic may be approximately 0.2 cc per square centimeter or approximately 0.15 cc per injection site. According to one embodiment of a procedure according to the invention in order to minimize the amount of fluid injected and, thus the changes to the tissue dielectric properties caused by the anesthesia, it may be necessary to utilize specialized anesthesia concentrations, such as, for example 4% lidocaine with 1 to 100,000 concentration of epinephrine, which may reduce the total amount of anesthetic fluid used by, for example, half. According to one embodiment of a procedure according to the invention using additional anesthesia may spread the energy more evenly across the target tissue, and may reduce the selectivity of the energy by reducing the energy density in a given tissue region.

According to one embodiment of the invention the invention includes a procedure for properly positioning an applicator 2320. According to one embodiment of a procedure according to the invention the treatment regimen may further include positioning the treatment apparatus such as, for example, applicator 2320 an disposable 2363 over an area to be treated in the treatment region, acquiring tissue in, for example tissue chamber 2338, using, for example, vacuum acquisition, treating the acquired tissue, by, for example, exposing it to microwave energy from applicator 2320, and releasing the acquired tissue, by, for example removing vacuum pressure from tissue chamber 2338. According to one embodiment of a procedure according to the invention the treatment apparatus may, thereafter be moved to a new treatment area within the treatment region and the procedure repeated as required until the area to be treated, or a defined subset thereof, has been treated. According to one embodiment of the invention as the treatment apparatus is moved from position to position, the roadmap treatment marks may be used to align the treatment apparatus over untreated tissue. According to one embodiment of the invention roadmap treatment marks may also be used to ensure that tissue in the treatment region is treated in a predetermined sequence.

According to one embodiment of the invention the invention includes a procedure for creating a lesion in a patient's skin. According to one embodiment of a procedure according to the invention proper positioning of applicator 2320 may be important to obtaining the desired tissue effect when energy is applied. According to one embodiment of a procedure according to the invention when applicator 2320 and disposable 2363 is placed against the skin surface, tissue may be acquired by pulling tissue into a tissue chamber 2338. According to one embodiment of a procedure according to the invention tissue acquisition may be accomplished by, for example, creating a vacuum in tissue chamber 2338. According to one embodiment of a procedure according to the invention once tissue is in tissue chamber 2338, microwave energy may be radiated into the tissue from the distal end of the treatment apparatus. According to one embodiment of a procedure according to the invention at least a portion of the radiated microwave energy may pass through the epidermis and dermis and, at least a portion of that microwave energy may reflect off of a critical interface in the skin, such as, for example, the dermal-hypodermal interface or an interface between the dermis and a glandular region. According to one embodiment of a procedure according to the invention as microwave energy is radiated into the acquired tissue and reflects off of the critical interface, a standing wave may be created which results in a peak SAR region in the dermis adjacent the critical interface. According to one embodiment of a procedure according to the invention tissue in the peak SAR region will be dielectrically heated, damaging or destroying tissue in the peak SAR region and generating heat which may be transmitted, through, for example, conduction or radiation, to surrounding tissue, including tissue which underlies the critical interface. According to one embodiment of a procedure according to the invention his transmitted heat may act to damage or destroy structures, including, for example, sweat glands or hair follicles located in the path of the transmitted heat. According to one embodiment of a procedure according to the invention the damage created by the transmitted heat may be augmented by direct dielectric heating caused by transmission of microwave energy into the damaged tissue. According to one embodiment of a procedure according to the invention tissue damage in the epidermis and upper layers of the dermis resulting from, for example, the transmitted heat, may be reduced or eliminated by, for example, controlling the temperature at the surface of the acquired tissue. According to one embodiment of a procedure according to the invention the temperature of the acquired tissue may be controlled by, for example, passing a cooling fluid 2361 through the distal end of applicator 2320 adjacent the surface of the acquired tissue. According to one embodiment of a procedure according to the invention the temperature at the surface of the acquired tissue may be controlled by, for example, cooling the skin surface prior to applying microwave energy, cooling the skin surface as microwave energy is applied or cooling the skin surface after microwave energy has been applied.

According to one embodiment of a procedure according to the invention the present procedure may be effective in creating desirable tissue effects in many types of skin, including human, porcine and mammalian. According to one embodiment of a procedure according to the invention when treating mammals other than humans or when treating different diseases, conditions or treatment regions, the procedure may be modified by using a modified treatment template to create a treatment roadmap.

According to one embodiment of the invention the invention includes a procedure for using a system according to the present invention. According to one embodiment of a procedure according to the invention in treatments using the present system, various power, time and cooling temperature settings and algorithms, as well as other variables, e.g. biobarrier configurations, may be used to generate acceptable clinical outcomes. According to one embodiment of a procedure according to the invention unacceptable clinical outcomes could include severe skin damage. According to one embodiment of a procedure according to the invention there should be no clinically relevant long term damage to the epidermis or upper dermis of the treatment subject (e.g. human or animal). According to one embodiment of a procedure according to the invention severe skin damage may include severe burns and blistering of the skin. According to one embodiment of a procedure according to the invention unacceptable clinical outcomes could include loss of physical integrity (i.e. ulcers or open sores which could lead to infection) or visible scarring of the epidermal layer. According to one embodiment of a procedure according to the invention unacceptable clinical outcomes could include aesthetic alteration of the skin which may include: displeasing appearance or texture changes to the treated sites which are a direct result of the application of microwave energy, including, permanent aesthetically displeasing changes in coloration to treatment sites and permanent aesthetically displeasing palpable changes in skin texture. According to one embodiment of a procedure according to the invention aesthetic changes which appear at the time of treatment or thereafter which resolver with time may not be undesirable aesthetic alterations. According to one embodiment of a procedure according to the invention in treatments using the present system damage to fat is expected but not at levels that will be detrimental to a treatment subject. According to one embodiment of a procedure according to the invention unacceptable clinical outcomes could include damage to large blood vessels and muscle.

According to one embodiment of a procedure according to the invention after treatments using the present system, apocrine glands (when present) in the dermal/subdermal interface region of the treatment site should appear abnormal when compared to control tissue samples. According to one embodiment of a procedure according to the invention after treatments using the present system, eccrine glands (when present) in the dermal/sub-dermal interface region of the treatment site should appear abnormal when compared to control tissue samples. According to one embodiment of a procedure according to the invention after treatments using the present system, gland structure should be structurally modified. According to one embodiment of a procedure according to the invention after treatments using the present system, damage to hair follicles may be a desirable result as it may aid in permanent hair removal.

According to one embodiment of a procedure according to the invention treatment is initiated by positioning applicator 2320 over tissue to be treated. According to one embodiment of a procedure according to the invention treatment is continued by clicking start button 2464 to initiate suction. According to one embodiment of a procedure according to the invention treatment is continued by acquiring tissue in chamber 2338. According to one embodiment of a procedure according to the invention treatment is continued by passing cooling fluid 2361 through applicator 2320, cooling tissue engaged in tissue chamber 2338. According to one embodiment of a procedure according to the invention treatment is continued by delivering power for a predetermined time. According to one embodiment of a procedure according to the invention treatment is continued by cycling microwave energy through waveguide antennas 2364 (including, in one embodiment. waveguide antennas 2364a, 2364b, 2364c and 2364d). According to one embodiment of a procedure according to the invention treatment is continued by continuing to cool tissue engaged in tissue chamber 2338 for a predetermined post-cool period after power delivery is stopped. According to one embodiment of a procedure according to the invention treatment is continued by releasing the vacuum pressure in tissue chamber 2338 after post-cool is finished. According to one embodiment of a procedure according to the invention treatment is continued by removing applicator 2320 and disposable 2363 from the treatment site. According to one embodiment of a procedure according to the invention treatment is continued by, where a procedure calls for additional treatment sites, moving applicator 2320 to the next site and repeating one or more of the previous steps. According to one embodiment of a procedure according to the invention treatment is continued all intended sites have been treated.

According to one embodiment of the invention the invention includes procedural elements. According to one embodiment of a procedure according to the invention key elements of the procedure may include the anesthesia used, the energy applied, the cooling applied, and the vacuum pressure applied. According to one embodiment of a procedure according to the invention procedural elements including, for example, anesthesia used, the energy applied, the cooling applied, and the vacuum pressure applied may be modified based upon patient characteristics such as, for example, skin thickness.

According to one embodiment of the invention the invention includes a procedure for applying energy to a treatment region within a patient. According to one embodiment of a procedure according to the invention energy applied to tissue may be a function of the power radiated into the tissue and the amount of time the power is on. According to one embodiment of a procedure according to the invention the maximum energy radiated into the tissue may be the amount of energy necessary to create a desired lesion size without damaging other tissue. According to one embodiment of a procedure according to the invention the minimum energy radiated into the tissue may be the amount of energy necessary to create the desired lesion. According to one embodiment of a procedure according to the invention tissue effects, including unwanted tissue effects, may be a function of energy per unit area. According to one embodiment of a procedure according to the invention the more the energy is spread out, the less the tissue effect. According to one embodiment of a procedure according to the invention the maximum energy delivered to the skin may be that energy which results in a lesion which does not extend into the epidermis. According to one embodiment of a procedure according to the invention the maximum energy delivered to the skin may be that energy which results in a lesion extending into the upper half of the dermis. According to one embodiment of a procedure according to the invention the maximum energy delivered to the skin may be that energy which results in a lesion extending into the upper two-thirds of the dermis. According to one embodiment of a procedure according to the invention power radiated into the tissue is a function of the power at the output generator and the applicator loss, including loss in applicator cables. According to one embodiment of a procedure according to the invention the applicator loss may be, for example approximately fifty percent, such that only approximately fifty percent of the power emitted by generator 2301 is actually coupled into the skin (in an ideal or lossless applicator, the power radiated into the tissue is substantially equal to the power at the generator output). According to one embodiment of the invention in an applicator 2320 according to the present invention, loss is a function of many factors, such as, for example, cooling fluid 2361 composition, coolant chamber 2360 thickness, cooling plate 2340 composition and cooling plate 2340 thickness. In a system 2309 according to an embodiment of the invention where the loss in applicator 2320 is approximately 50 percent, a generator radiating 80 Watts of microwave power for a period of between 2.5 and 3.5 seconds would be expected to couple approximately 100 joules into the dermis of tissue held in the distal end of the applicator. According to one embodiment of the invention when in one embodiment of the invention that microwave energy is radiated at a frequency of approximately 5.8 Gigahertz through applicator 2320 with cooling fluid 2361 cooled to a temperature of approximately 15 degrees centigrade and circulated through coolant chamber 2360 the treatment would be expected make a desirable lesion in the axilla of a human patient. In an embodiment of a procedure according to the invention such a treatment would be expected to damage or destroy at least the sweat glands, such as, for example apocrine glands or eccrine glands of a human patient without doing significant damage to skin outside a treatment zone. According to one embodiment of the invention in a procedure using an applicator 2320 with a four antenna array 2355 and a post cool period of approximately twenty seconds, a one by three centimeter area may be treated in approximately thirty five seconds.

According to one embodiment of the invention in a system 2309 where there is 2 dB of loss in the applicator cabling (which may consist of, for example a long, e.g. six foot, energy cable 2322, a antenna switch 2357 and interconnect cables 2372), the signal from generator 2301 would be expected to be reduced by approximately 37% before reaching waveguide antenna 2364. According to one embodiment of the invention in a system 2309 where there is 2 dB of loss from the input of waveguide antenna 2364 to the tissue engaged by tissue chamber 2338 as a result of, for example, absorption by cooling fluid 2361 and stray emissions, the signal from the input to waveguide antenna 2364 is reduced approximately 37% between the input to waveguide antenna 2364 and the skin surface. According to one embodiment of the invention in a system 2309 with 2 dB of cable loss and 2 dB of applicator antenna to tissue loss, the signal power is reduced approximately 60% between the generator 2301 output and the tissue load. According to one embodiment of the invention, in a system 2309 a generator 2301 output of 80 Watts would result in approximately 32 Watts of microwave power being coupled into the tissue while a generator 2301 output of 60 Watts would result in approximately 24 Watts of microwave power being coupled into the tissue and a generator output of 55 Watts would result in approximately 22 Watts of microwave power being coupled into the tissue. In a system 2309 according to one embodiment of the invention the power reaching the tissue may be adjusted by modifying the elements, e.g. the cabling, in the microwave circuit.

According to one embodiment of the invention the invention includes a procedure for applying a vacuum to acquire tissue in a tissue chamber 2338. According to one embodiment of the invention vacuum applied to disposable 2363 should be sufficient to engage skin in tissue chamber 2338 of the applicator such that the tissue is flat against tissue interface surface 2336 without damaging the tissue. According to one embodiment of the invention, for a tissue chamber 2338 having a volume of approximately one cubic inch TS and a tissue interface surface 2336 having an area of approximately 3.8 square inches, a suitable vacuum pressure may be between approximately twelve and twenty-seven and preferably approximately twenty inches of mercury, measured at the output of the vacuum pump. According to one embodiment of the invention in order to ensure full acquisition of the tissue prior to application of energy to the applicator, the vacuum may be applied for a vacuum acquisition period prior to energy application. According to one embodiment of the invention a suitable vacuum acquisition period may be, for example between two and three seconds. According to one embodiment of the invention a successful acquisition may be signaled by the absence of vacuum sounds at the distal end of applicator 2320. According to one embodiment of the invention successful vacuum acquisition may be indicated by an audible or visual signal from generator 2301. According to one embodiment of the invention vacuum acquisition may further be used to create suction marks on the skin which will assist the user in identifying regions which have been treated.

According to one embodiment of the invention, after applicator 2320 stops delivering energy to tissue, vacuum pressure may be maintained to hold the tissue in tissue chamber 2338 for a predetermined period of time. According to one embodiment of the invention the period of time may, for example, be a post treatment cooling period where the tissue is held against the cooling plate while cooling fluid continues to circulate through the applicator. According to one embodiment of the invention a suitable post cooling period may be between approximately zero and sixty seconds and preferably approximately twenty seconds. According to one embodiment of the invention a suitable post cooling period may be dictated by the amount of energy delivered to the tissue. According to one embodiment of the invention the generator may also generate an audible or visual signal when the applicator is in the post cool phase so that the applicator is not removed prematurely.

According to one embodiment of the invention the invention includes a procedure for delivering anesthesia prior to using a microwave treatment apparatus on a patient. According to one embodiment of the invention delivery of anesthesia may affect decisions on how much energy to deliver to tissue since the anesthesia may absorb some of the radiated energy, preventing it from reaching the treatment zone. According to one embodiment of the invention while anesthesia may be delivered using, for example, injections with a syringe, alternative methods of delivering anesthesia may include microneedle arrays or iontophoretic devices. According to one embodiment of the invention anesthesia may also be injected into the fat layer or in a manner which blocks all nerve sensations in the treatment area, such as, for example, the axilla of a human patient.

According to one embodiment of the invention the invention includes a method of measuring skin thickness. According to one embodiment of the invention skin thickness in the treatment region may also effect the amount of energy which should be delivered to get the required tissue effect. According to one embodiment of the invention thicker skin may require more energy to treat properly. According to one embodiment of the invention one way to measure the thickness of the skin in a particular region is to apply microwave energy through the skin surface and monitor the temperature at the skin surface. According to one embodiment of the invention in particular, the slope of the increase in temperature may provide an indication of the thickness of the skin underlying the applicator. According to one embodiment of the invention for example, a short burst of microwave energy prior to treating tissue may be used to provide an indication of skin thickness by looking at the skin temperature response to that burst and the skin temperature response may be used to modify the amount of energy delivered by, for example, increasing the amount of treatment energy delivered if the skin temperature response is relatively slow.

According to one embodiment of the invention the invention includes a treatment template. In performing a procedure according to one embodiment of the invention the user may create the roadmap using, for example, treatment template 2483. According to one embodiment of the invention when treating the axilla, for example, the user may employ a treatment template 2483 designed for use in the axilla region. According to one embodiment of the invention such a template would be selected to fit the axilla of the patient, the approximate size of the axilla and may be selected from an assortment of templates by, for example, using the length and width of the axilla or hair bearing area of the axilla as a selection criteria. According to one embodiment of the invention suitable template for use in the axilla may be oval or pear shaped.

According to one embodiment of the invention in addition to using the axilla size and shape to select appropriate treatment templates 2483, the characteristic of the axilla or any treatment region may be used to select appropriate applicators 2320 or to select appropriate firing algorithms for waveguide antennas 2364 in a particular applicator or antenna array.

According to one embodiment of the invention the invention includes a method of using a lubricant on the skin of a patient to facilitate the acquisition of tissue. According to one embodiment of the invention a procedure may include the use of a lubricant (such as, for example K-Y Jelly) on the skin to assist in acquisition. According to one embodiment of the invention a procedure may include use of lubricants to reduce friction as the skin is pulled into tissue chamber 2338. According to one embodiment of the invention a procedure may include use of lubricants to equalize force on tissue around tissue chamber 2338. According to one embodiment of the invention a procedure may include use of lubricants to assist in ensuring that targeted tissue is acquired in a manner which appropriately positions the target tissue in tissue chamber 2338. According to one embodiment of the invention a procedure may include use of lubricants may reduce the size and duration of suction marks. According to one embodiment of the invention a procedure may include use of lubricants to reduce the size of air pockets between the surface of skin positioned in tissue chamber 2338 and tissue interface surface 2336.

According to one embodiment of the invention the invention includes the treatment of a number of indications. According to one embodiment of the invention a method of reducing sweat is described. According to one embodiment of the invention a method of reducing sweat production in a patient is described. According to one embodiment of the invention a method of treating axillary hyperhidrosis is described. According to one embodiment of the invention a method of treating hyperhidrosis is described. According to one embodiment of the invention a method of removing hair is described. According to one embodiment of the invention a method of preventing the re-growth of hair is described. According to one embodiment of the invention, a method of treating osmidrosis is described. According to one embodiment of the invention, a method of denervating tissue is described. According to one embodiment of the invention, a method of treating port wine stains is described. According to one embodiment of the invention, a method of treating hemangiomas is described. According to one embodiment of the invention, a method of treating psoriasis is described. According to one embodiment of the invention, a method of reducing sweat is described. According to one embodiment of the invention, a method of reducing sweat is described. In embodiments of the invention, electromagnetic energy is used to treat acne. According to one embodiment of the invention, a method of treating sebaceous glands is described. According to one embodiment of the invention, a method of destroying bacteria is described. According to one embodiment of the invention, a method of destroying propionibacterium is described. According to one embodiment of the invention, a method of treating reducing inflammation is described.

According to one embodiment of the invention electromagnetic energy may be used to reduce sweat. According to one embodiment of the invention electromagnetic energy may be used to reduce sweat production in a patient. According to one embodiment of the invention electromagnetic energy may be used to treat axillary hyperhidrosis. According to one embodiment of the invention electromagnetic energy may be used to treat hyperhidrosis. According to one embodiment of the invention electromagnetic energy may be used to remove hair. According to one embodiment of the invention electromagnetic energy may be used to prevent the re-growth of hair. According to one embodiment of the invention electromagnetic energy may be used to treat osmidrosis. According to one embodiment of the invention, electromagnetic energy may be used to denervate tissue. According to one embodiment of the invention electromagnetic energy may be used to treat port wine stains. According to one embodiment of the invention electromagnetic energy may be used to treat hemangiomas. According to one embodiment of the invention electromagnetic energy may be used to treat psoriasis. According to one embodiment of the invention electromagnetic energy may be used to reduce sweat. In embodiments of the invention, electromagnetic energy may be used to treat acne. In embodiments of the invention, electromagnetic energy may be used to treat sebaceous glands. In embodiments of the invention, electromagnetic energy may be used to destroy bacteria. In embodiments of the invention, electromagnetic energy may be used to destroy propionibacterium. In embodiments of the invention, electromagnetic energy may be used to clear sebum from a hair follicle. In embodiments of the invention, electromagnetic energy may be used to clear obstructed hair follicles. In embodiments of the invention, electromagnetic energy may be used to reverse comedogenesis. In embodiments of the invention, electromagnetic energy may be used to clear blackheads. In embodiments of the invention, electromagnetic energy may be used to clear whiteheads. In embodiments of the invention, electromagnetic energy may be used to reducing inflammation. In embodiments of the invention, electromagnetic energy may be used to heat fat. In embodiments of the invention, electromagnetic energy may be used to reduce cellulite.

According to one embodiment of the invention a disposable medical apparatus is described which includes: a tissue chamber positioned at a distal end of the disposable member; an applicator chamber positioned at a proximal end of the disposable member; a tissue bio-barrier separating the tissue chamber and the applicator interface; and a vacuum circuit connecting the tissue chamber and the applicator chamber. According to one embodiment of the invention a tissue chamber may include: a tissue interface surface, the tissue interface surface comprising: vacuum channels surrounding the tissue bio-barrier; vacuum ports in flow communication with the vacuum channels and the vacuum circuit; and chamber walls surrounding the tissue chamber. According to one embodiment of the invention chamber walls further include a compliant member. According to one embodiment of the invention the compliant member has a height of between approximately 0.15 inches and approximately 0.25 inches. According to one embodiment of the invention the compliant member has a height of approximately 0.25 inches. According to one embodiment of the invention the chamber walls further include a lubricant coating at least a portion of the chamber walls. According to one embodiment of the invention the lubricant is selected from the group consisting of: silicone oil, Teflon, paralene or other suitable coating material to ease acquisition of tissue. According to one embodiment of the invention the applicator chamber includes: an applicator interface surface wherein the applicator interface surface surrounds the tissue bio-barrier; applicator interface walls surrounding the applicator interface surface; and a vacuum seal at a proximal end of the applicator chamber, the vacuum seal being positioned to hermetically seal the applicator chamber when an applicator is positioned in the applicator chamber. According to one embodiment of the invention the applicator chamber has a depth sufficient to receive and engage an applicator such that a distal end of the applicator contacts the tissue bio-barrier, creating an interference fit between the distal end of the applicator and the tissue bio-barrier. According to one embodiment of the invention the applicator chamber has a depth sufficient to ensure that an applicator positioned in the applicator chamber moves the bio-barrier between approximately 0.001 inches and approximately 0.030 inches into the tissue chamber. According to one embodiment of the invention the applicator chamber has a depth sufficient to ensure that an applicator positioned in the applicator chamber moves the bio-barrier approximately 0.010 inches into the tissue chamber. According to one embodiment of the invention the applicator chamber has a depth sufficient to receive and engage an applicator such that a distal end of the applicator contacts the tissue bio-barrier, creating an interference fit between the distal end of the applicator and the tissue bio-barrier when tissue is positioned in the tissue chamber. According to one embodiment of the invention the tissue bio-barrier is flexible. According to one embodiment of the invention the tissue bio-barrier is a film. According to one embodiment of the invention the tissue bio-barrier has a thickness of between 0.0001 inches and approximately 0.030 inches. According to one embodiment of the invention the tissue bio-barrier has a thickness of approximately 0.0005 inches. According to one embodiment of the invention the vacuum circuit includes: a main vacuum channel, the main vacuum passage being in flow communication with the applicator chamber; vacuum ports in flow communication with both the main vacuum channel and the tissue chamber. According to one embodiment of the invention the vacuum circuit further includes: a vacuum connector in flow communication with the main vacuum channel; an applicator bio-barrier positioned between the main vacuum channel and the applicator chamber. According to one embodiment of the invention the applicator bio-barrier is positioned on a first side of the disposable medical apparatus and the vacuum connector is positioned on a second side of the disposable medical apparatus. According to one embodiment of the invention the main vacuum channel includes a tortuous path between the vacuum connector and the applicator bio-barrier. According to one embodiment of the invention the main vacuum channel further includes vacuum baffles positioned adjacent the applicator bio-barrier. According to one embodiment of the invention the vacuum ports contact the main vacuum channel between the vacuum connector and the vacuum baffles.

According to one embodiment of the invention, the invention includes a method of balancing vacuum pressure in a medical treatment device, wherein the medical treatment device includes an applicator and a disposable, the disposable comprising a tissue chamber and an applicator chamber separated by a flexible tissue bio-barrier, the method comprising the steps of: positioning an applicator in the applicator chamber such that the applicator seals an applicator chamber opening; positioning tissue adjacent the tissue chamber such that the tissue at least partially seals a tissue chamber opening; drawing air from the tissue chamber; and drawing air from the applicator chamber. According to one embodiment of the invention a method of balancing vacuum pressure in a medical treatment device the method further including the step of positioning the applicator in the applicator chamber such that a distal end of the applicator forms an interference fit with the tissue bio-barrier. According to one embodiment of the invention a method of balancing vacuum pressure in a medical treatment device method further including the step of: positioning the applicator in the applicator chamber such that a distal end of the applicator stretches the tissue bio-barrier into the tissue chamber. According to one embodiment of the invention a method of balancing vacuum pressure in a medical treatment device further including the step of stretching the tissue bio-barrier into the tissue chamber a distance of between approximately 0.001 inches and approximately 0.030 inches. According to one embodiment of the invention a method of balancing vacuum pressure in a medical treatment device further including the step of stretching the tissue bio-barrier into the tissue chamber a distance of approximately 0.010 inches. According to one embodiment of the invention a method of balancing vacuum pressure in a medical treatment device wherein the step of drawing air from an applicator chamber includes the step of drawing air through a bio-barrier.

According to one embodiment of the invention a method of creating a lesion in a region of skin tissue below a first region of the dermis using a medical treatment device, wherein the medical treatment device includes an applicator, the applicator including a cooling plate, and a disposable, the disposable including a tissue chamber and an applicator chamber separated by a flexible tissue bio-barrier, the method including the steps of: positioning the applicator in the applicator chamber such that the applicator seals an applicator chamber opening; positioning the skin tissue adjacent the tissue chamber such that the tissue at least partially seals a tissue chamber opening; drawing air from the tissue chamber; drawing air from the applicator chamber to pull the tissue into the applicator chamber; transmitting electromagnetic energy through the cooling plate and the tissue bio-barrier. According to one embodiment of the invention a method of balancing vacuum pressure in a medical treatment device the method further including the step of positioning the applicator in the applicator chamber such that a distal end of the applicator forms an interference fit with the tissue bio-barrier. According to one embodiment of the invention a method of balancing vacuum pressure in a medical treatment device the method further including the step of positioning the applicator in the applicator chamber such that a distal end of the applicator stretches the tissue bio-barrier into the tissue chamber. According to one embodiment of the invention a method of balancing vacuum pressure in a medical treatment device further including the step of stretching the tissue bio-barrier into the tissue chamber a distance of between approximately 0.001 inches and approximately 0.030 inches. According to one embodiment of the invention a method of balancing vacuum pressure in a medical treatment device further including the step of stretching the tissue bio-barrier into the tissue chamber a distance of approximately 0.010 inches. According to one embodiment of the invention a method of balancing vacuum pressure in a medical treatment device the method further including the step of positioning the applicator in the applicator chamber such that a distal end of the applicator forms an interference fit with the tissue bio-barrier. According to one embodiment of the invention a method of balancing vacuum pressure in a medical treatment device wherein the step of drawing air from an applicator chamber includes the step of drawing air through a bio-barrier.

According to one embodiment of the invention an energy transmission applicator is described including: a disposable interface at a distal end of the applicator, the disposable interface including a disposable engagement mechanism; an antenna structure including at least one antenna aperture arranged to transmit energy through the distal end of the applicator; and a cooling circuit including a cooling plate, wherein at least a portion of the cooling circuit is positioned between the antenna and the distal end of the applicator. According to one embodiment of the invention the antenna includes: a plurality of antennas; a distribution element arranged to transmit the energy to the plurality of antennas. According to one embodiment of the invention the distribution element includes a microwave switch. According to one embodiment of the invention the distribution element includes a power splitter. According to one embodiment of the invention the energy transmission applicator further includes a scattering element positioned between the aperture and the distal end of the applicator. According to one embodiment of the invention the cooling circuit further includes a cooling chamber positioned between the antenna aperture and a proximal side of the cooling plate. According to one embodiment of the invention at least a portion of the cooling circuit is positioned between the antenna and the distal end of the applicator. According to one embodiment of the invention the waveguide assembly includes: a plurality of waveguide antennas positioned in an antenna cradle; a distribution element arranged to transmit the energy to the plurality of antennas. According to one embodiment of the invention the distribution element includes a microwave switch. According to one embodiment of the invention the distribution element includes a power splitter. According to one embodiment of the invention the energy transmission applicator further includes a plurality of scattering elements positioned between the apertures and the distal end of the applicator. According to one embodiment of the invention the cooling circuit further includes cooling chambers positioned between the antenna apertures and a proximal side of the cooling plate. According to one embodiment of the invention the waveguide assembly includes: a plurality of waveguide antennas positioned in an antenna cradle; a distribution element arranged to transmit the energy to the plurality of antennas. According to one embodiment of the invention the cooling circuit further includes cooling passages in the antenna cradle, the cooling passages being connected to the cooling chambers. According to one embodiment of the invention the waveguide assembly includes: a plurality of waveguide antennas; and a plurality of isolation elements positioned between the antennas. According to one embodiment of the invention the waveguide assembly further includes a first isolation element positioned at a first end of the waveguide assembly and a second isolation element positioned at a second end of the waveguide assembly. According to one embodiment of the invention the isolation elements comprise a shim of microwave absorption material. According to one embodiment of the invention the isolation elements comprise a microwave choke. According to one embodiment of the invention the waveguide antenna includes: an inner dielectric; an outer shell surrounding the inner dielectric on every side except the aperture. According to one embodiment of the invention the cooling plate includes: a proximal surface a distal surface; one or more thermocouple grooves in the distal surface; and one or more thermocouples positioned in the thermocouple grooves. According to one embodiment of the invention the thermocouple grooves are arranged parallel to an E-Field emitted by the waveguide assembly when the transmitted energy is microwave energy. According to one embodiment of the invention the microwave energy is transmitted in a TE10 mode.

According to one embodiment of the invention a method is described for cooling tissue using an energy transmission applicator including an antenna aperture and a cooling plate, the cooling plate having a proximal surface and a distal surface and being positioned at a distal end of the energy transmission applicator and the antenna aperture being positioned in the energy transmission applicator proximal to the cooling plate, the method including the steps of: engaging tissue in the energy transmission applicator adjacent the cooling plate; applying energy to the tissue, the energy passing through the cooling plate; and passing cooling fluid between the antenna aperture and a proximal surface of the cooling plate.

According to one embodiment of the invention method of distributing electromagnetic energy to tissue is described, the method including the steps of: radiating energy from an antenna aperture; radiating energy through cooling fluid wherein the cooling fluid flows through a cooling chamber beneath the aperture; radiating energy past scattering elements positioned in the cooling chamber; radiating energy through a cooling plate positioned opposite the aperture; radiating energy through a tissue bio-barrier on a distal side of the cooling plate.

According to one embodiment of the invention a method of supplying energy to an antenna array is described, the method including the steps of: supplying electromagnetic energy to a switch positioned in the applicator wherein the switch is connected to one or more waveguide antennas; supplying the electromagnetic energy through the switch to a first waveguide antenna for a predetermined period of time; supplying the electromagnetic energy through the switch to a second waveguide antenna for a predetermined period of time without repositioning the applicator. According to one embodiment of the invention a method of supplying energy to an antenna array wherein the first and the second waveguide antennas are adjacent to each other. According to one embodiment of the invention a method of supplying energy to an antenna array is described, the method including the steps of: supplying electromagnetic energy to an applicator including a power splitter wherein the power splitter is connected to one or more waveguide antennas; continuously connecting the power splitter to at least two of the one or more waveguide antennas; without repositioning the applicator; maintaining the energy supply to a single antenna for a predetermined period of time.

According to one embodiment of the invention microwave chain control circuitry for use in a medical device microwave generator is described the control circuitry including: a directional coupler coupled to an output of the microwave chain; power detectors coupled to the directional coupler, the power detectors including a forward power detector and a reverse power detector, the power detectors including a attenuators and detector diodes; a forward power lookup table coupled to the forward power detector, the forward power lookup table including data correlated to the characteristics of the forward power detector; a reverse power lookup table coupled to the reverse power detector, the reverse power lookup table including data correlated to the characteristics of the reverse power detector; a duty cycle circuit coupled to the forward power lookup table wherein the duty cycle circuit is coupled to a switch in the microwave chain, the switch being adapted to control the duty cycle of an input signal to an amplifier in the microwave chain.

According to one embodiment of the invention a method of controlling output power from a microwave chain in a medical device microwave generator is described, the method including the steps of: detecting a forward power signal at an output of the microwave chain; feeding the forward power signal into a forward power lookup table, the forward power lookup table including correlation data based upon the electrical characteristics of the forward power detector; modifying the forward power signal according to the correlation data; feeding the modified forward power signal to a duty cycle circuit wherein the duty cycle circuit is adapted to control the duty cycle of an input signal to an amplifier in the microwave chain.

According to one embodiment of the invention a patient support apparatus is described including: a center support; first and second arm supports connected to the center portion at a first predetermined angle of between approximately fifteen degrees an approximately thirty-five degrees. According to one embodiment of the invention the first predetermined angle is approximately twenty-five degrees.

According to one embodiment of the invention a treatment template is described including: a flexible transparent base, the flexible transparent base including: one or more treatment region outlines printed on the base; a plurality of anesthesia equally spaced injection sites printed on the base; a plurality of template positioning marks printed on the base; a plurality of applicator placement marks printed on the base.

According to one embodiment of the invention a method of treating hyperhidrosis in a patient is described including: positioning the patient on a patient support apparatus; aligning a treatment template to land marks on the patients axilla; marking anesthesia injection sites on the patients axilla; marking applicator positioning sites on the patients axilla; aligning an applicator with the applicator positioning sites; applying cooling to the patients axilla; applying energy to the patients axilla; switching energy through a plurality of antennas in the applicator; removing the applicator and moving the applicator to a second treatment site using the alignment markings.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A disposable medical apparatus for use with an applicator which radiates microwave energy, said disposable medical apparatus comprising:
   a tissue chamber at a distal end of said disposable medical apparatus, a distal end of said tissue chamber being adapted to form a vacuum seal when positioned against skin;
   an applicator chamber at a proximal end of said disposable member;
   a flexible film forming a tissue bio-barrier, said tissue bio-barrier separating said tissue chamber and said applicator chamber, said tissue bio-barrier being a material which is substantially transparent to microwave energy, and substantially impermeable to air and biological fluids;
   a filter forming an applicator bio-barrier separating air in said tissue chamber from air in said applicator chamber, said applicator bio-barrier being substantially permeable to air but substantially impermeable to biological fluids;
   a vacuum circuit connecting said tissue chamber and said applicator chamber, wherein said applicator bio-barrier is positioned in said vacuum circuit; and
   a vacuum seal at a proximal end of said applicator chamber, said vacuum seal being positioned to seal said applicator chamber when said applicator is positioned in said applicator chamber.

2. A disposable medical apparatus according to claim 1, wherein said tissue bio-barrier does not perturb microwave fields passing through said tissue bio-barrier.

3. A disposable medical apparatus according to claim 1, wherein said tissue bio-barrier is substantially lossless at a frequency of interest.

4. A disposable medical apparatus according to claim 3, wherein said frequency of interest is between approximately 5 GHz and 6.5 GHz.

5. A disposable medical apparatus according to claim 1, wherein said tissue bio-barrier has a Young's modulus of between approximately 0.1 GPa and 1.5 GPa.

6. A disposable medical apparatus according to claim 1, wherein said vacuum circuit provides a substantially free flow of air from said applicator chamber to said tissue chamber.

7. A disposable medical apparatus according to claim 1, wherein said tissue bio-barrier is less than approximately 0.001 inches thick.

8. A disposable medical apparatus according to claim 1, wherein the tissue bio-barrier comprises a dielectric material.

9. A disposable medical apparatus according to claim 1, wherein said vacuum circuit is adapted to split vacuum pressure between said tissue chamber and said actuator chamber.

10. A disposable medical apparatus according to claim 1, wherein said vacuum seal comprises a gasket around said applicator chamber.

11. A disposable medical apparatus according to claim 1 wherein said filter comprises a hydrophobic membrane filter.

12. A disposable medical apparatus according to claim 1 wherein said tissue chamber further comprises a flexible member positioned at a distal end thereof.

* * * * *